US012281339B2

(12) United States Patent
Brin et al.

(10) Patent No.: US 12,281,339 B2
(45) Date of Patent: Apr. 22, 2025

(54) COMBINATION CANCER IMMUNOTHERAPIES WITH ARGININE DEPLETION AGENTS

(71) Applicant: Polaris Group, Grand Cayman (KY)

(72) Inventors: Elena Brin, San Diego, CA (US); Wei He, San Diego, CA (US)

(73) Assignee: POLARIS GROUP, Grand Cayman (KY)

( * ) Notice: Subject to any disclaimer, the term of this patent is extended or adjusted under 35 U.S.C. 154(b) by 0 days.

(21) Appl. No.: 15/641,819

(22) Filed: Jul. 5, 2017

(65) Prior Publication Data

US 2018/0010114 A1  Jan. 11, 2018

Related U.S. Application Data

(60) Provisional application No. 62/515,807, filed on Jun. 6, 2017, provisional application No. 62/358,479, filed on Jul. 5, 2016.

(51) Int. Cl.
  *C12N 9/96* (2006.01)
  *A61K 47/10* (2017.01)

(52) U.S. Cl.
  CPC ............... *C12N 9/96* (2013.01); *A61K 47/10* (2013.01); *C12Y 305/03006* (2013.01)

(58) Field of Classification Search
  CPC ............ C12Y 305/03006; A61K 45/06; A61K 2300/00
  See application file for complete search history.

(56) References Cited

U.S. PATENT DOCUMENTS

| | | | |
|---|---|---|---|
| 5,658,565 A * | 8/1997 | Billiar | C12N 15/86 435/235.1 |
| 5,804,183 A | 9/1998 | Filpula et al. | |
| 6,132,713 A | 10/2000 | Fiipula et al. | |
| 6,180,387 B1 | 1/2001 | Biswas et al. | |
| 6,183,738 B1 | 2/2001 | Clark | |
| 6,635,462 B1 | 10/2003 | Ensor et al. | |
| 7,204,980 B2 | 4/2007 | Clark | |
| 7,323,167 B2 | 1/2008 | Clark et al. | |
| 7,413,735 B2 | 8/2008 | Min et al. | |
| 9,333,268 B2 | 5/2016 | Bomalaski et al. | |
| 9,731,028 B2 | 8/2017 | Bomalaski et al. | |
| 9,789,170 B2 | 10/2017 | Showalter et al. | |
| 2003/0215429 A1 | 11/2003 | de Simone | |
| 2004/0258675 A1 | 12/2004 | Ensor et al. | |
| 2005/0129706 A1 | 6/2005 | Clark | |
| 2006/0002915 A1 | 1/2006 | Min et al. | |
| 2007/0198198 A1 | 8/2007 | Burczynski et al. | |
| 2007/0212311 A1 | 9/2007 | Burne et al. | |
| 2009/0238813 A1 | 9/2009 | Georgiou et al. | |
| 2010/0197944 A1 | 8/2010 | Palle et al. | |
| 2010/0303893 A1 | 12/2010 | Luo et al. | |
| 2011/0111403 A1 | 5/2011 | Petrauskene et al. | |
| 2011/0268766 A1 * | 11/2011 | Beech | C12N 15/86 424/277.1 |
| 2011/0301189 A1 | 12/2011 | Hattar et al. | |
| 2012/0015049 A1 | 1/2012 | Zhang | |
| 2012/0148559 A1 | 6/2012 | Georgiou et al. | |
| 2013/0022625 A1 | 1/2013 | Igawa et al. | |
| 2013/0052179 A1 | 2/2013 | Huang et al. | |
| 2014/0348814 A1 | 11/2014 | Almassy et al. | |
| 2015/0132278 A1 | 5/2015 | Bomalaski et al. | |
| 2015/0231272 A1 | 8/2015 | Bomalaski et al. | |
| 2016/0074487 A1 | 3/2016 | Showalter et al. | |
| 2017/0000862 A1 | 1/2017 | Wu et al. | |

FOREIGN PATENT DOCUMENTS

| | | | |
|---|---|---|---|
| TW | 201340979 A | 10/2013 | |
| WO | WO-2013151568 A1 * | 10/2013 | |
| WO | WO-2016149562 A2 * | 9/2016 | ............. A61K 38/00 |

OTHER PUBLICATIONS

Pinton et al (Oncotarget, 2015, vol. 7, pp. 1168-1184) (Year: 2015).*
Pardoll (Nature Reviews Cancer, 2012, vol. 12, pp. 252-264) (Year: 2012).*
Abstract of Besse et al (European Journal of Cancer, Sep. 2015, vol. 51, suppl. 3, pp. S717-S718) (Year: 2015).*
Deeks (Drugs, 2014, vol. 74, pp. 1223-1239) (Year: 2014).*
Khoja et al (Journal for the Immunotherapy of Cancer, 2015, vol. 3, 13 pages) (Year: 2015).*
Raber et al (Oncotarget, Mar. 19, 2016, vol. 7, pp. 17565-17578) (Year: 2016).*
Fultang et al (International Journal of Cancer, Feb. 23, 2016, vol. 139, pp. 501-509) (Year: 2016).*
The abstract of Shim et al (Proc. Am Assoc. Cancer Res., 2009, Abstract No. LB-35) (Year: 2009).*
Yoon et al (International Journal of Cancer, 2006, vol. 120, pp. 897-905). (Year: 2006).*
Noh et al (Molecules and Cells, 2002, vol. 13, pp. 137-143) (Year: 2002).*
Amin et al (Oncology, 2013, vol. 27, pp. 680-691). (Year: 2013).*
Floros and Tarhini (Seminars in Oncology, 2015, vol. 42, pp. 539-548) (Year: 2016).*
Kryczek et al (Journal of Experimental Medicine, 2006, vol. 203, pp. 871-881) (Year: 2006).*
Smith et al (Gynecologic Oncology, 2014, vol. 134, pp. 181-189). (Year: 2014).*
Wheatley et al, Anti-Cancer Drugs, 2004, vol. 15, pp. 825-833 (Year: 2004).*
Murad, Rambam Maimonides Medical Journal, 2011, vol. 2, No. 2, e0038, 1-9 pages (Year: 2011).*
Garon et al (Seminars in Oncology, 2015, vol. 42, No. 5, suppl.2, pp. S11-S18) (Year: 2015).*
International Search Report and Written Opinion for International Application No. PCT/US2017/040700, mailed Nov. 17, 2017, 11 pages.

(Continued)

*Primary Examiner* — Karen A. Canella
(74) *Attorney, Agent, or Firm* — Carter, DeLuca & Farrell LLP

(57) ABSTRACT

Provided are arginine depletion agents such as ADI-PEG for use in combination with cancer immunotherapies, for example, immune checkpoint modulators and T-cell adoptive immunotherapies, for treating various cancers. Also provided are related methods, compositions, patient care kits, and cell cultures.

32 Claims, 12 Drawing Sheets

Specification includes a Sequence Listing.

(56) References Cited

OTHER PUBLICATIONS

Kuo, et al., "Targeted cellular metabolism for cancer chemotherapy with recombinant arginine-degrading enzymes." Oncotarget (2010); 1(4): 246-251.
Albina, et al., "Regulation of macrophage functions by L-arginine." J Exp Med. (1989); 169(3): 1021-1029.
Ascierto, et al., "Pegylated arginine deiminase treatment of patients with metastatic melanoma: results from phase I and II studies." J Clin Oncol. (2005); 23(30): 7660-7668.
Aulak, et al., "Molecular sites of regulation of expression of the rat cationic amino acid transporter gene." J Biol Chem. (1996); 271(47): 29799-29806.
Bansal, et al., "Citrulline can preserve proliferation and prevent the loss of CD3 zeta chain under conditions of low arginine." JPEN J Parenter Enteral Nutr. (2004); 28(6): 423-430.
Bomalaski, et al., "Comparative toxicity of arginine deiminase formulated with polyethylene glycol 5000 or 20,000 and the effects of arginine." Preclinica (2003); 1:284: 293.
Bottino, et al., "Identification of PVR (CD155) and Nectin-2 (CD112) as cell surface ligands for the human DNAM-1 (CD226) activating molecule." J Exp Med. (2003); 198(4): 557-567.
Bronte, et al., "Regulation of immune responses by L-arginine metabolism." Nat Rev Immunol. (2005); 5(8): 641-654.
De Graaf, et al., "Nonnatural amino acids for site-specific protein conjugation." Bioconjug Chem. (2009); 20(7): 1281-1295.
Delage, B. et al., "Arginine Deprivation and Argininosuccinate Synthetase Expression in the Treatment of Cancer," International Journal of Cancer, 126: 2762-2772 (2010).
Derre, et al., "BTLA mediates inhibition of human tumor-specific CD8+ T cells that can be partially reversed by vaccination." J Clin Invest. (2010); 120(1): 157-167.
Extended European Search Report for European Application No. 15765975.6, dated Oct. 27, 2017, 6 pages.
Feun, et al., "Arginine deprivation in cancer therapy." Curr Opin Clin Nutr Metab Care (2015); 18(1): 78-82.
Fletcher, et al., "l-Arginine depletion blunts antitumor T-cell responses by inducing myeloid-derived suppressor cells." Cancer Res. (2015); 75(2): 275-283.
Gazzola, et al., "Regulation of amino acid transport in chick embryo heart cells. I. Adaptive system of mediation for neutral amino acids." Biochim Biophys Acta. (1972); 266(2): 407-421.
He, et al., "Agonist anti-human CD27 monoclonal antibody induces T cell activation and tumor immunity in human CD27-transgenic mice." J Immunol. (2013); 191(8): 4174-4183.
Holtsberg, F. W. et al., "Poly(ethylene glycol) (PEG) Conjugated Arginine Deiminase: Effects of PEG Formulations on its Pharmacological Properties," Journal of Controlled Release, 80:259-271 (2002).
Huang, et al., "Role of LAG-3 in regulatory T cells." Immunity (2004); 21(4): 503-513.
Hyatt, et al., "Adaptive regulation of the cationic amino acid transporter-1 (Cat-1) in Fao cells." J Biol Chem. (1997); 272(32): 19951-19957.
Izzo, F., et al., "Pegylated arginine deiminase treatment of patients with unresectable hepatocellular carcinoma: results from phase I/II studies." J Clin Oncol. (2004); 22(10): 1815-1822.
Johnson, et al. "Clinical and biological effects of an agonist anti-CD40 antibody: a Cancer Research UK phase I study." Clin Cancer Res. (2015); 21(6): 1321-1328.
Johnston, et al., "The immunoreceptor TIGIT regulates antitumor and antiviral CD8(+) T cell effector function." Cancer Cell (2014); 26(6): 923-937.
June, C.H. "Adoptive T cell therapy for cancer in the clinic." J Clin Invest. (2007); 117(6): 1466-1476.
Kelly, M. P. et al., "Arginine Deiminase PEG20 Inhibits Growth of Small Cell Lung Cancers Lacking Expression of Argininosuccinate Synthetase," British Journal of Cancer, 106(2):324-332 (2012).
Kurtulus, et al., "TIGIT predominantly regulates the immune response via regulatory T cells." J Clin Invest. (2015); 125(11): 4053-4062.
Li, et al., "Emerging immune checkpoints for cancer therapy." Acta Oncol. (2015); 54(10): 1706-1713.
Lines, et al., "VISTA is an immune checkpoint molecule for human T cells." Cancer Res. (2014); 74(7): 1924-1932.
Lorentzen, et al., CD19-Chimeric Antigen Receptor T Cells for Treatment of Chronic Lymphocytic Leukaemia and Acute Lymphoblastic Leukaemia. Scand J Immunol. (2015); 82(4): 307-319.
Maude, et al., "CD19-targeted chimeric antigen receptor T-cell therapy for acute lymphoblastic leukemia." Blood (2015); 125(26): 4017-4023.
Park, et al., "Pharmacology of *Escherichia coli*-L-asparaginase polyethylene glycol adduct." Anticancer Res. (1981); 1(6): 373-6.
Peranzoni, et al., "Role of arginine metabolism in immunity and immunopathology." Immunobiology (2007); 212(9-10): 795-812.
Philips, et al., "Therapeutic uses of anti-PD-1 and anti-PD-L1 antibodies." Int Immunol. (2015); 27(1): 39-46.
Phillips, et al., "Targeting arginine-dependent cancers with arginine-degrading enzymes: opportunities and challenges." Cancer Res Treat. (2013); 45(4): 251-262.
Pilotte, et al., "Reversal of tumoral Immune resistance by inhibition of tryptophan 2,3-dioxygenase." Proc Natl Acad Sci U S A. (2012);109(7): 2497-2502.
Platten, et al., "Cancer Immunotherapy by Targeting IDO1/TDO and Their Downstream Effectors." Front Immunol. (2015); 5: 673.
Qiu, et al., "Targeting arginine metabolism pathway to treat arginine-dependent cancers." Cancer Lett. (2015); 364(1): 1-7.
Rath, et al., "Metabolism via Arginase or Nitric Oxide Synthase: Two Competing Arginine Pathways in Macrophages." Front Immunol. (2014); 5: 532.
Rodriguez, et al., "L-arginine availability regulates T-lymphocyte cell-cycle progression." Blood (2007); 109(4): 1568-1573.
Rodriguez, et al., "L-arginine consumption by macrophages modulates the expression of CD3zeta chain in T lymphocytes." J Immunol. (2003); 171(3): 1232-1239.
Rosenberg, et al., "Adoptive cell transfer as personalized immunotherapy for human cancer." Science (2015); 348(6230): 62-68.
Schaer, et al., "GITR pathway activation abrogates tumor immune suppression through loss of regulatory T cell lineage stability." Cancer Immunol Res. (2013); 1(5): 320-331.
Shao, et al., CD137 ligand, a member of the tumor necrosis factor family, regulates immune responses via reverse signal transduction. J Leukoc Biol. (2011); 89(1): 21-29.
Sharma, et al., "The future of immune checkpoint therapy." Science. (2015); 348(6230): 56-61.
Sheridan, C. "Ido inhibitors move center stage in immuno-oncology." Nat Biotechnol. (2015); 33(4): 321-322.
Tahara-Hanaoka, et al., "Functional characterization of DNAM-1 (CD226) interaction with its ligands PVR (CD155) and nectin-2 (PRR-2/CD112)." Int Immunol. (2004); 16(4): 533-538.
Tarasenko, et al., "Impaired T cell function in argininosuccinate synthetase deficiency." J Leukoc Biol. (2015); 97(2): 273-278.
Thomas, et al., "Targeting human CD27 with an agonist antibody stimulates T-cell activation and antitumor immunity." Oncoimmunology (2014); 3(1): e27255.
Topalian, et al., "Immune checkpoint blockade: a common denominator approach to cancer therapy." Cancer Cell. (2015); 27(4): 450-461.
Vonderheide, et al., "Agonistic CD40 antibodies and cancer therapy." Clin Cancer Res. (2013); 19(5): 1035-43.
Workman, et al., "Lymphocyte activation gene-3 (CD223) regulates the size of the expanding T cell population following antigen activation in vivo." J Immunol. (2004); 172(9): 5450-5455.
Workman, et al., "The CD4-related molecule, LAG-3 (CD223), regulates the expansion of activated T cells." Eur J Immunol. (2003); 33(4): 970-979.
English translation of Chinese Office Action dated Jan. 7, 2021, corresponding to counterpart Chinese Application No. 201780042314.X; 7 pages.
English translation of Chinese Office Action issued May 29, 2020, corresponding to counterpart Chinese Application No. 201780042314.X; 6 pages.

(56) References Cited

OTHER PUBLICATIONS

English translation of Taiwanese Search Report dated Sep. 24, 2021, corresponding to counterpart Taiwanese application No. 106122601; 1 page.
Bononi et al. "Latest Developments in our Understanding of the Pathogenesis of Mesothelioma and the Design of Targeted Therapies," Expert Rev. Respir Med., Oct. 2015; vol. 9, No. 5; pp. 633-654.
English translation of Chinese Office Action dated Sep. 28, 2021, corresponding to counterpart Chinese Application No. 201780042314.X; 6 pages.
English Translation of Taiwanese Office Action for application No. 106122601, Jun. 27, 2023, 11 pages.
English translation of Chinese Notification of Reexamination for application No. 201780042314.X, Nov. 14, 2023, 10 pages.
Yu, Boafa, "Interventional Oncology & Chemoimmunotherapy," Military Medical Science Press, 1st edition, 1st printing, Sep. 2014, pp. 44-53. Machine translation.
Shi, Yuankai, "Advances in Medical Oncology in China: Education for Chinese Oncologists," Peking Union Medical College Press, 1st edition, 1st printing, Jun. 2013, pp. 407-409. Machine Translation.
Croft, Michael, et al., "The significance of OX40 and OX40L to T-cell biology and immune disease," Immunological reviews, May 2009, pp. 173-191, 229.1.
Doherty, Daniel H., et al., "Site-specific PEGylation of engineered cysteine analogues of recombinant human granulocyte-macrophage colony-stimulating factor," Bioconjugate chemistry, Sep. 2005, pp. 1291-1298, 16.5.
Feun, Lynn, and Niramol Savaraj, "Pegylated arginine deiminase: a novel anticancer enzyme agent," Expert opinion on investigational drugs, Jul. 2006, pp. 815-822, 15.7.
Ramos, Carlos A., Barbara Savoldo, and Gianpietro Dotti, "CD19-CAR trials," The Cancer Journal, Mar. 2014, pp. 112-118, 20.2.
Raber, Patrick, Augusto C. Ochoa, and Paulo C. Rodriguez, "Metabolism of L-arginine by myeloid-derived suppressor cells in cancer: mechanisms of T cell suppression and therapeutic perspectives," Immunological investigations, Aug. 2012, pp. 614-634, 41.6-7.
Rodríguez, Paulo C., and Augusto C. Ochoa, "Arginine regulation by myeloid derived suppressor cells and tolerance in cancer: mechanisms and therapeutic perspectives," Immunological reviews, Apr. 2008, pp. 180-191, 222.1.
Feun, L., et al., "Arginine deprivation as a targeted therapy for cancer," Current pharmaceutical design, Apr. 2008, pp. 1049-1057, 14.11.
English translation of Chinese Office Action for application No. 201780042314X, Mar. 13, 2024, 8 pages.

* cited by examiner

COMBINATION CANCER IMMUNOTHERAPIES WITH ARGININE DEPLETION AGENTS

CROSS-REFERENCE TO RELATED APPLICATIONS

This application claims priority under 35 U.S.C. § 119(e) to U.S. Application No. 62/515,807, filed Jun. 6, 2017; and U.S. Application No. 62/358,479, filed Jul. 5, 2016, each of which is incorporated by reference in its entirety.

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is POLA_006_02 US_ST25.txt. The text file is about 196 KB, was created on Jul. 5, 2017, and is being submitted electronically via EFS-Web.

BACKGROUND

Technical Field

Embodiments of the present disclosure relate, inter alia, to the use of arginine depletion agents such as ADI-PEG in combination with cancer immunotherapies, for example, immune checkpoint modulators and T-cell adoptive immunotherapies, for treating various cancers.

Description of the Related Art

Arginine is used in a number of metabolic pathways, including those involved in modulating immune responses. It is a substrate for arginase and iNOS, enzymes that play important roles in immune cell regulation (see, e.g., Peranzoni et al., Immunobiology 2007; 212:795-812; Rodriguez and Ochoa, Immunol Rev 2008; 222:180-91; Rath et al., Front Immunol. 2014. Oct. 27; 5:532; Delage et al., Int J Cancer. 2010 Jun. 15; 126(12):2762-72; Bronte and Zanovello, Nat Rev Immunol. 2005 August; 5(8):641-54; Raber et al., Immunol Invest. 2012; 41(6-7):614-34; and Albina et al., J Exp Med. 1989 Mar. 1; 169(3):1021-9). T-cells need arginine for proliferation, TCR expression, and development of memory (Id.).

While arginine starvation has been shown to impede proliferation and cell cycle progression of activated T-cells in vitro this effect can be reversed by addition of citrulline (see, e.g., Bansal et al., JPEN J. Parenter. Enteral Nutr. 2004; 28, 423-430; Fletcher et al., Cancer Res 75, 275-83 (2015); and Rodriguez et al., Blood 2007; 109:1568-73). Similarly, prolonged loss of CD3 and T cell inhibition can be induced in vitro by macrophages expressing arginase I and not those producing NOS2 (converts arginine to citrulline and NO) (see, e.g., Rodriguez et al., J Immunol. 2003 Aug. 1; 171(3):1232-9).

Lack of arginine induces an increased transcription and stability of RNAs encoding a multi-amino acid transport system including CAT-1 which increases transport of cationic amino acids into the cell (see, e.g., Gazzola et al., Biochim Biophys Acta. 1972; 266:407-421; Hyatt et al., J Biol Chem. 1997; 272:19951-19957; Aulak et al., J Biol Chem. 1996; 271: 29799-29806;). Under low arginine conditions T-cells increase citrulline uptake and upregulate expression of ASS1 which converts citrulline into arginine (see, e.g., Bansal et al., 2004; Fletcher et al., 2015; and Tarasenko et al., J Leukoc Biol. 2015 February; 97(2):273-8). Therefore, while conversion of arginine into ornithine by arginase can lead to immunosuppression in the tumor microenvironment (Id.), conversion of arginine into citrulline may have a distinct outcome.

Pegylated arginine deiminase (ADI-PEG 20) depletes the external supply of arginine by converting it to citrulline and ammonia. ADI-PEG 20 is being investigated in clinic for tumors deficient in key enzyme argininosuccinate synthetase-1 (ASS1) involved in conversion of citrulline to arginine ADI-PEG 20 has been well-tolerated and showed promise in clinical studies (see, e.g., Qiu et al., Cancer Lett. 2015 Aug. 1; 364(1):1-7; Phillips et al., Cancer Res Treat. 2013 December; 45(4):251-62; Feun et al., Curr Pharm Des. 2008; 14(11):1049-57; Feun and Savarage, Expert Opin Investig Drugs. 2006 July; 15(7):815-22; Feun et al., Curr Opin Clin Nutr Metab Care. 2015 January; 18(1):78-82). The anti-tumor properties of ADI-PEG 20 have been extensively investigated; however, its impact on immune cells such as T-cells is largely unknown. Such provides the opportunity to explore new immunotherapeutic aspects of arginine depletion.

BRIEF SUMMARY

Embodiments of the present disclosure relate to the discovery that arginine depletion agents (that convert arginine to citrulline) have unexpected immunomodulatory properties. For example, the exemplary arginine depletion agent ADI-PEG 20 was shown to reduce immune-suppressive regulatory T-cells (Treg cells) moderate exhaustion of effector T-cells (Teff cells) in vitro, and to induce or increase T-cells infiltration into non-immunogenic tumors in vivo. As specific examples, ADI treatment during T-cell stimulation enhanced effector T cell activation (expression of CD69), blocked upregulation of immunosuppressive receptors PD-1 and CTLA-4 on T-cells, thereby reducing T-cell exhaustion, and reduced upregulation of PD-L1 on T-cells following stimulation.

These unexpected properties suggest that arginine depletion agents such as ADI-PEG 20 can be combined with other cancer immunotherapies to improve the same. Particular examples of cancer immunotherapies that can benefit from the combination with arginine depletion agents include PD-1 inhibitors, PD-L1 inhibitors, and T-cell adoptive immunotherapies, among others.

Certain embodiments therefore include methods of treating a cancer in a subject in need thereof, comprising administering to the subject
  (a) an arginine depletion agent which converts arginine to citrulline; and
  (b) a cancer immunotherapy agent.

In certain embodiments, the arginine depletion agent of (a) is an ADI polypeptide. In certain embodiments, the ADI polypeptide comprises, consists, or consists essentially of a sequence selected from Table A1, including variants and fragments which convert arginine to citrulline. In certain embodiments, the variant comprises a sequence that is at least 80%, 85%, 90%, 95%, 96%, 97%, 98%, or 99% identical to a sequence from Table A1, and which converts arginine to citrulline.

In some embodiments, the ADI polypeptide is covalently bonded via an optional linker to at least one PEG molecule. In certain embodiments, the ADI polypeptide is covalently bonded to more than one PEG molecule. In particular embodiments, the ADI polypeptide is covalently bonded to about 1 to about 10 PEG molecules. In certain embodiments, the ADI polypeptide is covalently bonded to about 2 to about 8 PEG molecules. In certain embodiments, the PEG molecules are straight chain or branch chain PEG molecules.

In some embodiments, the PEG has a total average molecular weight of from about 1,000 to about 40,000 Daltons. In certain embodiments, the PEG has a total average molecular weight of from about 10,000 to about 30,000 Daltons. In specific embodiments, the PEG has a total average molecular weight of about 20,000 Daltons.

In certain embodiments, the linker is a succinyl group, an amide group, an imide group, a carbamate group, an ester group, an epoxy group, a carboxyl group, a hydroxyl group, a carbohydrate, a tyrosine group, a cysteine group, a histidine group, a methylene group, or any combinations thereof. In certain embodiments, the source of the succinyl group is succinimidyl succinate.

In certain embodiments, the arginine depletion agent is pegylated arginine deiminase (ADI-PEG). In specific exemplary embodiments, the ADI-PEG is ADI-PEG 20.

In certain embodiments, the cancer immunotherapy agent of (b) is selected from one or more of an immune checkpoint modulatory agent, a cancer vaccine, an oncolytic virus, a cytokine, and a cell-based immunotherapies. In some embodiments, the immune checkpoint modulatory agent is a polypeptide, optionally an antibody or antigen-binding fragment thereof or a ligand, or a small molecule.

In certain embodiments, the immune checkpoint modulatory agent comprises
(i) an antagonist of a inhibitory immune checkpoint molecule; or
(ii) an agonist of a stimulatory immune checkpoint molecule.

In some embodiments, the immune checkpoint modulatory agent specifically binds to the immune checkpoint molecule.

In particular embodiments, the inhibitory immune checkpoint molecule is selected from one or more of Programmed Death-Ligand 1 (PD-L1), Programmed Death 1 (PD-1), Programmed Death-Ligand 2 (PD-L2), Cytotoxic T-Lymphocyte-Associated protein 4 (CTLA-4), Indoleamine 2,3-dioxygenase (IDO), tryptophan 2,3-dioxygenase (TDO), T-cell Immunoglobulin domain and Mucin domain 3 (TIM-3), Lymphocyte Activation Gene-3 (LAG-3), V-domain Ig suppressor of T cell activation (VISTA), B and T Lymphocyte Attenuator (BTLA), CD160, Herpes Virus Entry Mediator (HVEM), and T-cell immunoreceptor with Ig and ITIM domains (TIGIT).

In some embodiments, the antagonist is a PD-L1 antagonist optionally selected from one or more of an antibody or antigen-binding fragment or small molecule that specifically binds thereto, atezolizumab (MPDL3280A), avelumab (MSB0010718C), and durvalumab (MEDI4736), and wherein the cancer is optionally selected from one or more of colorectal cancer, melanoma, breast cancer, non-small-cell lung carcinoma, bladder cancer, and renal cell carcinoma. In certain embodiments, the antagonist is a PD-1 antagonist optionally selected from one or more of an antibody or antigen-binding fragment or small molecule that specifically binds thereto, nivolumab, pembrolizumab, PDR001, and pidilizumab. In some embodiments, the PD-1 antagonist is nivolumab and the cancer is optionally selected from one or more of Hodgkin's lymphoma, melanoma, non-small cell lung cancer, hepatocellular carcinoma, renal cell carcinoma, and ovarian cancer. In certain embodiments, the PD-1 antagonist is pembrolizumab and the cancer is optionally selected from one or more of melanoma, non-small cell lung cancer, small cell lung cancer, head and neck cancer, and urothelial cancer.

In some embodiments, the antagonist is a PD-L2 antagonist optionally selected from one or more of an antibody or antigen-binding fragment or small molecule that specifically binds thereto, In certain embodiments, the antagonist is a CTLA-4 antagonist optionally selected from one or more of an antibody or antigen-binding fragment or small molecule that specifically binds thereto, ipilimumab, tremelimumab. In particular embodiments, the cancer is selected from one or more of melanoma, prostate cancer, lung cancer, and bladder cancer.

In certain embodiments, the antagonist is an IDO antagonist optionally selected from one or more of an antibody or antigen-binding fragment or small molecule that specifically binds thereto, indoximod (NLG-8189), 1-methyl-tryptophan (1MT), β-Carboline (norharmane; 9H-pyrido[3,4-b]indole), rosmarinic acid, and epacadostat, and wherein the cancer is optionally selected from one or more of metastatic breast cancer and brain cancer optionally Glioblastoma Multiforme, glioma, gliosarcoma or malignant brain tumor.

In certain embodiments, the antagonist is a TDO antagonist optionally selected from one or more of an antibody or antigen-binding fragment or small molecule that specifically binds thereto, 680C91, and LM10.

In some embodiments, the antagonist is a TIM-3 antagonist optionally selected from one or more of an antibody or antigen-binding fragment or small molecule that specifically binds thereto.

In certain embodiments, the antagonist is a LAG-3 antagonist optionally selected from one or more of an antibody or antigen-binding fragment or small molecule that specifically binds thereto, and BMS-986016.

In certain embodiments, the antagonist is a VISTA antagonist optionally selected from one or more of an antibody or antigen-binding fragment or small molecule that specifically binds thereto.

In certain embodiments, the antagonist is a BTLA antagonist optionally selected from one or more of an antibody or antigen-binding fragment or small molecule that specifically binds thereto.

In some embodiments, the antagonist is a CD160 antagonist optionally selected from one or more of an antibody or antigen-binding fragment or small molecule that specifically binds thereto.

In certain embodiments, the antagonist is an HVEM antagonist optionally selected from one or more of an antibody or antigen-binding fragment or small molecule that specifically binds thereto.

In certain embodiments, the antagonist is a TIGIT antagonist optionally selected from one or more of an antibody or antigen-binding fragment or small molecule that specifically binds thereto.

In some embodiments, the stimulatory immune checkpoint molecule is selected from one or more of OX40, CD40, Glucocorticoid-Induced TNFR Family Related Gene (GITR), CD137 (4-1BB), CD27, CD28, CD226, and Herpes Virus Entry Mediator (HVEM).

In certain embodiments, the agonist is an OX40 agonist optionally selected from one or more of an antibody or antigen-binding fragment or small molecule or ligand that specifically binds thereto, OX86, Fc-OX40L, and GSK3174998.

In certain embodiments, the agonist is a CD40 agonist optionally selected from one or more of an antibody or antigen-binding fragment or small molecule or ligand that specifically binds thereto, CP-870,893, dacetuzumab, Chi Lob 7/4, ADC-1013, and rhCD40L, and wherein the cancer is optionally selected from one or more of melanoma, pancreatic carcinoma, mesothelioma, and hematological cancers optionally lymphoma such as Non-Hodgkin's lymphoma.

In certain embodiments, the agonist is a GITR agonist optionally selected from one or more of an antibody or antigen-binding fragment or small molecule or ligand that specifically binds thereto, INCAGN01876, DTA-1, and MEDI1873.

In some embodiments, the agonist is a CD137 agonist optionally selected from one or more of an antibody or antigen-binding fragment or small molecule or ligand that specifically binds thereto, utomilumab, and 4-1BB ligand.

In particular embodiments, the agonist is a CD27 agonist optionally selected from one or more of an antibody or antigen-binding fragment or small molecule or ligand that specifically binds thereto, varlilumab, and CDX-1127 (1F5).

In certain embodiments, the agonist is a CD28 agonist optionally selected from one or more of an antibody or antigen-binding fragment or small molecule or ligand that specifically binds thereto, and TAB08.

In certain embodiments, the agonist is a CD226 agonist optionally selected from one or more of an antibody or antigen-binding fragment or small molecule or ligand that specifically binds thereto In certain embodiments, the agonist is an HVEM agonist optionally selected from one or more of an antibody or antigen-binding fragment or small molecule or ligand that specifically binds thereto.

In certain embodiments, the cancer immunotherapy agent of (b) is a cancer vaccine is selected from one or more of Oncophage, a human papillomavirus HPV vaccine optionally Gardasil or Cervarix, a hepatitis B vaccine optionally Engerix-B, Recombivax HB, or Twinrix, and sipuleucel-T (Provenge), or comprises a cancer antigen selected from one or more of human Her2/neu, Her1/EGF receptor (EGFR), Her3, A33 antigen, B7H3, CD5, CD19, CD20, CD22, CD23 (IgE Receptor), MAGE-3, C242 antigen, 5T4, IL-6, IL-13, vascular endothelial growth factor VEGF (e.g., VEGF-A) VEGFR-1, VEGFR-2, CD30, CD33, CD37, CD40, CD44, CD51, CD52, CD56, CD74, CD80, CD152, CD200, CD221, CCR4, HLA-DR, CTLA-4, NPC-1C, tenascin, vimentin, insulin-like growth factor 1 receptor (IGF-1R), alpha-fetoprotein, insulin-like growth factor 1 (IGF-1), carbonic anhydrase 9 (CA-IX), carcinoembryonic antigen (CEA), guanylyl cyclase C, NY-ESO-1, p53, survivin, integrin $\alpha v \beta 3$, integrin $\alpha 5 \beta 1$, folate receptor 1, transmembrane glycoprotein NMB, fibroblast activation protein alpha (FAP), glycoprotein 75, TAG-72, MUC1, MUC16 (or CA-125), phosphatidylserine, prostate-specific membrane antigen (PMSA), NR-LU-13 antigen, TRAIL-R1, tumor necrosis factor receptor superfamily member 10b (TNFRSF10B or TRAIL-R2), SLAM family member 7 (SLAMF7), EGP40 pancarcinoma antigen, B-cell activating factor (BAFF), platelet-derived growth factor receptor, glycoprotein EpCAM (17-1A), Programmed Death-1, protein disulfide isomerase (PDI), Phosphatase of Regenerating Liver 3 (PRL-3), prostatic acid phosphatase, Lewis-Y antigen, GD2 (a disialoganglioside expressed on tumors of neuroectodermal origin), glypican-3 (GPC3), and mesothelin.

In certain embodiments, the cancer immunotherapy agent of (b) is an oncolytic virus selected from one or more of talimogene laherparepvec (T-VEC), coxsackievirus A21 (CAVATAK™), Oncorine (H101), pelareorep (REOLYSIN®), Seneca Valley virus (NTX-010), *Senecavirus* SVV-001, ColoAd1, SEPREHVIR (HSV-1716), CGTG-102 (Ad5/3-D24-GMCSF), GL-ONC1, MV-NIS, and DNX-2401.

In some embodiments, the cancer immunotherapy agent of (b) is a cytokine selected from one or more of interferon (IFN)-α, IL-2, IL-12, IL-7, IL-21, and Granulocyte-macrophage colony-stimulating factor (GM-CSF).

In some embodiments, the cancer immunotherapy agent of (b) is a cell-based immunotherapy that comprises cancer antigen-specific T-cells, optionally ex vivo-derived T-cells. In some embodiments, the cancer immunotherapy agent of the cancer antigen-specific T-cells are selected from one or more of chimeric antigen receptor (CAR)-modified T-cells, and T-cell Receptor (TCR)-modified T-cells, tumor infiltrating lymphocytes (TILs), and peptide-induced T-cells.

In some embodiments, the cancer immunotherapy agent of (b) is selected from one or more of an IDO antagonist, a CD20 antagonist, a B-Raf antagonist, IL-2, GM-CSF, and an oncolytic virus.

In some embodiments, the IDO antagonist is indoximod, and/or wherein the CD20 agonist is rituximab, and/or wherein the B-Raf antagonist is vemurafenib, and/or wherein the oncolytic virus is talimogene laherparepvec (T-VEC) or coxsackievirus A21 (CAVATAK™).

In some embodiments, the arginine depletion agent of (a) and the cancer immunotherapy agent of (b) are administered separately. In some embodiments, the arginine depletion agent of (a) and the cancer immunotherapy agent of (b) are administered together as part of the same composition.

In some embodiments, the cancer is selected from one or more of hepatocellular carcinoma, melanoma, metastatic melanoma, pancreatic cancer, prostate cancer, small cell lung cancer, mesothelioma, lymphocytic leukemia, chronic myelogenous leukemia, lymphoma, hepatoma, sarcoma, leukemia, acute myeloid leukemia, relapsed acute myeloid leukemia, breast cancer, ovarian cancer, colorectal cancer, gastric cancer, glioma, glioblastoma multiforme, non-small cell lung cancer (NSCLC), kidney cancer, bladder cancer, uterine cancer, esophageal cancer, brain cancer, head and neck cancers, cervical cancer, testicular cancer, and stomach cancer.

Also included are methods of adoptive T-cell immunotherapy for treating a cancer in a subject in need thereof, comprising
(a) incubating ex vivo-derived T-cells (i) with an arginine depletion agent or (ii) in arginine-free medium supplemented with citrulline;
(b) administering the ex vivo-derived T-cells to the subject In certain embodiments, the ex vivo-derived T-cells of (a) or (b) comprise cancer antigen-specific T-cells. In certain embodiments, the cancer antigen-specific T-cells are selected from one or more of chimeric antigen receptor (CAR)-modified T-cells, and T-cell Receptor (TCR)-modified T-cells, tumor infiltrating lymphocytes (TILs), and peptide-induced T-cells.

Also included are methods of increasing T-cell activation and/or regulatory T-cell (Treg) downregulation in vitro or ex vivo, comprising (a) incubating T-cells with an arginine depletion agent, (b) incubating T-cells in an arginine-free medium supplemented with citrulline, or both (a) and (b).

In certain embodiments, the arginine depletion agent is an ADI polypeptide. In certain embodiments, the ADI polypeptide comprises, consists, or consists essentially of a sequence selected from Table A1, including variants and fragments thereof having ADI activity. In certain embodiments, the variant comprises a sequence that is at least 80%, 85%, 90%, 95%, 96%, 97%, 98%, or 99% identical to a sequence from Table A1.

In certain embodiments, the ADI polypeptide is covalently bonded via an optional linker to at least one PEG molecule. In some embodiments, the ADI polypeptide is covalently bonded to more than one PEG molecule. In certain embodiments, the ADI polypeptide is covalently bonded to about 1 to about 10 PEG molecules. In certain embodiments, the ADI polypeptide is covalently bonded to about 2 to about 8 PEG molecules. In certain embodiments, the PEG molecules are straight chain or branch chain PEG molecules. In certain embodiments, the PEG has a total average molecular weight of from about 1,000 to about 40,000. In some embodiments, the PEG has a total average molecular weight of from about 10,000 to about 30,000. In specific embodiments, the PEG has a total average molecular weight of about 20,000.

In certain embodiments, the linker is a succinyl group, an amide group, an imide group, a carbamate group, an ester group, an epoxy group, a carboxyl group, a hydroxyl group, a carbohydrate, a tyrosine group, a cysteine group, a histidine group, a methylene group, or any combinations thereof. In certain embodiments, the source of the succinyl group is succinimidyl succinate.

In certain embodiments, the arginine depletion agent is pegylated arginine deiminase (ADI-PEG). In specific exemplary embodiments, the ADI-PEG is ADI-PEG 20.

Some embodiments include patient care kits, comprising:
(a) an arginine depletion agent which converts arginine to citrulline; and
(b) a cancer immunotherapy agent.

In some embodiments, (a) and (b) are in separate compositions. In certain embodiments, (a) and (b) are in the same composition.

DETAILED DESCRIPTION

Figures 1A, 1B, 1C:
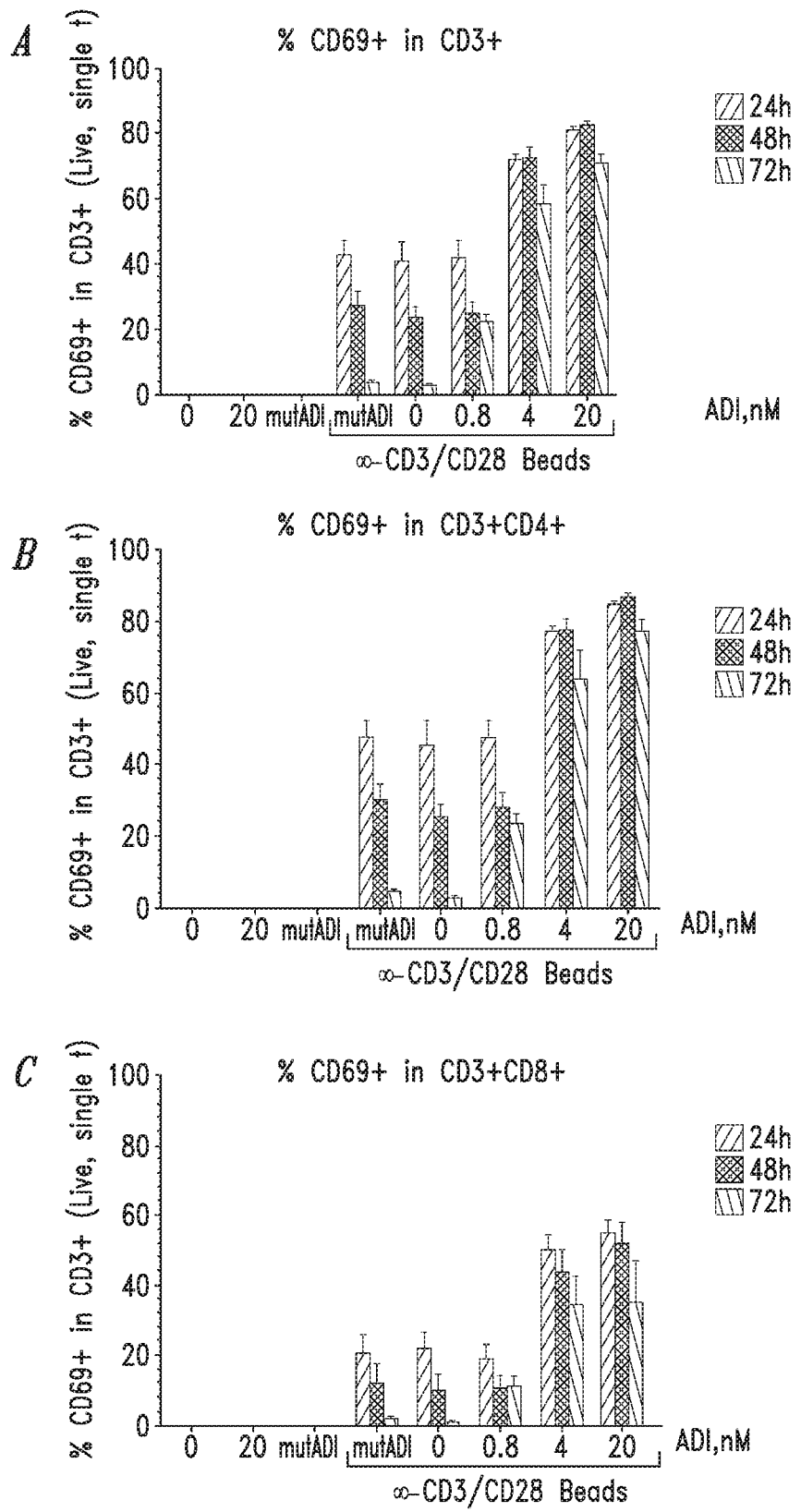
FIGS. 1A-1C show that ADI-PEG 20 enhances anti-CD3/CD28 induced T-cell activation. PBMCs were stimulated with anti-CD3/CD28 Dynabeads in the presence or absence of ADI-PEG 20 or mutADI-PEG 20. Percentages of CD69+ cells among all T-cells (A), CD4+ T-cells (B) and CD8+ T-cells (FIG. 1C) were determined by flow cytometry at 24, 48, and 72 hours.
Figures 2A, 2B, 2C:
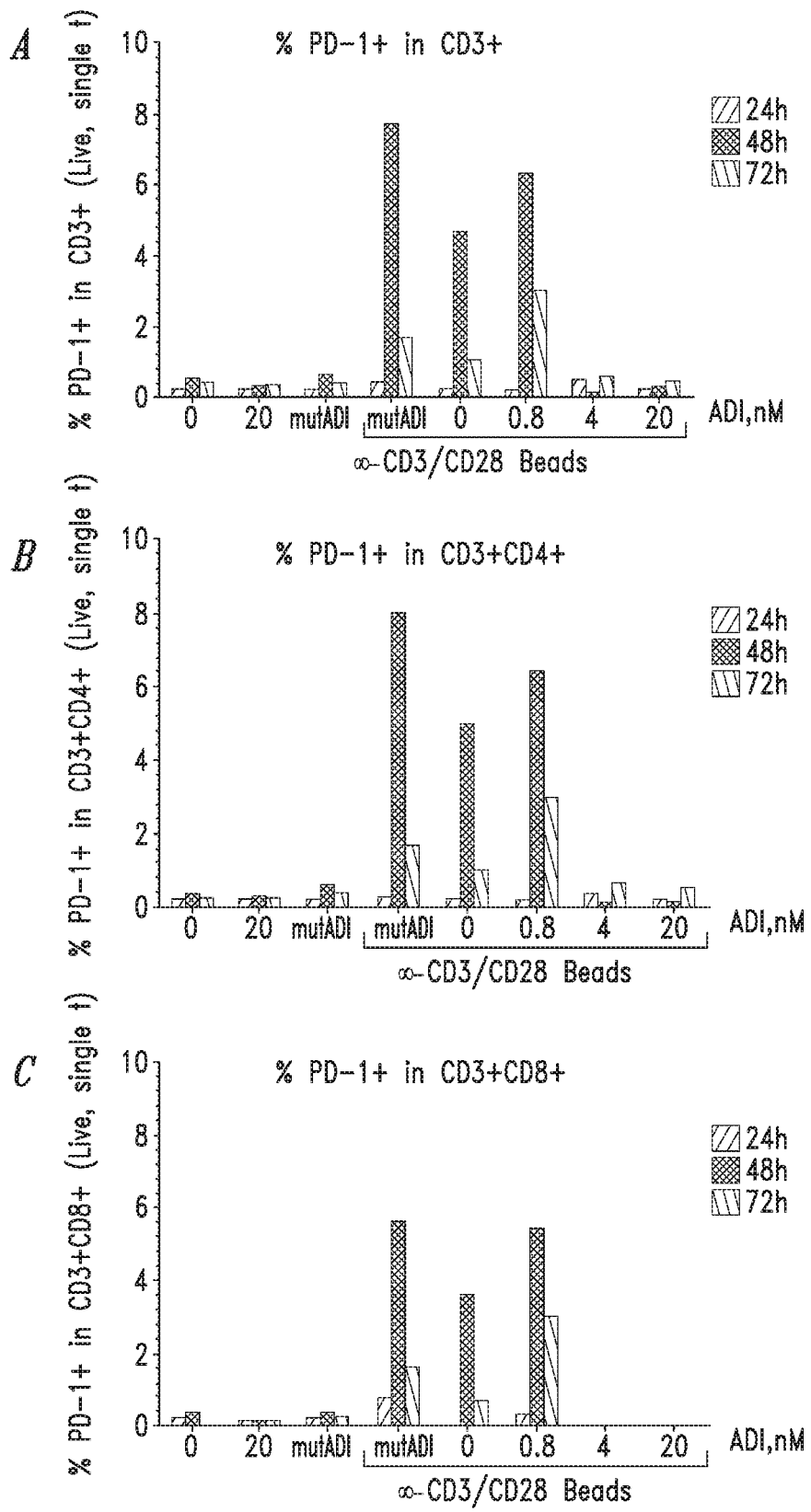
FIGS. 2A-2C show that ADI-PEG 20 blocks anti-CD3/CD28 induced PD-1 upregulation on T-cells. PBMCs were stimulated with anti-CD3/CD28 Dynabeads in the presence or absence of ADI-PEG 20 or mutADI-PEG 20. Percentages of PD-1+ cells among all T-cells (A), CD4+ T-cells (B) and CD8+ T-cells (C) were determined by flow cytometry at 24, 48, and 72 hours.

Unless defined otherwise, all technical and scientific terms used herein have the same meaning as commonly understood by those of ordinary skill in the art to which the disclosure belongs. Although any methods, materials, compositions, reagents, cells, similar or equivalent similar or equivalent to those described herein can be used in the practice or testing of the subject matter of the present disclosure, preferred methods and materials are described. All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

The practice of the present disclosure will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., *Current Protocols in Protein Science*, Current Protocols in Molecular Biology or Current Protocols in Immunology, John Wiley & Sons, New York, N.Y. (2009); Ausubel et al., Short Protocols in Molecular Biology, 3$^{rd}$ ed., Wiley & Sons, 1995; Sambrook and Russell, Molecular Cloning: A Laboratory Manual (3rd Edition, 2001); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984) and other like references.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well-known and commonly used in the art. Standard techniques may be used for recombinant technology, molecular biological, microbiological, chemical syntheses, chemical analyses, pharmaceutical preparation, formulation, and delivery, and treatment of patients.

For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

An "antagonist" refers to biological structure or chemical agent that interferes with or otherwise reduces the physiological action of another agent or molecule. In some instances, the antagonist specifically binds to the other agent or molecule. Included are full and partial antagonists.

An "agonist" refers to biological structure or chemical agent that increases or enhances the physiological action of another agent or molecule. In some instances, the agonist specifically binds to the other agent or molecule. Included are full and partial agonists.

As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like, which are known to a person skilled in the art. Amino acid analogs include modified forms of naturally and non-naturally occurring amino acids. Such modifications can include, for example, substitution or replacement of chemical groups and moieties on the amino acid or by derivatization of the amino acid. Amino acid mimetics include, for example, organic structures which exhibit functionally similar properties such as charge and charge spacing characteristic of the reference amino acid. For example, an organic structure which mimics Arginine (Arg or R) would have a positive charge moiety located in similar molecular space and having the same degree of mobility as the e-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

"Biocompatible" refers to materials or compounds which are generally not injurious to biological functions and which will not result in any degree of unacceptable toxicity, including allergenic and disease states.

By "coding sequence" is meant any nucleic acid sequence that contributes to the code for the polypeptide product of a gene. By contrast, the term "non-coding sequence" refers to any nucleic acid sequence that does not directly contribute to the code for the polypeptide product of a gene.

Throughout this disclosure, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The term "endotoxin free" or "substantially endotoxin free" relates generally to compositions, solvents, and/or vessels that contain at most trace amounts (e.g., amounts having no clinically adverse physiological effects to a subject) of endotoxin, and preferably undetectable amounts of endotoxin. Endotoxins are toxins associated with certain micro-organisms, such as bacteria, typically gram-negative bacteria, although endotoxins may be found in gram-positive bacteria, such as Listeria monocytogenes. The most prevalent endotoxins are lipopolysaccharides (LPS) or lipo-oligo-saccharides (LOS) found in the outer membrane of various Gram-negative bacteria, and which represent a central pathogenic feature in the ability of these bacteria to cause disease. Small amounts of endotoxin in humans may produce fever, a lowering of the blood pressure, and activation of inflammation and coagulation, among other adverse physiological effects.

Therefore, in pharmaceutical production, it is often desirable to remove most or all traces of endotoxin from drug products and/or drug containers, because even small amounts may cause adverse effects in humans. A depyrogenation oven may be used for this purpose, as temperatures in excess of 300° C. are typically required to break down most endotoxins. For instance, based on primary packaging material such as syringes or vials, the combination of a glass temperature of 250° C. and a holding time of 30 minutes is often sufficient to achieve a 3 log reduction in endotoxin levels. Other methods of removing endotoxins are contemplated, including, for example, chromatography and filtration methods, as described herein and known in the art.

Endotoxins can be detected using routine techniques known in the art. For example, the Limulus Amoebocyte Lysate assay, which utilizes blood from the horseshoe crab, is a very sensitive assay for detecting presence of endotoxin. In this test, very low levels of LPS can cause detectable coagulation of the limulus lysate due a powerful enzymatic cascade that amplifies this reaction. Endotoxins can also be quantitated by enzyme-linked immunosorbent assay (ELISA). To be substantially endotoxin free, endotoxin levels may be less than about 0.001, 0.005, 0.01, 0.02, 0.03, 0.04, 0.05, 0.06, 0.08, 0.09, 0.1, 0.5, 1.0, 1.5, 2, 2.5, 3, 4, 5, 6, 7, 8, 9, or 10 EU/mg of active compound. Typically, 1 ng lipopolysaccharide (LPS) corresponds to about 1-10 EU.

The "half-life" of a polypeptide can refer to the time it takes for the polypeptide to lose half of its pharmacologic, physiologic, or other activity, relative to such activity at the time of administration into the serum or tissue of an organism, or relative to any other defined time-point. "Half-life" can also refer to the time it takes for the amount or concentration of a polypeptide to be reduced by half of a starting amount administered into the serum or tissue of an organism, relative to such amount or concentration at the time of administration into the serum or tissue of an organism, or relative to any other defined time-point. The half-life can be measured in serum and/or any one or more selected tissues.

The terms "modulating" and "altering" include "increasing," "enhancing" or "stimulating," as well as "decreasing" or "reducing," typically in a statistically significant or a physiologically significant amount or degree relative to a control. An "increased," "stimulated" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and ranges in between e.g., 1.5, 1.6, 1.7. 1.8, etc.) the amount produced by no composition (e.g., the absence of agent) or a control composition. A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease (including all integers and ranges in between) in the amount produced by no composition (e.g., the absence of an agent) or a control composition. Examples of comparisons and "statistically significant" amounts are described herein.

The terms "polypeptide," "protein" and "peptide" are used interchangeably and mean a polymer of amino acids not limited to any particular length. The term "enzyme" includes polypeptide or protein catalysts, and with respect to ADI is used interchangeably with protein, polypeptide, or peptide. The terms include modifications such as myristoylation, sulfation, glycosylation, phosphorylation and addition or deletion of signal sequences. The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass the ADI enzymes/proteins described herein, or sequences that have deletions from, additions to, and/or substitutions of one or more amino acid of the ADI proteins. In certain embodiments, the polypeptide is a "recombinant" polypeptide, produced by recombinant cell that comprises one or more recombinant DNA molecules, which are typically made of heterologous polynucleotide sequences or combinations of polynucleotide sequences that would not otherwise be found in the cell.

The term "isolated" polypeptide or protein referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or non-covalent interaction) with portions of a protein with which the "isolated protein" is associated in nature, (6) is operably associated (by covalent or non-covalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially free from proteins or polypeptides or other contaminants that are found in its natural environment that would interfere with its use (therapeutic, diagnostic, prophylactic, research or otherwise).

In certain embodiments, the "purity" of any given agent (e.g., ADI, ADI-PEG) in a composition may be specifically defined. For instance, certain compositions may comprise an agent that is at least 80, 85, 90, 91, 92, 93, 94, 95, 96, 97, 98, 99, or 100% pure, including all decimals and ranges in between, as measured, for example and by no means limiting, by high performance liquid chromatography (HPLC), a well-known form of column chromatography used frequently in biochemistry and analytical chemistry to separate, identify, and quantify compounds.

The term "reference sequence" refers generally to a nucleic acid coding sequence, or amino acid sequence, to which another sequence is being compared. All polypeptide and polynucleotide sequences described herein are included as references sequences, including those described by name and those described in the Tables and the Sequence Listing.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., Nucl. Acids Res. 25:3389, 1997.

The term "solubility" refers to the property of an agent (e.g., ADI, ADI-PEG) provided herein to dissolve in a liquid solvent and form a homogeneous solution. Solubility is typically expressed as a concentration, either by mass of solute per unit volume of solvent (g of solute per kg of solvent, g per dL (100 mL), mg/ml, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 5.0, pH 6.0, pH 7.0, pH 7.4, pH 7.6, pH 7.8, or pH 8.0 (e.g., about pH 5-8). In certain embodiments, solubility is measured in water or a physiological buffer such as PBS or NaCl (with or without NaP). In specific embodiments, solubility is measured at relatively lower pH (e.g., pH 6.0) and relatively higher salt (e.g., 500 mM NaCl and 10 mM NaP). In certain embodiments, solubility is measured in a biological fluid (solvent) such as blood or serum. In certain embodiments, the temperature can be about room temperature (e.g., about 20, 21, 22, 23, 24, 25° C.) or about body temperature (37° C.). In certain embodiments, an agent has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 40, 50, 60, 70, 80, 90 or 100 mg/ml at room temperature or at 37° C.

A "subject" or a "subject in need thereof" or a "patient" or a "patient in need thereof" includes a mammalian subject such as a human subject.

"Substantially" or "essentially" means nearly totally or completely, for instance, 95%, 96%, 97%, 98%, 99% or greater of some given quantity.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

"Therapeutic response" refers to improvement of symptoms (whether or not sustained) based on administration of one or more therapeutic agents.

As used herein, "treatment" of a subject (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

The term "wild-type" refers to a gene or gene product (e.g., a polypeptide) that is most frequently observed in a population and is thus arbitrarily designed the "normal" or "wild-type" form of the gene.

Each embodiment in this specification is to be applied mutatis mutandis to every other embodiment unless expressly stated otherwise.

Throughout the present disclosure, the following abbreviations may be used: PEG, polyethylene glycol; ADI, arginine deiminase; SS, succinimidyl succinate; SSA, succinimidyl succinimide; SPA, succinimidyl propionate; NHS, N-hydroxy-succinimide; ASS1 or ASS, argininosuccinate synthetase.

Arginine Depletion Agents

Certain embodiments employ one or more arginine depletion agents. In certain instances, an arginine depletion agent converts arginine to citrulline (and ammonia), and thereby depletes or reduces the supply of arginine available to cells, for example, cancer cells and/or T-cells.

Certain exemplary arginine depletion agents include arginine deiminase (ADI) enzymes or polypeptides. In some embodiments, the ADI polypeptide is from *M hominis, M arginini, M arthritidis, M phocicerebrale, M gateae, M phocidae, M columbinum, M iowae, M crocodyli, M alligatoris, H. orenii,* or *M bovis*. In some embodiments, the ADI polypeptide is from *Mycoplasma salivarium, Mycoplasma spumans, Mycoplasma canadense, Mycoplasma auris, Mycoplasma hyosynoviae, Mycoplasma cloacale, Mycoplasma anseris, Mycoplasma alkalescens, Mycoplasma orale, Mycoplasma finers, Mycoplasma meleagridis, Mycoplasma alvi, Mycoplasma penetrans, Mycoplasma gallinarum, Mycoplasma pirum, Mycoplasma primatum, Mycoplasma fermentans, Mycoplasma lipofaciens, Mycoplasma felifaucium, Mycoplasma imitans, Mycoplasma opalescens, Mycoplasma moatsii, Mycoplasma elephantis, Mycoplasma pneumoniae, Mycoplasma testudinis, Mycoplasma* sp. CAG: 877, or *Mycoplasma* sp. CAG:472.

Illustrative ADI polypeptides are provided in Table A1 below.

TABLE A1

ADI Polypeptide Sequences

| Source | Sequence | SEQ ID NO: |
|---|---|---|
| Mycoplasma hominis | MSVFDSKFNGIHVYSEIGELETVLVHEPGREIDYITPARLDELLFSAILESHD ARKEHQSFVKIMKDRGINVVELTDLVAETYDLASKAAKEEFIETFLEETVPVL TEANKKAVRAFLLSKPTHEMVEFMMSGITKYELGVESENELIVDPMPNLYFTR DPFASVGNGVTIHFMRYIVRRRETLFARFVFRNHPKLVKTPWYYDPAMKMPIE GGDVFIYNNETLVVGVSERTDLDTITLLAKNIKANKEVEFKRIVAINVPKWTN LMHLDTWLTMLDKNKFLYSPIANDVFKFWDYDLVNGGAEPQPQLNGLPLDKLL | 1 |

TABLE A1-continued

ADI Polypeptide Sequences

| Source | Sequence | SEQ ID NO: |
|---|---|---|
| | ASIINKEPVLIPIGGAGATEMEIARETNFDGTNYLAIKPGLVIGYDRNEKTNA<br>ALKAAGITVLPFHGNQLSLGMGNARCMSMPLSRKDVKW | |
| PHX8 | MSVFDSKFNGIHVYSEIGELETVLVHEPGREIDYITPARLDELLFSAILESHD<br>ARKEHQSFVKIMKDRGINVVELTDLVAETYDLASKAAKEEFIETFLEETVPVL<br>TEANKEAVRAFLLSKPTHEMVEFMMSGITKYELGVESENELIVDPMPNLYFTR<br>DPFASVGNGVTIHFMRYIVRRRETLFARFVFRNHPKLVKTPWYYDPAMKMSIE<br>GGDVFIYNNETLVVGVSERTDLDTITLLAKNIKANKEVEFKRIVAINVPKWTN<br>LMHLDTWLTMLDKNKFLYSPIANDVFKFWDYDLVNGGAEPQPQLNGLPLDKLL<br>ASIINKEPVLIPIGGAGATEMEIARETNFDGTNYLAIKPGLVIGYDRNEKTNA<br>ALKAAGITVLPFHGNQLSLGMGNARCMSMPLSRKDVKW | 2 |
| Mycoplasma phocicerebrale | IHVYSEIGELETVLVHEPGREIDYITPARLDELLFSAILESHDARKEHQSFVK<br>QLKDNGINVVELTDLVAETFDLASKEEQEKLIEEFLEDSEPVLSEAHKTAVRK<br>FLTSRKSTREMVEFMMAGITKYDLGIEADHELIVDPMPNLYFTRDPFASVGNG<br>VTIHYMRYKVRQRETLFSRFVFSNHPKLVKTPWYYDPAMKMSIEGGDVFIYNN<br>DTLVVGVSERTDLETITLLAKNIKANKEVEFKRIVAINVPKWTNLMHLDTWLT<br>MLDKDKFLYSPIANDVFKFWDYDLVNGGAEPQPKENGLPLEGLLQSIINKKPV<br>LIPIAGNNASHIDIERETHFDGTNYLAIKPGVVIGYARNEKTNAALAAAGIKV<br>LPFHGNQLSLGMGNARCMSMP | 3 |
| Mycoplasma arginini | MSVFDSKFKGIHVYSEIGELESVLVHEPGREIDYITPARLDELLFSAILESHD<br>ARKEHKQFVAELKANDINVVELIDLVAETYDLASQEAKDKLIEEFLEDSEPVL<br>SEEHKVVVRNFLKAKKTSRELVEIMMAGITKYDLGIEADHELIVDPMPNLYFT<br>RDPFASVGNGVTIHYMRYKVRQRETLFSRFVFSNHPKLINTPWYYDPSLKLSI<br>EGGDVFIYNNDTLVVGVSERTDLQTVTLLAKNIVANKECEFKRIVAINVPKWT<br>NLMHLDTWLTMLDKDKFLYSPIANDVFKFWDYDLVNGGAEPQPVENGLPLEGL<br>LQSIINKKPVLIPIAGEGASQMEIERETHFDGTNYLAIRPGVVIGYSRNEKTN<br>AALEAAGIKVLPFHGNQLSLGMGNARCMSMPLSRKDVKW | 4 |
| Mycoplasma arthritidis | MSVFDSKFKGIHVYSEIGELETVLVHEPGKEIDYITPARLDELLFSAILESHD<br>ARKEHKEFVAELKKRGINVVELVDLIVETYDLASKEAKEKLLEEFLDDSVPVL<br>SDEHRAAVKKFLQSQKSTRSLVEYMIAGITKHDLKIESDLELIVDPMPNLYFT<br>RDPFASVGNGVTIHYMRYKVRQRETLFSRFVFSNHPKLVNTPWYYDPAEGLSI<br>EGGDVFIYNNDTLVVGVSERTDLQTITLLAKNIKANKECEFKRIVAINVPKWT<br>NLMHLDTWLTMLDKDKFLYSPIANDVFKFWDYDLVNGGDAPQPVDNGLPLEDL<br>LKSIIGKKPTLIPIAGAGASQIDIERETHFDGTNYLAVAPGIVIGYARNEKTN<br>AALEAAGITVLPFRGNQLSLGMGNARCMSMPLSRKDVK | 5 |
| Mycoplasma orale | SVFSDKFNGIHVYSEIGDLESVLVHEPGKEIDYITPARLDELLFSAILESTDA<br>RKEHKEFVEILKKQGINVVELVDLVVETYNLVDKKTQEKLLKDFLDDSEPVLS<br>PEHRKAVEKFLKSLKSTKELIQYMMAGITKYDLGIKADKELIVDPMPNLYFTR<br>DPFASVGNGVTIHYMRYKVRQRETLFSKFIFTNHPKLVKTPXYYDPAMKLSIE<br>GGDVFIYNNDTLVVGVSERTDLETITLLAKNIKANKECEFKRIVAINVPKXTN<br>LMHLDTXLTMLDKDKFLYSPIANDVFKFXDYDLVNGGSNPEPVVNGLPLDKLL<br>ESIINKKPVLIPIAGKGATEIETAVETHFDGTNYLAIKPGVVVGYSRNVKTNA<br>ALEANGIKVLPFKGNQLSLGMGNARCMSMPLSRKDVK | 6 |
| Mycoplasma gateae | IHVYSEIGELESVLVHEPGREIDYITPARLDELLFSAILESHDARKEHKLFVS<br>ELKKANDINVVELTDLVTETYDLASQEAKDNLIEEFLEDSEPVLTEELKSVVRT<br>YLKSIKSTRELIQMMMAGITKYDLGIEADHELIVDPMPNLYFTRDPFASVGNG<br>VTIHYMRYKVRQRETLFSRFVFSNHPKLVNTPWYYDPSLKLSIEGGDVFIYNN<br>NTLVVGVSERTDLETVTLLAKNIVANKECEFKRIVAINVPKWTNLMHLDTWLT<br>MLDKDKFLYSPIANDVFKFWDYDLVNGGEEPQPVENGLPLEGLLESIINKKPI<br>LIPIAGEGASQIDIERETHFDGTNYLAIRPGVVIGYSRNEKTNAALEAAGIKV<br>LPFHGNQLSLGMGNARCMSM | 7 |
| Mycoplasma phocidae | IHVYSEIGELQTVLVHEPGREIEYITPARLDELLFSAILESHDARKEHQEFVA<br>ELKKNNINVVELTDLVSETYDMVSKEKQEKLIEEFLEDSEPVLSEEHKGLVRK<br>FLKSLKSSKELIQYMMAGITKHDLNIEADHELIVDPMPNLYFTRDPFASVGNG<br>VTIHYMRYKVRQRETLFSRFIFANHPKLMNTPLYYNPDMKLSIEGGDVFVYNN<br>ETLVVGVSERTDLDTITLLAKNIKANKEREFKRIVAINVPKWTNLMHLDTWLT<br>MLDKDKFLYSPIANDVFKFWDYDLVNGGDEPQPKVNGLPLEKLLESIINKKPI<br>LIPIAGTSASNIDVERETHFDGTNYLAIAPGVVIGYSRNVKTNEALEAAGIKV<br>LPFKGNQLSLGMGNARCMSMP | 8 |
| Mycoplasma columbinum | MSKINVYSEIGELKEVLVHTPGDEIRRISPSRLDELLFSAILEPNEAIKEHKG<br>FLKILQDKGIKVIQLSDLVAETYTYHATQKEREAFIEKWLDEAEPALTKDLRA<br>KVKSYVLSKEGTPVAMVRTMMAGVSKQELNVESETELVVDPMPNLYFTRDPFA<br>SAGNGISLNNMKYVTRKRETIFAEFIFATHPDYKTTPHWFDRLDEGNIEGGDV<br>FIYNKDTLVIGVSERTNKEAILTIAKKKIKNNKEAKFKKIVAINVPPMPNLMHL<br>DTWLTMVDKDKFLYSPNMLSVLKWEIDLSKEIEMVETNKPLADVLESIIGVK<br>PVLIPIAGKGATQLDIDIETHFDGTNYLTIAPGVVVGYSRNIKTEAALRAAGV<br>TVLSFEGNQLSLGMGSARCMSMPLVREDVK | 9 |

TABLE A1-continued

ADI Polypeptide Sequences

| Source | Sequence | SEQ ID NO: |
|---|---|---|
| Mycoplasma iowae | MGNNIPKKINVFSEIGNLKRVLVHTPGKEIEYVTPQRLDELLFSAILDPVRAR EEHKEFIKILESQGVEVVQLVDLTAETYDVAESQAKENFIQKWLDESLPKLTD ENRNKVYSLLKSLEKDPKEMIRKMMSGVLASEIGVKSDVELIVDPMPNLYFTR DPFASVGNGITLHRMFRPTRRRETIFADFIFSNHPEYKSTQKYYEREDKFSLE GGDVFIYNNKTLVVGVSERTEKGAIKALAKAVQNNSNMSFEKIYAINVPKMSN LMHLDTWLTMLDTDKFLYSPNMMGVLKIWEIDLSDKSLKWKEIRDSLDHFLST IIGKKAITVPVAGKDAMQFEIDIETHFDATNFIAVAPGVVIGYDRNKKTNEAL KEAGIKVLSWNGDQLSLGMGSARCMTMPLYREELKK | 10 |
| Mycoplasma crocodyli | MNKINVYSEVGKLKEVLVHTPGDEIRRISPSRLEELLFSAILEPDSAIEEHKR FLKILEDNNIKVIQLDQLVADTYELVNPSVRDAFIEKWLNESEPKLDKKLREK VKEYLLHTQKTVGTKRMVRIMMAGVDRVELGVELDRQLVVDPMPNLYFTRDPF ASAGNGISLNNMKYVTRKRETIFSEFIFENHPDYKTTPHWFDRLDKGNIEGGD VFIYNRTTLVIGISERTNKDALLTIANNIKSNKESKFERIVAVNVPPMPNLMH LDTWLTMVDHDKFLYSPNMMKTLKFWTIDLTKPIKMVELEESLSDMIETIIGK KPVLIPIAGHDASPLDVDIETHFDGTNYLTIAPGVVVGYSRNKLTEKALTKAG VKVLSFEGNQLSLGMGSARCMSMPLVREDIK | 11 |
| Mycoplasma fermentans | MQIIAKIDLLTNMLIFMKIYFIGRLIMKKINVYSEYGKLKEVLVHTPGDEIRR IAPSRLDELLFSAILEPDSAIAEHKRFVQLLKDNGIKVIQLDELFAKTFDLVS ESVKQSLIERWLDECEPKLDATLRAKVKEYILELKAKSSKKMVRVMMAGIDKK ELGIELDRDLVVDPMPNLYFTRDPFASVGNGISLHHMKYVTRQRETIFSEFIF DNNLDYNTVPRWFDRKDEGRIEGGDVFIYSADTLVVGVSERTNKEAINVMARK IAADKEVKFKRIYAINVPPMPNLMHLDTWLTMLDKNKFLYSPNMLSVLKVWRI DLNDPDFVWHEIEGSLEEILEQIIGMKPILIPIAGKGASQLDIDIETHFDGTN YLTIAPSVVVGYSRNEKTEKALKAAKVKVLSFEGNQLSLGMGSARCMSMPLIR EDIKKK | 12 |
| Mycoplasma penetrans | MVITIALNILNKIYFKPQNRSILKLYRLPSLCTQISIFIGGKMSSIDKNSLGN GINVYSEIGELKEVLVHTPGDEIRYTAPSRLEELLFSAVLKADTAIEEHKGFV KILQNNGIKVIQLCDLVAETYELCSKEVRNSFIEQYLDEALPVLKKEIRPVVK DYLLSFPTVQMVRKMMSGILANELNIKQDNPLIIDGMPNLYFTRDPFASMGNG VSINCMKYPTRKREVIFSRFVFTNNPKYKNTPRYFDIVGNNGTIEGGDIFIYN SKTLVIGNSERTNFAAIESVAKNIQANKDCTFERIVVINVPPMPNLMHLDTWL TMLDYDKFLYSPNMMNVLKIWEIDLNVKPVKFVEKKGTLEEVLYSIIDKKPIL IPIAGKGANQLDIDIETHFDGTNYLTIAPGVVVGYERNEKTQKALVEAGIKVL SFNGSQLSLGMGSARCMSMPLIRENLKK | 13 |
| Mycoplasma gallisepticum | MFNKIRVYSEIGKLRKVLVHTPGKELDYVTPQRLDELLFSSLLNPIKARQEHE TFIKLLEDHDVECVQLSTLTAQTFQAVNSKIQEEFINRWLDECLPVLSEINRL KVYDYLKSLATNPQVMIRKMMSGILAKEVGIQSEVELVADPMPNLYFTRDPFA SIGKGITLHSMFHPTRKRETIFADFIFSHHPEYKNAPKYYSREDKYSIEGGDL FVYDDKTLVIGVSERTEKKAIQSLAEKLRQNDETSFEKIYAINVPKMSNLMHL DTWLTMLDYDKFLYSPNMMGVLKIWEIDLIHPTLIWRELNESLEGFLSMVIGK KATLIPVAGEDSTQIEIDVETNFDATNFLVIQPGVVVGYDRNYKTNQALRDAG VKVISWNGDQLSLGMGSARCMSMPLYRDPIKK | 14 |
| Mycoplasma alligatoris | MSKINVYSEVGRLKEVLVHTPGDEIRRISPTRLEELLFSAILEPDTAIEEHKR FLNVLEKNGIKAIQLDELVAQTYDVDQKIKDEFIDQWLQEAKPVLNDQLKKL VKNYLLKSQKEFSTKKMVRIMMAGIDKKEINIDLDRDLVVDPMPNLYFTRDPF ASVGNGISLHNMKYQTRKRETIFAQFIFKYNKDYKTTPHWFDRFDHGSIEGGD VFVYTKDTLVIGISERTTKEAVLNIAKKIKANTDSKFKKIVAINVPPMPNLMH LDTWITMVDHDKFLYSPNMMKSLKFWLIDLSKEIKMVELEESLSNMLEAIIGK KPILIPIAGKNASQLDIDIETHFDGTNYLTIAPGVVVGYSRNKLTQKALEDAG VKVLSFDGNQLSLGMGSARCMSMPLVREDIK | 15 |
| Mycoplasma pneumoniae | MSKKQLVKTDGHNQLDQPNTKALQLKKKQFNSGVRVTSEISFLREVIAHHPGI ETERVIDNQTFGSAMYLERAQKEHQLFIKILRQHGTKVHYLQDLLLEALSAAD PNVRQDFIKNFLLESGIKSVSTFEACLNFFRSLDSLVDVIKVMFGGIKVSDVP PITPQRFADIHVSNSPPFLIKPLSFSLYPHKFFNTLGTGVALFVTNDSELKRHS LVYEYIMRFHPRFDGVKLYTNRDFKNCLINSSDIIQISNEILLIGISHDTDVL GIESLARNLLSDHTNPIKQIIAINIHKFGAKTNLNKLIAMVDVDKFIIARKVL QATEIFELTATAQRDVDGLAQIKFKPLKFNFGEIIEAIIDKQPRFVIIGGGDE VAERKELLDCGMGVLNLSPGEIVVFDRNHYTNNLLNELGLIIHKIPASELSRG PSGPLEMVCSLWRE | 16 |
| Mycoplasma mobile | MKDTKDIINVFSEIGELKKVLIHTPGNELKYVSPYRLDELLFSNVLEWREAKK EHNEFIQKLKSEGVEPVELTDLVAESFEESSIKVKNDFIRQYLDEATPILDGL TKQKLLPFFLDIKHSTRKTIELMMSGITQKDISISHIERELIIDPMPNLYFSR DNFISIGNSVIISNMKYKTRKRETIFTDFIFKNHPLYKKVNMAFERKDLNNQI SIIEGGDVLVYSKEILIIGISERTTMSAILELAENFKKTKRSFKKIYGVEVPK MKNLMHLDTWLTMIDYDKFIYSPNVLTDLKFWEINLDYEKISSKELHASLSEF LKLIIGKDPILIPIGGKGASQITIDIETNFVAANYLVIRPGVVIGYSRNYETQ KALEGHGVKVIAFEGNQLSLGMGSSRCMSMPLIRSNLK | 17 |

TABLE A1-continued

ADI Polypeptide Sequences

| Source | Sequence | SEQ ID NO: |
|---|---|---|
| Streptococcus pyogenes | MTAQTPIHVYSEIGKLKKVLLHRPGKEIENLMPDYLERLLFDDIPFLEDAQKE HDAFAQALRDEGIEVLYLETLAAESLVTPEIREAFIDEYLSEANIRGRATKKA IRELLMAIEDNQELIEKTMAGVQKSELPEIPASEKGLTDLVESNYPFAIDPMP NLYFTRDPFATIGTGVSLNHMFSETRNRETLYGKYIFTHHPIYGGGKVPMVYD RNETTRIEGGDELVLSKDVLAVGISQRTDAASIEKLLVNIFKQNLGFKKVLAF EFANNRKFMHLDTVFTMVDYDKFTIHPEIEGDLRVYSVTYDNEELHIVEEKGD LAELLAANLGVEKVDLIRCGGDNLVAAGREQWNDGSNTLTIAPGVVVVYNRNT ITNAILESKGLKLIKIHGSELVRGRGGPRCMSMPFEREDI | 18 |
| Enterococcus faecalis | MSHPINVFSEIGKLKTVMLHRPGKELENLMPDYLERLLFDDIPFLEKAQAEHD AFAELLRSKDIEVVYLEDLAAEALINEEVRRQFIDQFLEEANIRSESAKEKVR ELMLEIDDNEELIQKAIAGIQKQELPKYEQEFLTDMVEADYPFIIDPMPNLYF TRDNFATMGHGISLNHMYSVTRQRETIFGQYIFDYHPRFAGKEVPRVYDRSES TRIEGGDELILSKEVVAIGISQRTDAASIEKIARNIFEQKLGFKNILAFDIGE HRKFMHLDTVFTMIDYDKFTIHPEIEGGLVVYSITEKADGDIQITKEKDTLDN ILCKYLHLDNVQLIRCGAGNLTAAAREQWNDGSNTLAIAPGEVVVYDRNTITN KALEEAGVKLNYIPGSELVRGRGGPRCMSMPLYREDL | 19 |
| Mycoplasma capricolum | MEKKINVFSEIGTLKTVLVHRPGDEIENLTPELLERLLFDDVPFKDVAVKEHD AFTKIMRDNGVEVLYIEKLAAETLDQHPDLREKFIDQFISEANIEDKYKEKYR DFISSLDNYRMIKKMIAGTKKLELGIDEGYKAYPFIADPLPNVLFQRDPFSSV GFGITMNRMWSVTRNRETIFPDLVFKHHNRFANQVPYYYERDWKEETIEGGDI LVLNKETLIIGVTQRTTLKAIEKFSERLFNDPESSYSKVIALDLPKSRAFMHL DTVFTNIDYDKFIAHPLIFDCIDEFKIYEVSKQGTKEVKKTLIELLSDAAGRE VQIIRCGGNDVVGASREQWNDGTNVVALRPGKVIAYERNWITIDLLRKAGVEV LTIASSELSRGRGGPRCMTMPLWREDLQEIKR | 20 |
| Halothermothrix orenii | MFKKSPLNVTSEIGKLKKVLLHRPGHEIENLTPDLLERLLFDDIPYLKVAQEE HDAFAQTLRDNGVEVLYLHELAAEAIQEDEIRKKFIEQFLDEAGVIGKGARQV LKEYFADMDNETLIRKMMAGVRKKEIPAIEKVASLNDMVEEDYPFVLDPMPNL YFTRDPFATIGTGITLNHMRTETRNREVIFAEYIFSYHPDFKDTEIPFWFDRN ETTSIEGGDELILSDKVLAMGISERTDAASIEKVARNIFTDGQPFETILAFKI PEKRAFMHLDTVFTMVDYDKFTIHAEIEGPLKVYSITKGDNDELKIDEEKATL EDTLKKYLGLDEVTLIRCAGGDYIDAGREQWNDGSNTLAIAPGEVVVYNRNHT TNRLLEEHGIKLHVIPSSELSRGRGGPRCMSMPLVREDI | 21 |
| Staphylococcus aureus | MTDGPIKVNSEIGALKTVLLKRPGKELENLVPDYLDGLLFDDIPYLEVAQKEH DHFAQVLREEGVEVLYLEKLAAESIENPQVRSEFIDDVLAESKKTILGHEEEI KALFATLSNQELVDKIMSGVRKEEINPKCTHLVEYMDDKYPFYLDPMPNLYFT RDPQASIGHGITINRMFWRARRRESIFIQYIVKHHPRFKDANIPIWLDRDCPF NIEGGDELVLSKDVLAIGVSERTSAQAIEKLARRIFENPQATFKKVVAIEIPT SRTFMHLDTVFTMIDYDKFTMHSAILKAEGNMNIFIIEYDDVNKDIAIKQSSH LKDTLEDVLGIDDIQFIPTGNGDVIDGAREQWNDGSNTLCIRPGVVVTYDRNY VSNDLLRQKGIKVIEISGSELVRGRGGPRCMSQPLFREDI | 22 |
| Pseudomonas plecoglossicida | MSAEKQKYGVHSEAGKLRKVMVCAPGLAHKRLTPSNCDELLFDDVIWVDQAKR DHFDFVTKMRERGVDVLEMHNLLTDIVQNPEALKWILDRKITPDTVGVGLTNE VRSWLEGQEPRHLAEFLIGGVAGQDLPESEGASVVKMYNDYLGHSSFILPPLP NTQFTRDTTCWIYGGVTLNPMYWPARRQETLLTTAIYKFHPEFTKADFQVWYG DPDQEHGQATLEGGDVMPIGKGIVLIGMGERTSRQAIGQLAQNLFAKGAVEQV IVAGLPKSRAAMHLDTVFSFCDRDLVTVFPPEVVREIVPFIIRPDESKPYGMDV RRENKSFIEVVGEQLGVKLRVVETGGNSFAAEREQWDDGNNVVALEPGVVIGY DRNTYTNTLLRKAGIEVITISAGELGRGRGGHCMTCPIVRDPINY | 23 |
| Pseudomonas putida | MSAEKQKYGVHSEAGKLRKVMVCAPGLAHKRLTPSNCDELLFDDVIWVDQAKR DHFDFVTKMRERGVDVLEMHNLLTDIVQNKDALKWILDRKITPDTVGVGLTNE VRSWLEGLEPRHLAEFLIGGVAGQDLPQSEGADVVKMYNDYLGHSSFILPPLP NTQFTRDTTCWIYGGVTLNPMYWPARRQETLLTTAIYKFHPQFTGADFQVWYG DPDKDHGNATLEGGDVMPIGKGIVLIGMGERTSRQAIGQLAQNLFAKGAVEKV IVAGLPKSRAAMHLDTVFSFCDRDLVTIFPPEVVKEIVPFIIRPDESKPYGMDV RRENKSFIEVVGEQLGVKLRVVETGGNSFAAEREQWDDGNNVVAVEPGVVIGY DRNTYTNTLLRKAGIEVITISAGELGRGRGGGHCMTCPIVRDPIDY | 24 |
| Pseudomonas aeruginosa | MSTEKTKLGVHSEAGKLRKVMVCSPGLAHQRLTPSNCDELLFDDVIWVNQAKR DHFDFVTKMRERGIDVLEMHNLLTETIQNPEALKWILDRKITADSVGLGLTSE LRSWLESLEPRKLAEYLIGGVAADDLPASEGANILKMYREYLGHSSFLLPPLP NTQFTRDTTCWIYGGVTLNPMYWPARRQETLLTTAIYKFHPEFANAEFEIWYG DPDKDHGSSTLEGGDVMPIGNGVVLIGMGERSSRQAIGQVAQSLFAKGAAERV IVAGLPKSRAAMHLDTVFSFCDRDLVTVFPPEVVKEIVPFSLRPDASSPYGMSI RREEKTFLEVVAESLGLKKLRVVETGGNSFAAEREQWDDGNNVVCLEPGVVVG YDRNTYTNTLLRKAGVEVITISASELGRGRGGGHCMTCPIIRDPIDY | 25 |

TABLE A1-continued

ADI Polypeptide Sequences

| Source | Sequence | SEQ ID NO: |
|---|---|---|
| *Mycobacterium tuberculosis* complex | MGVELGSNSEVGALRVVILHRPGAELRRLTPRNTDQLLFDGLPWVSRAQDEHD<br>EFAELLASRGAEVLLLSDLLTEALHHSGAARMQGIAAAVDAPRLGLPLAQELS<br>AYLRSLDPGRLAHVLTAGMTFNELPSDTRTDVSLVLRMHHGGDFVIEPLPNLV<br>FTRDSSIWIGPRVVIPSLALRARVREASLTDLIYAHHPRFTGVRRAYESRTAP<br>VEGGDVLLLAPGVVAVGVGERTTPAGAEALARSLFDDDLAHTVLAVPIAQQRA<br>QMHLDTVCTMVDTDTMVMYANVVDTLEAFTIQRTPDGVTIGDAAPFAEAAAKA<br>MGIDKLRVIHTGMDPVVAEREQWDDGNNTLALAPGVVVAYERNVQTNARLQDA<br>GIEVLTIAGSELGTGRGGPRCMSCPAARDPL | 26 |
| *Mycoplasma arthritidis* | MSVFDSKFKGIHVYSEIGELETVLVHEPGKEIDYITPARLDELLFSAILESHD<br>ARKEHKEFVAELKKRGINVVELVDLIVETYDLASKEAKEKLLEEFLDDSVPVL<br>SDEHRAAVKKFLQSQKSTRSLVEYMIAGITKHDLKIESDLELIVDPMPNLYFT<br>RDPFASVGNGVTIHYMRYKVRQRETLFSRFVFSNHPKLVNTPWYYDPAEGLSI<br>EGGDVFIYNNDTLVVGVSERTDLQTITTLLAKNIKANKECEFKRIVAINVPKWT<br>NLMHLDTWLTMLDKDKFLYSPIANDVFKFWDYDLVNGGDAPQPVDNGLPLEDL<br>LKSIIGKKPTLIPIAGAGASQIDIERETHFDGTNYLAVAPGIVIGYARNEKTN<br>AALEAAGITVLPFRGNQLSLGMGNARCMSMPLSRKDVK | 27 |
| *Mycoplasma phocicerebrale* Artificial full length from new species patent. | MSVFDSKFNGIHVYSEIGELETVLVHEPGREIDYITPARLDELLFSAILESHD<br>ARKEHQSFVKQLKDNGINVVELTDLVSETFDLASKEEQEKLIEEFLEDSEPVL<br>SEAHKTAVRKFLTSRKSTREMVEFMMAGITKYDLGIEADHELIVDPMPNLYFT<br>RDPFASVGNGVTIHYMRYKVRQRETLFSRFVFSNHPKLVKTPWYYDPAMKMSI<br>EGGDVFIYNNDTLVVGVSERTDLETITTLLAKNIKANKEVEFKRIVAINVPKWT<br>NLMHLDTWLTMLDKDKFLYSPIANDVFKFWDYDLVNGGAEPQPKENGLPLEGL<br>LQSIINKKPVLIPIAGNNASHIDIERETHFDGTNYLAIKPGVVIGYARNEKTN<br>AALAAAGIKVLPFHGNQLSLGMGNARCMSMPLSRKDVKW | 28 |
| *Mycoplasma gateae* Artificial full length from new species patent. | MSVFDSKFNGIHVYSEIGELESVLVHEPGREIDYITPARLDELLFSAILESHD<br>ARKEHKLFVSELKANDINVVELTDLVTETYDLASQEAKDNLIEEFLEDSEPVL<br>TEELKSVVRTYLKSIKSTRELIQMMMAGITKYDLGIEADHELIVDPMPNLYFT<br>RDPFASVGNGVTIHYMRYKVRQRETLFSRFVFSNHPKLVNTPWYYDPSLKLSI<br>EGGDVFIYNNNTLVVGVSERTDLETVTTLLAKNIVANKECEFKRIVAINVPKWT<br>NLMHLDTWLTMLDKDKFLYSPIANDVFKFWDYDLVNGGEEPQPVENGLPLEGL<br>LESIINKKPILIPIAGEGASQIDIERETHFDGTNYLAIRPGVVIGYSRNEKTN<br>AALEAAGIKVLPFHGNQLSLGMGNARCMSMPLSRKDVKW | 29 |
| *Mycoplasma phocidae* Artificial full length from new species patent. | MSVFDSKFNGIHVYSEIGELQTVLVHEPGREIEYITPARLDELLFSAILESHD<br>ARKEHQEFVAELKKNNINVVELTDLVSETYDMVSKEKQEKLIEEFLEDSEPVL<br>SEEHKGLVRKFLKSLKSSKELIQYMMAGITKHDLNIEADHELIVDPMPNLYFT<br>RDPFASVGNGVTIHYMRYKVRQRETLFSRFIFANHPKLMNTPLYYNPDMKLSI<br>EGGDVFVYNNETLVVGVSERTDLDTITTLLAKNIKANKEREFKRIVAINVPKWT<br>NLMHLDTWLTMLDKDKFLYSPIANDVFKFWDYDLVNGGDEPQPKVNGLPLEKL<br>LESIINKKPILIPIAGTSASNIDVERETHFDGTNYLAIAPGVVIGYSRNVKTN<br>EALEAAGIKVLPFKGNQLSLGMGNARCMSMPLSRKDVKW | 30 |
| *Mycoplasma salivarium* | MSVFSSKFNGIHVYSEIGELETVLVHEPGKEIDYITPSRLDELLFSAILESHD<br>ARKEHQEFVATLKKEKINVVELTDLVTETYDLVDQKTKDKLIDEFLEDSEPVL<br>TAELKATVKKFLKSFKETRKLIEVMMAGITKYDLGIKADRELIVDPMPNLYFT<br>RDPFASVGNGVTIHYMRYKVRQRETLFSRFIFNNHPKLVKTPWYYDPAMKMSI<br>EGGDVFIYNNDTLVVGVSERTDLDTITTLLAKNIKANKECEFKRIVAINVPKWT<br>NLMHLDTWLTMLDKDKFLYSPIANDIFKFWDYDLVNGGANPQPKDNGLPLDKL<br>LKSIIGKEPVLIPIAGHHATEIEVARETHFDGTNYLAIRPGVVIGYARNEKTN<br>EALKDAGITVLPFKGNQLSLGMGNARCMSMPLSRKDVKW | 31 |
| *Mycoplasma spumans* | MSVFDSKFKGIHVYSEIGELESVLVHEPGREIDYITPARLDELLFSAILESHD<br>ARKEHKGFVAELKKQNVNVIELTDLVAETYELASKEAQAKLIEDFIEDSEPVL<br>NAEEAQAVRKFLSERKSTREMVEYMMSGLTKYELGLESADRELIVDPMPNLYF<br>TRDPFASVGNGVTIHYMKYKVRQRETELTCFAKFVFSNHPKLVNTPRYYDPSMKLP<br>IEGGDVFIYNNETLVVGCSERTELETITLLAKNIKANKEVEFKRIVAINVPKW<br>TNLMHLDTWLTMLDKDKFLYSPIANDVFKFWDYDLVNGGEEPQPVENGLPLEE<br>LLASIINKKPTLIPIAGEGATHIDVERETHFDGTNYLAIAPALIIGYSRNEKT<br>NAALEKAGITVLPFHGNQLSLGMGNARCMSMPLSRKDVKW | 32 |
| *Mycoplasma auris* | MSVFDSKFKGIHVYSEIGELETVLVHEPGREIDYITPKRLDELLFSAILESHE<br>ARKEHKQFVAELKANDINVVELTDLVAETYDLVSQELKDKLIEEFLDDSYPVL<br>TEEHKKAVRSFLKSRSSTRELIEYMMAGITKYDLGIEAEGDLIVDPMPNLYFT<br>RDPFASVGNGVTIHYMRYKVRQRETLFSRFIFDNHPKLVNTPRYYDPSLKLSI<br>EGGDVFIYNNDTLVMGVSERTDLETVTTLLAKNIKANKECEFKRIVAINVPHWT<br>NLMHLDTWLTMLDKDKFLYSPIANDYFKFWDYDLVNGGAEPQPVVNELPLDKL<br>LESIIHKKPILIPIAGEGASQIDIERETHFDGTNYLVLRPGVVVGYARNEKTN<br>AALEAVGIKVLPFYGNQLSLGMGNSRCMSMPLSRKDVKW | 33 |
| *Mycoplasma hyosynoviae* | MSVFNSKFKGIHVYSEIGDLESVLVHEPGKEIDYITPSRLDELLFSAILESND<br>ARKEHKEFVEILKKEGVNVVELVDLIAETIDLVDAKKKEALIDEYIEDSEPVV<br>DAKVKPLVKKLLLGIKDTKELVKLMMAGITKYDLEIESEKELIIDPMPNLYFT | 34 |

TABLE A1-continued

ADI Polypeptide Sequences

| Source | Sequence | SEQ ID NO: |
|---|---|---|
| | RDPFASVGNGVTIHYMRYKVRQRETLFSRFVFRNHPKLTSTPWYYDPAMKLSI<br>EGGDVFIYNNDTLVVGVSERTDLDTITLLAKNIKANKECEFKRIVAINVPKWT<br>NLMHLDTWLTMLDKDKFLYSPIANDIFKFWDYDLVNGGSEPQPKDNGLPLEKL<br>LESIIGKKPVLIPIAGCCASDIEIARETHFDGTNYLAIKPGVVIGYARNEKTN<br>KALEKAGIKVLPFKGNQLSLGMGNARCMSMPLSRKDVKW | |
| Mycoplasma cloacale | MSVFDKRFKGIHVYSEIGELQTVLVHEPGREIDYITPARLDELLFSAILESHD<br>ARKEHKEFVKILESQGINVVELTDLIAETYELASEEAKDNLIEEFLDESEPVL<br>SEEHRILVRNFLKGITKTKELVKMMMAGITKYDLGIEADRELIVDPMPNLYFT<br>RDPFASVGNGVTIHYMRYKVRQRETLFSRFIFENHPKLVSTPIYYHPSQGLSI<br>EGGDVFIYNNDTLVVGVSERTDLQTITLLAKNIKANEECEFKRIVAINVPKWT<br>NLMHLDTWLTMLDKNKFLYSPIANDVFKFWDYDLVNGGDEPQPVDNGLPLNEL<br>LASIIGEEPVLVPIAGEGASKMDIERETHFDGTNYLAIAPGVVGYSRNEKTN<br>AALEKAGIKVLPFKGHQLSLGMGNARCMSMPLYRKDVK | 35 |
| Mycoplasma alkalescens | MSVFDSKFKGIHVYSEIGELESVLVHEPGHEIDYITPSRLDELLFSAMLESHD<br>ARKEHKQFVAELKANNVNVIELTDLVAETYDLASQEAKDKLIEEFLEDSEPVL<br>SEENKIAVRDFLKSRKTTRELIEVMMAGITKYDLGIKNCKCQDLVVDPMPNLY<br>FTRDPFASVGNGITIHYMRYKVRQRETLFSRFIFANHPKLVNTPIYYHPSLKL<br>SIEGGDVFIYNNDTLVVGVSERTDLETITLLAKNIVANKECEFKRIVAINVPK<br>WTNLMHLDTWLTMLDKDKFLYSPIANDVFKFWDYDLVNGGAEPKPVENGSSLE<br>AILESIIHKKPILIPIGGDSASQIEVERETHFDGTNYLAIRPGVVIGYSRNVK<br>TNAALEAAGIKVIPFHGNQLSLGMGNARCMSMPLSRKDVKW | 36 |
| Mycoplasma iners | MSKINVYSEIGVLKEVLVHTPGDEIRRIAPSRLDELLFSAILEPSAAIQEHKS<br>FLKILQDRGIKTIQLSDLVAETYKHYASEAEKEAFIEKYLDEATPVLSKDMRA<br>KVKNYILSMQGEPVKMVRTMMAGVSKQELNVESEVELIVDPMPNLYFTRDPFA<br>SAGNGISLNNMKYVVRKRETIFAEFIFSIHPEYKKTPHWFDRLDNGSIEGGDV<br>FIYNKDTLVIGVSERTNKEAIITIAKHIQDNKEAQFKKIVAINVPPMPNLMHL<br>DTWLTMVDKNKFLYSPNMLSVLKVWEIDLSKPIEMVETNKPLAEVLESIIGEK<br>PILIPIAGKDATQLDIDIETHFDGTNYLTIAPGVVVGYSRNVKTEAALRAAGV<br>TVLSFEGNQLSLGMGSARCMSMPLVREDVK | 37 |
| Mycoplasma gallinarum | MSKIRVYSEIGNLKKVLVHTPGDEIRRISPSRLEELLFSAVLEPNAAIEEHKR<br>FVKLLEDRGIQAIQLSDLVAETYVKYATAEQKAAFIEKYLDEATPALSAENRE<br>RAKKYILSLEMQPVKMIRTMMAGLSKYELNVESNIELIIDPMPNLYFTRDPFA<br>SAGNGISLNNMKYVVRKRETIFAEFIFAIHPEYKETPHWFDRLDHGSIEGGDV<br>FVYNKDTLVIGVSERTNKEAIITIAKHIQDNKEAEFKKIVAINVPPMPNLMHL<br>DTWLTMVDKNKFIYSPNMLSVLKIWEIDLAKPIEMVESNKSLTEVLESIIGEK<br>PILIPIAGEGASQLDIDIETHFDGTNYLTIAPGVVVGYSRNEKTEKALKAAGI<br>TVLSFEGNQLSLGMGSARCMSMPLVREDVK | 38 |
| Mycoplasma pirum | MNSNQKGIHVYSEIGKLKEVLVHRPGRELDFLDPTRLDELLFAATLEAETARL<br>EHDNFTNALKNQGVTVIELADLVAQTYSSSTPTIKAAFINKYLDEATPALTTK<br>LRTLVKDFLTKQKSVRKMVDYMIGGILSTDLNIKGKPELIVEPMPNAYFTHDP<br>FASVGNGVTLHYMKHNVRRREVLFSEFIFNNNERFQNTPRYIVPTKGLDIEGG<br>DVFVYNKNTLVVGVSERTKMVTIKELAKNILKNKECLFKKIYAINVPKMPNLM<br>HLDTWLTMLDHNKFLYSPNMLSVLKIWEIDISSGKSISSPKELNMDLSKALSI<br>IIGKKPILIPVAGENASQIDINIETNFDATNYLVTQPGVVVGYSRNKKTEAAL<br>IKAGIEVIPFQGNQLSLGMGSARCMSMPLIREDV | 39 |
| Mycoplasma primatum | MSKSKINVYSEYGNLKEVLVHTPGDEIRRITPSRLDELLFSAILEPKSAIAEH<br>KSFCQILKDNKVKAIQLDELVAATYKGVSESVQNSFVERWLDECEPKLENNVR<br>PIVKEYLLKAAEQSVKKMIRIMMAGIDKREIGVESEVDFIVDPMPNLYFTRDP<br>FASVGNGITLHHMKYVVRQRETLFSEFIFDNHPDYKFVPRYFDRDDEGKIEGG<br>DVFIYNSKTLVVGISERTNKDAIRIVAKKIQANADAKFEKIFAINVPPMPNLM<br>HLDTWLTMLDSNKFLYSPNMLSVLKVWEINLDDPALEWKEISGSLEEILTYII<br>GKKPILIPIAGKGASQFEIDIETHFDGTNYLAIAPSVVIGYSRNELTEKALKK<br>AGVKVLSLDGNQLSLGMGSARCMSMPLIREDVK | 40 |
| Mycoplasma lipofaciens | MSKINVYSEVGVLKEVLVHTPGDEIRRVAPSRLDELLFSAILEPQDAIAEHKR<br>FIKILEDNNIKVIQLDELVSETWEKATAEQRDAFIEKWLDEAEPVLKALRET<br>VKKYLLSLNPVKKMVRTMMAGIDKKELKIELDRDLVVDPMPNLYFTRDPFASA<br>GNGISLNNMKYVTRKRETIFAEFIFNIHPDYKTTPHWFDRLDKGNIEGGDVFI<br>YNKDTLVLGVSERTNKDAVMTIAKHIQSNEQAKFKKLVAINVPPMPNLMHLDT<br>WLTMVDHDKFLYSPNMLSVLKIWEIDLTPGKEIEMVESTKSLSDMLESIIGKK<br>PVLIPIAGKDASQLDIDIETHFDGTNYLTIRPGVVVGYSRNCLTEQALKDAGV<br>TVLSFDGNQLSLGMGSARCMSMPLVREDIK | 41 |
| Mycoplasma felifaucium | MNKINVYSEIGKLKEVLVHTPGNEIRRISPSRLDELLFSALLEPNFAAKEHTA<br>FCEILKENGIKAIQLVDLVSDTWRIASEKAKTEFIERWLDECEPKLDSNLREI<br>VRKHIYAIEKRSVKRMVKTMMAGIERRELPVTSKEVARELVVDPMPNLYFTRD<br>PFASVGNGISLHHMKYVTRQRETIFAEFVFGNHPDYIDTPRWFDRSDDGRIEG<br>GDVFIYGSKTLVIGVSERTNKEAIKVMAKKIQANKEATFEKIYAINVPPMPNL<br>MHLDTWLTMLDKNKFLYSPNMLAVLQVWEIDLKDPELTWHELSGSLEEILHKI | 42 |

TABLE A1-continued

ADI Polypeptide Sequences

| Source | Sequence | SEQ ID NO: |
|---|---|---|
| | IGRKPILIPIAGHGAQQIDIDIETHFDGTNYLAIAPGVVVGYNRNVLTERALK KAGIKVLSFEGNQLSLGMGSARCMSMPLIRENLK | |
| *Mycoplasma imitans* | MFNKIKVYSEIGRLRKVLVHTPGKELEYVTPQRLDELLFSSLLNPVKARQEHE AFIKILQDQGVECVQLTTLTAQTFQSATSEVKEKFINRWLDECLPKLSDDNRI KVYAYLKDLSSDPEVMIRKMMSGILAKEVNVQSDVELIADPMPNLYFTRDPFA SIGKGVTLHSMFHPTRKRETIFADFVFSHHPEYKQTPKYYSRLNEYSIEGGDL FVYDDKTLVIGVSERTEKKAIQFLAEKLRENYETTFEKIYAINVPKMSNLMHL DTWLTMLDYDKFLYSPNMMGVLKIWEIDLTHEQLSWRELNESLEEFLSMVIGK KATTIPVAGEDSTQIEIDVETNFDATNFLVIQPGVVVGYDRNYKTNQALVNAG IKVLSWNGDQLSLGMGSARCMSMPLYRDPIKKG | 43 |
| *Mycoplasma opalescens* | MSKINVYSEIGTLKEVLVHTPGDEIRRVAPARLDELLFSAILEPNHAIAEHKA FIKILEDNGIKVIQLDELVVQTWNQVDEATRKAFVTKWLDECEPKLESNVRVE VEKYIYSLAKEPKKMVRTMMAGISKEELPLNVNRPLVVDPMPNLYFTRDPFAS VGTGISLHHMKYVTRQRETIFAQFVFDNHKDYNTVPRWFDNKDQGRIEGGDVF IYNTKTLVIGVSERTDKDAIKIMAKKIQADKNCKFEKIFAINVPPMPNLMHLD TWLTMVDRNKFLYSPNMLSVLKVWEIDLKDASLAWKEIEGSLSQILEKIIGEK PILIPIAGENASQLDIDIETHFDGTNYLTIAPGVVVGYSRNVKTEQALKAAGV KVLSFEGNQLSLGMGSARCMSMPLIREDLK | 44 |
| *Mycoplasma moatsii* | MKKNAINVYSEIGKLKKVLVHRPGDELKYVTPQRMDELLMSAIIELEQAKEEH DAFTKILRDNGVEVIELADLTAEMYDSLTPSEKDAFLNQWVKEASWGKKSSID ALKIKKNLSKKVFDYVKSIKPTRKMIDKLMAGVLLSEIGEKSIILNKDKKNEM VIDLVVDPMPNLYFTRDPFASVGNGITLHNMKYPTRKRETIFAQWIFNKHPEY KDVPQFISKRDGKETIEGGDVFIYTKDVLAIGVSERTNMEAILRIATNIKKDK NCEFKKIVAINVPPMGNLMHDTWLTMLDKDLFLYSGNIKSALKVWEIDLTKP ITPKSPKLSTAKLADILAKIVGKKVRMIPIGGKDGNQMDIDIETHFDGTNYLA IAPGVVVGYHRNRKTQKALEEAGVKVLAFQGNQLSLGMGSARCMSMPLVREEV K | 45 |
| *Mycoplasma elephantis* | MSQINVFSEIGQLKEVLVHTPGDEIRRISPKRYNELLFSAILEADVAIKEHKS FVKILEENNVVKVIQLKDILLETWNICSKEAKNIFINKWIEEAQPVIHSSSLKE KIKLFLKSKTPLEIIDIMMKGILKQELGIEYKHELIIDPMPNLYFTRDPFTSM GSGITINNMKYQTRKRETIFSEFIFNNHPKYKNTPRWFDRFDSGNIEGGDLFV YTKETIVVGVSERTKKKAILKIAKNIQENNNSFKKIVVIKVPIMQNLMHLDTW IVMVDFDKFIYSPNVTKSLKFWEIDLTKKPKFIQLKNETLEDVLYRVIGKKPI LIPVAGENANQIDIDVETHFDATNYLTIRPGVVVGYSRNKKTEEALINAGVKV YAFEGNQLSLGMGSARCMSMPLIREDII | 46 |
| *Mycoplasma testudinis* | MKNINVYSEVGKLKEVVVHTPGEELHNVAPSRLQELLTSAVLEPEVARKEHLK FIKILNDYGVKVIQIVDLITETYEAVDSNKKEAFINNWLDNSVPKLTDKNRMI LRNYLTQFSTKAMIRKMISGIRAKELNLKTPSALLVDPMPNLCFARDTFACVG SAISLSTMKHPTRRREALLTEFIFQNHPKYKDVIKYFDSKNSKATIEGGDIFV YNPKTLVVGNSERTNMQACLLLAKKIQSNPNNKFEKIVIVNVPPLPHLMHLDT WLTMVDYDKFIYSPNILHTLKFWVIDLKKRKLEAVEKHNTLKAMLRMIIKKEP ILIPVGDVGADQLDIDLETHFDATNYLALAPGVVVGYDRNIKTQRALEKAGVK VLSFSGNQLSLAMGSARCLSMPLIREEN | 47 |
| *Mycoplasma canadense* | MSVFDSKFKGIHVYSEIGELESVLVHEPGREIDYITPARLDELLFSAILESHD ARKEHKQFVSELKANDINVVELTDLVAETYDLASQEAKDKLIEEFLEDSEPVL SEEHKAIVRKYLKGIQPTRKLIEMMMAGITKYDLGIEADHELIVDPMPNLYFT RDPFASVGNGVTIHYMRYKVRQRETLFSRFVFSNHPKLVNTPWYYDPSLKLSI EGGDVFVYNNDTLVVGVSERTDLQTVTLLAKNIVANKECEFKRIVAINVPKWT NLMHLDTWLTMLDKDKFLYSPIANDVFKFWDYDLVNGGSEPQPVENGLPLEGL LESIINKKPILIPIAGEGASQMEIERETHFDGTNYLAIRPGVVIGYSRNEKTN AALEAAGIKVLPFHGNQLSLGMGNARCMSMPLSRKDVKW | 48 |
| *Mycoplasma anseris* | MSVFDKRFKGIHVYSEIGELQTVLVHEPGREIDYITPARLDELLFSAILESHD ARAEHKKFVATLKEQGINTVELTDLVAETYDLASQEARDNLLEEFLDDSAPVL SEEHKEIVRTYLKGIKGTRKLIETMMAGITKYDLGIEAEQELIVDPMPNLYFT RDPFASVGNGVTIHYMRYKVRQRETLFSRFIFSNHPQLVNTPWYYNPAEGLSI EGGDVFIYNNDTLVVGVSERTDLQTITLLAKNIKANEECEFKRIVAINVPKWT NLMHLDTWLTMLDTNKFLYSPIANDVFKFWDYDLVNGGDEPQPVDNGLPLNEL LKSIIGEEPILIPIAGDGATQIEIERETHFDGTNYLAIAPGVVIGYSRNEKTN AALEAAGIKVLPFKGHQLSLGMGNARCMSMPLYRKDVK | 49 |
| *Mycoplasma meleagridis* | MSKINVYSEIGVLKEVLVHTPGDEIRRISPSRLDELLFSAILQPEQAIKEHQS FVKILQDRGIKVIQLSDLVAETYVKYATSKEKESFIEKWLDEATPALNSENRA RVKNYITAMQGQPVKMVRAMMAGVSKQELNIESDVELIVDPMPNLYFTRDPFA SAGNGISLNNMKYVVRKETIFAEFIFSIHPEYKQTPHWFDRLDKGNIEGGDV FIYNKDTLVIGVSERTNKEAILTIAEHIKNNKEAKFKKIVAINPPMPNLMHL DTWLTMVDKNKFLYSPNMLSVLKIWEIDLSKEIKMVETSKPLADVLESIIGEK PILIPIAGENASQLDIDIETHFDGTNYLTIAPGVVVGYSRNVKTEAALKAAGV TVYSFDGNQLSLGMGSGRCMSMPLVREDVK | 50 |

TABLE A1-continued

ADI Polypeptide Sequences

| Source | Sequence | SEQ ID NO: |
|---|---|---|
| Mycoplasma alvi | MSIKENGIHVYSEIGKLRDVLVHRPGRELNFLDPSRLDELLFAATLEPETARL EHDNFTTVLKNQGVNVIELADLVSQTYSKVDSKVKKEFIDQYLNEATPKLTSE LSKKVYDFLTKQKSNREMVDFMMGGILSSDLNIKGQPYLIVEPMPNLYFTRDP FASVGNGATIHWMKHNVRRREVLFANFIFKYNERFQNTPKYITPTKGLDIEGG DVFVYNKKTLVVGVSERTKMETIKELAKNISKNKECTFTKIYAINVPKMPNLM HLDTWLTMLDYNKFLYSPNMLSVLKVWEINISNNKVSAPKELNVNLEKALSMI IGKKPILIPVAGANASQIDINIETNFDATNYLVIEPGVVVGYSRNKKTEEALV KAGIKVLPFHGNQLSLGMGSARCMSMPLYREDV | 51 |
| Mycoplasma penetrans | MSSIDKNSLGNGINVYSEIGELKEVLVHTPGDEIRYTAPSRLEELLFSAVLKA DTAIEEHKGFVKILQNNGIKVIQLCDLVAETYELCSKEVRNSFIEQYLDEALP VLKKEIRPVVKDYLLSFPTVQMVRKMMSGILANELNIKQDNPLIIDGMPNLYF TRDPFASMGNGVSINCMKYPTRKREVIFSRFVFTNNPKYKNTPRYFDIVGNNG TIEGGDIFIYNSKTLVIGNSERTNFAAIESVAKNIQANKDCTFERIVVINVPP MPNLMHLDTWLTMLDYDKFLYSPNMMNVLKIWEIDLNVKPVKFVEKKGTLEEV LYSIIDKKPILIPIAGKGANQLDIDIETHFDGTNYLTIAPGVVVGYERNEKTQ KALVEAGIKVLSFNGSQLSLGMGSARCMSMPLIRENLKK | 52 |
| Mycoplasma fermentans | MKKINVYSEYGKLKEVLVHTPGDEIRRIAPSRLDELLFSAILEPDSAIAEHKR FVQLLKDNGIKVIQLDELFAKTFDLVSESVKQSFIERWLDECEPKLDATLRAK VKEYILELKAKSSKKMVRVMMAGIDKKELGIELDRDLVVDPMPNLYFTRDPFA SVGNGISLHHMKYVTRQRETIFSEFIFDNNLDYNTVPRWFDRKDEGRIEGGDV FIYSADTLVVGVSERTNKEAINVMARKIAADKEVKFKRIYAINVPPMPNLMHL DTWLTMLDKNKFLYSPNMLSVLKVWRIDLNDPDFVWHEIEGSLEEILEQIIGM KPILIPIAGKGASQLDIDIETHFDGTNYLTIAPSVVVGYSRNEKTEKALKAAK VKVLSFEGNQLSLGMGSARCMSMPLIREDIKKK | 53 |
| Mycoplasma pneumoniae | MKYNINVHSEIGQLQTVLVHTPGNEIRRISPRRLDDLLFSAVIEPDTAIQEHQ TFCQLLQEQNIEVVQLTDLTATTFDKANATAQNQFIETWLDQAEPKLTPEHRK VAKQYLLEQKAKSTLSMVRSMMGGIDKRKVAAANTINGDFLVDPMPNLYFTRD PFASIGHGISINRMKYLTRRRETLFASFIFANHPIIAARKFYFKPIDMGTIEG GDIFVYDQQTVVMGLSERTTEAAINVLAKKIQQDSSTSFKRIFVINVPQLPNL MHLDTWLTMLDRNKFLYSPNMLAVLKAWRIDFTDPALKWNEIAGDLSTILHTI IGQKPMLIPIAGADANQTEIDIETHFDGTNYLTIAPSVVVGYARNKLTHQTLE AAGVKVIAFKGNQLSLGMGSARCMSMPLVRKPL | 54 |
| Mycoplasma sp. CAG: 877 | MEKIHVTSEIGPLKKVLLHRPGNELLNLTPDTLSRLLFDDIPYLPDAIKEHDE FADALRANGVEVVYLENLMADVLDLSDEIRDKFIKQFIYEAGIRTPKYKYLVF DYLDQITNSKKLVLKTMEGIQISDIPRRKREIEKSLVDLIETEDEFIADPMPN LYFTRDPFASVGEGISLNKMYSVTRNRETIYAEYIFKYHPDYKDQARLYYDRY NPYHIEGGDVLNINDHVLAIGISQRTTAEAIDQIAKNLFKDPECKIDTILAFN IPESRAFMHLDTVFTQVDYDKFTYHPGIMGTLQVFEITEGDDPNSDEDLTVTE INAPLEEILTKYVGRKVTLIPCAGGDKVSAEREQWNDGSNTLCIAPGVVVVYD RNNLTNAVLRSYGLKVIEIHGAELSRGRGGPRCMSMPLVREDI | 55 |
| Mycoplasma sp. CAG: 472 | MHVTSEIKKLKKVLVHRPGKELLNLTPDTLGRLLFDDIPYLKDAILEHDEFCQ ILRDNDVEVVYLEDLMAETLDENPQVKPSFIRQFIYEAGVRTPKYKDLLFDYL MSYTNNKELVLKTMEGIKVSEVHRNKQDSEYSLVDQISEETKFLAEPMPNLYF TRDPFASVGDGIILNKMHSVTRSRETIYAYYIFNYHPDYMDKVPKYYDRENPF SIEGGDVLNLNEHTLAIGISQRTSAEAIDLVAKNMFNDEKCNIDTILAFKIPE CRAFMHLDTVFTQIDIDKFTYHPGIMDTLEVFEITKNEDDLDEVRVIKKEGSL ENILEEYLGIDITLIPCAGGDKIASEREQWNDGTNTLCIAPGVVVVYNRNNIT NEVLREKGIKVIEMNSAELSRGRGGPRCMSMPLERED | 56 |

Hence, in some embodiments, the ADI polypeptide comprises, consists, or consists essentially of an illustrative sequence from Table A1 (SEQ ID NOs:1-56), or a variant or fragment thereof having ADI activity.

Certain embodiments include variants of the reference ADI polypeptide sequences described herein, whether described by name or by reference to a Table or sequence identifier (e.g., Table A1, SEQ ID NOs:1-56). A "variant" sequence refers to a polypeptide or polynucleotide sequence that differs from a reference sequence by one or more substitutions, deletions (e.g., truncations), additions, and/or insertions. Certain variants thus include fragments of a reference sequence described herein. Variant polypeptides are biologically active, that is, they continue to possess the enzymatic or binding activity of a reference polypeptide. Such variants may result from, for example, genetic polymorphism and/or from human manipulation.

In many instances, a biologically active variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present disclosure and still obtain a functional molecule that encodes a variant or derivative polypeptide with desirable characteristics. When it is desired to alter the amino acid sequence of a polypeptide to create an equivalent, or even an improved, variant or portion of a polypeptide described herein, one skilled in the art will typically change one or more of the codons of the encoding DNA sequence.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their utility.

In making such changes, the hydropathic index of amino acids may be considered. The importance of the hydropathic amino acid index in conferring interactive biologic function on a protein is generally understood in the art (Kyte & Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte & Doolittle, 1982). These values are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A variant may also, or alternatively, contain non-conservative changes. In a preferred embodiment, variant polypeptides differ from a native or reference sequence by substitution, deletion or addition of fewer than about 10, 9, 8, 7, 6, 5, 4, 3, 2 amino acids, or even 1 amino acid. Variants may also (or alternatively) be modified by, for example, the deletion or addition of amino acids that have minimal influence on the immunogenicity, secondary structure, enzymatic activity, and/or hydropathic nature of the polypeptide.

In certain embodiments, a polypeptide sequence is about, at least about, or up to about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700. 700, 710, 720, 730, 740, 750, 760, 770, 780, 790, 800, 800, 810, 820, 830, 840, 850, 860, 870, 880, 890, 900, 900, 910, 920, 930, 940, 950, 960, 970, 980, 990, 1000 or more contiguous amino acids in length, including all integers in between, and which may comprise all or a portion of a reference sequence (see, e.g., Sequence Listing).

In some embodiments, a polypeptide sequence consists of about or no more than about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800. 800, 810, 820, 830, 840, 850, 860, 870, 880, 890, 900, 900, 910, 920, 930, 940, 950, 960, 970, 980, 990, 1000 or more contiguous amino acids, including all integers in between, and which may comprise all or a portion of a reference sequence (see, e.g., sequence listing).

In certain embodiments, a polypeptide sequence is about 10-1000, 10-900, 10-800, 10-700, 10-600, 10-500, 10-400, 10-300, 10-200, 10-100, 10-50, 10-40, 10-30, 10-20, 20-1000, 20-900, 20-800, 20-700, 20-600, 20-500, 20-400, 20-300, 20-200, 20-100, 20-50, 20-40, 20-30, 50-1000, 50-900, 50-800, 50-700, 50-600, 50-500, 50-400, 50-300, 50-200, 50-100, 100-1000, 100-900, 100-800, 100-700, 100-600, 100-500, 100-400, 100-300, 100-200, 200-1000, 200-900, 200-800, 200-700, 200-600, 200-500, 200-400, or 200-300 contiguous amino acids, including all ranges in between, and comprises all or a portion of a reference sequence. In certain embodiments, the C-terminal or N-terminal region of any reference polypeptide may be truncated by about 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 250, 300, 350, 400, 450, 500, 550, 600, 650, 700, 750, or 800 or more amino acids, or by about 10-50, 20-50, 50-100, 100-150, 150-200, 200-250, 250-300, 300-350, 350-400, 400-450, 450-500, 500-550, 550-600, 600-650, 650-700, 700-750, 750-800 or more amino acids, including all integers and ranges in between (e.g., 101, 102, 103, 104, 105), so long as the truncated polypeptide retains the binding properties and/or activity of the reference polypeptide. Typically, the biologically-active fragment has no less than about 1%, about 5%, about 10%, about 25%, or about 50% of an activity of the biologically-active reference polypeptide from which it is derived.

In general, variants will display at least about 30%, 40%, 50%, 55%, 60%, 65%, 70%, 75%, 80%, 85%, 90%, 91%, 92%, 93%, 94%, 95%, 96%, 97%, 98%, 99% similarity or sequence identity or sequence homology to a reference polypeptide sequence. Moreover, sequences differing from the native or parent sequences by the addition (e.g., C-terminal addition, N-terminal addition, both), deletion, truncation, insertion, or substitution (e.g., conservative substitution) of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 amino acids (including all integers and ranges in between) but which retain the properties or activities of a parent or reference polypeptide sequence are contemplated.

In some embodiments, variant polypeptides differ from reference sequence by at least one but by less than 50, 40, 30, 20, 15, 10, 8, 6, 5, 4, 3 or 2 amino acid residue(s). In certain embodiments, variant polypeptides differ from a reference sequence by at least 1% but less than 20%, 15%, 10% or 5% of the residues. (If this comparison requires alignment, the sequences should be aligned for maximum similarity. "Looped" out sequences from deletions or insertions, or mismatches, are considered differences.)

Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (J. Mol. Biol. 48: 444-453, 1970) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (*Cabios*. 4:11-17, 1989) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, *J. Mol. Biol*, 215: 403-10). BLAST nucleotide searches can be performed with the NBLAST program, score=100, wordlength=12 to obtain nucleotide sequences homologous to nucleic acid molecules described herein. BLAST protein searches can be performed with the XBLAST program, score=50, wordlength=3 to obtain amino acid sequences homologous to protein molecules described herein. To obtain gapped alignments for comparison purposes, Gapped BLAST can be utilized as described in Altschul et al., (*Nucleic Acids Res.* 25: 3389-3402, 1997). When utilizing BLAST and Gapped BLAST programs, the default parameters of the respective programs (e.g., XBLAST and NBLAST) can be used.

In some embodiments, as noted above, polynucleotides and/or polypeptides can be evaluated using a BLAST alignment tool. A local alignment consists simply of a pair of sequence segments, one from each of the sequences being compared. A modification of Smith-Waterman or Sellers algorithms will find all segment pairs whose scores cannot be improved by extension or trimming, called high-scoring segment pairs (HSPs). The results of the BLAST alignments include statistical measures to indicate the likelihood that the BLAST score can be expected from chance alone.

The raw score, S, is calculated from the number of gaps and substitutions associated with each aligned sequence wherein higher similarity scores indicate a more significant alignment. Substitution scores are given by a look-up table (see PAM, BLOSUM).

Gap scores are typically calculated as the sum of G, the gap opening penalty and L, the gap extension penalty. For a gap of length n, the gap cost would be G+Ln. The choice of gap costs, G and L is empirical, but it is customary to choose a high value for G (10-15), e.g., 11, and a low value for L (1-2) e.g., 1.

The bit score, S', is derived from the raw alignment score S in which the statistical properties of the scoring system used have been taken into account. Bit scores are normalized with respect to the scoring system, therefore they can be used to compare alignment scores from different searches. The terms "bit score" and "similarity score" are used interchangeably. The bit score gives an indication of how good the alignment is; the higher the score, the better the alignment.

The E-Value, or expected value, describes the likelihood that a sequence with a similar score will occur in the database by chance. It is a prediction of the number of different alignments with scores equivalent to or better than S that are expected to occur in a database search by chance. The smaller the E-Value, the more significant the alignment. For example, an alignment having an E value of $e^{-117}$ means that a sequence with a similar score is very unlikely to occur simply by chance. Additionally, the expected score for aligning a random pair of amino acids is required to be negative, otherwise long alignments would tend to have high score independently of whether the segments aligned were related. Additionally, the BLAST algorithm uses an appropriate substitution matrix, nucleotide or amino acid and for gapped alignments uses gap creation and extension penalties. For example, BLAST alignment and comparison of polypeptide sequences are typically done using the BLOSUM62 matrix, a gap existence penalty of 11 and a gap extension penalty of 1.

In some embodiments, sequence similarity scores are reported from BLAST analyses done using the BLOSUM62 matrix, a gap existence penalty of 11 and a gap extension penalty of 1.

In a particular embodiment, sequence identity/similarity scores provided herein refer to the value obtained using GAP Version 10 (GCG, Accelrys, San Diego, Calif.) using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix (Henikoff and Henikoff, *PNAS USA*. 89:10915-10919, 1992). GAP uses the algorithm of Needleman and Wunsch (*J Mol Biol*. 48:443-453, 1970) to find the alignment of two complete sequences that maximizes the number of matches and minimizes the number of gaps.

In particular embodiments, the variant polypeptide comprises an amino acid sequence that can be optimally aligned with a reference polypeptide sequence (see, e.g., Sequence Listing) to generate a BLAST bit scores or sequence similarity scores of at least about 50, 60, 70, 80, 90, 100, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or more, including all integers and ranges in between, wherein the BLAST alignment used the BLOSUM62 matrix, a gap existence penalty of 11, and a gap extension penalty of 1.

As noted above, a reference polypeptide may be altered in various ways including amino acid substitutions, deletions, truncations, additions, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (*PNAS USA*. 82: 488-492, 1985); Kunkel et al., (*Methods in Enzymol*. 154: 367-382, 1987), U.S. Pat. No. 4,873,192, Watson, J. D. et al., ("Molecular Biology of the Gene," Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Methods for screening gene products of combinatorial libraries made by such modifications, and for screening cDNA libraries for gene products having a selected property are known in the art. Such methods are adaptable for rapid screening of the gene libraries generated by combinatorial mutagenesis of reference polypeptides. As one example, recursive ensemble mutagenesis (REM), a technique which enhances the frequency of functional mutants in the libraries, can be used in combination with the screening assays to identify polypeptide variants (Arkin and Yourvan, *PNAS USA* 89: 7811-7815, 1992; Delgrave et al., *Protein Engineering*. 6: 327-331, 1993).

In some instances, a native ADI may be derived from microorganisms and can thus be immunogenic and/or rapidly cleared from circulation in a patient. Such problems may be overcome by modifying an ADI to create a "modified ADI" enzyme. Thus, certain embodiments include an ADI enzyme that comprises a "modifying agent," examples of which included but are not limited to macromolecule polymers, proteins, peptides, polysaccharides, and other compounds. The ADI enzyme and the modifying agent may be linked by either covalent bonds or non-covalent interaction to form a stable conjugate or a stable composition to achieve a desired effect. In certain embodiments, the modified ADI retains the biological activity of a corresponding unmodified ADI (e.g., of the same or similar sequence) and has a longer half-life in vivo and lower antigenicity than the corresponding unmodified ADI. In certain embodiments, the modified ADI retains at least 30%, 35%, 40%, 45%, 50%, 55%, 60%, 65%, 70%, 75%, 80%, 85%, 90%, 95%, 96%, 97%, 98%, 99% or more of the biological activity of the corresponding unmodified ADI. Generally, the modified ADI retains biological activity sufficient for therapeutic use.

In some embodiments, a modifying agent can be a polymer or a protein or a fragment thereof that is biocompatible and can increase the half-life of ADI in blood. The modifying agent can be either chemically coupled to ADI or where applicable, linked to the ADI via fusion protein expression.

Macromolecule polymers may include a non-peptide macromolecule polymer, which in certain embodiments, may have its own bioactivity. Suitable polymers include, but are not limited to, polyenol compounds, polyether compounds, polyvinylpyrrolidone, poly amino acids, copolymer of divinyl ether and maleic anhydride, N-(2-hydroxypropyl)-methacrylamide, polysaccharide, polyoxyethylated polyol, heparin or its fragment, poly-alkyl-ethylene glycol and its derivatives, copolymers of poly-alkyl-ethylene glycol and its derivatives, poly(vinyl ethyl ether), a,P-Poly[(2-hydroxyethyl)-DL-aspartamide], polycarboxylates, poly oxyethylene-oxymethylenes, poly acryloyl morpholines, copolymer of amino compounds and oxyolefin, poly hyaluronic acid, polyoxiranes, copolymer of ethanedioic acid and malonic acid, poly (1,3-dioxolane), ethylene and maleic hydrazide copolymer, poly sialic acid, cyclodextrin, etc. In certain embodiments, the polymer is polyethylene glycol.

The polyenol compounds as used herein include, but are not limited to, polyethylene glycol (including monomethoxy polyethylene glycol, monohydroxyl polyethylene glycol), polyvinyl alcohol, polyallyl alcohol, polybutenol and the like, and their derivatives, such as lipids.

The polyether compounds include, but are not limited to poly alkylene glycol (HO((CH2)$_x$O)$_n$H), polypropylene glycol, polyoxyrehylene (HO((CH$_2$)$_2$O)$_n$H), polyvinyl alcohol ((CH2CHOH)$_n$).

Poly amino acids include, but are not limited to, polymers of one type of amino acid or copolymers of two or more types of amino acids, for example, polyalanine or polylysine, or block co-polymers thereof.

Polysaccharides include but are not limited to, glucosan and its derivatives, for example dextran sulfate, cellulose and its derivatives (including methyl cellulose and carboxymethyl cellulose), starch and its derivatives, polysucrose, etc.

In specific embodiments, the ADI is modified by coupling with protein(s) or peptide(s), wherein one or more proteins or peptides are directly or indirectly linked to ADI. The proteins can either be naturally-existing proteins or their fragments, including but not limited to naturally existing human serum proteins or their fragments, such as thyroxine-binding protein, transthyretin, al-acid glycoprotein, transferrin, fibrinogen, immunoglobulin, Ig Fc regions, albumin, and fragments thereof. By "fragment" is meant any portion of a protein that is smaller than the whole protein but which retains the desired function of the protein. The ADI as described herein may be directly or indirectly linked to a protein via a covalent bond. Direct linking means that one amino acid of ADI is directly linked to one amino acid of the modifying protein, via a peptide bond or a disulfide bridge. Indirect linking refers to the linkages between an ADI and a modifying protein, via originally existing chemical groups there between or specific chemical groups added through biological or chemical means, or the combination of the above-mentioned linkages.

In particular embodiments, the ADI is modified by covalent attachment to one or more PEG molecules. ADI covalently modified with PEG (with or without a linker) may be hereinafter referred to as "ADI-PEG." When compared to unmodified ADI, ADI-PEG retains most of its enzymatic activity, is far less immunogenic or antigenic, has a greatly extended circulating half-life, and is more efficacious in the treatment of tumors.

"Polyethylene glycol" or "PEG" refers to mixtures of condensation polymers of ethylene oxide and water, in a branched or straight chain, represented by the general formula H(OCH$_2$CH2)$_n$OH, wherein n is at least 4. "Polyethylene glycol" or "PEG" is used in combination with a numeric suffix to indicate the approximate weight average molecular weight thereof. For example, PEG5,000 refers to PEG having a total weight average molecular weight of about 5,000; PEG12,000 refers to PEG having a total weight average molecular weight of about 12,000; and PEG20,000 refers to PEG having a total weight average molecular weight of about 20,000.

In some embodiments, the PEG has a total weight average molecular weight of about 1,000 to about 50,000; about 3,000 to about 40,000; about 5,000 to about 30,000; about 8,000 to about 30,000; about 11,000 to about 30,000; about 12,000 to about 28,000; about 16,000 to about 24,000; about 18,000 to about 22,000; or about 19,000 to about 21,000. In some embodiments, the PEG has a total weight average molecular weight of about 1,000 to about 50,000; about 3,000 to about 30,000; about 3,000 to about 20,000; about 4,000 to about 12,000; about 4,000 to about 10,000; about 4,000 to about 8,000; about 4,000 to about 6,000; or about 5,000. In specific embodiments, the PEG has a total weight average molecular weight of about 20,000. Generally, PEG with a molecular weight of 30,000 or more is difficult to dissolve, and yields of the formulated product may be reduced. The PEG may be a branched or straight chain Generally, increasing the molecular weight of the PEG decreases the immunogenicity of the ADI. The PEG may be a branched or straight chain, and in certain embodiments is a straight chain. The PEG having a molecular weight described herein may be used in conjunction with ADI, and optionally, a biocompatible linker.

Certain embodiments employ thiol, sulfhydryl, or cysteine-reactive PEG(s). In some embodiments, the thiol, sulfhydryl, or cysteine-reactive PEG(s) are attached to one or more naturally-occurring cysteine residues, one or more introduced cysteine residues (e.g., substitution of one or more wild-type residues with cysteine residue(s)), insertion of one or more cysteine residues), or any combination thereof (see, e.g., Doherty et al., Bioconjug Chem. 16:1291-98, 2005). In certain embodiments, certain of the wild-type ADI cysteines residues may be first substituted with another amino acid to prevent attachment of the PEG polymer to wild-type cysteines, for example, to prevent the PEG(s) from disrupting an otherwise desirable biological activity. Some embodiments employ one or more non-natural cysteine derivatives (e.g., homocysteine) instead of cysteine.

Non-limiting examples of thiol, sulfhydryl, or cysteine-reactive PEGs include Methoxy PEG Maleimides (M-PEG-MAL) (e.g., MW 2000, MW 5000, MW 10000, MW 20000, MW 30000, MW 40000). M-PEG-MALs react with the thiol groups on cysteine side chains in proteins and peptides to generate a stable 3-thiosuccinimidyl ether linkage. This reaction is highly selective and can take place under mild conditions at about pH 5.0-6.5 in the presence of other functional groups. Particular examples of commercially-available thiol, sulfhydryl, or cysteine-reactive PEG molecules are illustrated in FIGS. 1A-1D. Thus, in certain embodiments, an ADI enzyme is conjugated to any one or more of the thiol, sulfhydryl, or cysteine-reactive PEG molecules described herein.

ADI may be covalently bonded to a modifying agent, such as PEG, with or without a linker, although a preferred embodiment utilizes a linker. ADI may be covalently bonded to PEG via a biocompatible linker using methods known in the art, as described, for example, by Park et al, Anticancer Res., 1:373-376 (1981); and Zaplipsky and Lee, Polyethylene Glycol Chemistry: Biotechnical and Biomedical Applications, J. M. Harris, ed., Plenum Press, NY, Chapter 21 (1992), the disclosures of which are hereby incorporated by reference herein in their entirety. In some instances, ADI may be coupled directly (i.e., without a linker) to a modifying agent such as PEG, for example, through an amino group, a sulfhydryl group, a hydroxyl group, a carboxyl group, or other group.

The linker used to covalently attach ADI to a modifying agent (e.g. PEG) can be any biocompatible linker. As discussed above, "biocompatible" indicates that the compound or group is non-toxic and may be utilized in vitro or in vivo without causing injury, sickness, disease, or death. A modifying agent such as PEG can be bonded to the linker, for example, via an ether bond, a thiol bond, an amide bond, or other bond.

In some embodiments, suitable linkers can have an overall chain length of about 1-100 atoms, 1-80 atoms, 1-60 atoms, 1-40 atoms, 1-30 atoms, 1-20 atoms, or 1, 2, 3, 4, 5, 6, 7, 8, 9, 10, 11, 12, 13, 14, 15, 16, 17, 18, 19, or 20 atoms, for example, wherein the atoms in the chain comprise C, S, N, P, and/or O. In certain embodiments, a linker is optional, e.g., a PEG conjugated ADI enzyme does not comprise a linker. In some instances, a linker group includes, for example, a succinyl group, an amide group, an imide group, a carbamate group, an ester group, an epoxy group, a carboxyl group, a hydroxyl group, a carbohydrate, a tyrosine group, a cysteine group, a histidine group, a methylene group, and combinations thereof. Particular examples of stable linkers includesuccinimide, propionic acid, carboxymethylate linkages, ethers, carbamates, amides, amines, carbamides, imides, aliphatic C—C bonds, and thio ethers. In certain embodiments, the biocompatible linker is a succinimidyl succinate (SS) group.

Other suitable linkers include an oxycarbonylimidazole group (including, for example, carbonylimidazole (CDI)), a nitro phenyl group (including, for example, nitrophenyl carbonate (NCP) or trichlorophenyl carbonate (TCP)), a trysylate group, an aldehyde group, an isocyanate group, a vinylsulfone group, or a primary amine. In certain embodiments, the linker is derived from SS, SPA, SCM, or NHS; in certain embodiments, SS, SPA, or NHS are used, and in some embodiments, SS or SPA are used. Thus, in certain embodiments, potential linkers can be formed from methoxy-PEG succinimidyl succinate (SS), methoxy-PEG succinimidyl glutarate (SG), methoxy-PEG succinimidyl carbonate (SC), methoxy-PEG succinimidyl carboxymethyl ester (SCM), methoxy-PEG2 N-hydroxy succinimide (NHS), methoxy-PEG succinimidyl butanoate (SBA), methoxy-PEG succinimidyl propionate (SPA), methoxy-PEG succinimidyl glutaramide, and/or methoxy-PEG succinimidyl succinimide.

Additional examples of linkers include, but are not limited to, one or more of the following: —O—, —NH—, —S—, —C(O)—, C(O)—NH, NH—C(O)—NH, O—C(O)—NH, —C(S)—, —CH2—, —CH2—CH2—, —CH2—CH2—CH2—, —CH2—CH2—CH2—CH2—, —O—CH2—, —CH2—O—, —O—CH2—CH2—, —CH2—O—CH2—, —CH2—CH2—O—, —O—CH2—CH2—CH2—, —CH2—O—CH2—CH2—, —CH2—CH2—O—CH2—, —CH2—CH2—CH2—O—, —O—CH2—CH2—CH2—CH2—, —CH2—O—CH2—CH2—CH2—, —CH2—CH2—O—CH2—CH2—, —CH2—CH2—CH2—O—CH2—, —CH2—CH2—CH2—CH2—O—, —C(O)—NH—CH2—, —C(O)—NH—CH2—CH2—, —CH2—C(O)—NH—CH2—, —CH2—CH2—C(O)—NH—, —C(O)—NH—CH2—CH2—, —CH2—C(O)—NH—CH2—CH2—, —CH2—CH2—C(O)—NH—CH2—, —CH2—CH2—C(O)—NH—CH2—CH2—CH2—C(O)—NH—, —C(O)—NH—CH2—CH2—CH2—, —CH2—CH2—C(O)—NH—CH2—CH2—, —CH2—, —CH2—CH2—CH2—C(O)—NH—CH2—CH2—, —CH2—CH2—CH2—C(O)—NH—, —CH2—, —CH2—CH2—CH2—C(O)—NH—, —NH—C(O)—CH2—, —CH2—NH—C(O)—CH2—, —CH2—CH2—NH—C(O)—CH2—, —NH—C(O)—CH2—CH2—, —CH2—NH—C(O)—CH2—CH2, —CH2—CH2—NH—C(O)—CH2—CH2, —C(O)—NH—CH2—, —C(O)—NH—CH2—CH2—, —O—C(O)—NH—CH2—, —O—C(O)—NH—CH2—CH2—, —NH—CH2—, —NH—CH2—CH2—, —CH2—NH—CH2—, —CH2—CH2—NH—CH2—, —C(O)—CH2—, —C(O)—CH2—CH2—, —CH2—C(O)—CH2—, —CH2—CH2—C(O)—CH2—, —CH2—CH2—C(O)—CH2—CH2—, —CH2—CH2—C(O)—, —CH2—CH2—CH2—C(O)—NH—CH2—CH2—NH—, —CH2—CH2—CH2—C(O)—NH—CH2—CH2—NH—C(O)—, —CH2—CH2—CH2—C(O)—NH—CH2—CH2—NH—C(O)—CH2—, bivalent cycloalkyl group, —N(R6)—, R6 is H or an organic radical selected from the group consisting of alkyl, substituted alkyl, alkenyl, substituted alkenyl, alkynyl, substituted alkynyl, aryl and substituted aryl. Additionally, any of the linker moieties described herein may further include an ethylene oxide oligomer chain comprising 1 to 20 ethylene oxide monomer units [i.e., —(CH$_2$CH$_2$O)$_{1-20}$-].That is, the ethylene oxide oligomer chain can occur before or after the linker, and optionally in between any two atoms of a linker moiety comprised of two or more atoms. Also, the oligomer chain would not be considered part of the linker moiety if the oligomer is adjacent to a polymer segment and merely represent an extension of the polymer segment.

Specific exemplary PEG molecules and linkers are described in Table A2 below.

TABLE A2

PEG and Linkers

| PEG | Linker | Comments |
|---|---|---|
| Methoxy-PEG succinimidyl hexanoate | amide | pH 7-8, lower reactivity |
| Methoxy-PEG succinimidyl butanoate (SBA) | amide | pH 7-8, longer hydrolysis time than SPA (~23 min) |
| Methoxy-PEG succinimidyl propionate (SPA) | amide | Tan, 1998, Metase; Basu, IFN; Games, Phe Am. Lyase; better than SCM (~16 min) |
| Methoxy-PEG succinimidyl carboxymethyl ester (SCM) | amide | pH 7-8, RT, 1 hr rxn time, extremely reactive, 0.75 min at pH 8, 25° C., arginase |
| Methoxy-PEG succinimidyl glutaramide | amide | pH 7-8, RT, 90% complete |
| Methoxy-PEG succinimidyl succinamide | amide | pH 7-8, RT, 95% complete |
| MethoxyPEG2 NHS | | Gamez, Phe Am. Lyase; Basu, IFNa2a40K, Nulasta (G-CSF), pegfilgrastim (G-CSF) |
| Methoxy-PEG succinimidyl carbonate (SC) | urethane | Hydrolysis ½ longer than SCM, Wang, 2006, M. art. ADI, Basu, |
| Methoxy-PEG succinimidyl glutarate (SG) | ester | Yang, 2004, Metase |
| Methoxy-PEG succinimidyl succinate (SS) | ester | Adenosine deaminase, asparginase, ADI-PEG 20 |
| PEG-maleimide | | |
| PEG-vinylsulfone | | |
| PEG-iodoacetamide | | |
| orthopyridyl disulfide-PEG | | |

In certain embodiments, the ADI enzyme comprises one or more PEG molecules and/or linkers as described herein (e.g., in Table A2).

The attachment of PEG to ADI increases the circulating half-life of ADI. Generally, PEG is attached to a primary amine of ADI. Selection of the attachment site of PEG, or other modifying agent, on the ADI is determined by the role of each of the sites within the active domain of the protein, as would be known to the skilled artisan. PEG may be attached to the primary amines of ADI without substantial loss of enzymatic activity. For example, the lysine residues present in ADI are all possible points at which ADI as described herein can be attached to PEG via a biocompatible linker, such as SS, SPA, SCM, SSA and/or NHS. PEG may also be attached to other sites on ADI, as would be apparent to one skilled in the art in view of the present disclosure.

From 1 to about 30 PEG molecules may be covalently bonded to ADI. In certain embodiments, ADI is modified with (i.e., comprises) one PEG molecule. In some embodiments, the ADI is modified with more than one PEG molecule. In particular embodiments, the ADI is modified with about 1 to about 10, or from about 7 to about 15 PEG molecules, or from about 2 to about 8 or about 9 to about 12 PEG molecules. In some embodiments, the ADI is modified with about 2, 3, 4, 5, 6, 7, 8, 9, 10, 11, 12, 13, 14, or 15 PEG molecules. In specific embodiments, ADI is modified with 4.5-5.5 PEG molecules per ADI. In some embodiment, ADI is modified with 5±1.5 PEG molecules.

In certain embodiments, about 15% to about 70% of the primary amino groups in ADI are modified with PEG, in some embodiments about 20% to about 65%, about 25% to about 60%, or in certain embodiments about 30% to about 55%, or 45% to about 50%, or in some embodiments about 50% of the primary amino groups in arginine deiminase are modified with PEG. When PEG is covalently bonded to the end terminus of ADI, it may be desirable to have only 1 PEG molecule utilized. Increasing the number of PEG units on ADI increases the circulating half-life of the enzyme. However, increasing the number of PEG units on ADI decreases the specific activity of the enzyme. Thus, a balance needs to be achieved between the two, as would be apparent to one skilled in the art in view of the present disclosure.

In some embodiments, a common feature of biocompatible linkers is that they attach to a primary amine of arginine deiminase via a succinimide group. Once coupled with ADI, SS-PEG has an ester linkage next to the PEG, which may render this site sensitive to serum esterase, which may release PEG from ADI in the body. SPA-PEG and PEG2-NHS do not have an ester linkage, so they are not sensitive to serum esterase.

PEG which is attached to the protein may be either a straight chain, as with SS-PEG, SPA-PEG and SC-PEG, or a branched chain of PEG may be used, as with PEG2-NHS.

In certain embodiments, pegylation sites associated with ADI located at or adjacent to the catalytic region of the enzyme are modified. In certain embodiments, the phrase "pegylation site" is defined as any site or position of ADI that may be covalently modified with polyethylene glycol. A "pegylation site" can be considered located at or adjacent the catalytic region of the enzyme where pegylation of the site results in a significant reduction in catalytic activity of the enzyme. The pegylation of such sites has traditionally resulted in the inactivation of the enzyme. For example, ADI from *Mycoplasma hominis* has a lysine at the 112 position which can be considered to be at or adjacent the catalytic region of the enzyme. The attachment of PEG to this lysine at the 112 position can inactivate the enzyme. In addition, ADI from *Mycoplasma hominis* has a cysteine at the 397 position which can be considered to be at or adjacent the catalytic region of the enzyme. The amino acid substitutions for cysteine at the 397 position can inactivate the enzyme. In particular, substituting alanine, histidine, arginine, serine, lysine or tyrosine for cysteine at the 397 position can result in a loss of all detectable enzyme activity. ADI from *Mycoplasma hominis* also has three lysine residues located near this conserved cysteine, in particular Lys374, Lys405 and Lys408. The attachment of PEG to Lys374, Lys405, Lys408 or combinations thereof can inactivate the enzyme.

It is to be understood that ADI derived from other organisms may also have pegylation sites corresponding to 112 position of ADI from *Mycoplasma hominis*. In addition, ADI from some organisms may have lysine residues corresponding to the same general location as the 112 position of ADI from *Mycoplasma hominis*. The location of lysine in ADI from such organisms are known to the skilled person and are described in U.S. Pat. No. 6,635,462.

Thus, some embodiments provide for certain amino acid substitutions in the polypeptide chain of ADI. These amino acid substitutions provide for modified ADI that loses less activity when modified by a modifying agent, e.g., upon pegylation. By eliminating pegylation sites, or other known modification sites, at or adjacent to the catalytic region of enzyme, optimal modification, e.g., pegylation, can be achieved without the loss of activity.

In some embodiments, for example, as noted above, the amino acid substitutions employ non-natural amino acids for conjugation to PEG or other modifying agent (see, e.g., de Graaf et al., Bioconjug Chem. 20:1281-95, 2009). Certain embodiments thus include an ADI enzyme that is conjugated to one or more PEGs via one or more non-natural amino acids. In some embodiments the non-natural amino acid comprises a side chain having a functional group selected from the group consisting of: an alkyl, aryl, aryl halide, vinyl halide, alkyl halide, acetyl, ketone, aziridine, nitrile, nitro, halide, acyl, keto, azido, hydroxyl, hydrazine, cyano, halo, hydrazide, alkenyl, alkynyl, ether, thio ether, epoxide, sulfone, boronic acid, boronate ester, borane, phenylboronic acid, thiol, seleno, sulfonyl, borate, boronate, phospho, phosphono, phosphine, heterocyclic-, pyridyl, naphthyl, benzophenone, a constrained ring such as a cyclooctyne, thioester, enone, imine, aldehyde, ester, thioacid, hydroxylamine, amino, carboxylic acid, alpha-keto carboxylic acid, alpha or beta unsaturated acids and amides, glyoxyl amide, and an organosilane group. In some embodiments, the non-natural amino acid is selected from the group consisting of: p-acetyl-L-phenylalanine, O-methyl-L-tyrosine, L-3-(2-naphthyl)alanine, 3-methyl-phenylalanine, O-4-allyl-L-tyrosine, homocysteine, 4-propyl-L-tyrosine, tri-O-acetyl-GlcNAcβ-serine, β-O-GlcNAc-L-serine, tri-O-acetyl-GalNAc-α-threonine, α-GalNAc-L-threonine, L-Dopa, a fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, and isopropyl-L-phenylalanine.

While ADI-PEG is the illustrative modified ADI described herein, as would be recognized by the skilled person ADI may be modified with other polymers or appropriate molecules for the desired effect, in particular reducing antigenicity and increasing serum half-life.

It is to be understood that some embodiments are based on the understanding that certain structural characteristics of arginine deiminase may prevent or interfere with the proper and rapid renaturation when produced via recombinant technology. In particular, these structural characteristics hinder or prevent the enzyme from assuming an active conformation during recombinant production. In some embodiments, the term "active conformation" is defined as a three-dimensional structure that allows for enzymatic activity by unmodified or modified arginine deiminase. The active conformation may, in particular, be necessary for catalyzing the conversion of arginine into citrulline. The term "structural characteristic" may be defined as any trait, quality or property of the polypeptide chain resulting from a particular amino acid or combination of amino acids. For instance, arginine deiminase may contain an amino acid that results in a bend or kink in the normal peptide chain and thus hinders the enzyme from assuming an active conformation during renaturation of the enzyme. In particular, arginine deiminase from *Mycoplasma hominis* has a proline at the 210 position that may result in a bend or kink in the peptide chain, making it more difficult to renature the enzyme during recombinant production. It is to be understood that arginine deiminase derived from other organisms may also have sites corresponding to the 210 position of arginine deiminase from *Mycoplasma hominis*.

Some embodiments thus provide for certain amino acid substitutions in the polypeptide chain of wild type arginine deiminases. Examples include substitutions that eliminate the problematic structural characteristics in the peptide chain of arginine deiminase. Also included are substitutions that provide for improved renaturation of the modified arginine deiminase. These amino acid substitutions make possible rapid renaturation of modified arginine deiminases using reduced amounts of buffer. These amino acid substitutions may also provide for increased yields of renatured modified arginine deiminase. In some embodiments, the modified arginine deiminase has an amino acid substitution at P210 or the equivalent residue. As mentioned above, arginine deiminase derived from *Mycoplasma hominis* has the amino acid proline located at the 210 position. While not limiting, it is believed that the presence of the amino acid proline at position 210 results in a bend or kink in the normal polypeptide chain that increases the difficulty of renaturing (i.e., refolding) certain arginine deiminase enzymes. Substitutions for proline at position 210 make possible the rapid renaturation of modified arginine deiminase using reduced amounts of buffer. Substitutions for proline at position 210 (or the equivalent residue) may also provide for increased yields of renatured modified arginine deiminase. In some embodiments, the proline at position 210 (or the equivalent residue) is substituted with serine. Non-limiting examples of other substitutions include Pro210 to Thr210, Pro210 to Arg210, Pro210 to Asn210, Pro210 to Gln210 or Pro210 to Met210. By eliminating those structural characteristics associated with the amino acid of position 210 of the wild-type arginine deiminase, optimal refolding of the enzyme can be achieved.

In specific embodiments, the modified ADI is ADI-PEG 20. ADI-PEG 20 refers to the ADI molecule described. for example. in U.S. Pat. Nos. 6,183,738; 6,635,462; Ascierto P A, et al. (2005) Pegylated arginine deiminase treatment of patients with metastatic melanoma: results from phase I and II studies. J Clin Oncol 23(30): 7660-7668; Izzo F, et al. (2004) Pegylated arginine deiminase treatment of patients with unresectable hepatocellular carcinoma: results from phase I/II studies. J Clin Oncol 22(10): 1815-1822; Holtsberg F W, et al. (2002), Poly(ethylene glycol) (PEG) conjugated arginine deiminase: effects of PEG formulations on its pharmacological properties. J Control Release 80(1-3): 259-271; and Kelly et al., (2012) British Journal of Cancer 106, 324-332. As would be recognized by the skilled artisan, ADI-PEG 20 is a pegylated ADI enzyme derived from *M hominis* (5.5±1.0 bonded PEG 20,000), which has two substitutions (K112E; P210S) relative to the wild type *M hominis* ADI sequence.

The skilled artisan will appreciate that the various arginine depletion agents described herein can be combined with any one or more of the various cancer immunotherapy agents described herein, and used according to any one or more of the methods or compositions described herein.
Immunotherapy Agents Certain embodiments employ one or more cancer immunotherapy agents. In certain instances, an immunotherapy agent modulates the immune response of a subject, for example, to increase or maintain a cancer-related or cancer-specific immune response, and thereby results in increased immune cell inhibition or reduction of cancer cells. Exemplary immunotherapy agents include polypeptides, for example, antibodies and antigen-binding fragments thereof, ligands, and small peptides, and mixtures thereof. Also include as immunotherapy agents are small molecules, cells (e.g., immune cells such as T-cells), various cancer vaccines, gene therapy or other polynucleotide-based agents, including viral agents such as oncolytic viruses, and others known in the art. Thus, in certain embodiments, the cancer immunotherapy agent is selected from one or more of immune checkpoint modulatory agents, cancer vaccines, oncolytic viruses, cytokines, and a cell-based immunotherapies.

In certain embodiments, the cancer immunotherapy agent is an immune checkpoint modulatory agent. Particular examples include "antagonists" of one or more inhibitory immune checkpoint molecules, and "agonists" of one or more stimulatory immune checkpoint molecules. Generally, immune checkpoint molecules are components of the immune system that either turn up a signal (co-stimulatory molecules) or turn down a signal, the targeting of which has therapeutic potential in cancer because cancer cells can perturb the natural function of immune checkpoint molecules (see, e.g., Sharma and Allison, Science. 348:56-61, 2015; Topalian et al., Cancer Cell. 27:450-461, 2015; Pardoll, Nature Reviews Cancer. 12:252-264, 2012). In some embodiments, the immune checkpoint modulatory agent (e.g., antagonist, agonist) "binds" or "specifically binds" to the one or more immune checkpoint molecules, as described herein.

In particular embodiments, the immune checkpoint modulatory agent is a polypeptide or peptide. The terms "peptide" and "polypeptide" are used interchangeably herein, however, in certain instances, the term "peptide" can refer to shorter polypeptides, for example, polypeptides that consist of about 2, 3, 4, 5, 6, 7, 8, 9, 10, 11, 12, 13, 14, 15, 16, 17, 18, 19, 20, 25, 30, 35, 40, 45, or 50 amino acids, including all integers and ranges (e.g., 5-10, 8-12, 10-15) in between. Polypeptides and peptides can be composed of naturally-occurring amino acids and/or non-naturally occurring amino acids, as described herein. Antibodies are also included as polypeptides.

The binding properties of polypeptides can be quantified using methods well known in the art (see Davies et al., Annual Rev. Biochem. 59:439-473, 1990). In some embodiments, a polypeptide specifically binds to a target molecule, for example, an immune checkpoint molecule or an epitope thereof, with an equilibrium dissociation constant that is about or ranges from about ≤10-7 to about 10-8 M. In some embodiments, the equilibrium dissociation constant is about or ranges from about ≤10-9 M to about ≤10-10 M. In certain illustrative embodiments, the polypeptide has an affinity (Kd) for target described herein (to which it specifically binds) of about, at least about, or less than about, 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM.

In some embodiments, the immune checkpoint modulatory polypeptide agent is an antibody or "antigen-binding fragment thereof." The antibody or antigen-binding fragment can be of essentially any type. As is well known in the art, an antibody is an immunoglobulin molecule capable of specific binding to a target, such as an immune checkpoint molecule, through at least one epitope recognition site, located in the variable region of the immunoglobulin molecule.

As used herein, the term "antibody" encompasses not only intact polyclonal or monoclonal antibodies, but also fragments thereof (such as dAb, Fab, Fab', F(ab')2, Fv), single chain (ScFv), synthetic variants thereof, naturally occurring variants, fusion proteins comprising an antibody portion with an antigen-binding fragment of the required specificity, humanized antibodies, chimeric antibodies, and any other modified configuration of the immunoglobulin molecule that comprises an antigen-binding site or fragment (epitope recognition site) of the required specificity. Certain features and characteristics of antibodies (and antigen-binding fragments thereof) are described in greater detail herein.

The term "antigen-binding fragment" as used herein refers to a polypeptide fragment that contains at least one CDR of an immunoglobulin heavy and/or light chain that binds to the antigen of interest. In this regard, an antigen-binding fragment of the herein described antibodies may comprise 1, 2, 3, 4, 5, or all 6 CDRs of a VH and VL sequence from antibodies that bind to a target molecule.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "epitope" includes any determinant, preferably a polypeptide determinant, capable of specific binding to an immunoglobulin or T-cell receptor. An epitope is a region of an antigen that is bound by an antibody. In certain embodiments, epitope determinants include chemically active surface groupings of molecules such as amino acids, sugar side chains, phosphoryl or sulfonyl, and may in certain embodiments have specific three-dimensional structural characteristics, and/or specific charge characteristics. Epitopes can be contiguous or non-contiguous in relation to the primary structure of the antigen.

A molecule such as a polypeptide or antibody is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances, for example, by a statistically significant amount. For instance, an antibody that specifically or preferentially binds to a specific epitope is an antibody that binds that specific epitope with greater affinity, avidity, more readily, and/or with greater duration than it binds to other epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

Immunological binding generally refers to the non-covalent interactions of the type which occur between an immunoglobulin molecule and an antigen for which the immunoglobulin is specific, for example by way of illustration and not limitation, as a result of electrostatic, ionic, hydrophilic and/or hydrophobic attractions or repulsion, steric forces, hydrogen bonding, van der Waals forces, and other interactions. The strength, or affinity of immunological binding interactions can be expressed in terms of the dissociation constant (Kd) of the interaction, wherein a smaller Kd represents a greater affinity Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" (Kon) and the "off rate constant" (Koff) can be determined by calculation of the concentrations and the actual rates of association and dissociation. The ratio of Koff/Kon enables cancellation of all parameters not related to affinity, and is thus equal to the dissociation constant Kd.

Antibodies may be prepared by any of a variety of techniques known to those of ordinary skill in the art. See, e.g., Harlow and Lane, Antibodies: A Laboratory Manual, Cold Spring Harbor Laboratory, 1988. Monoclonal antibodies specific for a polypeptide of interest may be prepared, for example, using the technique of Kohler and Milstein, Eur. J. Immunol. 6:511-519, 1976, and improvements thereto. Also included are methods that utilize transgenic animals such as mice to express human antibodies. See, e.g., Neuberger et al., Nature Biotechnology 14:826, 1996; Lonberg et al., Handbook of Experimental Pharmacology 113:49-101, 1994; and Lonberg et al., Internal Review of Immunology 13:65-93, 1995. Particular examples include the VELOCIMMUNE® platform by REGENEREX® (see, e.g., U.S. Pat. No. 6,596,541).

Antibodies can also be generated or identified by the use of phage display or yeast display libraries (see, e.g., U.S. Pat. No. 7,244,592; Chao et al., Nature Protocols. 1:755-768, 2006). Non-limiting examples of available libraries include cloned or synthetic libraries, such as the Human Combinatorial Antibody Library (HuCAL), in which the structural diversity of the human antibody repertoire is represented by seven heavy chain and seven light chain variable region genes. The combination of these genes gives rise to 49 frameworks in the master library. By superimposing highly variable genetic cassettes (CDRs=complementarity determining regions) on these frameworks, the vast human antibody repertoire can be reproduced. Also included are human libraries designed with human-donor-sourced fragments encoding a light-chain variable region, a heavy-chain CDR-3, synthetic DNA encoding diversity in heavy-chain CDR-1, and synthetic DNA encoding diversity in heavy-chain CDR-2. Other libraries suitable for use will be apparent to persons skilled in the art.

In certain embodiments, antibodies and antigen-binding fragments thereof as described herein include a heavy chain and a light chain CDR set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

The structures and locations of immunoglobulin variable domains may be determined by reference to Kabat, E. A. et al., Sequences of Proteins of Immunological Interest. 4th Edition. US Department of Health and Human Services. 1987, and updates thereof.

Also include are "monoclonal" antibodies, which refer to a homogeneous antibody population wherein the monoclonal antibody is comprised of amino acids (naturally occurring and non-naturally occurring) that are involved in the selective binding of an epitope. Monoclonal antibodies are highly specific, being directed against a single epitope. The term "monoclonal antibody" encompasses not only intact monoclonal antibodies and full-length monoclonal antibodies, but also fragments thereof (such as Fab, Fab', F(ab')2, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals). The term includes whole immunoglobulins as well as the fragments etc. described above under the definition of "antibody."

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')2 fragment which comprises both antigen-binding sites. An Fv fragment for use according to certain embodiments of the present invention can be produced by preferential proteolytic cleavage of an IgM, and on rare occasions of an IgG or IgA immunoglobulin molecule. Fv fragments are, however, more commonly derived using recombinant techniques known in the art. The Fv fragment includes a non-covalent VH::VL heterodimer including an antigen-binding site which retains much of the antigen recognition and binding capabilities of the native antibody molecule. See Inbar et al., PNAS USA. 69:2659-2662, 1972; Hochman et al., Biochem. 15:2706-2710, 1976; and Ehrlich et al., Biochem. 19:4091-4096, 1980.

In certain embodiments, single chain Fv or scFV antibodies are contemplated. For example, Kappa bodies (Ill et al., Prot. Eng. 10:949-57, 1997); minibodies (Martin et al., EMBO J 13:5305-9, 1994); diabodies (Holliger et al., PNAS 90: 6444-8, 1993); or Janusins (Traunecker et al., EMBO J 10: 3655-59, 1991; and Traunecker et al., Int. J. Cancer Suppl. 7:51-52, 1992), may be prepared using standard molecular biology techniques following the teachings of the present application with regard to selecting antibodies having the desired specificity.

A single chain Fv (sFv) polypeptide is a covalently linked VH::VL heterodimer which is expressed from a gene fusion including VH- and VL-encoding genes linked by a peptide-encoding linker. Huston et al. (PNAS USA. 85(16):5879-5883, 1988). A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

In certain embodiments, an antibody as described herein is in the form of a "diabody." Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804). A dAb fragment of an antibody consists of a VH domain (Ward et al., Nature 341:544-546, 1989). Diabodies and other multivalent or multispecific fragments can be constructed, for example, by gene fusion (see WO94/13804; and Holliger et al., PNAS USA. 90:6444-6448, 1993)).

Minibodies comprising a scFv joined to a CH3 domain are also included (see Hu et al., Cancer Res. 56:3055-3061, 1996). See also Ward et al., Nature. 341:544-546, 1989; Bird et al., Science. 242:423-426, 1988; Huston et al., PNAS USA. 85:5879-5883, 1988); PCT/US92/09965; WO94/13804; and Reiter et al., Nature Biotech. 14:1239-1245, 1996.

Where bispecific antibodies are to be used, these may be conventional bispecific antibodies, which can be manufactured in a variety of ways (Holliger and Winter, Current Opinion Biotechnol. 4:446-449, 1993), e.g. prepared chemically or from hybrid hybridomas, or may be any of the bispecific antibody fragments mentioned above. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in E. coli. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected. Bispecific whole antibodies may be made by knobs-into-holes engineering (Ridgeway et al., Protein Eng., 9:616-621, 1996).

In certain embodiments, the antibodies described herein may be provided in the form of a UniBody®. A UniBody® is an IgG4 antibody with the hinge region removed (see GenMab Utrecht, The Netherlands; see also, e.g., US20090226421). This antibody technology creates a stable, smaller antibody format with an anticipated longer therapeutic window than current small antibody formats. IgG4 antibodies are considered inert and thus do not interact with the immune system. Fully human IgG4 antibodies may be modified by eliminating the hinge region of the antibody to obtain half-molecule fragments having distinct stability properties relative to the corresponding intact IgG4 (GenMab, Utrecht). Halving the IgG4 molecule leaves only one area on the UniBody® that can bind to cognate antigens (e.g., disease targets) and the UniBody® therefore binds univalently to only one site on target cells. For certain cancer cell surface antigens, this univalent binding may not stimulate the cancer cells to grow as may be seen using bivalent antibodies having the same antigen specificity, and hence UniBody® technology may afford treatment options for some types of cancer that may be refractory to treatment with conventional antibodies. The small size of the UniBody® can be a great benefit when treating some forms of cancer, allowing for better distribution of the molecule over larger solid tumors and potentially increasing efficacy.

In certain embodiments, the antibodies provided herein may take the form of a nanobody. Minibodies are encoded by single genes and are efficiently produced in almost all prokaryotic and eukaryotic hosts, for example, *E. coli* (see U.S. Pat. No. 6,765,087), molds (for example *Aspergillus* or *Trichoderma*) and yeast (for example *Saccharomyces, Kluyvermyces, Hansenula* or *Pichia* (see U.S. Pat. No. 6,838,254). The production process is scalable and multi-kilogram quantities of nanobodies have been produced. Nanobodies may be formulated as a ready-to-use solution having a long shelf life. The Nanoclone method (see WO 06/079372) is a proprietary method for generating Nano-bodies against a desired target, based on automated high-throughput selection of B-cells.

In certain embodiments, the antibodies or antigen-binding fragments thereof are humanized. These embodiments refer to a chimeric molecule, generally prepared using recombi-nant techniques, having an antigen-binding site derived from an immunoglobulin from a non-human species and the remaining immunoglobulin structure of the molecule based upon the structure and/or sequence of a human immuno-globulin. The antigen-binding site may comprise either complete variable domains fused onto constant domains or only the CDRs grafted onto appropriate framework regions in the variable domains Epitope binding sites may be wild type or modified by one or more amino acid substitutions. This eliminates the constant region as an immunogen in human individuals, but the possibility of an immune response to the foreign variable region remains (LoBuglio et al., PNAS USA 86:4220-4224, 1989; Queen et al., PNAS USA. 86:10029-10033, 1988; Riechmann et al., Nature. 332:323-327, 1988). Illustrative methods for humanization of antibodies include the methods described in U.S. Pat. No. 7,462,697.

Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When nonhuman antibodies are prepared with respect to a particular epitope, the variable regions can be "reshaped" or "humanized" by grafting CDRs derived from nonhuman antibody on the FRs present in the human anti-body to be modified. Application of this approach to various antibodies has been reported by Sato et al., Cancer Res. 53:851-856, 1993; Riechmann et al., Nature 332:323-327, 1988; Verhoeyen et al., Science 239:1534-1536, 1988; Kettleborough et al., Protein Engineering. 4:773-3783, 1991; Maeda et al., Human Antibodies Hybridoma 2:124-134, 1991; Gorman et al., PNAS USA. 88:4181-4185, 1991; Tempest et al., Bio/Technology 9:266-271, 1991; Co et al., PNAS USA. 88:2869-2873, 1991; Carter et al., PNAS USA. 89:4285-4289, 1992; and Co et al., J Immunol. 148:1149-1154, 1992. In some embodiments, humanized antibodies preserve all CDR sequences (for example, a humanized mouse antibody which contains all six CDRs from the mouse antibodies). In other embodiments, humanized anti-bodies have one or more CDRs (one, two, three, four, five, six) which are altered with respect to the original antibody, which are also termed one or more CDRs "derived from" one or more CDRs from the original antibody.

In certain embodiments, the antibodies may be chimeric antibodies. In this regard, a chimeric antibody is comprised of an antigen-binding fragment of an antibody operably linked or otherwise fused to a heterologous Fc portion of a different antibody. In certain embodiments, the heterologous Fc domain is of human origin. In other embodiments, the heterologous Fc domain may be from a different Ig class from the parent antibody, including IgA (including sub-classes IgA1 and IgA2), IgD, IgE, IgG (including subclasses IgG1, IgG2, IgG3, and IgG4), and IgM. In further embodi-ments, the heterologous Fc domain may be comprised of CH2 and CH3 domains from one or more of the different Ig classes. As noted above with regard to humanized antibod-ies, the antigen-binding fragment of a chimeric antibody may comprise only one or more of the CDRs of the antibodies described herein (e.g., 1, 2, 3, 4, 5, or 6 CDRs of the antibodies described herein), or may comprise an entire variable domain (VL, VH or both).

In some embodiments, the agent is or comprises a "ligand," for example, a natural ligand, of the immune checkpoint molecule. A "ligand" refers generally to a sub-stance or molecule that forms a complex with a target molecule (e.g., biomolecule) to serve a biological purpose, and includes a "protein ligand," which generally produces a signal by binding to a site on a target molecule or target protein. Thus, certain agents are protein ligands that, in nature, bind to an immune checkpoint molecule and produce a signal. Also included are "modified ligands," for example, protein ligands that are fused to a pharmacokinetic modifier, for example, an Fc region derived from an immunoglobulin.

In some embodiments, the agent is a "small molecule," which refers to an organic compound that is of synthetic or biological origin (biomolecule), but is typically not a poly-mer. Organic compounds refer to a large class of chemical compounds whose molecules contain carbon, typically excluding those that contain only carbonates, simple oxides of carbon, or cyanides. A "biomolecule" refers generally to an organic molecule that is produced by a living organism, including large polymeric molecules (biopolymers) such as peptides, polysaccharides, and nucleic acids as well, and small molecules such as primary secondary metabolites, lipids, phospholipids, glycolipids, sterols, glycerolipids, vitamins, and hormones. A "polymer" refers generally to a large molecule or macromolecule composed of repeating structural units, which are typically connected by covalent chemical bond.

In certain embodiments, a small molecule has a molecular weight of about or less than about 1000-2000 Daltons, typically between about 300 and 700 Daltons, and including about or less than about 50, 100, 150, 200, 250, 300, 350, 400, 450, 500, 550, 500, 650, 600, 750, 700, 850, 800, 950, 1000 or 2000 Daltons.

Certain small molecules can have the "specific binding" characteristics described for herein polypeptides such as antibodies. For instance, in some embodiments a small molecule specifically binds to a target, for example, an immune checkpoint molecule, with a binding affinity (Kd) of about, at least about, or less than about, 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM.

In some embodiments, the immune checkpoint modulatory agent is an antagonist or inhibitor of one or more inhibitory immune checkpoint molecules. Exemplary inhibitory immune checkpoint molecules include Programmed Death-Ligand 1 (PD-L1), Programmed Death-Ligand 2 (PD-L2), Programmed Death 1 (PD-1), Cytotoxic T-Lymphocyte-Associated protein 4 (CTLA-4), Indoleamine 2,3-dioxygenase (IDO), tryptophan 2,3-dioxygenase (TDO), T-cell Immunoglobulin domain and Mucin domain 3 (TIM-3), Lymphocyte Activation Gene-3 (LAG-3), V-domain Ig suppressor of T cell activation (VISTA), B and T Lymphocyte Attenuator (BTLA), CD160, and T-cell immunoreceptor with Ig and ITIM domains (TIGIT).

In certain embodiments, the agent is a PD-1 (receptor) antagonist or inhibitor, the targeting of which has been shown to restore immune function in the tumor environment (see, e.g., Phillips et al., Int Immunol. 27:39-46, 2015). PD-1 is a cell surface receptor that belongs to the immunoglobulin superfamily and is expressed on T cells and pro-B cells. PD-1 interacts with two ligands, PD-L1 and PD-L2. PD-1 functions as an inhibitory immune checkpoint molecule, for example, by reducing or preventing the activation of T-cells, which in turn reduces autoimmunity and promotes self-tolerance. The inhibitory effect of PD-1 is accomplished at least in part through a dual mechanism of promoting apoptosis in antigen specific T-cells in lymph nodes while also reducing apoptosis in regulatory T cells (suppressor T cells). Some examples of PD-1 antagonists or inhibitors include an antibody or antigen-binding fragment or small molecule that specifically binds to PD-1 and reduces one or more of its immune-suppressive activities, for example, its downstream signaling or its interaction with PD-L1. Specific examples of PD-1 antagonists or inhibitors include the antibodies nivolumab, pembrolizumab, PDR001, and pidilizumab, and antigen-binding fragments thereof.

In some embodiments, the agent is a PD-L1 antagonist or inhibitor. As noted above, PD-L1 is one of the natural ligands for the PD-1 receptor. General examples of PD-L1 antagonists or inhibitors include an antibody or antigen-binding fragment or small molecule that specifically binds to PD-L1 and reduces one or more of its immune-suppressive activities, for example, its binding to the PD-1 receptor. Specific examples of PD-L1 antagonists include the antibodies atezolizumab (MPDL3280A), avelumab (MSB0010718C), and durvalumab (MEDI4736), and antigen-binding fragments thereof.

In some embodiments, the agent is a PD-L2 antagonist or inhibitor. As noted above, PD-L2 is one of the natural ligands for the PD-1 receptor. General examples of PD-L2 antagonists or inhibitors include an antibody or antigen-binding fragment or small molecule that specifically binds to PD-L2 and reduces one or more of its immune-suppressive activities, for example, its binding to the PD-1 receptor.

In some embodiments, the agent is a CTLA-4 antagonist or inhibitor. CTLA4 or CTLA-4 (cytotoxic T-lymphocyte-associated protein 4), also known as CD152 (cluster of differentiation 152), is a protein receptor that functions as an inhibitory immune checkpoint molecule, for example, by transmitting inhibitory signals to T-cells when it is bound to CD80 or CD86 on the surface of antigen-presenting cells. General examples CTLA-4 antagonists or inhibitors include an antibody or antigen-binding fragment or small molecule that specifically binds to CTLA-4. Particular examples include the antibodies ipilimumab and tremelimumab, and antigen-binding fragments thereof. At least some of the activity of ipilimumab is believed to be mediated by antibody-dependent cell-mediated cytotoxicity (ADCC) killing of suppressor Tregs that express CTLA-4. Thus, the ability of ADI to down-regulate suppressor Tregs parallels that of certain CTLA-4 antagonists or inhibitors, suggesting that ADI can be useful not only in the same clinical situations as the CTLA-4 inhibitors (e.g., ipilimumab), but also in combination with the same.

In some embodiments, the agent is an IDO antagonist or inhibitor, or a TDO antagonist or inhibitor. IDO and TDO are tryptophan catabolic enzymes with immune-inhibitory properties. For example, IDO is known to suppress T-cells and NK cells, generate and activate Tregs and myeloid-derived suppressor cells, and promote tumor angiogenesis. General examples of IDO and TDO antagonists or inhibitors include an antibody or antigen-binding fragment or small molecule that specifically binds to IDO or TDO (see, e.g., Platten et al., Front Immunol. 5: 673, 2014) and reduces or inhibits one or more immune-suppressive activities. Specific examples of IDO antagonists or inhibitors include indoximod (NLG-8189), 1-methyl-tryptophan (IMT), β-Carboline (norharmane; 9H-pyrido[3,4-b]indole), rosmarinic acid, and epacadostat (see, e.g., Sheridan, Nature Biotechnology. 33:321-322, 2015). Specific examples of TDO antagonists or inhibitors include 680C91 and LM10 (see, e.g., Pilotte et al., PNAS USA. 109:2497-2502, 2012).

In some embodiments, the agent is a TIM-3 antagonist or inhibitor. T-cell Immunoglobulin domain and Mucin domain 3 (TIM-3) is expressed on activated human CD4+ T-cells and regulates Th1 and Th17 cytokines. TIM-3 also acts as a negative regulator of Th1/Tc1 function by triggering cell death upon interaction with its ligand, galectin-9. TIM-3 contributes to the suppressive tumor microenvironment and its overexpression is associated with poor prognosis in a variety of cancers (see, e.g., Li et al., Acta Oncol. 54:1706-13, 2015). General examples of TIM-3 antagonists or inhibitors include an antibody or antigen-binding fragment or small molecule that specifically binds to TIM-3 and reduces or inhibits one or more of its immune-suppressive activities.

In some embodiments, the agent is a LAG-3 antagonist or inhibitor. Lymphocyte Activation Gene-3 (LAG-3) is expressed on activated T-cells, natural killer cells, B-cells and plasmacytoid dendritic cells. It negatively regulates cellular proliferation, activation, and homeostasis of T-cells, in a similar fashion to CTLA-4 and PD-1 (see, e.g., Workman and Vignali. European Journal of Immun 33: 970-9, 2003; and Workman et al., Journal of Immun 172: 5450-5, 2004), and has been reported to play a role in Treg suppressive function (see, e.g., Huang et al., Immunity. 21: 503-13, 2004). LAG3 also maintains CD8+ T-cells in a tolerogenic state and combines with PD-1 to maintain CD8 T-cell exhaustion. General examples of LAG-3 antagonists or inhibitors include an antibody or antigen-binding fragment or small molecule that specifically binds to LAG-3 and inhibits one or more of its immune-suppressive activities. Specific examples include the antibody BMS-986016, and antigen-binding fragments thereof.

In some embodiments, the agent is a VISTA antagonist or inhibitor. V-domain Ig suppressor of T cell activation (VISTA) is primarily expressed on hematopoietic cells and is an inhibitory immune checkpoint regulator that suppresses T-cell activation, induces Foxp3 expression, and is highly expressed within the tumor microenvironment where it suppresses anti-tumor T cell responses (see, e.g., Lines et al., Cancer Res. 74:1924-32, 2014). General examples of VISTA antagonists or inhibitors include an antibody or antigen-binding fragment or small molecule that specifically binds to VISTA and reduces one or more of its immune-suppressive activities.

In some embodiments, the agent is a BTLA antagonist or inhibitor. B- and T-lymphocyte attenuator (BTLA; CD272) expression is induced during activation of T-cells, and it inhibits T-cells via interaction with tumor necrosis family receptors (TNF-R) and B7 family of cell surface receptors. BTLA is a ligand for tumor necrosis factor (receptor) superfamily, member 14 (TNFRSF14), also known as herpes virus entry mediator (HVEM). BTLA-HVEM complexes negatively regulate T-cell immune responses, for example, by inhibiting the function of human CD8+ cancer-specific T-cells (see, e.g., Derré et al., J Clin Invest 120:157-67, 2009). General examples of BTLA antagonists or inhibitors include an antibody or antigen-binding fragment or small molecule that specifically binds to BTLA-4 and reduce one or more of its immune-suppressive activities.

In some embodiments, the agent is an HVEM antagonist or inhibitor, for example, an antagonist or inhibitor that specifically binds to HVEM and interferes with its interaction with BTLA or CD160. General examples of HVEM antagonists or inhibitors include an antibody or antigen-binding fragment or small molecule that specifically binds to HVEM, optionally reduces the HVEM/BTLA and/or HVEM/CD160 interaction, and thereby reduces one or more of the immune-suppressive activities of HVEM.

In some embodiments, the agent is a CD160 antagonist or inhibitor, for example, an antagonist or inhibitor that specifically binds to CD160 and interferes with its interaction with HVEM. General examples of CD160 antagonists or inhibitors include an antibody or antigen-binding fragment or small molecule that specifically binds to CD160, optionally reduces the CD160/HVEM interaction, and thereby reduces or inhibits one or more of its immune-suppressive activities.

In some embodiments, the agent is a TIGIT antagonist or inhibitor. T cell Ig and ITIM domain (TIGIT) is a coinhibitory receptor that is found on the surface of a variety of lymphoid cells, and suppresses antitumor immunity, for example, via Tregs (Kurtulus et al., J Clin Invest. 125:4053-4062, 2015). General examples of TIGIT antagonists or inhibitors include an antibody or antigen-binding fragment or small molecule that specifically binds to TIGIT and reduce one or more of its immune-suppressive activities (see, e.g., Johnston et al., Cancer Cell. 26:923-37, 2014).

In certain embodiments, the immune checkpoint modulatory agent is an agonist of one or more stimulatory immune checkpoint molecules. Exemplary stimulatory immune checkpoint molecules include OX40, CD40, Glucocorticoid-Induced TNFR Family Related Gene (GITR), CD137 (4-1BB), CD27, CD28, CD226, and Herpes Virus Entry Mediator (HVEM).

In some embodiments, the agent is an OX40 agonist. OX40 (CD134) promotes the expansion of effector and memory T cells, and suppresses the differentiation and activity of T-regulatory cells (see, e.g., Croft et al., Immunol Rev. 229:173-91, 2009). Its ligand is OX40L (CD252). Since OX40 signaling influences both T-cell activation and survival, it plays a key role in the initiation of an anti-tumor immune response in the lymph node and in the maintenance of the anti-tumor immune response in the tumor microenvironment. General examples of OX40 agonists include an antibody or antigen-binding fragment or small molecule or ligand that specifically binds to OX40 and increases one or more of its immunostimulatory activities. Specific examples include OX86, OX-40L, Fc-OX40L, GSK3174998, MEDI0562 (a humanized OX40 agonist), MEDI6469 (murine OX4 agonist), and MEDI6383 (an OX40 agonist), and antigen-binding fragments thereof.

In some embodiments, the agent is a CD40 agonist. CD40 is expressed on antigen-presenting cells (APC) and some malignancies. Its ligand is CD40L (CD154). On APC, ligation results in upregulation of costimulatory molecules, potentially bypassing the need for T-cell assistance in an antitumor immune response. CD40 agonist therapy plays an important role in APC maturation and their migration from the tumor to the lymph nodes, resulting in elevated antigen presentation and T cell activation. Anti-CD40 agonist antibodies produce substantial responses and durable anticancer immunity in animal models, an effect mediated at least in part by cytotoxic T-cells (see, e.g., Johnson et al. Clin Cancer Res. 21: 1321-1328, 2015; and Vonderheide and Glennie, Clin Cancer Res. 19:1035-43, 2013). General examples of CD40 agonists include an antibody or antigen-binding fragment or small molecule or ligand that specifically binds to CD40 and increases one or more of its immunostimulatory activities. Specific examples include CP-870,893, dacetuzumab, Chi Lob 7/4, ADC-1013, CD40L, rhCD40L, and antigen-binding fragments thereof.

In some embodiments, the agent is a GITR agonist. Glucocorticoid-Induced TNFR family Related gene (GITR) increases T cell expansion, inhibits the suppressive activity of Tregs, and extends the survival of T-effector cells. GITR agonists have been shown to promote an anti-tumor response through loss of Treg lineage stability (see, e.g., Schaer et al., Cancer Immunol Res. 1:320-31, 2013). These diverse mechanisms show that GITR plays an important role in initiating the immune response in the lymph nodes and in maintaining the immune response in the tumor tissue. Its ligand is GITRL. General examples of GITR agonists include an antibody or antigen-binding fragment or small molecule or ligand that specifically binds to GITR and increases one or more of its immunostimulatory activities. Specific examples include GITRL, INCAGN01876, DTA-1, MEDI1873, and antigen-binding fragments thereof.

In some embodiments, the agent is a CD137 agonist. CD137 (4-1BB) is a member of the tumor necrosis factor (TNF) receptor family, and crosslinking of CD137 enhances T-cell proliferation, IL-2 secretion, survival, and cytolytic activity. CD137-mediated signaling also protects T-cells such as CD8+ T-cells from activation-induced cell death. General examples of CD137 agonists include an antibody or antigen-binding fragment or small molecule or ligand that specifically binds to CD137 and increases one or more of its immunostimulatory activities. Specific examples include the CD137 (or 4-1BB) ligand (see, e.g., Shao and Schwarz, J Leukoc Biol. 89:21-9, 2011) and the antibody utomilumab, including antigen-binding fragments thereof.

In some embodiments, the agent is a CD27 agonist. Stimulation of CD27 increases antigen-specific expansion of naïve T cells and contributes to T-cell memory and long-term maintenance of T-cell immunity. Its ligand is CD70. The targeting of human CD27 with an agonist antibody stimulates T-cell activation and antitumor immunity (see, e.g., Thomas et al., Oncoimmunology. 2014; 3:e27255. doi:10.4161/onci.27255; and He et al., J Immunol. 191: 4174-83, 2013). General examples of CD27 agonists include an antibody or antigen-binding fragment or small molecule or ligand that specifically binds to CD27 and increases one or more of its immunostimulatory activities. Specific examples include CD70 and the antibodies varlilumab and CDX-1127 (1F5), including antigen-binding fragments thereof.

In some embodiments, the agent is a CD28 agonist. CD28 is constitutively expressed CD4+ T cells some CD8+ T cells. Its ligands include CD80 and CD86, and its stimulation increases T-cell expansion. General examples of CD28 agonists include an antibody or antigen-binding fragment or small molecule or ligand that specifically binds to CD28 and increases one or more of its immunostimulatory activities. Specific examples include CD80, CD86, the antibody TAB08, and antigen-binding fragments thereof.

In some embodiments, the agent is CD226 agonist. CD226 is a stimulating receptor that shares ligands with TIGIT, and opposite to TIGIT, engagement of CD226 enhances T-cell activation (see, e.g., Kurtulus et al., J Clin Invest. 125:4053-4062, 2015; Bottino et al., J Exp Med. 1984:557-567, 2003; and Tahara-Hanaoka et al., Int Immunol. 16:533-538, 2004). General examples of CD226 agonists include an antibody or antigen-binding fragment or small molecule or ligand (e.g., CD112, CD155) that specifically binds to CD226 and increases one or more of its immunostimulatory activities.

In some embodiments, the agent is an HVEM agonist. Herpesvirus entry mediator (HVEM), also known as tumor necrosis factor receptor superfamily member 14 (TNFRSF14), is a human cell surface receptor of the TNF-receptor superfamily. HVEM is found on a variety of cells including T-cells, APCs, and other immune cells. Unlike other receptors, HVEM is expressed at high levels on resting T-cells and down-regulated upon activation. It has been shown that HVEM signaling plays a crucial role in the early phases of T-cell activation and during the expansion of tumor-specific lymphocyte populations in the lymph nodes. General examples of HVEM agonists include an antibody or antigen-binding fragment or small molecule or ligand that specifically binds to HVEM and increases one or more of its immunostimulatory activities.

In certain embodiments, the cancer immunotherapy agent is a cancer vaccine. The efficacy of cancer vaccines can be limited by the activity of Tregs in a subject, and the ability of arginine depletion agents such as ADI to reduce Tregs (among other properties described herein) can be used to increase the efficacy of any variety of cancer vaccines. Exemplary cancer vaccines include Oncophage, human papillomavirus HPV vaccines such Gardasil or Cervarix, hepatitis B vaccines such as Engerix-B, Recombivax HB, or Twinrix, and sipuleucel-T (Provenge). In some embodiments, the cancer vaccine comprises or utilizes one or more cancer antigens, or cancer-associate d antigens. Exemplary cancer antigens include, without limitation, human Her2/neu, Her1/EGF receptor (EGFR), Her3, A33 antigen, B7H3, CD5, CD19, CD20, CD22, CD23 (IgE Receptor), MAGE-3, C242 antigen, 5T4, IL-6, IL-13, vascular endothelial growth factor VEGF (e.g., VEGF-A) VEGFR-1, VEGFR-2, CD30, CD33, CD37, CD40, CD44, CD51, CD52, CD56, CD74, CD80, CD152, CD200, CD221, CCR4, HLA-DR, CTLA-4, NPC-1C, tenascin, vimentin, insulin-like growth factor 1 receptor (IGF-1R), alpha-fetoprotein, insulin-like growth factor 1 (IGF-1), carbonic anhydrase 9 (CA-IX), carcinoembryonic antigen (CEA), guanylyl cyclase C, NY-ESO-1, p53, survivin, integrin $\alpha v \beta 3$, integrin $\alpha 5 \beta 1$, folate receptor 1, transmembrane glycoprotein NMB, fibroblast activation protein alpha (FAP), glycoprotein 75, TAG-72, MUC1, MUC16 (or CA-125), phosphatidylserine, prostate-specific membrane antigen (PSMA), NR-LU-13 antigen, TRAIL-R1, tumor necrosis factor receptor superfamily member 10b (TNFRSF10B or TRAIL-R2), SLAM family member 7 (SLAMF7), EGP40 pancarcinoma antigen, B-cell activating factor (BAFF), platelet-derived growth factor receptor, glycoprotein EpCAM (17-1A), Programmed Death-1, protein disulfide isomerase (PDI), Phosphatase of Regenerating Liver 3 (PRL-3), prostatic acid phosphatase, Lewis-Y antigen, GD2 (a disialoganglioside expressed on tumors of neuroectodermal origin), glypican-3 (GPC3), and mesothelin.

In certain embodiments, the cancer immunotherapy agent is an oncolytic virus. An oncolytic virus is a virus that preferentially infects and kills cancer cells. Included are naturally-occurring and man-made or engineered oncolytic viruses. Similar to above, the efficacy of oncolytic viruses can be limited by the activity of Tregs in a subject, and the ability of arginine depletion agents such as ADI to reduce Tregs (among other properties described herein) can be used to increase the efficacy of any variety of oncolytic viruses. Most oncolytic viruses are engineered for tumor selectivity, although there are naturally-occurring examples such as Reovirus and the SVV-001 Seneca Valley virus. General examples of oncolytic viruses include VSV, Poliovirus, Reovirus, *Senecavirus*, and RIGVIR, and engineered versions thereof. Non-limiting examples of oncolytic viruses include herpes simplex virus (HSV) and engineered version thereof, talimogene laherparepvec (T-VEC), coxsackievirus A21 (CAVATAK™), Oncorine (H101), pelareorep (REOLYSINθ), Seneca Valley virus (NTX-010), *Senecavirus* SVV-001, ColoAd1, SEPREHVIR (HSV-1716), CGTG-102 (Ad5/3-D24-GMCSF), GL-ONC1, MV-NIS, and DNX-2401, among others.

In certain embodiments, the cancer immunotherapy agent is a cytokine. Exemplary cytokines include interferon (IFN)-α, IL-2, IL-12, IL-7, IL-21, and Granulocyte-macrophage colony-stimulating factor (GM-CSF).

In certain embodiments, the cancer immunotherapy agent is cell-based immunotherapy, for example, a T-cell based adoptive immunotherapy. In some embodiments, the cell-based immunotherapy comprises cancer antigen-specific T-cells, optionally ex vivo-derived T-cells. In some embodiments, the cancer antigen-specific T-cells are selected from one or more of chimeric antigen receptor (CAR)-modified T-cells, and T-cell Receptor (TCR)-modified T-cells, tumor infiltrating lymphocytes (TILs), and peptide-induced T-cells. In specific embodiments, the CAR-modified T-cell is targeted against CD-19 (see, e.g., Maude et al., Blood. 125: 4017-4023, 2015).

In particular embodiments, the cancer immunotherapy agent is selected from one or more of an IDO antagonist, a CD20 antagonist, a B-Raf antagonist, IL-2, GM-CSF, and an oncolytic virus. In specific embodiments, the IDO antagonist is indoximod, and/or the CD20 agonist is rituximab, and/or the B-Raf antagonist is vemurafenib, and/or the oncolytic virus is talimogene laherparepvec (T-VEC) or coxsackievirus A21 (CAVATAK™).

The skilled artisan will appreciate that the various cancer immunotherapy agents described herein can be combined with any one or more of the various arginine depletion agents described herein, and used according to any one or more of the methods or compositions described herein.

Methods of Use

As noted above, embodiments of the present disclosure relate to the discovery that arginine depletion agents have unexpected immunomodulatory properties. For example, the exemplary arginine depletion agent ADI-PEG 20 was shown in vitro to reduce immune-suppressive regulatory T-cells (Treg cells), which would otherwise minimize the magnitude and duration of an inflammatory response, particularly anti-tumor responses. It was also shown to moderate exhaustion of effector T-cells (Teff cells) in vitro, and increase tumor infiltration by T-cells in vivo. Accordingly, arginine depletion agents such as ADI can be used to increase anti-tumor T-cell responses, for example, by enhancing T-cell priming and trafficking into the tumor microenvironment, and thereby potentiate other cancer immunotherapies.

Certain embodiments therefore include methods of treating ameliorating the symptoms of, or inhibiting the progression of, a cancer in a subject in need thereof, comprising administering to the subject (a) an arginine depletion agent which converts arginine to citrulline; and (b) a cancer immunotherapy agent. Arginine depletion agents and cancer immunotherapy agents are described elsewhere herein, as are combinations thereof.

In some instances, (a) the arginine depletion agent and (b) the cancer immunotherapy agent are administered separately, for example, in separate compositions and at different times. In some embodiments, (a) the arginine depletion agent and (b) the cancer immunotherapy agent are administered as part of the same composition, at the same time.

In certain embodiments, administration of the arginine depletion agent (e.g., ADI, ADI-PEG, ADI-PEG 20), reduces immune-suppressive regulatory T-cells (Treg cells), for example, in a tumor microenvironment in the subject. In some instances, Tregs are reduced by about or at least about 10, 20, 30, 40, 50, 60, 70, 80, 90, or 100% or more relative to a control, for example, a control composition (with no agent) or a control timepoint, for example, an earlier timepoint.

In certain embodiments, administration of the arginine depletion agent (e.g., ADI, ADI-PEG, ADI-PEG 20), reduces or moderates exhaustion of effector T-cells (Teff cells), for example, in a tumor microenvironment in the subject. In some instances, Teff cell exhaustion is reduced by about or at least about 10, 20, 30, 40, 50, 60, 70, 80, 90, or 100% or more relative to a control, for example, a control composition (with no agent) or a control timepoint, for example, an earlier timepoint.

In some embodiments, administration of the arginine depletion agent (e.g., ADI, ADI-PEG, ADI-PEG 20), increases tumor infiltration by T-cells. In some instances, tumor infiltration by T-cells is increased by about or at least about 10, 20, 30, 40, 50, 60, 70, 80, 90, or 100% or more relative to a control, for example, a control composition (with no agent) or a control timepoint, for example, an earlier timepoint. Tumor infiltration can be measured according to routine techniques in the art (see, e.g., Example 2).

In some instances, administration of the arginine depletion agent (e.g., ADI, ADI-PEG, ADI-PEG 20) enhances effector T cell activation (expression of CD69) and/or reduces upregulation of immunosuppressive receptors PD-1 and CTLA-4 on T-cells. In some instances, CD69 expression on effector T-cells is increased by about or at least about 10, 20, 30, 40, 50, 60, 70, 80, 90, or 100% or more relative to a control, for example, a control composition (with no agent) or a control timepoint, for example, an earlier timepoint. In some instances, PD-1 expression on T-cells is reduced by about or at least about 10, 20, 30, 40, 50, 60, 70, 80, 90, or 100% or more relative to a control, for example, a control composition (with no agent) or a control timepoint, for example, an earlier timepoint. In certain instances, CTLA-4 expression on T-cells is reduced by about or at least about 10, 20, 30, 40, 50, 60, 70, 80, 90, or 100% or more relative to a control, for example, a control composition (with no agent) or a control timepoint, for example, an earlier timepoint.

In some embodiments, the combination therapies described herein increase median survival time of a patient by 4 weeks, 5 weeks, 6 weeks, 7 weeks, 8 weeks, 9 weeks, 10 weeks, 15 weeks, 20 weeks, 25 weeks, 30 weeks, 40 weeks, or longer. In certain embodiments, the combination therapies described herein increase median survival time of a patient by 1 year, 2 years, 3 years, or longer. In some embodiments, the combination therapies described herein increase progression-free survival by 2 weeks, 3 weeks, 4 weeks, 5 weeks, 6 weeks, 7 weeks, 8 weeks, 9 weeks, 10 weeks or longer. In certain embodiments, the combination therapies described herein increase progression-free survival by 1 year, 2 years, 3 years, or longer.

In certain embodiments, the combination administered is sufficient to result in tumor regression, as indicated by a statistically significant decrease in the amount of viable tumor, for example, at least a 10%, 20%, 30%, 40%, 50% or greater decrease in tumor mass, or by altered (e.g., decreased with statistical significance) scan dimensions. In certain embodiments, the combination administered is sufficient to result in stable disease. In certain embodiments, the combination administered is sufficient to result in clinically relevant reduction in symptoms of a particular disease indication known to the skilled clinician. In some embodiments, the arginine depletion agent increases, complements, or otherwise enhances the anti-tumor and/or immunostimulatory activity of the cancer immunotherapy agent, relative to the cancer immunotherapy agent alone.

The methods and compositions described herein can be used in the treatment of any variety of cancers. In some embodiments, the cancer is selected from one or more of hepatocellular carcinoma (HCC), melanoma, metastatic melanoma, pancreatic cancer, prostate cancer, small cell lung cancer, mesothelioma, lymphocytic leukemia, chronic myelogenous leukemia, lymphoma, hepatoma, sarcoma, leukemia, acute myeloid leukemia, relapsed acute myeloid leukemia, B-cell malignancy, breast cancer, ovarian cancer, colorectal cancer, gastric cancer, glioma (e.g., astrocytoma, oligodendroglioma, ependymoma, or a choroid plexus papilloma), glioblastoma multiforme (e.g., giant cell gliobastoma or a gliosarcoma), meningioma, pituitary adenoma, vestibular schwannoma, primary CNS lymphoma, or primitive neuroectodermal tumor (medulloblastoma), non-small cell lung cancer (NSCLC), kidney cancer, bladder cancer, uterine cancer, esophageal cancer, brain cancer, head and neck cancers, cervical cancer, testicular cancer, and stomach cancer.

Certain specific combinations include an arginine depletion agent and a PD-L1 antagonist or inhibitor, for example, atezolizumab (MPDL3280A) avelumab (MSB0010718C), and durvalumab (MEDI4736), for treating a cancer selected from one or more of colorectal cancer, melanoma, breast cancer, non-small-cell lung carcinoma, bladder cancer, and renal cell carcinoma.

Some specific combinations include an arginine depletion agent and a PD-1 antagonist, for example, nivolumab, for treating a cancer selected from one or more of Hodgkin's lymphoma, melanoma, non-small cell lung cancer, hepatocellular carcinoma, renal cell carcinoma, and ovarian cancer.

Particular specific combinations include an arginine depletion agent and a PD-1 antagonist, for example, pembrolizumab, for treating a cancer selected from one or more of melanoma, non-small cell lung cancer, small cell lung cancer, head and neck cancer, and urothelial cancer.

Certain specific combinations include an arginine depletion agent and a CTLA-4 antagonist, for example, ipilimumab and tremelimumab, for treating a cancer selected from one or more of melanoma, prostate cancer, lung cancer, and bladder cancer.

Some specific combinations include an arginine depletion agent and an IDO antagonist, for example, indoximod (NLG-8189), 1-methyl-tryptophan (1MT), β-Carboline (norharmane; 9H-pyrido[3,4-b]indole), rosmarinic acid, or epacadostat, for treating a cancer selected from one or more of metastatic breast cancer and brain cancer optionally Glioblastoma Multiforme, glioma, gliosarcoma or malignant brain tumor.

Certain specific combinations include an arginine depletion agent and the cytokine INF-α for treating melanoma, Kaposi sarcoma, and hematologic cancers. Also included is the combination of an arginine depletion agent and IL-2 (e.g., Aldesleukin) for treating metastatic kidney cancer or metastatic melanoma.

Some specific combinations include an arginine depletion agent and a T-cell based adoptive immunotherapy, for example, comprising CAR-modified T-cells targeted against CD-19, for treating hematological cancers such as acute lymphoblastic leukemia (ALL), chronic lymphocytic leukemia (CLL), and B-cell neoplasms (see, e.g., Maude et al., 2015, supra; Lorentzen and Straten, Scand J Immunol. 82:307-19, 2015; and Ramos et al., Cancer J. 20:112-118, 2014).

In some embodiments, as noted above, administration of the arginine depletion agent (e.g., ADI, ADI-PEG, ADI-PEG 20) reduces upregulation of the immunosuppressive receptor CTLA-4 on T-cells, and downregulates Tregs. Without being limited by any one theory, such activities parallel at least in part the anti-tumor activities of the anti-CTLA4 monoclonal antibody ipilimumab (YERVOY®). Thus, arginine depletion agents should find therapeutic utility in clinical situations or combinations similar to those being identified for ipilimumab. Particular examples include administering an arginine depletion agent in combination with one or more of an IDO antagonist, a CD20 antagonist, a B-Raf antagonist, IL-2, GM-CSF, and an oncolytic virus. In particular embodiments, the IDO antagonist is indoximod, the CD20 agonist is rituximab, the B-Raf antagonist is vemurafenib, and/or the oncolytic virus is talimogene laherparepvec (T-VEC) or coxsackievirus A21 (CAVATAK™).

The methods for treating cancers can be combined with other therapeutic modalities. For example, a combination therapy described herein can be administered to a subject before, during, or after other therapeutic interventions, including symptomatic care, radiotherapy, surgery, transplantation, hormone therapy, photodynamic therapy, antibiotic therapy, or any combination thereof. Symptomatic care includes administration of corticosteroids, to reduce cerebral edema, headaches, cognitive dysfunction, and emesis, and administration of anti-convulsants, to reduce seizures. Radiotherapy includes whole-brain irradiation, fractionated radiotherapy, and radiosurgery, such as stereotactic radiosurgery, which can be further combined with traditional surgery.

Methods for identifying subjects with one or more of the diseases or conditions described herein are known in the art.

For in vivo use, for instance, for the treatment of human disease or testing, the agents described herein are generally incorporated into one or more pharmaceutical or therapeutic compositions prior to administration. In some instances, a pharmaceutical or therapeutic composition comprises one or more of the agents described herein in combination with a physiologically acceptable carrier or excipient.

To prepare a pharmaceutical composition, an effective or desired amount of one or more agents is mixed with any pharmaceutical carrier(s) or excipient known to those skilled in the art to be suitable for the particular agent and/or mode of administration. A pharmaceutical carrier may be liquid, semi-liquid or solid. Solutions or suspensions used for parenteral, intradermal, subcutaneous or topical application may include, for example, a sterile diluent (such as water), saline solution (e.g., phosphate buffered saline; PBS), fixed oil, polyethylene glycol, glycerin, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously (e.g., by IV infusion), suitable carriers include physiological saline or phosphate buffered saline (PBS), and solutions containing thickening and solubilizing agents, such as glucose, polyethylene glycol, polypropylene glycol and mixtures thereof.

Administration of agents described herein, in pure form or in an appropriate pharmaceutical composition, can be carried out via any of the accepted modes of administration of agents for serving similar utilities. The pharmaceutical compositions can be prepared by combining an agent-containing composition with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other small molecules as described elsewhere herein) and/or suitable excipients such as salts, buffers and stabilizers may, but need not, be present within the composition.

Administration may be achieved by a variety of different routes, including oral, parenteral, nasal, intravenous, intradermal, intramuscular, subcutaneous or topical. Preferred modes of administration depend upon the nature of the condition to be treated or prevented. Particular embodiments include administration by IV infusion.

Carriers can include, for example, pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as polysorbate 20 (TWEEN™) polyethylene glycol (PEG), and poloxamers (PLURONICS™), and the like.

In some embodiments, one or more agents can be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nanoparticles and nanocapsules), or in macroemulsions. Such techniques are disclosed in Remington's Pharmaceutical Sciences, 16th edition, Oslo, A., Ed., (1980). The particle(s) or liposomes may further comprise other therapeutic or diagnostic agents.

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

Typical routes of administering these and related pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions according to certain embodiments of the present invention are formulated so as to allow the active ingredients contained therein to be bioavailable upon administration of the composition to a patient. Compositions that will be administered to a subject or patient may take the form of one or more dosage units, where for example, a tablet may be a single dosage unit, and a container of a herein described agent in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will typically contain a therapeutically effective amount of an agent described herein, for treatment of a disease or condition of interest.

A pharmaceutical composition may be in the form of a solid or liquid. In one embodiment, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration should contain an amount of an agent such that a suitable dosage will be obtained. Typically, this amount is at least 0.01% of the agent of interest in the composition. When intended for oral administration, this amount may be varied to be between 0.1 and about 70% of the weight of the composition. Certain oral pharmaceutical compositions contain between about 4% and about 75% of the agent of interest. In certain embodiments, pharmaceutical compositions and preparations according to the present invention are prepared so that a parenteral dosage unit contains between 0.01 to 10% by weight of the agent of interest prior to dilution.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter, and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The pharmaceutical composition in solid or liquid form may include a component that binds to agent and thereby assists in the delivery of the compound. Suitable components that may act in this capacity include monoclonal or polyclonal antibodies, one or more proteins or a liposome.

The pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The compositions described herein may be prepared with carriers that protect the agents against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

The pharmaceutical compositions may be prepared by methodology well known in the pharmaceutical art. For example, a pharmaceutical composition intended to be administered by injection may comprise one or more of salts, buffers and/or stabilizers, with sterile, distilled water so as to form a solution. A surfactant may be added to facilitate the formation of a homogeneous solution or suspension. Surfactants are compounds that non-covalently interact with the agent so as to facilitate dissolution or homogeneous suspension of the agent in the aqueous delivery system.

The compositions may be administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. In some instances, a therapeutically effective daily dose is (for a 70 kg mammal) from about 0.001 mg/kg (i.e., ~0.07 mg) to about 100 mg/kg (i.e., ~7.0 g); preferably a therapeutically effective dose is (for a 70 kg mammal) from about 0.01 mg/kg (i.e., ~0.7 mg) to about 50 mg/kg (i.e., ~3.5 g); more preferably a therapeutically effective dose is (for a 70 kg mammal) from about 1 mg/kg (i.e., ~70 mg) to about 25 mg/kg (i.e., ~1.75 g).

In some embodiments, a composition comprising ADI (e.g., ADI-PEG, ADI-PEG 20) has a pH of about 5 to about 9, about 6 to about 8, or about 6.5 to about 7.5. In some embodiments, the composition comprising ADI (e.g., ADI-PEG, ADI-PEG 20) has a pH of about 6.8±1.0.

In some embodiments, free PEG in a composition comprising ADI (e.g., ADI-PEG, ADI-PEG 20) is between 1-10%. In some embodiments, it is less than 7%, less than 6%, less than 5%, less than 4%, less than 3%, less than 2% or less than 1% of the total PEG. In certain embodiments, the unmodified ADI in a composition comprising ADI-PEG (e.g., ADI-PEG 20) is less than about 1%, 0.9%, 0.8%, 0.7%, 0.6%, 0.5%, 0.4%, 0.3%, 0.2% or less than 0.1%. Generally, compositions comprising ADI (e.g., ADI-PEG, ADI-PEG 20) have total impurities less than or equal to about 4%, 3%, 2%, 1.5%, 1% or 0.5%. In some embodiments, the endotoxin limit meets the requirements stated in USP, i.e., ≤50 EU/mL.

In some embodiments, the free sulfhydryl in a composition comprising ADI (e.g., ADI-PEG, ADI-PEG 20) is greater than about 90%. In some embodiments, the free sulfhydryl in a composition comprising ADI (e.g., ADI-PEG, ADI-PEG 20) is about 91%, about 92%, about 93%, about 94% or about 95%, about 96% about 97%, about 98% about 99% or more.

In some embodiments, the ADI (e.g., ADI-PEG, ADI-PEG 20) in a composition has a Km of from about 0.1 µM or 0.5 µM to about 15 µM, or is from about 1 µM to about 12 µM, about 1 µM to about 10 µM, about 1.5 µM to about 9 µM, about 1.5 µM to about 8 µM or about 1.5 µM to about 7 µM. In certain embodiments, the ADI (e.g., ADI-PEG, ADI-PEG 20) in a composition has a Km of about 1.0 µM to about 10 µM or about 1.5 µM to about 6.5 µM. In some embodiments, the ADI (e.g., ADI-PEG, ADI-PEG 20) in a composition has a Km of about, at least about, or less than about 0.1 µM, about 0.5 µM, about 1.0 µM, about 1.5 µM, about 2 µM, about 2.5 µM, about 3 µM, about 3.5 µM, about 4 µM, about 4.5 µM, about 5 µM, about 5.5 µM, about 6 µM, about 6.5 µM, or about 7 µM, or about 8 µM, or about 9 µM, or about 10 µM.

In some embodiments, the ADI (e.g., ADI-PEG, ADI-PEG 20) in a composition has a Kcat of from about 0.5 sec$^{-1}$ to about 80 sec$^{-1}$, or about 0.5 sec$^{-1}$ to about 70 sec$^{-1}$, or about 0.5 sec$^{-1}$ to about 60 sec$^{-1}$, or about 0.5 sec$^{-1}$ to about 50 sec$^{-1}$, or about 0.5 sec$^{-1}$ to about 40 sec$^{-1}$, or about 0.5 sec$^{-1}$ to about 30 sec$^{-1}$, or about 0.5 sec$^{-1}$ to about 20 sec$^{-1}$, or about 0.5 sec$^{-1}$ to about 15 sec$^{-1}$, or is from about 0.5 sec$^{-1}$ to about 80 sec$^{-1}$, or about 1 sec$^{-1}$ to about 80 sec$^{-1}$, or about 5 sec$^{-1}$ to about 80 sec$^{-1}$, or about 10 sec$^{-1}$ to about 80 sec$^{-1}$, or about 20 sec$^{-1}$ to about 80 sec$^{-1}$, or about 30 sec$^{-1}$ to about 80 sec$^{-1}$, or about 40 sec$^{-1}$ to about 80 sec$^{-1}$, or about 50 sec$^{-1}$ to about 80 sec$^{-1}$, or about 60 sec$^{-1}$ to about 80 sec$^{-1}$, or about 70 sec$^{-1}$ to about 80 sec$^{-1}$, or about 1 sec$^{-1}$ to about 12 sec$^{-1}$, about 1 sec$^{-1}$ to about 10 sec$^{-1}$, about 1.5 sec$^{-1}$ to about 9 sec$^{-1}$, about 2 sec$^{-1}$ to about 8 sec$^{-1}$ or about 2.5 sec$^{-1}$ to about 7 sec$^{-1}$. In certain embodiments, the ADI (e.g., ADI-PEG, ADI-PEG 20) in a composition has a Kcat of about 2.5 sec$^{-1}$ to about 7.5 sec$^{-1}$. In some embodiments, the ADI (e.g., ADI-PEG, ADI-PEG 20) in a composition has a Kcat of about or at least about 2.5 sec$^{-1}$, about 3 sec$^{-1}$, about 3.5 sec$^{-1}$, about 4 sec$^{-1}$, about 4.5 sec$^{-1}$, about 5 sec$^{-1}$, about 5.5 sec$^{-1}$, about 6 sec$^{-1}$, about 6.5 sec$^{-1}$, about 7 sec$^{-1}$, about 7.5 sec$^{-1}$ or about 8 sec$^{-1}$, about 10 sec$^{-1}$, about 15 sec$^{-1}$, about 20 sec$^{-1}$, about 25 sec$^{-1}$, about 30 sec$^{-1}$, about 35 sec$^{-1}$, about 40 sec$^{-1}$, about 45 sec$^{-1}$, about 50 sec$^{-1}$, about 55 sec$^{-1}$, about 60 sec$^{-1}$, about 65 sec$^{-1}$, about 70 sec$^{-1}$, about 75 sec$^{-1}$, about 80 sec$^{-1}$, about 85 sec$^{-1}$, about 90 sec$^{-1}$, about 95 sec$^{-1}$, or about 100 sec$^{-1}$.

In some embodiments, the ADI (e.g., ADI-PEG, ADI-PEG 20) in a composition has a conductivity (also referred to in the art as specific conductance) of about 5 mS/cm to about 20 mS/cm, or about 5 mS/cm to about 15 mS/cm, about 7 mS/cm to about 15 mS/cm, about 9 mS/cm to about 15 mS/cm or about 10 mS/cm to about 15 mS/cm. In some embodiments, the ADI (e.g., ADI-PEG, ADI-PEG 20) in a composition has a conductivity of about 9 mS/cm, about 10 mS/cm, about 11 mS/cm, about 12 mS/cm or about 13 mS/cm, about 14 mS/cm or about 15 mS/cm. In certain embodiments, the ADI (e.g., ADI-PEG, ADI-PEG 20) in a composition has a conductivity of about 13 mS/cm±1.0 mS/cm.

In some embodiments, the ADI (e.g., ADI-PEG, ADI-PEG 20) in a composition has an osmolality of about 50 mOsm/kg to about 500 mOsm/kg, about 100 mOsm/kg to about 400 mOsm/kg, about 150 mOsm/kg to about 350 mOsm/kg, about 200 mOsm/kg to about 350 mOsm/kg or about 250 mOsm/kg to about 350 mOsm/kg. In certain embodiments, the ADI (e.g., ADI-PEG, ADI-PEG 20) in a composition has an osmolality of about 300±30 mOsm/kg.

In certain embodiments, the protein concentration is between about 8 and about 15 mg/mL. In certain embodiments, the protein concentration is about 8, 9, 10, 10.5, 11, 11.5, 12, 12.5, 13, 13.5, 14, or 15 mg/mL.

In some embodiments, the specific enzyme activity of the ADI (e.g., ADI-PEG, ADI-PEG 20) is between about 5.0 and 90 IU/mg or between about 5 and 55 IU/mg, where 1 IU is defined as the amount of enzyme that converts one µmol of arginine into one µmol of citrulline and 1 µmol of ammonia in one minute at 37° C. and the potency is 100±20 IU/mL. In certain embodiments, the specific enzyme activity is about 5.5, 6, 6.5, 7, 7.5, 8, 8.5, 9.0, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 35, 40, 45, 50, 55, 55, 60, 65, 70, 75, 80, 85, 90, 95, or 100±2.0 IU/mg.

The combination therapies described herein may include administration of a single pharmaceutical dosage formulation, which contains an arginine depletion agent and an immunotherapy agent (optionally with one or more additional active agents), as well as administration of compositions comprising an arginine depletion agent and a cancer immunotherapy agent in its own separate pharmaceutical dosage formulation. For example, an arginine depletion agent as described herein and a cancer immunotherapy agent can be administered to the patient together in a single oral dosage composition such as a tablet or capsule, or each agent administered in separate oral dosage formulations. Similarly, an arginine depletion agent as described herein and a cancer immunotherapy agent can be administered to the patient together in a single parenteral dosage composition such as in a saline solution or other physiologically acceptable solution, or each agent administered in separate parenteral dosage formulations. As another example, for cell-based therapies, the arginine depletion agent can be mixed with the cells prior to administration, administered as part of a separate composition, or both. Where separate dosage formulations are used, the compositions can be administered at essentially the same time, i.e., concurrently, or at separately staggered times, i.e., sequentially and in any order; combination therapy is understood to include all these regimens.

Also included are in vitro or ex vivo uses of the arginine depletion agents and related embodiments described herein. Generally, arginine depletion can be used, for instance, to increase in vitro T-cell activation and/or Treg downregulation in tissue culture studies or as a primer for T-cell based immunotherapies. Certain embodiments therefore relate to methods of increasing T-cell activation and/or Treg downregulation in vitro or ex vivo, comprising incubating or contacting T-cells with one or more arginine depletion agents, which are described elsewhere herein. Also included are methods of increasing T-cell activation and/or Treg downregulation in vitro or ex vivo, comprising incubating the T-cells in arginine-free medium supplemented with citrulline. In certain embodiments, the T-cells are primary T-cells, for example, isolated or obtained from a subject or patient.

Particular embodiments relate to methods of adoptive T-cell immunotherapy for treating a cancer in a subject in need thereof, comprising (a) incubating ex vivo-derived T-cells (i) with an arginine depletion agent or (ii) in arginine-free medium supplemented with citrulline; and (b) administering the ex vivo-derived T-cells to the subject. See, for example, June, J Clin Invest. 117: 1466-1476, 2007; and Rosenberg and Restifo, Science. 348:62-68, 2015, for descriptions of adoptive T-cell immunotherapies. In some instances, the ex vivo-derived T-cells are obtained from the subject to be treated. In certain embodiments, arginine depletion enhances the efficacy of the adoptively transferred T-cells.

Exemplary arginine depletion agents are described elsewhere herein. Arginine-free media and citrulline supplements are commercially-available (see, e.g., ThermoFisher Scientific). In some instances, the arginine-free media comprises citrulline ranging from about 0.01-100 mM, or at about, at least about, or no more than about, 0.01, 0.05, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 60, 70, 80, 90, or 100 mM.

Similar to above, exemplary cancers for treatment by adoptive T-cell immunotherapy combined with arginine depletion include hepatocellular carcinoma (HCC), melanoma, metastatic melanoma, pancreatic cancer, prostate cancer, small cell lung cancer, mesothelioma, lymphocytic leukemia, chronic myelogenous leukemia, lymphoma, hepatoma, sarcoma, leukemia, acute myeloid leukemia, relapsed acute myeloid leukemia, B-cell malignancy, breast cancer, ovarian cancer, colorectal cancer, gastric cancer, glioma (e.g., astrocytoma, oligodendroglioma, ependymoma, or a choroid plexus papilloma), glioblastoma multiforme (e.g., giant cell gliobastoma or a gliosarcoma), meningioma, pituitary adenoma, vestibular schwannoma, primary CNS lymphoma, or primitive neuroectodermal tumor (medulloblastoma), non-small cell lung cancer (NSCLC), kidney cancer, bladder cancer, uterine cancer, esophageal cancer, brain cancer, head and neck cancers, cervical cancer, testicular cancer, and stomach cancer.

In some embodiments, the T-cells (e.g., ex vivo-derived T-cells) comprise cancer antigen-specific T-cells. Cancer antigen-specific T-cells can be expanded, enriched, engineered, or otherwise prepared before, during, and/or after exposure to arginine depletion (e.g., contacting with arginine depletion agent, incubating in arginine-free media supplemented with citrulline). In certain instances, the cancer to be treated associates with the cancer antigen, that is, the cancer antigen-specific T-cells are targeted against or enriched for at least one antigen that is known to associate with the cancer to be treated. In some embodiments, the cancer antigen is selected from one or more of CD19, human Her2/neu, Her1/EGF receptor (EGFR), Her3, A33 antigen, B7H3, CD5, CD20, CD22, CD23 (IgE Receptor), MAGE-3, C242 antigen, 5T4, IL-6, IL-13, vascular endothelial growth factor VEGF (e.g., VEGF-A) VEGFR-1, VEGFR-2, CD30, CD33, CD37, CD40, CD44, CD51, CD52, CD56, CD74, CD80, CD152, CD200, CD221, CCR4, HLA-DR, CTLA-4, NPC-1C, tenascin, vimentin, insulin-like growth factor 1 receptor (IGF-1R), alpha-fetoprotein, insulin-like growth factor 1 (IGF-1), carbonic anhydrase 9 (CA-IX), carcinoembryonic antigen (CEA), guanylyl cyclase C, NY-ESO-1, p53, survivin, integrin αvβ3, integrin α5β1, folate receptor 1, transmembrane glycoprotein NMB, fibroblast activation protein alpha (FAP), glycoprotein 75, TAG-72, MUC1, MUC16 (or CA-125), phosphatidylserine, prostate-specific membrane antigen (PMSA), NR-LU-13 antigen, TRAIL-R1, tumor necrosis factor receptor superfamily member 10b (TNFRSF10B or TRAIL-R2), SLAM family member 7 (SLAMF7), EGP40 pancarcinoma antigen, B-cell activating factor (BAFF), platelet-derived growth factor receptor, glycoprotein EpCAM (17-1A), Programmed Death-1, protein disulfide isomerase (PDI), Phosphatase of Regenerating Liver 3 (PRL-3), prostatic acid phosphatase, Lewis-Y antigen, GD2 (a disialoganglioside expressed on tumors of neuroectodermal origin), glypican-3 (GPC3), and mesothelin. In some instances, the cancer antigen-specific T-cells are selected from one or more of chimeric antigen receptor (CAR)-modified T-cells (e.g., targeted against a cancer antigen), and T-cell Receptor (TCR)-modified T-cells, tumor infiltrating lymphocytes (TILs), and peptide-induced T-cells.

Also included are patient care kits, comprising (a) one or more arginine depletion agents which converts arginine to citrulline; and one or more cancer immunotherapy agents. In certain kits, (a) and (b) are in separate compositions. In some kits, (a) and (b) are in the same composition.

The kits herein may also include a one or more additional therapeutic agents or other components suitable or desired for the indication being treated, or for the desired diagnostic application. The kits herein can also include one or more syringes or other components necessary or desired to facilitate an intended mode of delivery (e.g., stents, implantable depots, etc.).

All publications, patent applications, and issued patents cited in this specification are herein incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

ADI-PEG 20 Modulates Stimulated and not Resting T-Cells

The effect of ADI PEG-20 on T-cells was tested, as described below.
Reagents.

ADI-PEG 20 is a recombinant protein cloned from *Mycoplasma hominis*, produced in *Escherichia coli.*, and PEGylated with 20,000 MW PEG (see, e.g., Feun and Savaraj, Expert Opin Investig Drugs. 2006 July; 15(7):815-22; Holtsberg et al., J Control Release. 2002 Apr. 23; 80(1-3):259-71; and Bomalaski et al., Preclinica (2003), Vol. 1 pages 284-293). A C397A substitution was used to generate an inactive ADI-PEG 20 mutant (mutADI).

Frozen healthy donor PBMCs were purchased from AllCells. PBMCs from two different donors were tested in three repeat experiments. PBMCs were thawed, washed and rested overnight (18 hours). The next day cells were collected, resuspended in AIM-V medium supplemented with Glutamax, and counted. Cell concentration was adjusted to $2\times10^6$ cells per mL and 2 mL of cells were added per well of a 6-well plates. PBMCs were treated with 0, 0.8, 4, or 20 nM of ADI-PEG 20 in the presence or absence of CD3/CD28 Dynabeads or PHA. CD3/CD28 Dynabeads were prepared according to manufacturer's instructions. Cells were analyzed after 24, 48, and 72 hours of treatment.
Flow Cytometry Analysis.

Prior to flow cytometry analysis Dynabeads were removed from samples. Cells were blocked in human Fc block, stained with Live/Dead fixable Near-IR stain following by appropriate antibody solution mixes. For effector T-cell (Teff) analyses antibody mix contained: CD3-PE-Cy7, CD8-FITC, CD4-PerCP-Cy5.5, CD69-APC and either CD274-PE, CD279-PE or CD152-PE. For analysis of regulatory T-cells (Treg) antibody mix included CD3-PE-Cy7, CD4-PerCP-Cy5.5, CD25-APC and either CD127-PE, CD274-PE, CD279-PE or CD152-PE. After surface staining samples were washed, those stained with Teff antibody mix were immediately analyzed by flow cytometry, while samples stained with Treg antibody mix were permeabilized with human FoxP3 buffer set and intracellularly stained with FoxP3-FITC antibody. 50,000 events were acquired for each sample on a Guava EasyCyte 8HT (Millipore). Data acquisition and analysis was performed with InCyte software (Millipore). AbC total antibody compensation bead kit and ArC amine reactive bead kit were used to create single stained fluorophore controls and perform spectral overlap compensation on the cytometer.
Gating Strategy.

Singlet gate was determined by FSC-H versus FSC-A plot. Fluorescent minus one (FMO) controls were used to set up other analyses gates. Singlet cells were gated on live cells based on Live/Dead fixable Near-IR stain and singlet and live cells were further analyzed for the presence of CD3 T-cell marker. Within CD3+ live and singlet cells CD4+ and CD8+ gates were set up, then each of these populations were analyzed for the presence of other markers—CD69, CD274, CD279, CD152. For Treg analysis singlet and live CD3+ CD4+ cells were analyzed for the presence of CD25, FoxP3, CD127, CD274, CD279 and CD152 markers.
Experimental Summary.

PBMCs were rested overnight and treated for 24, 48, or 72 hours with 0, 0.8, 4, or 20 nM ADI-PEG 20 in the presence or absence of CD3/CD28 beads or PHA. To control for any potential effects of PEG 20 and verify that the observed treatment outcomes with ADI-PEG 20 were mediated by ADI activity, the effect of 20 nM of an inactive ADI mutant (mutADI) was evaluated as a control (ADI with C397A substitution and PEGylated with 20K PEG).

After incubation was complete cells were collected, stained for expression of surface markers and analyzed by immune cell phenotyping using flow cytometry. Three independent experiments were conducted with PBMCs from two different donors and the obtained results were consistent between experimental repeats, representative data is shown in FIGS. 1-5.

While having no effect on T-cells under resting conditions, ADI-PEG 20 treatment during stimulation with anti-CD3/CD28 beads (FIG. 1-5) or PHA (data not shown) resulted in modulation of T-cells, as detailed below. Non-functional mutADI-PEG 20 did not modulate T-cells under any experimental conditions.

Results.

ADI-PEG 20 boosted stimulation-induced T-cell activation manifested by CD69 expression. CD69 upregulation on T-cells after 24h stimulation was enhanced by ADI-PEG 20 in a concentration-dependent manner. Moreover at 48h and 72h time points, while CD69 levels subsided (as expected) in the absence of ADI-PEG 20, stimulated T-cells maintained high CD69 levels in its presence.

The 0.8 nM dose of ADI-PEG 20 had no apparent effect at 24 and 48h time points and induced a modest increase in CD69 expression at 72h, which must have been enough time to convert critical amount of arginine to citrulline. Both 4 nM and 20 nM doses greatly augmented CD69 expression (inducing it in ~80% of T-cells) with the 20 nM dose having only slightly larger effect than 4 nM dose; ADI-PEG 20 at 100 nM had the same effect as at 20 nM (data not shown).

ADI-PEG 20 dose-dependent enhancement of surface CD69 was evident on both CD4+ and CD8+ T-cells. Representative data is shown in FIG. 1.

ADI-PEG 20 also moderated T-cell exhaustion. Induction of PD-1 on T-cells at 48 and 72 hours following stimulation was prevented by the treatment with 4 or 20 nM ADI-PEG 20 (see FIG. 2). When ADI-PEG 20 was present during PBMC stimulation PD-1 levels remained low in T-cells, similar to that at a resting state.

Figures 3A, 3B, 3C:
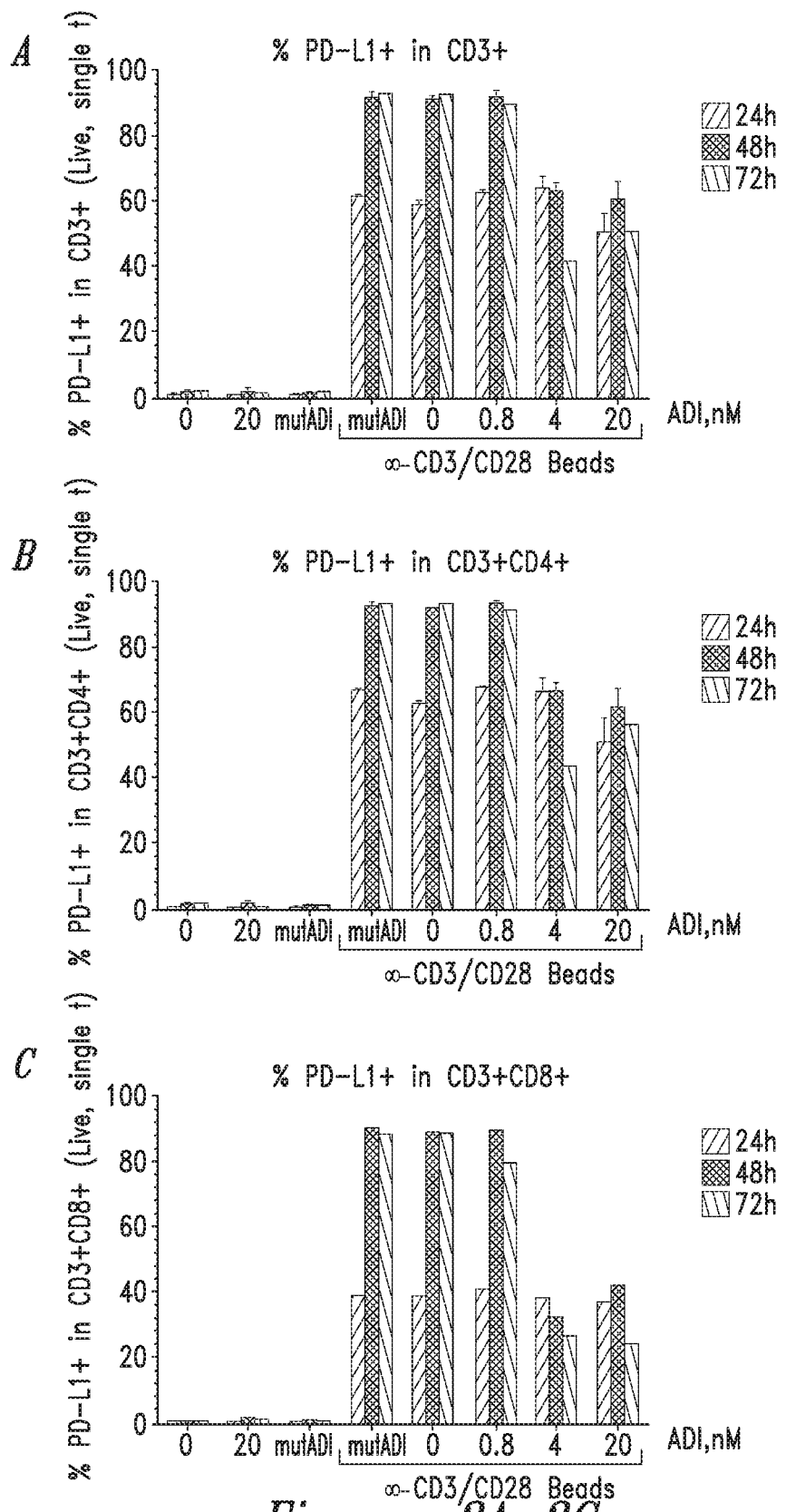
FIGS. 3A-3C show that ADI-PEG 20 moderates anti-CD3/CD28 induced PD-L1 upregulation on T-cells. PBMCs were stimulated with anti-CD3/CD28 Dynabeads in the presence or absence of ADI-PEG 20 or mutADI-PEG 20. Percentages of PD-L1+ cells among all T-cells (A), CD4+ T-cells (B) and CD8+ T-cells (C) were determined by flow cytometry at 24, 48, 72 hours.
Figures 4A, 4B, 4C:
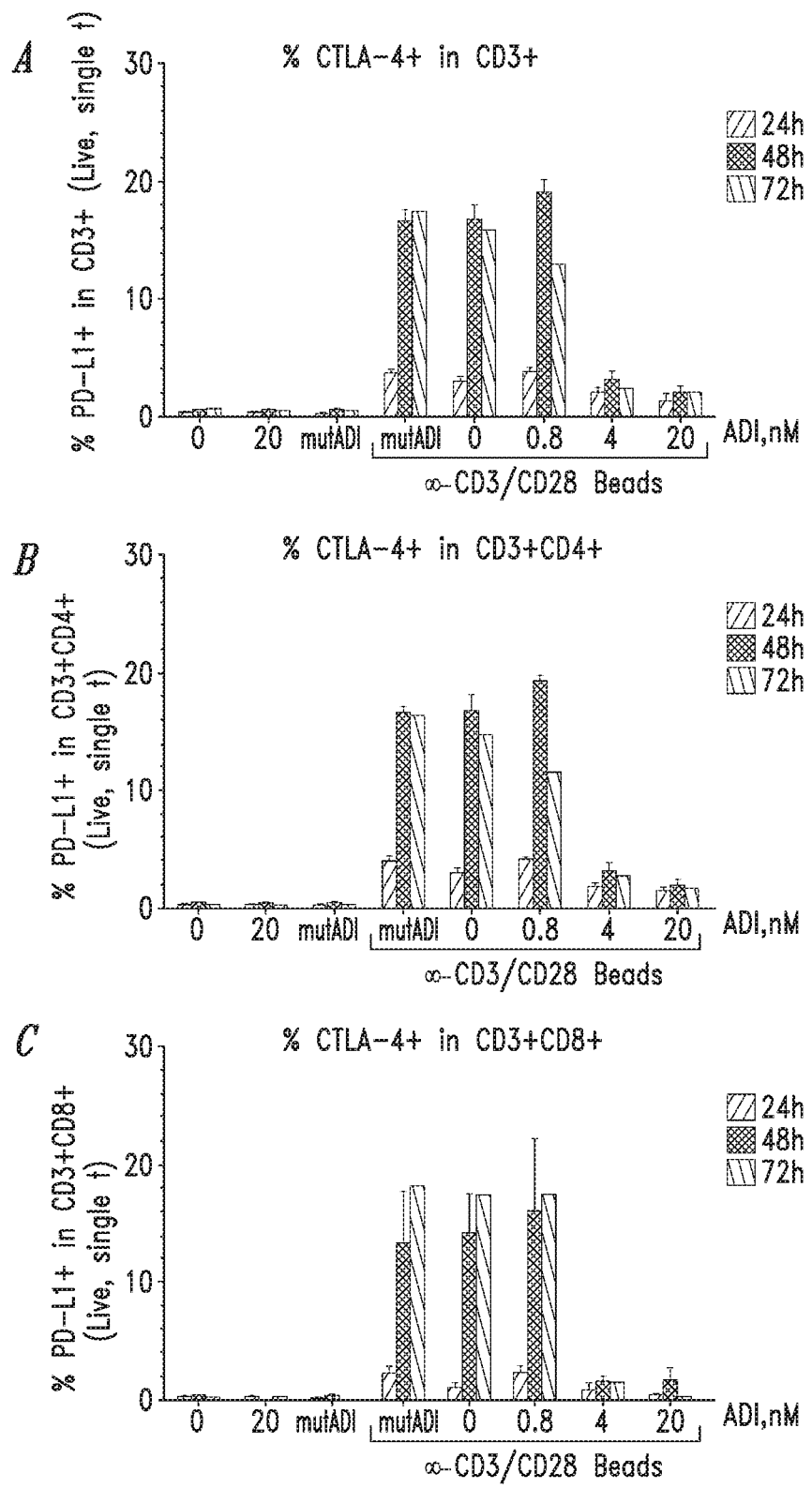
FIGS. 4A-4C show that ADI-PEG 20 inhibits anti-CD3/CD28 induced CTLA-4 upregulation on T-cells. PBMCs were stimulated with anti-CD3/CD28 Dynabeads in the presence or absence of ADI-PEG 20 or mutADI-PEG 20. Percentages of CTLA-4+ cells among all T-cells (A), CD4+ T-cells (B) and CD8+ T-cells (C) were determined by flow cytometry at 24, 48, and 72 hours.
Figures 5A, 5B, 5C:
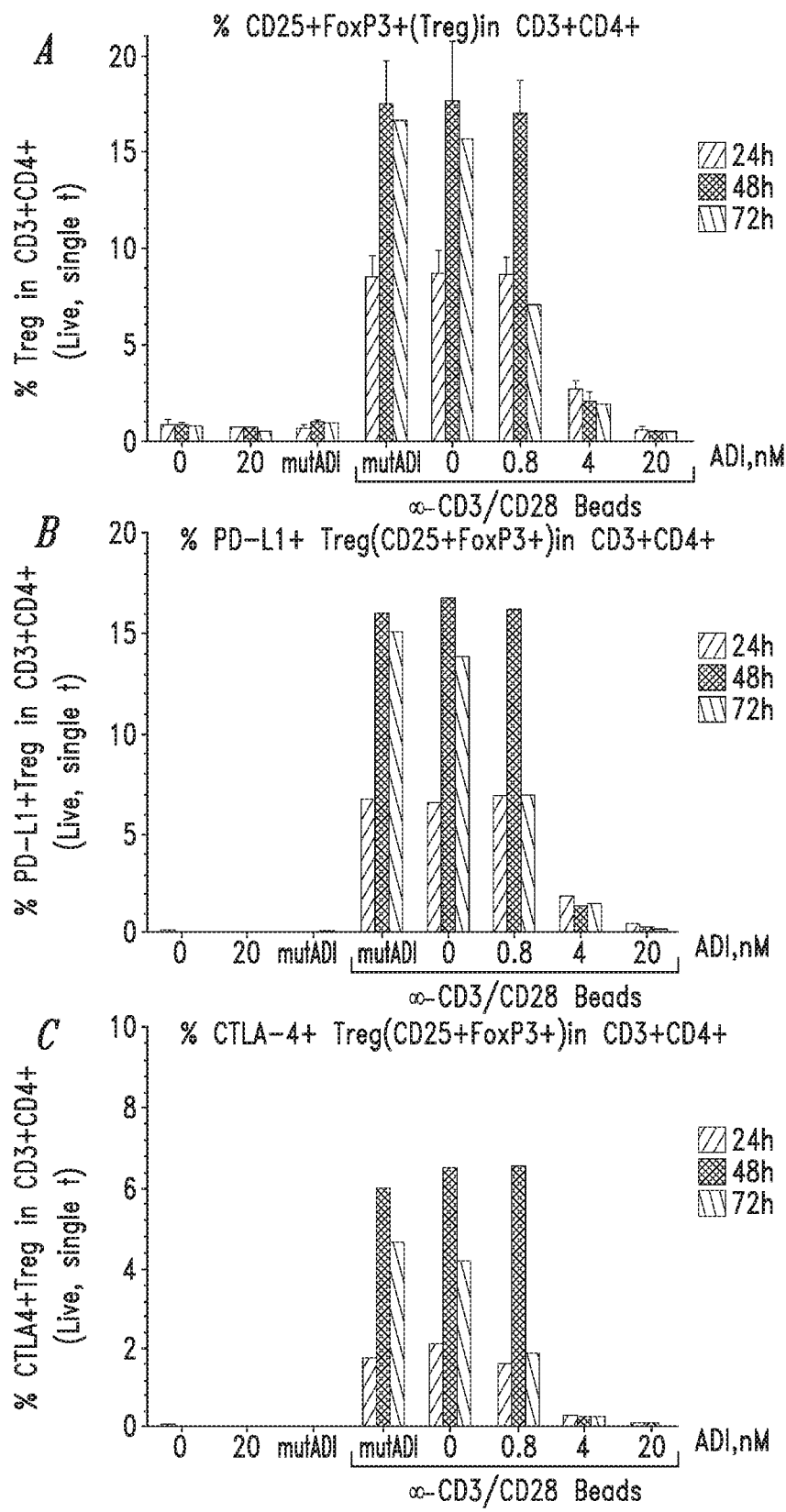
FIGS. 5A-5C show that ADI-PEG 20 reverses anti-CD3/CD28 induced Treg accumulation. PBMCs were stimulated with anti-CD3/CD28 Dynabeads in the presence or absence of ADI-PEG 20 or mutADI-PEG 20. Percentages of Treg cells among CD4+ T-cells were determined by flow cytometry at 24, 48, and 72 hours. Treg cells were determined by CD3+CD4+CD25+FoxP3+(A), CD3+CD4+CD25+FoxP3+PD-L1+(B) or CD3+CD4+CD25+FoxP3+CTLA-4+(C) markers.

Analysis of CTLA-4 expression on T-cell subsets revealed that 4 and 20 nM doses of ADI-PEG 20 also greatly reduced upregulation of CTLA-4 on both CD4+ and CD8+ cells following stimulation while 20 nM mutADI-PEG 20 or 0.8 nM ADI-PEG-20 did not noticeably affect CTLA-4 levels (see FIG. 3).

PD-L1 surface levels on T-cells were greatly upregulated following anti-CD3/CD28 beads (or PHA) stimulation with surface PD-L1 detectable on almost all T-cells by 48 hours. Presence of 4 or 20 nM (and not 0.8 nM) ADI-PEG 20 somewhat moderated this induction though percentage of PD-L1+ T-cells was still much higher than in the non-stimulated control. ADI-PEG 20 mediated reduction in PD-L1+ activated T-cells was more pronounced in CD8+ than in CD4+ cells (see FIG. 4).

ADI-PEG 20 down-modulated regulatory T-cells (Tregs). CD3/CD28 bead stimulation induced CD3+CD4+CD25+FoxP3+Tregs and ADI-PEG 20 reversed this effect in a concentration dependent manner (see FIG. 5). ADI-PEG 20 at 4 nM and 20 nM doses dramatically reduced Treg levels at all three tested time points with 20 nM dose producing a greater effect and bringing Treg levels to those found in non-stimulated PBMCs.

Similar to the T-cell activation data (CD69 levels) 0.8 nM ADI-PEG 20 didn't affect Treg cells at 24 and 48h time points but modulated them at 72 hours. Percentage of Treg among CD4+ cells in PBMC samples stimulated with anti-CD3/CD28 beads and treated with 0.8 nM ADI-PEG 20 was reduced ~2.x from 48h to 72h time point while in non-treated or mutADI-PEG 20 treated controls they decreased only slightly. This suggests that ADI-PEG 20 not only prevents accumulation of Treg cells but also reverses the same.

Treg cells were further analyzed for their expression of PD-L1 and CTLA-4 markers. Dose-dependent effects of ADI-PEG-20 on Treg cells expressing PD-L1+(majority of the Treg cells) or CTLA-4+ were similar to those observed with all Treg cells (CD3+CD4+CD25+FoxP3+). These results were similar whether or not gating on CD127-cells was included (almost all CD3+CD4+CD25+FoxP3+ were CD127-, data not shown).

Example 2

ADI-PEG 20 Induced T-Cell Infiltration and Showed Efficacy in B16-F10 Syngeneic Mouse Melanoma Model To assess the efficacy and effect of ADI-PEG 20 on T-cell activity in vivo, C57BL/6 mice were implanted with B16-F10 melanoma cells ($5\times10^5$ B16-F10 cells were implanted subcutaneously into the right flank of C57BL/6 mice in 0.1 ml PBS) and treated with test agents.

Figure 6A:
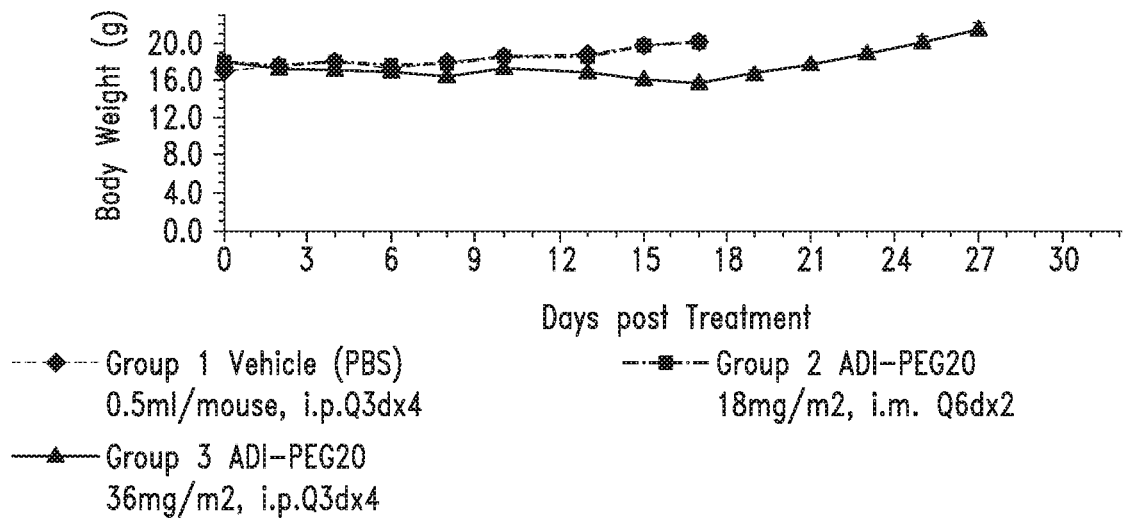
FIG. 6A shows the effect of ADI-PEG 20 on the body weight.
Figure 6B:
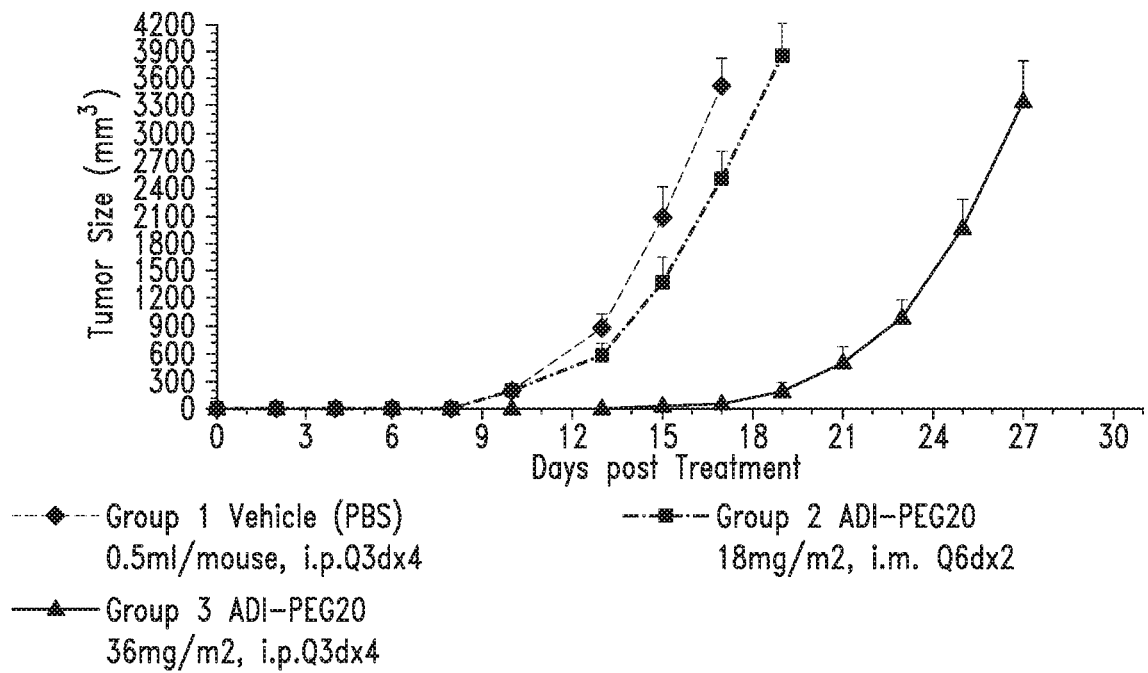
FIG. 6B shows the effect of ADI-PEG 20 on dynamic tumor volume, of C57BL/6 mice implanted with B16-F10 syngeneic tumors and treated with vehicle (PBS; control) versus ADI-PEG 20.

For efficacy, animals were randomized into three groups of eight mice each (n=8). The treatments were started the day after tumor inoculation. Each mouse in Group 1 received 0.5 ml vehicle (PBS) by intraperitoneal injection every 3 days for 4 times. Each mouse in Group 2 received 18 mg/m$^2$ ADI-PEG20 in 40 µl by intramuscular injection every 6 days for 2 times. Each mouse in Group 3 received 36 mg/m$^2$ ADI-PEG20 in 0.25 ml by intraperitoneal injection every 3 days for 4 times. Tumor size was measured three times per week until the average tumor volume of each group reached 3500-4000 mm$^3$, and the tumor volume was expressed in mm$^3$ using the formula:: $V=0.536\ a\times b2$ where a and b are the long and short diameters of the tumor, respectively. Body weight was measured and recorded three times a week during this period. The results were expressed as mean±S.E.M. as indicated. FIG. 6A shows the effect of ADI-PEG 20 on the body weight of inoculated mice, and FIG. 6B shows the effect of ADI-PEG 20 on dynamic tumor volume. These results show that ADI-PEG 20 significantly reduced tumor volume relative to time.

For tumor T-cell infiltration analysis, animals were randomized into two groups: 4 mice in the control group and 6 mice in the ADI-PEG 20 treatment group. Treatments were administered on day 1 and day 7 after tumor implantation. The control animals were injected intramuscularly with vehicle (PBS) and mice in the experimental group with 36 mg/m$^2$ of ADI-PEG 20, both in a 40 µl volume.

On day 14 after tumor implantation animals were euthanized and their tumors were removed, preserved in 4% paraformaldehyde solution for at least 24 hours, and paraffin-embedded for immunohistochemistry (IHC) analysis. Tumor sections were stained with anti-CD3 mAb to examine the presence of T-cells. Three sections were stained for each animal's tumor and level of T-cell infiltration was similar between the sections derived from the same tumor.

Figure 7:
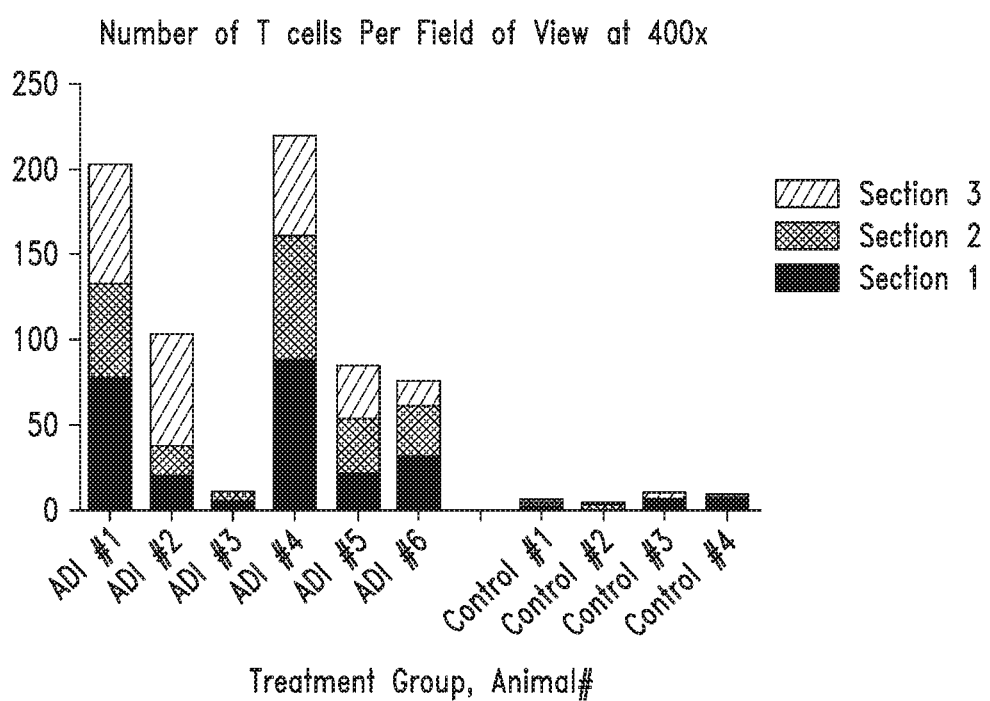
FIG. 7 shows that ADI-PEG 20 treatment induced T-cell infiltration in B16-F10 tumors in C57BL/6 mice. Number of T-cells detected in tumor sections of ADI-PEG 20 treated mice versus vehicle treated controls are shown.
Figure 8:
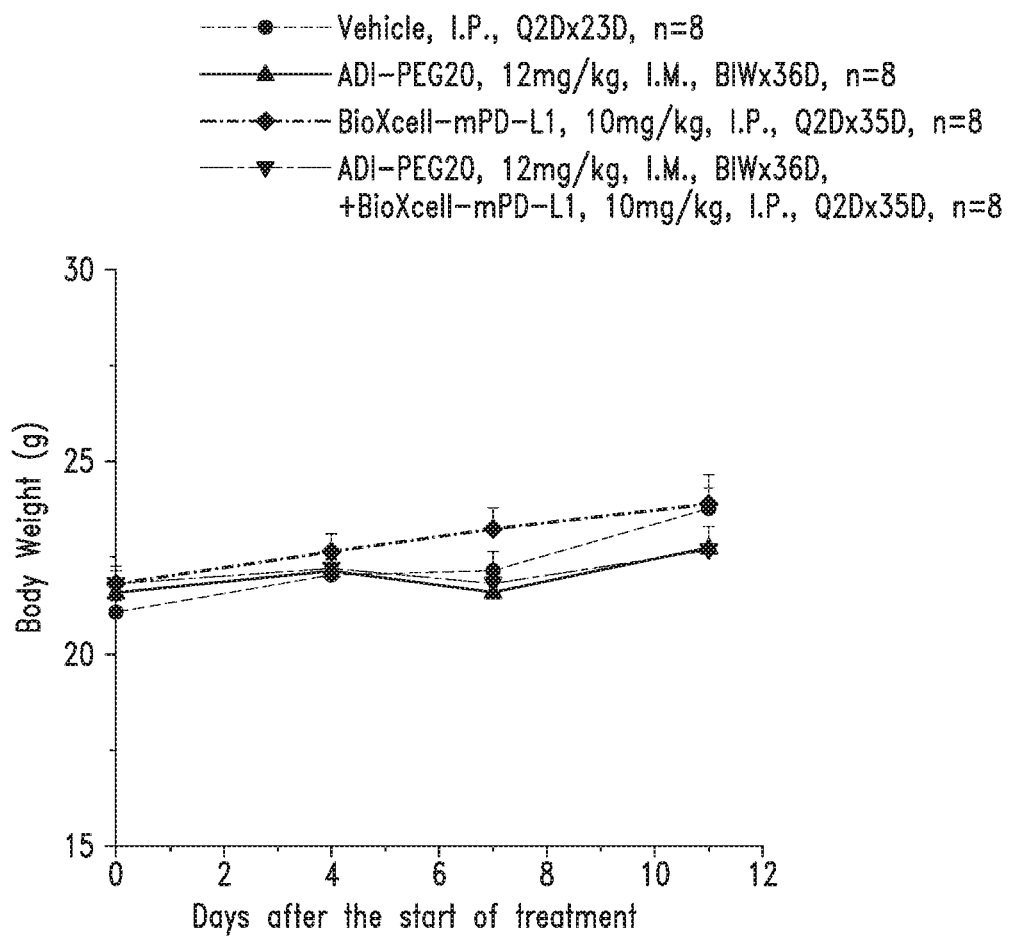
FIG. 8 shows body weight after administration of ADI-PEG20 and/or anti-PD-L1 mAb to female Balb/c mice bearing CT26 established tumors. Data points represent group mean body weights. Error bars represent standard error of the mean (SEM).

Five out of six animals treated with ADI-PEG 20 had a large presence of T-cells in their tumors (see FIG. 7), demonstrating that ADI-PEG 20 induced tumor infiltration by T-cells into a non-immunogenic B16-F10 tumor. Tumor sections from only one ADI-PEG 20 treated animal had very few infiltrating T-cells, similar to the levels observed in tumor sections from the control non-treated mice.

Example 3

Anti-Tumor Efficacy of ADI-PEG20 and Mouse Specific PD-1 and PD-L1 Antibodies in Syngeneic Mouse Models The efficacy of ADI-PEG in combination with PD-1 and PD-L1 antibodies was tested in two different mouse models of colorectal cancer.

CT26 Mouse Colorectal Cancer Model.

Balb/c mice were inoculated subcutaneously at the right flank with CT26 tumor cells ($2\times10^5$) in 0.1 ml of PBS for tumor development. The animals were randomized based on the tumor size, and treatment was started when the average tumor size reached 81 mm$^3$ for the efficacy study.

ADI-PEG20 was administrated via intramuscular injection (i.m.) and mouse-specific anti-PD-L1 antibody was administered intraperitoneally (i.p.)

Figure 9:
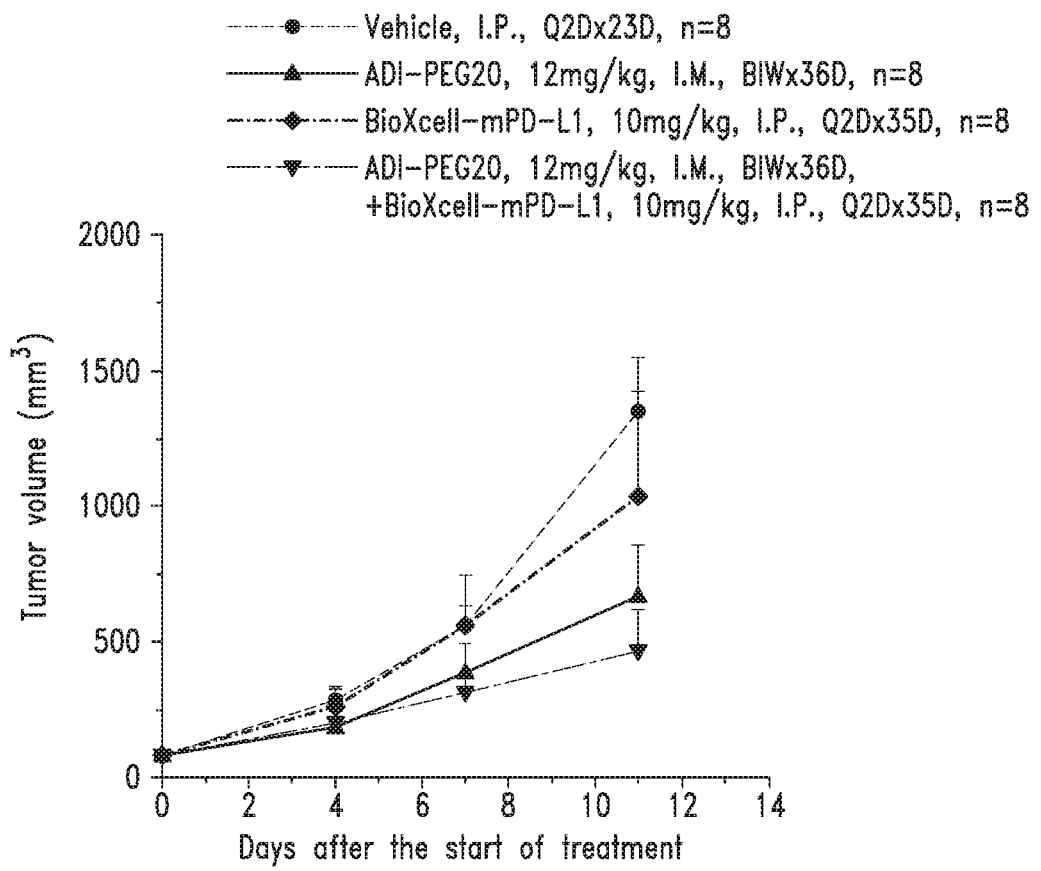
FIG. 9 shows tumor volume trace (Tumor Growth Curve) after administration of ADI-PEG20 and/or anti-PD-L1 mAb to female BALB/C mice bearing CT26 established tumors. Data points represent group mean, error bars represent standard error of the mean (SEM).

FIG. 9 and Table E1 (below) show the effects of ADI-PEG20, PD-L1 inhibitor, and combination therapy on tumor volume of tumor bearing mice.

TABLE E1

| Treatment | Tumor Size (mm$^3$)[a] at day 11 | T/C[b] (%) | TGI (%) | p value |
|---|---|---|---|---|
| Vehicle | 1347 ± 203 | — | — | — |
| ADI-PEG20, 12 mg/kg | 667 ± 189 | 50 | 54 | 0.113[c] |
| BioXcell-mPD-L1, 10 mg/kg | 1033 ± 388 | 77 | 25 | 0.889[c] |
| ADI-PEG20, 12 mg/kg + BioXcell-mPD-L1, 10 mg/kg | 469 ± 145 | 35 | 69 | 0.018[c] |

[a]Mean ± SEM.
[b]Tumor Growth Inhibition is calculated by dividing the group average tumor volume for the treated group by the group average tumor volume for the control group (T/C). For a test article to be considered to have anti-tumor activity, T/C must be 50% or less.
[c]p value is calculated based on tumor size with Games-Howell test.

The mean tumor size of control group reached 1,347 mm$^3$ at day 11 post treatment. Treatment of BioXcell-mPD-L1 at dose of 10 mg/kg presented significant antitumor activity, the mean tumor size reached 1,033 mm$^3$ (T/C value=77%; TGI value=25% and p=0.889 vs vehicle group). Treatment of ADI-PEG20 at dose of 12 mg/kg presented moderate antitumor activity; the mean tumor sizes were 667 mm$^3$ (T/C value=50%; TGI value=54% and p=0.113 vs vehicle group). ADI-PEG20 combined with BioXcell-mPD-L1 showed a significant antitumor activity as well; the mean tumor size was 469 mm$^3$ (T/C value=35%; TGI value=69% and p=0.018).

Figure 10:
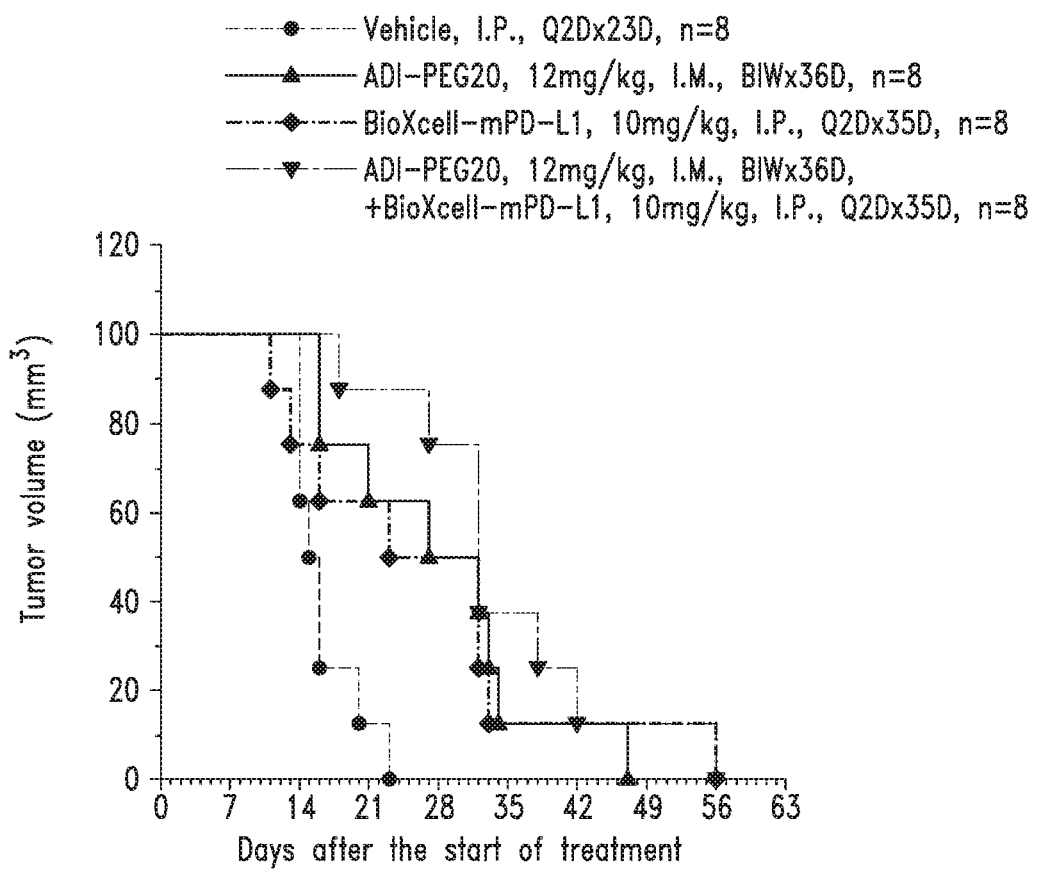
FIG. 10 shows the survival curve after administration of ADI-PEG20 and/or anti-PD-L1 mAb to female BALB/C mice bearing CT26 established tumors. Each animal was sacrificed when the tumor reached 3000 mm$^3$.
Figure 11:
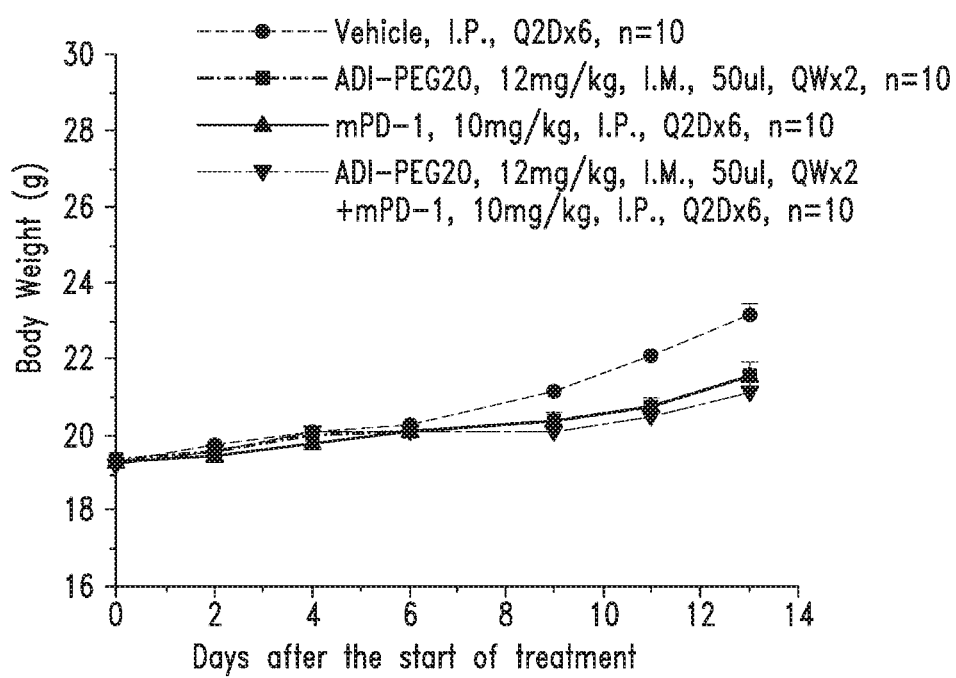
FIG. 11 shows body weight after administration of ADI-PEG 20 and/or anti-PD-1 mAb to female C57BL/6J mice bearing B16F10 established tumors. Data points represent group mean body weight. Error bars represent standard error of the mean (SEM).

FIG. 10 and Table E2 (below) show the effects of ADI-PEG20, PD-L1 inhibitor, and combination therapy on the survival of tumor bearing mice.

TABLE E2

| | | Survival. | | |
|---|---|---|---|---|
| Group | Treatment | MST (days) | ILS (%) | p value |
| 1 | Vehicle | 15.50[a] | — | — |
| 2 | ADI-PEG20, 12 mg/kg | 29.50 | 90 | 0.003[b] |
| 3 | BioXcell-mPD-L1, 10 mg/kg | 27.50 | 77 | 0.052[b] |
| 4 | ADI-PEG20, 12 mg/kg + BioXcell-mPD-L1, 10 mg/kg | 32.00 | 106 | 0.000[b] |

[a]The range of survival times;
[b]p value is calculated based on MST with Dunnett test.

The life span of the PBS treated control mice ranged from 14 to 21 days with an MST of 15.5 days. The ADI-PEG20 (12 mg/kg) treatment resulted in an MST value of 29.5 days, which represented an ILS of 90% (p=0.003) when compared with the control group. The dose of BioXcell-mPD-L1 (10 mg/kg) treatment produced an MST of 27.5 days (ILS=77%, p=0.052). ADI-PEG20 combined with BioXcell-mPD-L1 presented an MST of 32 days (ILS=106%, p=0.0002).

B16F10 Mouse Colorectal Cancer Model.

Female C57BL/6J mice were inoculated subcutaneously at the right flank with B16F10 tumor cells ($2\times10^5$) in 0.1 ml of PBS (containing 0.05 ml matrigel) for tumor development. The animals were randomized based on the body weight, and treatment was started the next day after the cell inoculation.

ADI-PEG20 was administrated via intramuscular injection (i.m.) and mouse-specific anti-PD-1 antibody was administered intraperitoneally (i.p.).

Figure 12:
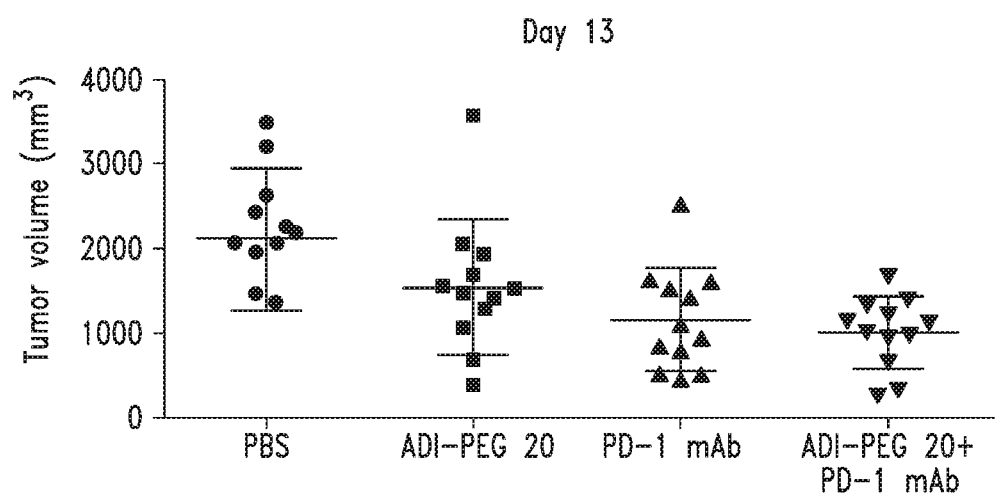
FIG. 12 shows tumor volume on day 13 after administration of ADI-PEG 20 and/or anti-PD-1 mAb to female C57BL/6J mice bearing B16F10 established tumors.

FIG. 12 shows the effects of ADI-PEG20, PD-1 inhibitor, and combination therapy on the survival of tumor bearing mice. The mean tumor size of control group reached 2,157 mm3 at day 13 after the start of treatment. The mean tumor size of the anti-PD-1 mAb (10 mg/kg) treated mice reached 1,078 mm3 (T/C value=50%; TGI value=50% and p<0.001 vs vehicle group). Treatment of ADI-PEG 20 at dose of 12 mg/kg produced antitumor activity; the mean tumor sizes were 1,466 mm3 (T/C value=68%; TGI value=32% and p=0.003 vs vehicle group). ADI-PEG 20 combined with anti-PD-1 mAb produced a significant antitumor activity; the mean tumor size was 1,002 mm3 (T/C value=46%; TGI value=54% and p<0.001).

The invention claimed is:

1. A method of treating a cancer in a subject in need thereof, comprising administering to the subject
   (a) an ADI polypeptide; and
   (b) an immune checkpoint modulatory agent wherein said agent is a PD-1 antagonist or a PD-L1 antagonist; and wherein (i) the cancer in the subject is one targeted for immunotherapy treatment and (ii) the ADI-polypeptide is administered to enhance the immune activity of the immune checkpoint modulatory agent.

2. The method of claim 1, wherein the ADI polypeptide comprises, consists, or consists essentially of
   (i) a sequence selected from SEQ ID NO: 1-56; or
   (ii) a sequence that is at least 95%, identical to a sequence selected from SEQ ID NO: 1-56.

3. The method of claim 1, wherein the ADI polypeptide is covalently bonded via an optional linker to at least one PEG molecule.

4. The method of claim 3, wherein the ADI polypeptide is covalently bonded to more than one PEG molecule.

5. The method of claim 3, wherein the ADI polypeptide is covalently bonded to about 1 to about 10 PEG molecules.

6. The method of claim 5, wherein the ADI polypeptide is covalently bonded to about 2 to about 8 PEG molecules.

7. The method of claim 3, wherein the PEG molecules are straight chain or branch chain PEG molecules.

8. The method of claim 3, wherein the PEG has a total average molecular weight of from about 1,000 to about 40,000 Daltons.

9. The method of claim 3, wherein the PEG has a total average molecular weight of from about 10,000 to about 30,000 Daltons.

10. The method of claim 9, wherein the PEG has a total average molecular weight of about 20,000 Daltons.

11. The method of claim 3, wherein the linker is a succinyl group, an amide group, an imide group, a carbamate group, an ester group, an epoxy group, a carboxyl group, a hydroxyl group, a carbohydrate, a tyrosine group, a cysteine group, a histidine group, a methylene group, or any combinations thereof.

12. The method of claim 11, wherein the source of the succinyl group is succinimidyl succinate.

13. The method of claim 1, wherein the ADI polypeptide is pegylated arginine deiminase (ADI-PEG).

14. The method of claim 13, wherein the ADI-PEG is ADI-PEG 20.

15. The method of claim 1, wherein the antagonist is a PD-LI antagonist selected from one or more of an antibody or antigen-binding fragment or small molecule that specifically binds thereto, atezolizumab (MPDL3280A), avelumab (MSB0010718C), and durvalumab (MEDI4736), and wherein the cancer is optionally selected from one or more of colorectal cancer, melanoma, breast cancer, non-small-cell lung carcinoma, bladder cancer, and renal cell carcinoma.

16. The method of claim 1, wherein the PD-I antagonist selected from one or more of an antibody or antigen-binding fragment or small molecule that specifically binds thereto, nivolumab, pembrolizumab, PDR00I, and pidilizumab.

17. The method of claim 16, wherein the PD-I antagonist is nivolumab and the cancer is optionally selected from one or more of Hodgkin's lymphoma, melanoma, non-small cell lung cancer, hepatocellular carcinoma, renal cell carcinoma, and ovarian cancer.

18. The method of claim 16, wherein the PD-I antagonist is pembrolizumab and the cancer is optionally selected from one or more of melanoma, non-small cell lung cancer, small cell lung cancer, head and neck cancer, and urothelial cancer.

19. The method of claim 1, wherein (a) and (b) are administered separately.

20. The method of claim 1, wherein (a) and (b) are administered together as part of the same composition.

21. The method of claim 1, wherein the cancer is selected from one or more of hepatocellular carcinoma, melanoma, pancreatic cancer, prostate cancer, small cell lung cancer, mesothelioma, lymphoma, hepatoma, sarcoma, leukemia, breast cancer, ovarian cancer, colorectal cancer, gastric cancer, non-small cell lung cancer (NSCLC), kidney cancer, bladder cancer, uterine cancer, esophageal cancer, brain cancer, head and neck cancers, cervical cancer, and testicular cancer.

22. The method of claim 21, wherein:
   (i) the melanoma is metastatic melanoma;
   (ii) the leukemia is selected from the group consisting of lymphocytic leukemia, chronic myelogenous leukemia, acute myeloid leukemia and relapsed acute myeloid leukemia;
   (iii) the gastric cancer is stomach cancer; and
   (iv) the brain cancer is selected from the group consisting of glioma and glioblastoma multiforme.

23. The method of claim 1 wherein the cancer is an argininosuccinate synthetase (ASS)- or argininosuccinate lyase (ASL)-deficient cancer.

24. A method of adoptive T-cell immunotherapy for treating a cancer in a subject in need thereof, comprising
   (a) incubating ex vivo-derived T-cells (i) with or (ii) in arginine-free medium supplemented with citrulline;
   (b) administering the ex vivo-derived T-cells to the subject.

25. The method of claim 24, wherein the ADI polypeptide is pegylated arginine deiminase (ADI-PEG).

26. The method of claim 25, wherein the ADI-PEG is ADI-PEG 20.

27. A method of increasing T-cell activation and/or regulatory T-cell (Treg) downregulation in vitro or ex vivo, comprising (a) incubating T-cells with an ADI polypeptide wherein said ADI polypeptide converts arginine to citrulline, (b) incubating T-cells in an arginine-free medium supplemented with citrulline, or both (a) and (b).

28. The method of claim 27, wherein the arginine depletion agent is pegylated arginine deiminase (ADI-PEG).

29. The method of claim 28, wherein the ADI-PEG is ADI-PEG 20.

30. A composition or patient care kit, comprising:
  (a) an ADI polypeptide which converts arginine to citrulline; and
  (b) an immune checkpoint modulatory agent wherein said agent is a PD-1 antagonist or a PD-L1 antagonist.

31. The composition or patient care kit of claim 30, wherein the arginine depletion agent is pegylated arginine deiminase (ADI-PEG).

32. The composition or patient care kit of claim 31, wherein the ADI-PEG is ADI-PEG 20.

\* \* \* \* \*

SEQUENCE LISTING

<160> NUMBER OF SEQ ID NOS: 56

<210> SEQ ID NO 1
<211> LENGTH: 409
<212> TYPE: PRT
<213> ORGANISM: Mycoplasma hominis

<400> SEQUENCE: 1

Met Ser Val Phe Asp Ser Lys Phe Asn Gly Ile His Val Tyr Ser Glu

```
1               5                   10                  15
Ile Gly Glu Leu Glu Thr Val Leu Val His Glu Pro Gly Arg Glu Ile
                20                  25                  30
Asp Tyr Ile Thr Pro Ala Arg Leu Asp Glu Leu Leu Phe Ser Ala Ile
                35                  40                  45
Leu Glu Ser His Asp Ala Arg Lys Glu His Gln Ser Phe Val Lys Ile
                50                  55                  60
Met Lys Asp Arg Gly Ile Asn Val Val Glu Leu Thr Asp Leu Val Ala
65                  70                  75                  80
Glu Thr Tyr Asp Leu Ala Ser Lys Ala Ala Lys Glu Glu Phe Ile Glu
                85                  90                  95
Thr Phe Leu Glu Glu Thr Val Pro Val Leu Thr Glu Ala Asn Lys Lys
                100                 105                 110
Ala Val Arg Ala Phe Leu Leu Ser Lys Pro Thr His Glu Met Val Glu
                115                 120                 125
Phe Met Met Ser Gly Ile Thr Lys Tyr Glu Leu Gly Val Glu Ser Glu
130                 135                 140
Asn Glu Leu Ile Val Asp Pro Met Pro Asn Leu Tyr Phe Thr Arg Asp
145                 150                 155                 160
Pro Phe Ala Ser Val Gly Asn Gly Val Thr Ile His Phe Met Arg Tyr
                165                 170                 175
Ile Val Arg Arg Arg Glu Thr Leu Phe Ala Arg Phe Val Phe Arg Asn
                180                 185                 190
His Pro Lys Leu Val Lys Thr Pro Trp Tyr Tyr Asp Pro Ala Met Lys
                195                 200                 205
Met Pro Ile Glu Gly Gly Asp Val Phe Ile Tyr Asn Asn Glu Thr Leu
210                 215                 220
Val Val Gly Val Ser Glu Arg Thr Asp Leu Asp Thr Ile Thr Leu Leu
225                 230                 235                 240
Ala Lys Asn Ile Lys Ala Asn Lys Glu Val Glu Phe Lys Arg Ile Val
                245                 250                 255
Ala Ile Asn Val Pro Lys Trp Thr Asn Leu Met His Leu Asp Thr Trp
                260                 265                 270
Leu Thr Met Leu Asp Lys Asn Lys Phe Leu Tyr Ser Pro Ile Ala Asn
                275                 280                 285
Asp Val Phe Lys Phe Trp Asp Tyr Asp Leu Val Asn Gly Gly Ala Glu
                290                 295                 300
Pro Gln Pro Gln Leu Asn Gly Leu Pro Leu Asp Lys Leu Leu Ala Ser
305                 310                 315                 320
Ile Ile Asn Lys Glu Pro Val Leu Ile Pro Ile Gly Gly Ala Gly Ala
                325                 330                 335
Thr Glu Met Glu Ile Ala Arg Glu Thr Asn Phe Asp Gly Thr Asn Tyr
                340                 345                 350
Leu Ala Ile Lys Pro Gly Leu Val Ile Gly Tyr Asp Arg Asn Glu Lys
                355                 360                 365
Thr Asn Ala Ala Leu Lys Ala Ala Gly Ile Thr Val Leu Pro Phe His
                370                 375                 380
Gly Asn Gln Leu Ser Leu Gly Met Gly Asn Ala Arg Cys Met Ser Met
385                 390                 395                 400
Pro Leu Ser Arg Lys Asp Val Lys Trp
                405

<210> SEQ ID NO 2
```

```
<211> LENGTH: 409
<212> TYPE: PRT
<213> ORGANISM: Artificial Sequence
<220> FEATURE:
<223> OTHER INFORMATION: Mutated arginine deaminase

<400> SEQUENCE: 2

Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Gln Ser Phe Val Lys Ile
    50                  55                  60

Met Lys Asp Arg Gly Ile Asn Val Val Glu Leu Thr Asp Leu Val Ala
65                  70                  75                  80

Glu Thr Tyr Asp Leu Ala Ser Lys Ala Ala Lys Glu Glu Phe Ile Glu
                85                  90                  95

Thr Phe Leu Glu Glu Thr Val Pro Val Leu Thr Glu Ala Asn Lys Glu
            100                 105                 110

Ala Val Arg Ala Phe Leu Leu Ser Lys Pro Thr His Glu Met Val Glu
        115                 120                 125

Phe Met Met Ser Gly Ile Thr Lys Tyr Glu Leu Gly Val Glu Ser Glu
130                 135                 140

Asn Glu Leu Ile Val Asp Pro Met Pro Asn Leu Tyr Phe Thr Arg Asp
145                 150                 155                 160

Pro Phe Ala Ser Val Gly Asn Gly Val Thr Ile His Phe Met Arg Tyr
                165                 170                 175

Ile Val Arg Arg Arg Glu Thr Leu Phe Ala Arg Phe Val Phe Arg Asn
            180                 185                 190

His Pro Lys Leu Val Lys Thr Pro Trp Tyr Tyr Asp Pro Ala Met Lys
        195                 200                 205

Met Ser Ile Glu Gly Gly Asp Val Phe Ile Tyr Asn Asn Glu Thr Leu
210                 215                 220

Val Val Gly Val Ser Glu Arg Thr Asp Leu Asp Thr Ile Thr Leu Leu
225                 230                 235                 240

Ala Lys Asn Ile Lys Ala Asn Lys Glu Val Glu Phe Lys Arg Ile Val
                245                 250                 255

Ala Ile Asn Val Pro Lys Trp Thr Asn Leu Met His Leu Asp Thr Trp
            260                 265                 270

Leu Thr Met Leu Asp Lys Asn Lys Phe Leu Tyr Ser Pro Ile Ala Asn
        275                 280                 285

Asp Val Phe Lys Phe Trp Asp Tyr Asp Leu Val Asn Gly Gly Ala Glu
    290                 295                 300

Pro Gln Pro Gln Leu Asn Gly Leu Pro Leu Asp Lys Leu Leu Ala Ser
305                 310                 315                 320

Ile Ile Asn Lys Glu Pro Val Leu Ile Pro Ile Gly Gly Ala Gly Ala
                325                 330                 335

Thr Glu Met Glu Ile Ala Arg Glu Thr Asn Phe Asp Gly Thr Asn Tyr
            340                 345                 350

Leu Ala Ile Lys Pro Gly Leu Val Ile Gly Tyr Asp Arg Asn Glu Lys
        355                 360                 365

Thr Asn Ala Ala Leu Lys Ala Ala Gly Ile Thr Val Leu Pro Phe His
    370                 375                 380
```

Gly Asn Gln Leu Ser Leu Gly Met Gly Asn Ala Arg Cys Met Ser Met
385                 390                 395                 400

Pro Leu Ser Arg Lys Asp Val Lys Trp
                405

<210> SEQ ID NO 3
<211> LENGTH: 392
<212> TYPE: PRT
<213> ORGANISM: Mycoplasma phocicerebrale

<400> SEQUENCE: 3

Ile His Val Tyr Ser Glu Ile Gly Glu Leu Glu Thr Val Leu Val His
1               5                   10                  15

Glu Pro Gly Arg Glu Ile Asp Tyr Ile Thr Pro Ala Arg Leu Asp Glu
                20                  25                  30

Leu Leu Phe Ser Ala Ile Leu Glu Ser His Asp Ala Arg Lys Glu His
                35                  40                  45

Gln Ser Phe Val Lys Gln Leu Lys Asp Asn Gly Ile Asn Val Val Glu
50                  55                  60

Leu Thr Asp Leu Val Ala Glu Thr Phe Asp Leu Ala Ser Lys Glu Glu
65                  70                  75                  80

Gln Glu Lys Leu Ile Glu Glu Phe Leu Glu Asp Ser Glu Pro Val Leu
                85                  90                  95

Ser Glu Ala His Lys Thr Ala Val Arg Lys Phe Leu Thr Ser Arg Lys
                100                 105                 110

Ser Thr Arg Glu Met Val Glu Phe Met Met Ala Gly Ile Thr Lys Tyr
                115                 120                 125

Asp Leu Gly Ile Glu Ala Asp His Glu Leu Ile Val Asp Pro Met Pro
                130                 135                 140

Asn Leu Tyr Phe Thr Arg Asp Pro Phe Ala Ser Val Gly Asn Gly Val
145                 150                 155                 160

Thr Ile His Tyr Met Arg Tyr Lys Val Arg Gln Arg Glu Thr Leu Phe
                165                 170                 175

Ser Arg Phe Val Phe Ser Asn His Pro Lys Leu Val Lys Thr Pro Trp
                180                 185                 190

Tyr Tyr Asp Pro Ala Met Lys Met Ser Ile Glu Gly Gly Asp Val Phe
                195                 200                 205

Ile Tyr Asn Asn Asp Thr Leu Val Val Gly Val Ser Glu Arg Thr Asp
                210                 215                 220

Leu Glu Thr Ile Thr Leu Leu Ala Lys Asn Ile Lys Ala Asn Lys Glu
225                 230                 235                 240

Val Glu Phe Lys Arg Ile Val Ala Ile Asn Val Pro Lys Trp Thr Asn
                245                 250                 255

Leu Met His Leu Asp Thr Trp Leu Thr Met Leu Asp Lys Asp Lys Phe
                260                 265                 270

Leu Tyr Ser Pro Ile Ala Asn Asp Val Phe Lys Phe Trp Asp Tyr Asp
                275                 280                 285

Leu Val Asn Gly Gly Ala Glu Pro Gln Pro Lys Glu Asn Gly Leu Pro
                290                 295                 300

Leu Glu Gly Leu Leu Gln Ser Ile Ile Asn Lys Lys Pro Val Leu Ile
305                 310                 315                 320

Pro Ile Ala Gly Asn Asn Ala Ser His Ile Asp Ile Glu Arg Glu Thr
                325                 330                 335

His Phe Asp Gly Thr Asn Tyr Leu Ala Ile Lys Pro Gly Val Val Ile

```
                    340             345             350
Gly Tyr Ala Arg Asn Glu Lys Thr Asn Ala Ala Leu Ala Ala Ala Gly
        355                 360                 365

Ile Lys Val Leu Pro Phe His Gly Asn Gln Leu Ser Leu Gly Met Gly
    370                 375                 380

Asn Ala Arg Cys Met Ser Met Pro
385                 390

<210> SEQ ID NO 4
<211> LENGTH: 410
<212> TYPE: PRT
<213> ORGANISM: Mycoplasma arginini

<400> SEQUENCE: 4

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Lys Gln Phe Val Ala Glu
    50                  55                  60

Leu Lys Ala Asn Asp Ile Asn Val Val Glu Leu Ile Asp Leu Val Ala
65                  70                  75                  80

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu Glu His Lys Val
            100                 105                 110

Val Val Arg Asn Phe Leu Lys Ala Lys Lys Thr Ser Arg Glu Leu Val
        115                 120                 125

Glu Ile Met Met Ala Gly Ile Thr Lys Tyr Asp Leu Gly Ile Glu Ala
    130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Ile Asn Thr Pro Trp Tyr Tyr Asp Pro Ser Leu
        195                 200                 205

Lys Leu Ser Ile Glu Gly Gly Asp Val Phe Ile Tyr Asn Asn Asp Thr
    210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Ala
    290                 295                 300

Glu Pro Gln Pro Val Glu Asn Gly Leu Pro Leu Glu Gly Leu Leu Gln
305                 310                 315                 320
```

```
Ser Ile Ile Asn Lys Lys Pro Val Leu Ile Pro Ile Ala Gly Glu Gly
            325                 330                 335

Ala Ser Gln Met Glu Ile Glu Arg Glu Thr His Phe Asp Gly Thr Asn
        340                 345                 350

Tyr Leu Ala Ile Arg Pro Gly Val Val Ile Gly Tyr Ser Arg Asn Glu
            355                 360                 365

Lys Thr Asn Ala Ala Leu Glu Ala Ala Gly Ile Lys Val Leu Pro Phe
370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
            405                 410

<210> SEQ ID NO 5
<211> LENGTH: 409
<212> TYPE: PRT
<213> ORGANISM: Mycoplasma arthritidis

<400> SEQUENCE: 5

Met Ser Val Phe Asp Ser Lys Phe Lys Gly Ile His Val Tyr Ser Glu
1               5                   10                  15

Ile Gly Glu Leu Glu Thr Val Leu Val His Glu Pro Gly Lys Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Lys Glu Phe Val Ala Glu
50                  55                  60

Leu Lys Lys Arg Gly Ile Asn Val Val Glu Leu Val Asp Leu Ile Val
65                  70                  75                  80

Glu Thr Tyr Asp Leu Ala Ser Lys Glu Ala Lys Glu Lys Leu Leu Glu
            85                  90                  95

Glu Phe Leu Asp Asp Ser Val Pro Val Leu Ser Asp Glu His Arg Ala
        100                 105                 110

Ala Val Lys Lys Phe Leu Gln Ser Gln Lys Ser Thr Arg Ser Leu Val
    115                 120                 125

Glu Tyr Met Ile Ala Gly Ile Thr Lys His Asp Leu Lys Ile Glu Ser
130                 135                 140

Asp Leu Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
            165                 170                 175

Tyr Lys Val Arg Gln Arg Glu Thr Leu Phe Ser Arg Phe Val Phe Ser
        180                 185                 190

Asn His Pro Lys Leu Val Asn Thr Pro Trp Tyr Tyr Asp Pro Ala Glu
    195                 200                 205

Gly Leu Ser Ile Glu Gly Gly Asp Val Phe Ile Tyr Asn Asn Asp Thr
210                 215                 220

Leu Val Val Gly Val Ser Glu Arg Thr Asp Leu Gln Thr Ile Thr Leu
225                 230                 235                 240

Leu Ala Lys Asn Ile Lys Ala Asn Lys Glu Cys Glu Phe Lys Arg Ile
            245                 250                 255

Val Ala Ile Asn Val Pro Lys Trp Thr Asn Leu Met His Leu Asp Thr
        260                 265                 270

Trp Leu Thr Met Leu Asp Lys Asp Lys Phe Leu Tyr Ser Pro Ile Ala
    275                 280                 285
```

```
Asn Asp Val Phe Lys Phe Trp Asp Tyr Asp Leu Val Asn Gly Gly Asp
        290                 295                 300

Ala Pro Gln Pro Val Asp Asn Gly Leu Pro Leu Glu Asp Leu Leu Lys
305                 310                 315                 320

Ser Ile Ile Gly Lys Lys Pro Thr Leu Ile Pro Ile Ala Gly Ala Gly
                325                 330                 335

Ala Ser Gln Ile Asp Ile Glu Arg Glu Thr His Phe Asp Gly Thr Asn
                340                 345                 350

Tyr Leu Ala Val Ala Pro Gly Ile Val Ile Gly Tyr Ala Arg Asn Glu
            355                 360                 365

Lys Thr Asn Ala Ala Leu Glu Ala Ala Gly Ile Thr Val Leu Pro Phe
        370                 375                 380

Arg Gly Asn Gln Leu Ser Leu Gly Met Gly Asn Ala Arg Cys Met Ser
385                 390                 395                 400

Met Pro Leu Ser Arg Lys Asp Val Lys
                405

<210> SEQ ID NO 6
<211> LENGTH: 408
<212> TYPE: PRT
<213> ORGANISM: Mycoplasma orale
<220> FEATURE:
<221> NAME/KEY: misc_feature
<222> LOCATION: (201)..(201)
<223> OTHER INFORMATION: Xaa can be any naturally occurring amino acid
<220> FEATURE:
<221> NAME/KEY: misc_feature
<222> LOCATION: (263)..(263)
<223> OTHER INFORMATION: Xaa can be any naturally occurring amino acid
<220> FEATURE:
<221> NAME/KEY: misc_feature
<222> LOCATION: (272)..(272)
<223> OTHER INFORMATION: Xaa can be any naturally occurring amino acid
<220> FEATURE:
<221> NAME/KEY: misc_feature
<222> LOCATION: (294)..(294)
<223> OTHER INFORMATION: Xaa can be any naturally occurring amino acid

<400> SEQUENCE: 6

Ser Val Phe Ser Asp Lys Phe Asn Gly Ile His Val Tyr Ser Glu Ile
1               5                   10                  15

Gly Asp Leu Glu Ser Val Leu Val His Glu Pro Gly Lys Glu Ile Asp
            20                  25                  30

Tyr Ile Thr Pro Ala Arg Leu Asp Glu Leu Leu Phe Ser Ala Ile Leu
        35                  40                  45

Glu Ser Thr Asp Ala Arg Lys Glu His Lys Glu Phe Val Glu Ile Leu
50                  55                  60

Lys Lys Gln Gly Ile Asn Val Val Glu Leu Val Asp Leu Val Val Glu
65                  70                  75                  80

Thr Tyr Asn Leu Val Asp Lys Lys Thr Gln Glu Lys Leu Leu Lys Asp
                85                  90                  95

Phe Leu Asp Asp Ser Glu Pro Val Leu Ser Pro Glu His Arg Lys Ala
            100                 105                 110

Val Glu Lys Phe Leu Lys Ser Leu Lys Ser Thr Lys Glu Leu Ile Gln
        115                 120                 125

Tyr Met Met Ala Gly Ile Thr Lys Tyr Asp Leu Gly Ile Lys Ala Asp
130                 135                 140

Lys Glu Leu Ile Val Asp Pro Met Pro Asn Leu Tyr Phe Thr Arg Asp
145                 150                 155                 160
```

-continued

Pro Phe Ala Ser Val Gly Asn Gly Val Thr Ile His Tyr Met Arg Tyr
            165                 170                 175

Lys Val Arg Gln Arg Glu Thr Leu Phe Ser Lys Phe Ile Phe Thr Asn
            180                 185                 190

His Pro Lys Leu Val Lys Thr Pro Xaa Tyr Tyr Asp Pro Ala Met Lys
            195                 200                 205

Leu Ser Ile Glu Gly Gly Asp Val Phe Ile Tyr Asn Asn Asp Thr Leu
210                 215                 220

Val Val Gly Val Ser Glu Arg Thr Asp Leu Thr Ile Thr Leu Leu
225                 230                 235                 240

Ala Lys Asn Ile Lys Ala Asn Lys Glu Cys Glu Phe Lys Arg Ile Val
            245                 250                 255

Ala Ile Asn Val Pro Lys Xaa Thr Asn Leu Met His Leu Asp Thr Xaa
            260                 265                 270

Leu Thr Met Leu Asp Lys Asp Lys Phe Leu Tyr Ser Pro Ile Ala Asn
            275                 280                 285

Asp Val Phe Lys Phe Xaa Asp Tyr Asp Leu Val Asn Gly Gly Ser Asn
            290                 295                 300

Pro Glu Pro Val Val Asn Gly Leu Pro Leu Asp Lys Leu Leu Glu Ser
305                 310                 315                 320

Ile Ile Asn Lys Lys Pro Val Leu Ile Pro Ile Ala Gly Lys Gly Ala
            325                 330                 335

Thr Glu Ile Glu Thr Ala Val Glu Thr His Phe Asp Gly Thr Asn Tyr
            340                 345                 350

Leu Ala Ile Lys Pro Gly Val Val Val Gly Tyr Ser Arg Asn Val Lys
            355                 360                 365

Thr Asn Ala Ala Leu Glu Ala Asn Gly Ile Lys Val Leu Pro Phe Lys
            370                 375                 380

Gly Asn Gln Leu Ser Leu Gly Met Gly Asn Ala Arg Cys Met Ser Met
385                 390                 395                 400

Pro Leu Ser Arg Lys Asp Val Lys
            405

<210> SEQ ID NO 7
<211> LENGTH: 391
<212> TYPE: PRT
<213> ORGANISM: Mycoplasma gateae

<400> SEQUENCE: 7

Ile His Val Tyr Ser Glu Ile Gly Glu Leu Glu Ser Val Leu Val His
1               5                   10                  15

Glu Pro Gly Arg Glu Ile Asp Tyr Ile Thr Pro Ala Arg Leu Asp Glu
            20                  25                  30

Leu Leu Phe Ser Ala Ile Leu Glu Ser His Asp Ala Arg Lys Glu His
            35                  40                  45

Lys Leu Phe Val Ser Glu Leu Lys Ala Asn Asp Ile Asn Val Val Glu
            50                  55                  60

Leu Thr Asp Leu Val Thr Glu Thr Tyr Asp Leu Ala Ser Gln Glu Ala
65                  70                  75                  80

Lys Asp Asn Leu Ile Glu Glu Phe Leu Glu Asp Ser Glu Pro Val Leu
            85                  90                  95

Thr Glu Glu Leu Lys Ser Val Val Arg Thr Tyr Leu Lys Ser Ile Lys
            100                 105                 110

Ser Thr Arg Glu Leu Ile Gln Met Met Met Ala Gly Ile Thr Lys Tyr
            115                 120                 125

Asp Leu Gly Ile Glu Ala Asp His Glu Leu Ile Val Asp Pro Met Pro
            130                 135                 140

Asn Leu Tyr Phe Thr Arg Asp Pro Phe Ala Ser Val Gly Asn Gly Val
145                 150                 155                 160

Thr Ile His Tyr Met Arg Tyr Lys Val Arg Gln Arg Glu Thr Leu Phe
                165                 170                 175

Ser Arg Phe Val Phe Ser Asn His Pro Lys Leu Val Asn Thr Pro Trp
            180                 185                 190

Tyr Tyr Asp Pro Ser Leu Lys Leu Ser Ile Glu Gly Asp Val Phe
            195                 200                 205

Ile Tyr Asn Asn Asn Thr Leu Val Val Gly Val Ser Glu Arg Thr Asp
210                 215                 220

Leu Glu Thr Val Thr Leu Leu Ala Lys Asn Ile Val Ala Asn Lys Glu
225                 230                 235                 240

Cys Glu Phe Lys Arg Ile Val Ala Ile Asn Val Pro Lys Trp Thr Asn
                245                 250                 255

Leu Met His Leu Asp Thr Trp Leu Thr Met Leu Asp Lys Asp Lys Phe
            260                 265                 270

Leu Tyr Ser Pro Ile Ala Asn Asp Val Phe Lys Phe Trp Asp Tyr Asp
            275                 280                 285

Leu Val Asn Gly Gly Glu Glu Pro Gln Pro Val Glu Asn Gly Leu Pro
290                 295                 300

Leu Glu Gly Leu Leu Glu Ser Ile Ile Asn Lys Lys Pro Ile Leu Ile
305                 310                 315                 320

Pro Ile Ala Gly Glu Gly Ala Ser Gln Ile Asp Ile Glu Arg Glu Thr
                325                 330                 335

His Phe Asp Gly Thr Asn Tyr Leu Ala Ile Arg Pro Gly Val Val Ile
            340                 345                 350

Gly Tyr Ser Arg Asn Glu Lys Thr Asn Ala Ala Leu Glu Ala Ala Gly
            355                 360                 365

Ile Lys Val Leu Pro Phe His Gly Asn Gln Leu Ser Leu Gly Met Gly
370                 375                 380

Asn Ala Arg Cys Met Ser Met
385                 390

<210> SEQ ID NO 8
<211> LENGTH: 392
<212> TYPE: PRT
<213> ORGANISM: Mycoplasma phocidae

<400> SEQUENCE: 8

Ile His Val Tyr Ser

```
                100             105             110
    Ser Ser Lys Glu Leu Ile Gln Tyr Met Met Ala Gly Ile Thr Lys His
            115                 120                 125

Asp Leu Asn Ile Glu Ala Asp His Glu Leu Ile Val Asp Pro Met Pro
        130                 135                 140

Asn Leu Tyr Phe Thr Arg Asp Pro Phe Ala Ser Val Gly Asn Gly Val
    145                 150                 155                 160

Thr Ile His Tyr Met Arg Tyr Lys Val Arg Gln Arg Glu Thr Leu Phe
                    165                 170                 175

Ser Arg Phe Ile Phe Ala Asn His Pro Lys Leu Met Asn Thr Pro Leu
                        180                 185                 190

Tyr Tyr Asn Pro Asp Met Lys Leu Ser Ile Glu Gly Gly Asp Val Phe
                    195                 200                 205

Val Tyr Asn Asn Glu Thr Leu Val Val Gly Val Ser Glu Arg Thr Asp
        210                 215                 220

Leu Asp Thr Ile Thr Leu Leu Ala Lys Asn Ile Lys Ala Asn Lys Glu
    225                 230                 235                 240

Arg Glu Phe Lys Arg Ile Val Ala Ile Asn Val Pro Lys Trp Thr Asn
                    245                 250                 255

Leu Met His Leu Asp Thr Trp Leu Thr Met Leu Asp Lys Asp Lys Phe
                        260                 265                 270

Leu Tyr Ser Pro Ile Ala Asn Asp Val Phe Lys Phe Trp Asp Tyr Asp
                    275                 280                 285

Leu Val Asn Gly Gly Asp Glu Pro Gln Pro Lys Val Asn Gly Leu Pro
        290                 295                 300

Leu Glu Lys Leu Leu Glu Ser Ile Ile Asn Lys Lys Pro Ile Leu Ile
    305                 310                 315                 320

Pro Ile Ala Gly Thr Ser Ala Ser Asn Ile Asp Val Glu Arg Glu Thr
                    325                 330                 335

His Phe Asp Gly Thr Asn Tyr Leu Ala Ile Ala Pro Gly Val Val Ile
                        340                 345                 350

Gly Tyr Ser Arg Asn Val Lys Thr Asn Glu Ala Leu Glu Ala Ala Gly
                    355                 360                 365

Ile Lys Val Leu Pro Phe Lys Gly Asn Gln Leu Ser Leu Gly Met Gly
        370                 375                 380

Asn Ala Arg Cys Met Ser Met Pro
    385                 390

<210> SEQ ID NO 9
<211> LENGTH: 401
<212> TYPE: PRT
<213> ORGANISM: Mycoplasma columbinum

<400> SEQUENCE: 9

Met Ser Lys Ile Asn Val Tyr Ser Glu Ile Gly Glu Leu Lys Glu Val
    1               5                   10                  15

Leu Val His Thr Pro Gly Asp Glu Ile Arg Arg Ile Ser Pro Ser Arg
                    20                  25                  30

Leu Asp Glu Leu Leu Phe Ser Ala Ile Leu Glu Pro Asn Glu Ala Ile
                        35                  40                  45

Lys Glu His Lys Gly Phe Leu Lys Ile Leu Gln Asp Lys Gly Ile Lys
                    50                  55                  60

Val Ile Gln Leu Ser Asp Leu Val Ala Glu Thr Tyr Thr Tyr His Ala
    65                  70                  75                  80
```

```
Thr Gln Lys Glu Arg Glu Ala Phe Ile Glu Lys Trp Leu Asp Glu Ala
                85                  90                  95

Glu Pro Ala Leu Thr Lys Asp Leu Arg Ala Lys Val Lys Ser Tyr Val
            100                 105                 110

Leu Ser Lys Glu Gly Thr Pro Val Ala Met Val Arg Thr Met Met Ala
        115                 120                 125

Gly Val Ser Lys Gln Glu Leu Asn Val Glu Ser Glu Thr Glu Leu Val
    130                 135                 140

Val Asp Pro Met Pro Asn Leu Tyr Phe Thr Arg Asp Pro Phe Ala Ser
145                 150                 155                 160

Ala Gly Asn Gly Ile Ser Leu Asn Asn Met Lys Tyr Val Thr Arg Lys
                165                 170                 175

Arg Glu Thr Ile Phe Ala Glu Phe Ile Phe Ala Thr His Pro Asp Tyr
            180                 185                 190

Lys Thr Thr Pro His Trp Phe Asp Arg Leu Asp Glu Gly Asn Ile Glu
        195                 200                 205

Gly Gly Asp Val Phe Ile Tyr Asn Lys Asp Thr Leu Val Ile Gly Val
    210                 215                 220

Ser Glu Arg Thr Asn Lys Glu Ala Ile Leu Thr Ile Ala Lys Lys Ile
225                 230                 235                 240

Lys Asn Asn Lys Glu Ala Lys Phe Lys Lys Ile Val Ala Ile Asn Val
                245                 250                 255

Pro Pro Met Pro Asn Leu Met His Leu Asp Thr Trp Leu Thr Met Val
            260                 265                 270

Asp Lys Asp Lys Phe Leu Tyr Ser Pro Asn Met Leu Ser Val Leu Lys
        275                 280                 285

Val Trp Glu Ile Asp Leu Ser Lys Glu Ile Glu Met Val Glu Thr Asn
    290                 295                 300

Lys Pro Leu Ala Asp Val Leu Glu Ser Ile Ile Gly Val Lys Pro Val
305                 310                 315                 320

Leu Ile Pro Ile Ala Gly Lys Gly Ala Thr Gln Leu Asp Ile Asp Ile
                325                 330                 335

Glu Thr His Phe Asp Gly Thr Asn Tyr Leu Thr Ile Ala Pro Gly Val
            340                 345                 350

Val Val Gly Tyr Ser Arg Asn Ile Lys Thr Glu Ala Ala Leu Arg Ala
        355                 360                 365

Ala Gly Val Thr Val Leu Ser Phe Glu Gly Asn Gln Leu Ser Leu Gly
    370                 375                 380

Met Gly Ser Ala Arg Cys Met Ser Met Pro Leu Val Arg Glu Asp Val
385                 390                 395                 400

Lys
```

<210> SEQ ID NO 10
<211> LENGTH: 407
<212> TYPE: PRT
<213> ORGANISM: Mycoplasma iowae

<400> SEQUENCE: 10

```
Met Gly Asn Asn Ile Pro Lys Lys Ile Asn Val Phe Ser Glu Ile Gly
1               5                   10                  15

Asn Leu Lys Arg Val Leu Val His Thr Pro Gly Lys Glu Ile Glu Tyr
            20                  25                  30

Val Thr Pro Gln Arg Leu Asp Glu Leu Leu Phe Ser Ala Ile Leu Asp
        35                  40                  45
```

```
Pro Val Arg Ala Arg Glu Glu His Lys Glu Phe Ile Lys Ile Leu Glu
    50                  55                  60

Ser Gln Gly Val Glu Val Val Gln Leu Val Asp Leu Thr Ala Glu Thr
65                  70                  75                  80

Tyr Asp Val Ala Glu Ser Gln Ala Lys Glu Asn Phe Ile Gln Lys Trp
                85                  90                  95

Leu Asp Glu Ser Leu Pro Lys Leu Thr Asp Glu Asn Arg Asn Lys Val
            100                 105                 110

Tyr Ser Leu Leu Lys Ser Leu Glu Lys Asp Pro Lys Glu Met Ile Arg
        115                 120                 125

Lys Met Met Ser Gly Val Leu Ala Ser Glu Ile Gly Val Lys Ser Asp
130                 135                 140

Val Glu Leu Ile Val Asp Pro Met Pro Asn Leu Tyr Phe Thr Arg Asp
145                 150                 155                 160

Pro Phe Ala Ser Val Gly Asn Gly Ile Thr Leu His Arg Met Phe Arg
                165                 170                 175

Pro Thr Arg Arg Arg Glu Thr Ile Phe Ala Asp Phe Ile Phe Ser Asn
            180                 185                 190

His Pro Glu Tyr Lys Ser Thr Gln Lys Tyr Tyr Glu Arg Glu Asp Lys
        195                 200                 205

Phe Ser Leu Glu Gly Gly Asp Val Phe Ile Tyr Asn Asn Lys Thr Leu
210                 215                 220

Val Val Gly Val Ser Glu Arg Thr Glu Lys Gly Ala Ile Lys Ala Leu
225                 230                 235                 240

Ala Lys Ala Val Gln Asn Asn Ser Asn Met Ser Phe Glu Lys Ile Tyr
                245                 250                 255

Ala Ile Asn Val Pro Lys Met Ser Asn Leu Met His Leu Asp Thr Trp
            260                 265                 270

Leu Thr Met Leu Asp Thr Asp Lys Phe Leu Tyr Ser Pro Asn Met Met
        275                 280                 285

Gly Val Leu Lys Ile Trp Glu Ile Asp Leu Ser Asp Lys Ser Leu Lys
290                 295                 300

Trp Lys Glu Ile Arg Asp Ser Leu Asp His Phe Leu Ser Thr Ile Ile
305                 310                 315                 320

Gly Lys Lys Ala Ile Thr Val Pro Val Ala Gly Lys Asp Ala Met Gln
                325                 330                 335

Phe Glu Ile Asp Ile Glu Thr His Phe Asp Ala Thr Asn Phe Ile Ala
            340                 345                 350

Val Ala Pro Gly Val Val Ile Gly Tyr Asp Arg Asn Lys Lys Thr Asn
        355                 360                 365

Glu Ala Leu Lys Glu Ala Gly Ile Lys Val Leu Ser Trp Asn Gly Asp
370                 375                 380

Gln Leu Ser Leu Gly Met Gly Ser Ala Arg Cys Met Thr Met Pro Leu
385                 390                 395                 400

Tyr Arg Glu Glu Leu Lys Lys
                405

<210> SEQ ID NO 11
<211> LENGTH: 402
<212> TYPE: PRT
<213> ORGANISM: Mycoplasma crocodyli

<400> SEQUENCE: 11

Met Asn Lys Ile Asn Val Tyr Ser Glu Val Gly Lys Leu Lys Glu Val
1               5                   10                  15
```

Leu Val His Thr Pro Gly Asp Glu Ile Arg Arg Ile Ser Pro Ser Arg
            20                  25                  30

Leu Glu Glu Leu Leu Phe Ser Ala Ile Leu Glu Pro Asp Ser Ala Ile
        35                  40                  45

Glu Glu His Lys Arg Phe Leu Lys Ile Leu Glu Asp Asn Asn Ile Lys
    50                  55                  60

Val Ile Gln Leu Asp Gln Leu Val Ala Asp Thr Tyr Glu Leu Val Asn
65                  70                  75                  80

Pro Ser Val Arg Asp Ala Phe Ile Glu Lys Trp Leu Asn Glu Ser Glu
                85                  90                  95

Pro Lys Leu Asp Lys Lys Leu Arg Glu Lys Val Lys Glu Tyr Leu Leu
            100                 105                 110

His Thr Gln Lys Thr Val Gly Thr Lys Arg Met Val Arg Ile Met Met
        115                 120                 125

Ala Gly Val Asp Arg Val Glu Leu Gly Val Glu Leu Asp Arg Gln Leu
    130                 135                 140

Val Val Asp Pro Met Pro Asn Leu Tyr Phe Thr Arg Asp Pro Phe Ala
145                 150                 155                 160

Ser Ala Gly Asn Gly Ile Ser Leu Asn Asn Met Lys Tyr Val Thr Arg
                165                 170                 175

Lys Arg Glu Thr Ile Phe Ser Glu Phe Ile Phe Glu Asn His Pro Asp
            180                 185                 190

Tyr Lys Thr Thr Pro His Trp Phe Asp Arg Leu Asp Lys Gly Asn Ile
        195                 200                 205

Glu Gly Gly Asp Val Phe Ile Tyr Asn Arg Thr Thr Leu Val Ile Gly
    210                 215                 220

Ile Ser Glu Arg Thr Asn Lys Asp Ala Leu Leu Thr Ile Ala Asn Asn
225                 230                 235                 240

Ile Lys Ser Asn Lys Glu Ser Lys Phe Glu Arg Ile Val Ala Val Asn
                245                 250                 255

Val Pro Pro Met Pro Asn Leu Met His Leu Asp Thr Trp Leu Thr Met
            260                 265                 270

Val Asp His Asp Lys Phe Leu Tyr Ser Pro Asn Met Met Lys Thr Leu
        275                 280                 285

Lys Phe Trp Thr Ile Asp Leu Thr Lys Pro Ile Lys Met Val Glu Leu
    290                 295                 300

Glu Glu Ser Leu Ser Asp Met Ile Glu Thr Ile Ile Gly Lys Lys Pro
305                 310                 315                 320

Val Leu Ile Pro Ile Ala Gly His Asp Ala Ser Pro Leu Asp Val Asp
                325                 330                 335

Ile Glu Thr His Phe Asp Gly Thr Asn Tyr Leu Thr Ile Ala Pro Gly
            340                 345                 350

Val Val Val Gly Tyr Ser Arg Asn Lys Leu Thr Glu Lys Ala Leu Thr
        355                 360                 365

Lys Ala Gly Val Lys Val Leu Ser Phe Glu Gly Asn Gln Leu Ser Leu
    370                 375                 380

Gly Met Gly Ser Ala Arg Cys Met Ser Met Pro Leu Val Arg Glu Asp
385                 390                 395                 400

Ile Lys

<210> SEQ ID NO 12
<211> LENGTH: 430
<212> TYPE: PRT

```
<213> ORGANISM: Mycoplasma fermentans

<400> SEQUENCE: 12

Met Gln Ile Ile Ala Lys Ile Asp Leu Leu Thr Asn Met Leu Ile Phe
1               5                   10                  15

Met Lys Ile Tyr Phe Ile Gly Arg Leu Ile Met Lys Lys Ile Asn Val
            20                  25                  30

Tyr Ser Glu Tyr Gly Lys Leu Lys Glu Val Leu Val His Thr Pro Gly
        35                  40                  45

Asp Glu Ile Arg Arg Ile Ala Pro Ser Arg Leu Asp Glu Leu Leu Phe
    50                  55                  60

Ser Ala Ile Leu Glu Pro Asp Ser Ala Ile Ala Glu His Lys Arg Phe
65                  70                  75                  80

Val Gln Leu Leu Lys Asp Asn Gly Ile Lys Val Ile Gln Leu Asp Glu
                85                  90                  95

Leu Phe Ala Lys Thr Phe Asp Leu Val Ser Glu Ser Val Lys Gln Ser
            100                 105                 110

Leu Ile Glu Arg Trp Leu Asp Glu Cys Glu Pro Lys Leu Asp Ala Thr
        115                 120                 125

Leu Arg Ala Lys Val Lys Glu Tyr Ile Leu Glu Leu Lys Ala Lys Ser
    130                 135                 140

Ser Lys Lys Met Val Arg Val Met Met Ala Gly Ile Asp Lys Lys Glu
145                 150                 155                 160

Leu Gly Ile Glu Leu Asp Arg Asp Leu Val Val Asp Pro Met Pro Asn
                165                 170                 175

Leu Tyr Phe Thr Arg Asp Pro Phe Ala Ser Val Gly Asn Gly Ile Ser
            180                 185                 190

Leu His His Met Lys Tyr Val Thr Arg Gln Arg Glu Thr Ile Phe Ser
        195                 200                 205

Glu Phe Ile Phe Asp Asn Asn Leu Asp Tyr Asn Thr Val Pro Arg Trp
    210                 215                 220

Phe Asp Arg Lys Asp Glu Gly Arg Ile Glu Gly Gly Asp Val Phe Ile
225                 230                 235                 240

Tyr Ser Ala Asp Thr Leu Val Val Gly Val Ser Glu Arg Thr Asn Lys
                245                 250                 255

Glu Ala Ile Asn Val Met Ala Arg Lys Ile Ala Ala Asp Lys Glu Val
            260                 265                 270

Lys Phe Lys Arg Ile Tyr Ala Ile Asn Val Pro Pro Met Pro Asn Leu
        275                 280                 285

Met His Leu Asp Thr Trp Leu Thr Met Leu Asp Lys Asn Lys Phe Leu
    290                 295                 300

Tyr Ser Pro Asn Met Leu Ser Val Leu Lys Val Trp Arg Ile Asp Leu
305                 310                 315                 320

Asn Asp Pro Asp Phe Val Trp His Glu Ile Glu Gly Ser Leu Glu Glu
                325                 330                 335

Ile Leu Glu Gln Ile Ile Gly Met Lys Pro Ile Leu Ile Pro Ile Ala
            340                 345                 350

Gly Lys Gly Ala Ser Gln Leu Asp Ile Asp Ile Glu Thr His Phe Asp
        355                 360                 365

Gly Thr Asn Tyr Leu Thr Ile Ala Pro Ser Val Val Val Gly Tyr Ser
    370                 375                 380

Arg Asn Glu Lys Thr Glu Lys Ala Leu Lys Ala Ala Lys Val Lys Val
385                 390                 395                 400
```

```
Leu Ser Phe Glu Gly Asn Gln Leu Ser Leu Gly Met Gly Ser Ala Arg
                405                 410                 415

Cys Met Ser Met Pro Leu Ile Arg Glu Asp Ile Lys Lys Lys
            420                 425                 430

<210> SEQ ID NO 13
<211> LENGTH: 452
<212> TYPE: PRT
<213> ORGANISM: Mycoplasma penetrans

<400> SEQUENCE: 13

Met Val Ile Thr Ile Ala Leu Asn Ile Leu Asn Lys Ile Tyr Phe Lys
1               5                   10                  15

Pro Gln Asn Arg Ser Ile Leu Lys Leu Tyr Arg Leu Pro Ser Leu Cys
            20                  25                  30

Thr Gln Ile Ser Ile Phe Ile Gly Gly Lys Met Ser Ser Ile Asp Lys
        35                  40                  45

Asn Ser Leu Gly Asn Gly Ile Asn Val Tyr Ser Glu Ile Gly Glu Leu
    50                  55                  60

Lys Glu Val Leu Val His Thr Pro Gly Asp Glu Ile Arg Tyr Thr Ala
65                  70                  75                  80

Pro Ser Arg Leu Glu Glu Leu Leu Phe Ser Ala Val Leu Lys Ala Asp
                85                  90                  95

Thr Ala Ile Glu Glu His Lys Gly Phe Val Lys Ile Leu Gln Asn Asn
            100                 105                 110

Gly Ile Lys Val Ile Gln Leu Cys Asp Leu Val Ala Glu Thr Tyr Glu
        115                 120                 125

Leu Cys Ser Lys Glu Val Arg Asn Ser Phe Ile Glu Gln Tyr Leu Asp
    130                 135                 140

Glu Ala Leu Pro Val Leu Lys Lys Glu Ile Arg Pro Val Val Lys Asp
145                 150                 155                 160

Tyr Leu Leu Ser Phe Pro Thr Val Gln Met Val Arg Lys Met Met Ser
                165                 170                 175

Gly Ile Leu Ala Asn Glu Leu Asn Ile Lys Gln Asp Asn Pro Leu Ile
            180                 185                 190

Ile Asp Gly Met Pro Asn Leu Tyr Phe Thr Arg Asp Pro Phe Ala Ser
        195                 200                 205

Met Gly Asn Gly Val Ser Ile Asn Cys Met Lys Tyr Pro Thr Arg Lys
    210                 215                 220

Arg Glu Val Ile Phe Ser Arg Phe Val Phe Thr Asn Asn Pro Lys Tyr
225                 230                 235                 240

Lys Asn Thr Pro Arg Tyr Phe Asp Ile Val Gly Asn Asn Gly Thr Ile
                245                 250                 255

Glu Gly Gly Asp Ile Phe Ile Tyr Asn Ser Lys Thr Leu Val Ile Gly
            260                 265                 270

Asn Ser Glu Arg Thr Asn Phe Ala Ala Ile Glu Ser Val Ala Lys Asn
        275                 280                 285

Ile Gln Ala Asn Lys Asp Cys Thr Phe Glu Arg Ile Val Val Ile Asn
    290                 295                 300

Val Pro Pro Met Pro Asn Leu Met His Leu Asp Thr Trp Leu Thr Met
305                 310                 315                 320

Leu Asp Tyr Asp Lys Phe Leu Tyr Ser Pro Asn Met Met Asn Val Leu
                325                 330                 335

Lys Ile Trp Glu Ile Asp Leu Asn Val Lys Pro Val Lys Phe Val Glu
            340                 345                 350
```

```
Lys Lys Gly Thr Leu Glu Glu Val Leu Tyr Ser Ile Ile Asp Lys Lys
            355                 360                 365

Pro Ile Leu Ile Pro Ile Ala Gly Lys Gly Ala Asn Gln Leu Asp Ile
    370                 375                 380

Asp Ile Glu Thr His Phe Asp Gly Thr Asn Tyr Leu Thr Ile Ala Pro
385                 390                 395                 400

Gly Val Val Gly Tyr Glu Arg Asn Glu Lys Thr Gln Lys Ala Leu
                405                 410                 415

Val Glu Ala Gly Ile Lys Val Leu Ser Phe Asn Gly Ser Gln Leu Ser
                420                 425                 430

Leu Gly Met Gly Ser Ala Arg Cys Met Ser Met Pro Leu Ile Arg Glu
            435                 440                 445

Asn Leu Lys Lys
    450

<210> SEQ ID NO 14
<211> LENGTH: 403
<212> TYPE: PRT
<213> ORGANISM: Mycoplasma gallisepticum

<400> SEQUENCE: 14

Met Phe Asn Lys Ile Arg Val Tyr Ser Glu Ile Gly Lys Leu Arg Lys
1               5                   10                  15

Val Leu Val His Thr Pro Gly Lys Glu Leu Asp Tyr Val Thr Pro Gln
                20                  25                  30

Arg Leu Asp Glu Leu Leu Phe Ser Ser Leu Leu Asn Pro Ile Lys Ala
            35                  40                  45

Arg Gln Glu His Glu Thr Phe Ile Lys Leu Leu Glu Asp His Asp Val
        50                  55                  60

Glu Cys Val Gln Leu Ser Thr Leu Thr Ala Gln Thr Phe Gln Ala Val
65                  70                  75                  80

Asn Ser Lys Ile Gln Glu Glu Phe Ile Asn Arg Trp Leu Asp Glu Cys
                85                  90                  95

Leu Pro Val Leu Ser Glu Ile Asn Arg Leu Lys Val Tyr Asp Tyr Leu
            100                 105                 110

Lys Ser Leu Ala Thr Asn Pro Gln Val Met Ile Arg Lys Met Met Ser
        115                 120                 125

Gly Ile Leu Ala Lys Glu Val Gly Ile Gln Ser Glu Val Glu Leu Val
    130                 135                 140

Ala Asp Pro Met Pro Asn Leu Tyr Phe Thr Arg Asp Pro Phe Ala Ser
145                 150                 155                 160

Ile Gly Lys Gly Ile Thr Leu His Ser Met Phe His Pro Thr Arg Lys
                165                 170                 175

Arg Glu Thr Ile Phe Ala Asp Phe Ile Phe Ser His His Pro Glu Tyr
            180                 185                 190

Lys Asn Ala Pro Lys Tyr Tyr Ser Arg Glu Asp Lys Tyr Ser Ile Glu
        195                 200                 205

Gly Gly Asp Leu Phe Val Tyr Asp Asp Lys Thr Leu Val Ile Gly Val
    210                 215                 220

Ser Glu Arg Thr Glu Lys Lys Ala Ile Gln Ser Leu Ala Glu Lys Leu
225                 230                 235                 240

Arg Gln Asn Asp Glu Thr Ser Phe Glu Lys Ile Tyr Ala Ile Asn Val
                245                 250                 255

Pro Lys Met Ser Asn Leu Met His Leu Asp Thr Trp Leu Thr Met Leu
```

```
            260                 265                 270
Asp Tyr Asp Lys Phe Leu Tyr Ser Pro Asn Met Met Gly Val Leu Lys
            275                 280                 285

Ile Trp Glu Ile Asp Leu Ile His Pro Thr Leu Ile Trp Arg Glu Leu
            290                 295                 300

Asn Glu Ser Leu Glu Gly Phe Leu Ser Met Val Ile Gly Lys Lys Ala
305                 310                 315                 320

Thr Leu Ile Pro Val Ala Gly Glu Asp Ser Thr Gln Ile Glu Ile Asp
            325                 330                 335

Val Glu Thr Asn Phe Asp Ala Thr Asn Phe Leu Val Ile Gln Pro Gly
            340                 345                 350

Val Val Val Gly Tyr Asp Arg Asn Tyr Lys Thr Asn Gln Ala Leu Arg
            355                 360                 365

Asp Ala Gly Val Lys Val Ile Ser Trp Asn Gly Asp Gln Leu Ser Leu
            370                 375                 380

Gly Met Gly Ser Ala Arg Cys Met Ser Met Pro Leu Tyr Arg Asp Pro
385                 390                 395                 400

Ile Lys Lys

<210> SEQ ID NO 15
<211> LENGTH: 402
<212> TYPE: PRT
<213> ORGANISM: Mycoplasma alligatoris

<400> SEQUENCE: 15

Met Ser Lys Ile Asn Val Tyr Ser Glu Val Gly Arg Leu Lys Glu Val
1               5                   10                  15

Leu Val His Thr Pro Gly Asp Glu Ile Arg Arg Ile Ser Pro Thr Arg
            20                  25                  30

Leu Glu Glu Leu Leu Phe Ser Ala Ile Leu Glu Pro Asp Thr Ala Ile
            35                  40                  45

Glu Glu His Lys Arg Phe Leu Asn Val Leu Glu Lys Asn Gly Ile Lys
        50                  55                  60

Ala Ile Gln Leu Asp Glu Leu Val Ala Gln Thr Tyr Asp Gln Val Asp
65                  70                  75                  80

Gln Lys Ile Lys Asp Glu Phe Ile Asp Gln Trp Leu Gln Glu Ala Lys
                85                  90                  95

Pro Val Leu Asn Asp Gln Leu Lys Lys Leu Val Lys Asn Tyr Leu Leu
            100                 105                 110

Lys Ser Gln Lys Glu Phe Ser Thr Lys Lys Met Val Arg Ile Met Met
        115                 120                 125

Ala Gly Ile Asp Lys Lys Glu Ile Asn Ile Asp Leu Asp Arg Asp Leu
130                 135                 140

Val Val Asp Pro Met Pro Asn Leu Tyr Phe Thr Arg Asp Pro Phe Ala
145                 150                 155                 160

Ser Val Gly Asn Gly Ile Ser Leu His Asn Met Lys Tyr Gln Thr Arg
                165                 170                 175

Lys Arg Glu Thr Ile Phe Ala Gln Phe Ile Phe Lys Tyr Asn Lys Asp
            180                 185                 190

Tyr Lys Thr Thr Pro His Trp Phe Asp Arg Phe Asp His Gly Ser Ile
            195                 200                 205

Glu Gly Gly Asp Val Phe Val Tyr Thr Lys Asp Thr Leu Val Ile Gly
        210                 215                 220

Ile Ser Glu Arg Thr Thr Lys Glu Ala Val Leu Asn Ile Ala Lys Lys
```

```
                225                 230                 235                 240
Ile Lys Ala Asn Thr Asp Ser Lys Phe Lys Ile Val Ala Ile Asn
                    245                 250                 255

Val Pro Pro Met Pro Asn Leu Met His Leu Asp Thr Trp Ile Thr Met
                    260                 265                 270

Val Asp His Asp Lys Phe Leu Tyr Ser Pro Asn Met Met Lys Ser Leu
                    275                 280                 285

Lys Phe Trp Leu Ile Asp Leu Ser Lys Glu Ile Lys Met Val Glu Leu
                    290                 295                 300

Glu Glu Ser Leu Ser Asn Met Leu Glu Ala Ile Ile Gly Lys Lys Pro
305                 310                 315                 320

Ile Leu Ile Pro Ile Ala Gly Lys Asn Ala Ser Gln Leu Asp Ile Asp
                    325                 330                 335

Ile Glu Thr His Phe Asp Gly Thr Asn Tyr Leu Thr Ile Ala Pro Gly
                    340                 345                 350

Val Val Val Gly Tyr Ser Arg Asn Lys Leu Thr Gln Lys Ala Leu Glu
                    355                 360                 365

Asp Ala Gly Val Lys Val Leu Ser Phe Asp Gly Asn Gln Leu Ser Leu
370                 375                 380

Gly Met Gly Ser Ala Arg Cys Met Ser Met Pro Leu Val Arg Glu Asp
385                 390                 395                 400

Ile Lys

<210> SEQ ID NO 16
<211> LENGTH: 438
<212> TYPE: PRT
<213> ORGANISM: Mycoplasma pneumoniae

<400> SEQUENCE: 16

Met Ser Lys Lys Gln Leu Val Lys Thr Asp Gly His Asn Gln Leu Asp
1               5                   10                  15

Gln Pro Asn Thr Lys Ala Leu Gln Leu Lys Lys Lys Gln Phe Asn Ser
                    20                  25                  30

Gly Val Arg Val Thr Ser Glu Ile Ser Phe Leu Arg Glu Val Ile Ala
                    35                  40                  45

His His Pro Gly Ile Glu Thr Glu Arg Val Ile Asp Asn Gln Thr Phe
                    50                  55                  60

Gly Ser Ala Met Tyr Leu Glu Arg Ala Gln Lys Glu His Gln Leu Phe
65                  70                  75                  80

Ile Lys Ile Leu Arg Gln His Gly Thr Lys Val His Tyr Leu Gln Asp
                    85                  90                  95

Leu Leu Leu Glu Ala Leu Ser Ala Ala Asp Pro Asn Val Arg Gln Asp
                    100                 105                 110

Phe Ile Lys Asn Phe Leu Leu Glu Ser Gly Ile Lys Ser Val Ser Thr
                    115                 120                 125

Phe Glu Ala Cys Leu Asn Phe Phe Arg Ser Leu Asp Ser Leu Val Asp
                    130                 135                 140

Val Ile Lys Val Met Phe Gly Gly Ile Lys Val Ser Asp Val Pro Pro
145                 150                 155                 160

Ile Thr Pro Gln Arg Phe Ala Asp Ile His Val Ser Asn Ser Pro Phe
                    165                 170                 175

Leu Ile Lys Pro Leu Ser Phe Ser Leu Tyr Pro His Lys Phe Phe Asn
                    180                 185                 190

Thr Leu Gly Thr Gly Val Ala Leu Phe Val Thr Asn Asp Ser Glu Leu
```

```
            195                 200                 205
Lys Arg His Ser Leu Val Tyr Glu Tyr Ile Met Arg Phe His Pro Arg
    210                 215                 220

Phe Asp Gly Val Lys Leu Tyr Thr Asn Arg Asp Phe Lys Asn Cys Leu
225                 230                 235                 240

Ile Asn Ser Ser Asp Ile Ile Gln Ile Ser Asn Glu Ile Leu Leu Ile
                245                 250                 255

Gly Ile Ser His Asp Thr Asp Val Leu Gly Ile Glu Ser Leu Ala Arg
            260                 265                 270

Asn Leu Leu Ser Asp His Thr Asn Pro Ile Lys Gln Ile Ile Ala Ile
        275                 280                 285

Asn Ile His Lys Phe Gly Ala Lys Thr Asn Leu Asn Lys Leu Ile Ala
    290                 295                 300

Met Val Asp Val Asp Lys Phe Ile Ile Ala Arg Lys Val Leu Gln Ala
305                 310                 315                 320

Thr Glu Ile Phe Glu Leu Thr Ala Thr Ala Gln Arg Asp Val Asp Gly
                325                 330                 335

Leu Ala Gln Ile Lys Phe Lys Pro Leu Lys Phe Asn Phe Gly Glu Ile
            340                 345                 350

Ile Glu Ala Ile Ile Asp Lys Gln Pro Arg Phe Val Ile Ile Gly Gly
        355                 360                 365

Gly Asp Glu Val Ala Glu Arg Lys Glu Leu Leu Asp Cys Gly Met Gly
    370                 375                 380

Val Leu Asn Leu Ser Pro Gly Glu Ile Val Val Phe Asp Arg Asn His
385                 390                 395                 400

Tyr Thr Asn Asn Leu Leu Asn Glu Leu Gly Leu Ile Ile His Lys Ile
                405                 410                 415

Pro Ala Ser Glu Leu Ser Arg Gly Pro Ser Gly Pro Leu Glu Met Val
            420                 425                 430

Cys Ser Leu Trp Arg Glu
            435

<210> SEQ ID NO 17
<211> LENGTH: 409
<212> TYPE: PRT
<213> ORGANISM: Mycoplasma mobile

<400> SEQUENCE: 17

Met Lys Asp Thr Lys Asp Ile Ile Asn Val Phe Ser Glu Ile Gly Glu
1               5                   10                  15

Leu Lys Lys Val Leu Ile His Thr Pro Gly Asn Glu Leu Lys Tyr Val
                20                  25                  30

Ser Pro Tyr Arg Leu Asp Glu Leu Leu Phe Ser Asn Val Leu Glu Trp
            35                  40                  45

Arg Glu Ala Lys Lys Glu His Asn Glu Phe Ile Gln Lys Leu Lys Ser
        50                  55                  60

Glu Gly Val Glu Pro Val Glu Leu Thr Asp Leu Val Ala Glu Ser Phe
65                  70                  75                  80

Glu Glu Ser Ser Ile Lys Val Lys Asn Asp Phe Ile Arg Gln Tyr Leu
                85                  90                  95

Asp Glu Ala Thr Pro Ile Leu Asp Gly Leu Thr Lys Gln Lys Leu Leu
            100                 105                 110

Pro Phe Phe Leu Asp Ile Lys His Ser Thr Arg Lys Thr Ile Glu Leu
        115                 120                 125
```

-continued

```
Met Met Ser Gly Ile Thr Gln Lys Asp Ile Ser Ile Ser His Ile Glu
    130                 135                 140

Arg Glu Leu Ile Ile Asp Pro Met Pro Asn Leu Tyr Phe Ser Arg Asp
145                 150                 155                 160

Asn Phe Ile Ser Ile Gly Asn Ser Val Ile Ile Ser Asn Met Lys Tyr
                165                 170                 175

Lys Thr Arg Lys Arg Glu Thr Ile Phe Thr Asp Phe Ile Phe Lys Asn
            180                 185                 190

His Pro Leu Tyr Lys Lys Val Asn Met Ala Phe Glu Arg Lys Asp Leu
        195                 200                 205

Asn Asn Gln Ile Ser Ile Ile Glu Gly Gly Asp Val Leu Val Tyr Ser
210                 215                 220

Lys Glu Ile Leu Ile Ile Gly Ile Ser Glu Arg Thr Thr Met Ser Ala
225                 230                 235                 240

Ile Leu Glu Leu Ala Glu Asn Phe Lys Lys Thr Lys Arg Ser Phe Lys
                245                 250                 255

Lys Ile Tyr Gly Val Glu Val Pro Lys Met Lys Asn Leu Met His Leu
            260                 265                 270

Asp Thr Trp Leu Thr Met Ile Asp Tyr Asp Lys Phe Ile Tyr Ser Pro
        275                 280                 285

Asn Val Leu Thr Asp Leu Lys Phe Trp Glu Ile Asn Leu Asp Tyr Glu
290                 295                 300

Lys Ile Ser Ser Lys Glu Leu His Ala Ser Leu Ser Glu Phe Leu Lys
305                 310                 315                 320

Leu Ile Ile Gly Lys Asp Pro Ile Leu Ile Pro Ile Gly Gly Lys Gly
                325                 330                 335

Ala Ser Gln Ile Thr Ile Asp Ile Glu Thr Asn Phe Val Ala Ala Asn
            340                 345                 350

Tyr Leu Val Ile Arg Pro Gly Val Val Ile Gly Tyr Ser Arg Asn Tyr
        355                 360                 365

Glu Thr Gln Lys Ala Leu Glu Gly His Gly Val Lys Val Ile Ala Phe
370                 375                 380

Glu Gly Asn Gln Leu Ser Leu Gly Met Gly Ser Ser Arg Cys Met Ser
385                 390                 395                 400

Met Pro Leu Ile Arg Ser Asn Leu Lys
                405

<210> SEQ ID NO 18
<211> LENGTH: 411
<212> TYPE: PRT
<213> ORGANISM: Streptococcus pyogenes

<400> SEQUENCE: 18

Met Thr Ala Gln Thr Pro Ile His Val Tyr Ser Glu Ile Gly Lys Leu
1               5                   10                  15

Lys Lys Val Leu Leu His Arg Pro Gly Lys Glu Ile Glu Asn Leu Met
            20                  25                  30

Pro Asp Tyr Leu Glu Arg Leu Leu Phe Asp Asp Ile Pro Phe Leu Glu
        35                  40                  45

Asp Ala Gln Lys Glu His Asp Ala Phe Ala Gln Ala Leu Arg Asp Glu
    50                  55                  60

Gly Ile Glu Val Leu Tyr Leu Glu Thr Leu Ala Ala Glu Ser Leu Val
65                  70                  75                  80

Thr Pro Glu Ile Arg Glu Ala Phe Ile Asp Glu Tyr Leu Ser Glu Ala
                85                  90                  95
```

```
Asn Ile Arg Gly Arg Ala Thr Lys Lys Ala Ile Arg Glu Leu Leu Met
                100                 105                 110

Ala Ile Glu Asp Asn Gln Glu Leu Ile Glu Lys Thr Met Ala Gly Val
            115                 120                 125

Gln Lys Ser Glu Leu Pro Glu Ile Pro Ala Ser Glu Lys Gly Leu Thr
        130                 135                 140

Asp Leu Val Glu Ser Asn Tyr Pro Phe Ala Ile Asp Pro Met Pro Asn
145                 150                 155                 160

Leu Tyr Phe Thr Arg Asp Pro Phe Ala Thr Ile Gly Thr Gly Val Ser
                165                 170                 175

Leu Asn His Met Phe Ser Glu Thr Arg Asn Arg Glu Thr Leu Tyr Gly
            180                 185                 190

Lys Tyr Ile Phe Thr His His Pro Ile Tyr Gly Gly Lys Val Pro
        195                 200                 205

Met Val Tyr Asp Arg Asn Glu Thr Thr Arg Ile Glu Gly Gly Asp Glu
    210                 215                 220

Leu Val Leu Ser Lys Asp Val Leu Ala Val Gly Ile Ser Gln Arg Thr
225                 230                 235                 240

Asp Ala Ala Ser Ile Glu Lys Leu Leu Val Asn Ile Phe Lys Gln Asn
                245                 250                 255

Leu Gly Phe Lys Lys Val Leu Ala Phe Glu Phe Ala Asn Asn Arg Lys
            260                 265                 270

Phe Met His Leu Asp Thr Val Phe Thr Met Val Asp Tyr Asp Lys Phe
        275                 280                 285

Thr Ile His Pro Glu Ile Glu Gly Asp Leu Arg Val Tyr Ser Val Thr
    290                 295                 300

Tyr Asp Asn Glu Glu Leu His Ile Val Glu Glu Lys Gly Asp Leu Ala
305                 310                 315                 320

Glu Leu Leu Ala Ala Asn Leu Gly Val Glu Lys Val Asp Leu Ile Arg
                325                 330                 335

Cys Gly Gly Asp Asn Leu Val Ala Ala Gly Arg Glu Gln Trp Asn Asp
            340                 345                 350

Gly Ser Asn Thr Leu Thr Ile Ala Pro Gly Val Val Val Tyr Asn
        355                 360                 365

Arg Asn Thr Ile Thr Asn Ala Ile Leu Glu Ser Lys Gly Leu Lys Leu
    370                 375                 380

Ile Lys Ile His Gly Ser Glu Leu Val Arg Gly Arg Gly Pro Arg
385                 390                 395                 400

Cys Met Ser Met Pro Phe Glu Arg Glu Asp Ile
                405                 410

<210> SEQ ID NO 19
<211> LENGTH: 408
<212> TYPE: PRT
<213> ORGANISM: Enterococcus faecalis

<400> SEQUENCE: 19

Met Ser His Pro Ile Asn Val Phe Ser Glu Ile Gly Lys Leu Lys Thr
1               5                   10                  15

Val Met Leu His Arg Pro Gly Lys Glu Leu Glu Asn Leu Met Pro Asp
            20                  25                  30

Tyr Leu Glu Arg Leu Leu Phe Asp Asp Ile Pro Phe Leu Glu Lys Ala
        35                  40                  45

Gln Ala Glu His Asp Ala Phe Ala Glu Leu Leu Arg Ser Lys Asp Ile
```

-continued

```
                50                  55                  60
Glu Val Val Tyr Leu Glu Asp Leu Ala Ala Glu Ala Leu Ile Asn Glu
 65                  70                  75                  80

Glu Val Arg Arg Gln Phe Ile Asp Gln Phe Leu Glu Glu Ala Asn Ile
                 85                  90                  95

Arg Ser Glu Ser Ala Lys Glu Lys Val Arg Glu Leu Met Leu Glu Ile
                100                 105                 110

Asp Asp Asn Glu Glu Leu Ile Gln Lys Ala Ile Ala Gly Ile Gln Lys
            115                 120                 125

Gln Glu Leu Pro Lys Tyr Glu Gln Glu Phe Leu Thr Asp Met Val Glu
        130                 135                 140

Ala Asp Tyr Pro Phe Ile Ile Asp Pro Met Pro Asn Leu Tyr Phe Thr
145                 150                 155                 160

Arg Asp Asn Phe Ala Thr Met Gly His Gly Ile Ser Leu Asn His Met
                165                 170                 175

Tyr Ser Val Thr Arg Gln Arg Glu Thr Ile Phe Gly Gln Tyr Ile Phe
            180                 185                 190

Asp Tyr His Pro Arg Phe Ala Gly Lys Glu Val Pro Arg Val Tyr Asp
        195                 200                 205

Arg Ser Glu Ser Thr Arg Ile Glu Gly Gly Asp Glu Leu Ile Leu Ser
210                 215                 220

Lys Glu Val Val Ala Ile Gly Ile Ser Gln Arg Thr Asp Ala Ala Ser
225                 230                 235                 240

Ile Glu Lys Ile Ala Arg Asn Ile Phe Glu Gln Lys Leu Gly Phe Lys
                245                 250                 255

Asn Ile Leu Ala Phe Asp Ile Gly Glu His Arg Lys Phe Met His Leu
            260                 265                 270

Asp Thr Val Phe Thr Met Ile Asp Tyr Asp Lys Phe Thr Ile His Pro
        275                 280                 285

Glu Ile Glu Gly Gly Leu Val Val Tyr Ser Ile Thr Glu Lys Ala Asp
290                 295                 300

Gly Asp Ile Gln Ile Thr Lys Glu Lys Asp Thr Leu Asp Asn Ile Leu
305                 310                 315                 320

Cys Lys Tyr Leu His Leu Asp Asn Val Gln Leu Ile Arg Cys Gly Ala
                325                 330                 335

Gly Asn Leu Thr Ala Ala Arg Glu Gln Trp Asn Asp Gly Ser Asn
            340                 345                 350

Thr Leu Ala Ile Ala Pro Gly Glu Val Val Tyr Asp Arg Asn Thr
        355                 360                 365

Ile Thr Asn Lys Ala Leu Glu Glu Ala Gly Val Lys Leu Asn Tyr Ile
    370                 375                 380

Pro Gly Ser Glu Leu Val Arg Gly Arg Gly Pro Arg Cys Met Ser
385                 390                 395                 400

Met Pro Leu Tyr Arg Glu Asp Leu
            405
```

<210> SEQ ID NO 20
<211> LENGTH: 403
<212> TYPE: PRT
<213> ORGANISM: Mycoplasma capricolum

<400> SEQUENCE: 20

```
Met Glu Lys Lys Ile Asn Val Phe Ser Glu Ile Gly Thr Leu Lys Thr
 1               5                  10                  15
```

Val Leu Val His Arg Pro Gly Asp Glu Ile Glu Asn Leu Thr Pro Glu
            20                  25                  30

Leu Leu Glu Arg Leu Leu Phe Asp Asp Val Pro Phe Lys Asp Val Ala
        35                  40                  45

Val Lys Glu His Asp Ala Phe Thr Lys Ile Met Arg Asp Asn Gly Val
50                  55                  60

Glu Val Leu Tyr Ile Glu Lys Leu Ala Ala Glu Thr Leu Asp Gln His
65                  70                  75                  80

Pro Asp Leu Arg Glu Lys Phe Ile Asp Gln Phe Ile Ser Glu Ala Asn
                85                  90                  95

Ile Glu Asp Lys Tyr Lys Glu Lys Tyr Arg Asp Phe Ile Ser Ser Leu
            100                 105                 110

Asp Asn Tyr Arg Met Ile Lys Lys Met Ile Ala Gly Thr Lys Lys Leu
        115                 120                 125

Glu Leu Gly Ile Asp Glu Gly Tyr Lys Ala Tyr Pro Phe Ile Ala Asp
130                 135                 140

Pro Leu Pro Asn Val Leu Phe Gln Arg Asp Pro Phe Ser Ser Val Gly
145                 150                 155                 160

Phe Gly Ile Thr Met Asn Arg Met Trp Ser Val Thr Arg Asn Arg Glu
                165                 170                 175

Thr Ile Phe Pro Asp Leu Val Phe Lys His His Asn Arg Phe Ala Asn
            180                 185                 190

Gln Val Pro Tyr Tyr Glu Arg Asp Trp Lys Glu Thr Ile Glu
        195                 200                 205

Gly Gly Asp Ile Leu Val Leu Asn Lys Glu Thr Leu Ile Ile Gly Val
210                 215                 220

Thr Gln Arg Thr Thr Leu Lys Ala Ile Glu Lys Phe Ser Glu Arg Leu
225                 230                 235                 240

Phe Asn Asp Pro Glu Ser Ser Tyr Ser Lys Val Ile Ala Leu Asp Leu
                245                 250                 255

Pro Lys Ser Arg Ala Phe Met His Leu Asp Thr Val Phe Thr Asn Ile
            260                 265                 270

Asp Tyr Asp Lys Phe Ile Ala His Pro Leu Ile Phe Asp Cys Ile Asp
        275                 280                 285

Glu Phe Lys Ile Tyr Glu Val Ser Lys Gln Gly Thr Lys Glu Val Lys
290                 295                 300

Lys Thr Leu Ile Glu Leu Leu Ser Asp Ala Ala Gly Arg Glu Val Gln
305                 310                 315                 320

Ile Ile Arg Cys Gly Gly Asn Asp Val Val Gly Ala Ser Arg Glu Gln
                325                 330                 335

Trp Asn Asp Gly Thr Asn Val Val Ala Leu Arg Pro Gly Lys Val Ile
            340                 345                 350

Ala Tyr Glu Arg Asn Trp Ile Thr Ile Asp Leu Leu Arg Lys Ala Gly
        355                 360                 365

Val Glu Val Leu Thr Ile Ala Ser Ser Glu Leu Ser Arg Gly Arg Gly
370                 375                 380

Gly Pro Arg Cys Met Thr Met Pro Leu Trp Arg Glu Asp Leu Gln Glu
385                 390                 395                 400

Ile Lys Arg

<210> SEQ ID NO 21
<211> LENGTH: 410
<212> TYPE: PRT
<213> ORGANISM: Halothermothrix orenii

<400> SEQUENCE: 21

Met Phe Lys Lys Ser Pro Leu Asn Val Thr Ser Glu Ile Gly Lys Leu
1               5                   10                  15

Lys Lys Val Leu Leu His Arg Pro Gly His Glu Ile Glu Asn Leu Thr
            20                  25                  30

Pro Asp Leu Leu Glu Arg Leu Leu Phe Asp Asp Ile Pro Tyr Leu Lys
        35                  40                  45

Val Ala Gln Glu Glu His Asp Ala Phe Ala Gln Thr Leu Arg Asp Asn
50                  55                  60

Gly Val Glu Val Leu Tyr Leu His Glu Leu Ala Ala Glu Ala Ile Gln
65                  70                  75                  80

Glu Asp Glu Ile Arg Lys Lys Phe Ile Glu Gln Phe Leu Asp Glu Ala
                85                  90                  95

Gly Val Ile Gly Lys Gly Ala Arg Gln Val Leu Lys Glu Tyr Phe Ala
            100                 105                 110

Asp Met Asp Asn Glu Thr Leu Ile Arg Lys Met Met Ala Gly Val Arg
            115                 120                 125

Lys Lys Glu Ile Pro Ala Ile Glu Lys Val Ala Ser Leu Asn Asp Met
130                 135                 140

Val Glu Glu Asp Tyr Pro Phe Val Leu Asp Pro Met Pro Asn Leu Tyr
145                 150                 155                 160

Phe Thr Arg Asp Pro Phe Ala Thr Ile Gly Thr Gly Ile Thr Leu Asn
                165                 170                 175

His Met Arg Thr Glu Thr Arg Asn Arg Glu Val Ile Phe Ala Glu Tyr
            180                 185                 190

Ile Phe Ser Tyr His Pro Asp Phe Lys Asp Thr Glu Ile Pro Phe Trp
        195                 200                 205

Phe Asp Arg Asn Glu Thr Thr Ser Ile Glu Gly Gly Asp Glu Leu Ile
210                 215                 220

Leu Ser Asp Lys Val Leu Ala Met Gly Ile Ser Glu Arg Thr Asp Ala
225                 230                 235                 240

Ala Ser Ile Glu Lys Val Ala Arg Asn Ile Phe Thr Asp Gly Gln Pro
                245                 250                 255

Phe Glu Thr Ile Leu Ala Phe Lys Ile Pro Glu Lys Arg Ala Phe Met
            260                 265                 270

His Leu Asp Thr Val Phe Thr Met Val Asp Tyr Asp Lys Phe Thr Ile
        275                 280                 285

His Ala Glu Ile Glu Gly Pro Leu Lys Val Tyr Ser Ile Thr Lys Gly
290                 295                 300

Asp Asn Asp Glu Leu Lys Ile Asp Glu Glu Lys Ala Thr Leu Glu Asp
305                 310                 315                 320

Thr Leu Lys Lys Tyr Leu Gly Leu Asp Glu Val Thr Leu Ile Arg Cys
                325                 330                 335

Ala Gly Gly Asp Tyr Ile Asp Ala Gly Arg Gln Trp Asn Asp Gly
            340                 345                 350

Ser Asn Thr Leu Ala Ile Ala Pro Gly Glu Val Val Tyr Asn Arg
        355                 360                 365

Asn His Thr Thr Asn Arg Leu Leu Glu His Gly Ile Lys Leu His
370                 375                 380

Val Ile Pro Ser Ser Glu Leu Ser Arg Gly Arg Gly Pro Arg Cys
385                 390                 395                 400

Met Ser Met Pro Leu Val Arg Glu Asp Ile

<210> SEQ ID NO 22
<211> LENGTH: 411
<212> TYPE: PRT
<213> ORGANISM: Staphylococcus aureus

<400> SEQUENCE: 22

Met Thr Asp Gly Pro Ile Lys Val Asn Ser Glu Ile Gly Ala Leu Lys
1               5                   10                  15

Thr Val Leu Leu Lys Arg Pro Gly Lys Glu Leu Glu Asn Leu Val Pro
                20                  25                  30

Asp Tyr Leu Asp Gly Leu Leu Phe Asp Asp Ile Pro Tyr Leu Glu Val
            35                  40                  45

Ala Gln Lys Glu His Asp His Phe Ala Gln Val Leu Arg Glu Glu Gly
        50                  55                  60

Val Glu Val Leu Tyr Leu Glu Lys Leu Ala Ala Glu Ser Ile Glu Asn
65                  70                  75                  80

Pro Gln Val Arg Ser Glu Phe Ile Asp Asp Val Leu Ala Glu Ser Lys
                85                  90                  95

Lys Thr Ile Leu Gly His Glu Glu Ile Lys Ala Leu Phe Ala Thr
                100                 105                 110

Leu Ser Asn Gln Glu Leu Val Asp Lys Ile Met Ser Gly Val Arg Lys
            115                 120                 125

Glu Glu Ile Asn Pro Lys Cys Thr His Leu Val Glu Tyr Met Asp Asp
130                 135                 140

Lys Tyr Pro Phe Tyr Leu Asp Pro Met Pro Asn Leu Tyr Phe Thr Arg
145                 150                 155                 160

Asp Pro Gln Ala Ser Ile Gly His Gly Ile Thr Ile Asn Arg Met Phe
                165                 170                 175

Trp Arg Ala Arg Arg Glu Ser Ile Phe Ile Gln Tyr Ile Val Lys
            180                 185                 190

His His Pro Arg Phe Lys Asp Ala Asn Ile Pro Ile Trp Leu Asp Arg
        195                 200                 205

Asp Cys Pro Phe Asn Ile Glu Gly Gly Asp Glu Leu Val Leu Ser Lys
    210                 215                 220

Asp Val Leu Ala Ile Gly Val Ser Glu Arg Thr Ser Ala Gln Ala Ile
225                 230                 235                 240

Glu Lys Leu Ala Arg Arg Ile Phe Glu Asn Pro Gln Ala Thr Phe Lys
                245                 250                 255

Lys Val Val Ala Ile Glu Ile Pro Thr Ser Arg Thr Phe Met His Leu
            260                 265                 270

Asp Thr Val Phe Thr Met Ile Asp Tyr Asp Lys Phe Thr Met His Ser
        275                 280                 285

Ala Ile Leu Lys Ala Glu Gly Asn Met Asn Ile Phe Ile Glu Tyr
    290                 295                 300

Asp Asp Val Asn Lys Asp Ile Ala Ile Lys Gln Ser Ser His Leu Lys
305                 310                 315                 320

Asp Thr Leu Glu Asp Val Leu Gly Ile Asp Asp Ile Gln Phe Ile Pro
                325                 330                 335

Thr Gly Asn Gly Asp Val Ile Asp Gly Ala Arg Glu Gln Trp Asn Asp
            340                 345                 350

Gly Ser Asn Thr Leu Cys Ile Arg Pro Gly Val Val Thr Tyr Asp
        355                 360                 365

```
Arg Asn Tyr Val Ser Asn Asp Leu Leu Arg Gln Lys Gly Ile Lys Val
    370                 375                 380

Ile Glu Ile Ser Gly Ser Glu Leu Val Arg Gly Arg Gly Gly Pro Arg
385                 390                 395                 400

Cys Met Ser Gln Pro Leu Phe Arg Glu Asp Ile
                405                 410

<210> SEQ ID NO 23
<211> LENGTH: 417
<212> TYPE: PRT
<213> ORGANISM: Pseudomonas plecoglossicida

<400> SEQUENCE: 23

Met Ser Ala Glu Lys Gln Lys Tyr Gly Val His Ser Glu Ala Gly Lys
1               5                   10                  15

Leu Arg Lys Val Met Val Cys Ala Pro Gly Leu Ala His Lys Arg Leu
                20                  25                  30

Thr Pro Ser Asn Cys Asp Glu Leu Leu Phe Asp Asp Val Ile Trp Val
            35                  40                  45

Asp Gln Ala Lys Arg Asp His Phe Asp Phe Val Thr Lys Met Arg Glu
        50                  55                  60

Arg Gly Val Asp Val Leu Glu Met His Asn Leu Leu Thr Asp Ile Val
65                  70                  75                  80

Gln Asn Pro Glu Ala Leu Lys Trp Ile Leu Asp Arg Lys Ile Thr Pro
                85                  90                  95

Asp Thr Val Gly Val Gly Leu Thr Asn Glu Val Arg Ser Trp Leu Glu
            100                 105                 110

Gly Gln Glu Pro Arg His Leu Ala Glu Phe Leu Ile Gly Gly Val Ala
        115                 120                 125

Gly Gln Asp Leu Pro Glu Ser Glu Gly Ala Ser Val Val Lys Met Tyr
    130                 135                 140

Asn Asp Tyr Leu Gly His Ser Ser Phe Ile Leu Pro Pro Leu Pro Asn
145                 150                 155                 160

Thr Gln Phe Thr Arg Asp Thr Thr Cys Trp Ile Tyr Gly Gly Val Thr
                165                 170                 175

Leu Asn Pro Met Tyr Trp Pro Ala Arg Arg Gln Glu Thr Leu Leu Thr
            180                 185                 190

Thr Ala Ile Tyr Lys Phe His Pro Glu Phe Thr Lys Ala Asp Phe Gln
        195                 200                 205

Val Trp Tyr Gly Asp Pro Asp Gln Glu His Gly Gln Ala Thr Leu Glu
    210                 215                 220

Gly Gly Asp Val Met Pro Ile Gly Lys Gly Ile Val Leu Ile Gly Met
225                 230                 235                 240

Gly Glu Arg Thr Ser Arg Gln Ala Ile Gly Gln Leu Ala Gln Asn Leu
                245                 250                 255

Phe Ala Lys Gly Ala Val Glu Gln Val Ile Val Ala Gly Leu Pro Lys
            260                 265                 270

Ser Arg Ala Ala Met His Leu Asp Thr Val Phe Ser Phe Cys Asp Arg
        275                 280                 285

Asp Leu Val Thr Val Phe Pro Glu Val Val Arg Glu Ile Val Pro Phe
    290                 295                 300

Ile Ile Arg Pro Asp Glu Ser Lys Pro Tyr Gly Met Asp Val Arg Arg
305                 310                 315                 320

Glu Asn Lys Ser Phe Ile Glu Val Val Gly Glu Gln Leu Gly Val Lys
                325                 330                 335
```

```
Leu Arg Val Val Glu Thr Gly Gly Asn Ser Phe Ala Ala Glu Arg Glu
            340                 345                 350

Gln Trp Asp Asp Gly Asn Asn Val Val Ala Leu Glu Pro Gly Val Val
        355                 360                 365

Ile Gly Tyr Asp Arg Asn Thr Tyr Thr Asn Thr Leu Leu Arg Lys Ala
370                 375                 380

Gly Ile Glu Val Ile Thr Ile Ser Ala Gly Glu Leu Gly Arg Gly Arg
385                 390                 395                 400

Gly Gly Gly His Cys Met Thr Cys Pro Ile Val Arg Asp Pro Ile Asn
                405                 410                 415

Tyr

<210> SEQ ID NO 24
<211> LENGTH: 417
<212> TYPE: PRT
<213> ORGANISM: Pseudomonas putida

<400> SEQUENCE: 24

Met Ser Ala Glu Lys Gln Lys Tyr Gly Val His Ser Glu Ala Gly Lys
1               5                   10                  15

Leu Arg Lys Val Met Val Cys Ala Pro Gly Leu Ala His Lys Arg Leu
            20                  25                  30

Thr Pro Ser Asn Cys Asp Glu Leu Leu Phe Asp Val Ile Trp Val
        35                  40                  45

Asp Gln Ala Lys Arg Asp His Phe Asp Phe Val Thr Lys Met Arg Glu
    50                  55                  60

Arg Gly Val Asp Val Leu Glu Met His Asn Leu Leu Thr Asp Ile Val
65                  70                  75                  80

Gln Asn Lys Asp Ala Leu Lys Trp Ile Leu Asp Arg Lys Ile Thr Pro
                85                  90                  95

Asp Thr Val Gly Val Gly Leu Thr Asn Glu Val Arg Ser Trp Leu Glu
            100                 105                 110

Gly Leu Glu Pro Arg His Leu Ala Glu Phe Leu Ile Gly Gly Val Ala
        115                 120                 125

Gly Gln Asp Leu Pro Gln Ser Glu Gly Ala Asp Val Val Lys Met Tyr
    130                 135                 140

Asn Asp Tyr Leu Gly His Ser Ser Phe Ile Leu Pro Pro Leu Pro Asn
145                 150                 155                 160

Thr Gln Phe Thr Arg Asp Thr Thr Cys Trp Ile Tyr Gly Gly Val Thr
                165                 170                 175

Leu Asn Pro Met Tyr Trp Pro Ala Arg Arg Gln Glu Thr Leu Leu Thr
            180                 185                 190

Thr Ala Ile Tyr Lys Phe His Pro Gln Phe Thr Gly Ala Asp Phe Gln
        195                 200                 205

Val Trp Tyr Gly Asp Pro Asp Lys Asp His Gly Asn Ala Thr Leu Glu
    210                 215                 220

Gly Gly Asp Val Met Pro Ile Gly Lys Gly Ile Val Leu Ile Gly Met
225                 230                 235                 240

Gly Glu Arg Thr Ser Arg Gln Ala Ile Gly Gln Leu Ala Gln Asn Leu
                245                 250                 255

Phe Ala Lys Gly Ala Val Glu Lys Val Ile Val Ala Gly Leu Pro Lys
            260                 265                 270

Ser Arg Ala Ala Met His Leu Asp Thr Val Phe Ser Phe Cys Asp Arg
        275                 280                 285
```

```
Asp Leu Val Thr Ile Phe Pro Glu Val Val Lys Glu Ile Val Pro Phe
    290                 295                 300

Ile Ile Arg Pro Asp Glu Ser Lys Pro Tyr Gly Met Asp Val Arg Arg
305                 310                 315                 320

Glu Asn Lys Ser Phe Ile Glu Val Val Gly Glu Gln Leu Gly Val Lys
                325                 330                 335

Leu Arg Val Val Glu Thr Gly Gly Asn Ser Phe Ala Ala Glu Arg Glu
            340                 345                 350

Gln Trp Asp Asp Gly Asn Asn Val Val Ala Val Glu Pro Gly Val Val
        355                 360                 365

Ile Gly Tyr Asp Arg Asn Thr Tyr Thr Asn Thr Leu Leu Arg Lys Ala
    370                 375                 380

Gly Ile Glu Val Ile Thr Ile Ser Ala Gly Glu Leu Gly Arg Gly Arg
385                 390                 395                 400

Gly Gly Gly His Cys Met Thr Cys Pro Ile Val Arg Asp Pro Ile Asp
                405                 410                 415

Tyr

<210> SEQ ID NO 25
<211> LENGTH: 418
<212> TYPE: PRT
<213> ORGANISM: Pseudomonas aeruginosa

<400> SEQUENCE: 25

Met Ser Thr Glu Lys Thr Lys Leu Gly Val His Ser Glu Ala Gly Lys
1               5                   10                  15

Leu Arg Lys Val Met Val Cys Ser Pro Gly Leu Ala His Gln Arg Leu
            20                  25                  30

Thr Pro Ser Asn Cys Asp Glu Leu Leu Phe Asp Asp Val Ile Trp Val
        35                  40                  45

Asn Gln Ala Lys Arg Asp His Phe Asp Phe Val Thr Lys Met Arg Glu
    50                  55                  60

Arg Gly Ile Asp Val Leu Glu Met His Asn Leu Leu Thr Glu Thr Ile
65                  70                  75                  80

Gln Asn Pro Glu Ala Leu Lys Trp Ile Leu Asp Arg Lys Ile Thr Ala
                85                  90                  95

Asp Ser Val Gly Leu Gly Leu Thr Ser Glu Leu Arg Ser Trp Leu Glu
            100                 105                 110

Ser Leu Glu Pro Arg Lys Leu Ala Glu Tyr Leu Ile Gly Gly Val Ala
        115                 120                 125

Ala Asp Asp Leu Pro Ala Ser Glu Gly Ala Asn Ile Leu Lys Met Tyr
    130                 135                 140

Arg Glu Tyr Leu Gly His Ser Ser Phe Leu Leu Pro Pro Leu Pro Asn
145                 150                 155                 160

Thr Gln Phe Thr Arg Asp Thr Thr Cys Trp Ile Tyr Gly Gly Val Thr
                165                 170                 175

Leu Asn Pro Met Tyr Trp Pro Ala Arg Arg Gln Glu Thr Leu Leu Thr
            180                 185                 190

Thr Ala Ile Tyr Lys Phe His Pro Glu Phe Ala Asn Ala Glu Phe Glu
        195                 200                 205

Ile Trp Tyr Gly Asp Pro Asp Lys Asp His Gly Ser Ser Thr Leu Glu
    210                 215                 220

Gly Gly Asp Val Met Pro Ile Gly Asn Gly Val Val Leu Ile Gly Met
225                 230                 235                 240
```

```
Gly Glu Arg Ser Ser Arg Gln Ala Ile Gly Gln Val Ala Gln Ser Leu
                245                 250                 255

Phe Ala Lys Gly Ala Ala Glu Arg Val Ile Val Ala Gly Leu Pro Lys
            260                 265                 270

Ser Arg Ala Ala Met His Leu Asp Thr Val Phe Ser Phe Cys Asp Arg
        275                 280                 285

Asp Leu Val Thr Val Phe Pro Glu Val Lys Glu Ile Val Pro Phe
    290                 295                 300

Ser Leu Arg Pro Asp Ala Ser Ser Pro Tyr Gly Met Ser Ile Arg Arg
305                 310                 315                 320

Glu Glu Lys Thr Phe Leu Glu Val Val Ala Glu Ser Leu Gly Leu Lys
                325                 330                 335

Lys Leu Arg Val Val Glu Thr Gly Gly Asn Ser Phe Ala Ala Glu Arg
            340                 345                 350

Glu Gln Trp Asp Asp Gly Asn Asn Val Val Cys Leu Glu Pro Gly Val
        355                 360                 365

Val Val Gly Tyr Asp Arg Asn Thr Tyr Thr Asn Thr Leu Leu Arg Lys
    370                 375                 380

Ala Gly Val Glu Val Ile Thr Ile Ser Ala Ser Glu Leu Gly Arg Gly
385                 390                 395                 400

Arg Gly Gly Gly His Cys Met Thr Cys Pro Ile Ile Arg Asp Pro Ile
                405                 410                 415

Asp Tyr

<210> SEQ ID NO 26
<211> LENGTH: 402
<212> TYPE: PRT
<213> ORGANISM: Mycobacterium tuberculosis complex

<400> SEQUENCE: 26

Met Gly Val Glu Leu Gly Ser Asn Ser Glu Val Gly Ala Leu Arg Val
1               5                   10                  15

Val Ile Leu His Arg Pro Gly Ala Glu Leu Arg Arg Leu Thr Pro Arg
            20                  25                  30

Asn Thr Asp Gln Leu Leu Phe Asp Gly Leu Pro Trp Val Ser Arg Ala
        35                  40                  45

Gln Asp Glu His Asp Glu Phe Ala Glu Leu Leu Ala Ser Arg Gly Ala
    50                  55                  60

Glu Val Leu Leu Leu Ser Asp Leu Leu Thr Glu Ala Leu His His Ser
65                  70                  75                  80

Gly Ala Ala Arg Met Gln Gly Ile Ala Ala Ala Val Asp Ala Pro Arg
                85                  90                  95

Leu Gly Leu Pro Leu Ala Gln Glu Leu Ser Ala Tyr Leu Arg Ser Leu
            100                 105                 110

Asp Pro Gly Arg Leu Ala His Val Leu Thr Ala Gly Met Thr Phe Asn
        115                 120                 125

Glu Leu Pro Ser Asp Thr Arg Thr Asp Val Ser Leu Val Leu Arg Met
    130                 135                 140

His His Gly Gly Asp Phe Val Ile Glu Pro Leu Pro Asn Leu Val Phe
145                 150                 155                 160

Thr Arg Asp Ser Ser Ile Trp Ile Gly Pro Arg Val Val Ile Pro Ser
                165                 170                 175

Leu Ala Leu Arg Ala Arg Val Arg Glu Ala Ser Leu Thr Asp Leu Ile
            180                 185                 190
```

```
Tyr Ala His His Pro Arg Phe Thr Gly Val Arg Arg Ala Tyr Glu Ser
        195                 200                 205

Arg Thr Ala Pro Val Glu Gly Gly Asp Val Leu Leu Leu Ala Pro Gly
210                 215                 220

Val Val Ala Val Gly Val Gly Glu Arg Thr Thr Pro Ala Gly Ala Glu
225                 230                 235                 240

Ala Leu Ala Arg Ser Leu Phe Asp Asp Leu Ala His Thr Val Leu
        245                 250                 255

Ala Val Pro Ile Ala Gln Gln Arg Ala Gln Met His Leu Asp Thr Val
        260                 265                 270

Cys Thr Met Val Asp Thr Asp Thr Met Val Met Tyr Ala Asn Val Val
        275                 280                 285

Asp Thr Leu Glu Ala Phe Thr Ile Gln Arg Thr Pro Asp Gly Val Thr
290                 295                 300

Ile Gly Asp Ala Ala Pro Phe Ala Glu Ala Ala Lys Ala Met Gly
305                 310                 315                 320

Ile Asp Lys Leu Arg Val Ile His Thr Gly Met Asp Pro Val Val Ala
                325                 330                 335

Glu Arg Glu Gln Trp Asp Asp Gly Asn Asn Thr Leu Ala Leu Ala Pro
            340                 345                 350

Gly Val Val Ala Tyr Glu Arg Asn Val Gln Thr Asn Ala Arg Leu
        355                 360                 365

Gln Asp Ala Gly Ile Glu Val Leu Thr Ile Ala Gly Ser Glu Leu Gly
370                 375                 380

Thr Gly Arg Gly Gly Pro Arg Cys Met Ser Cys Pro Ala Ala Arg Asp
385                 390                 395                 400

Pro Leu

<210> SEQ ID NO 27
<211> LENGTH: 409
<212> TYPE: PRT
<213> ORGANISM: Mycoplasma arthritidis

<400> SEQUENCE: 27

Met Ser Val Phe Asp Ser Lys Phe Lys Gly Ile His Val Tyr Ser Glu
1               5                   10                  15

Ile Gly Glu Leu Glu Thr Val Leu Val His Glu Pro Gly Lys Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Lys Glu Phe Val Ala Glu
    50                  55                  60

Leu Lys Lys Arg Gly Ile Asn Val Val Glu Leu Val Asp Leu Ile Val
65                  70                  75                  80

Glu Thr Tyr Asp Leu Ala Ser Lys Glu Ala Lys Glu Lys Leu Leu Glu
                85                  90                  95

Glu Phe Leu Asp Asp Ser Val Pro Val Leu Ser Asp Glu His Arg Ala
            100                 105                 110

Ala Val Lys Lys Phe Leu Gln Ser Gln Lys Ser Thr Arg Ser Leu Val
        115                 120                 125

Glu Tyr Met Ile Ala Gly Ile Thr Lys His Asp Leu Lys Ile Glu Ser
    130                 135                 140

Asp Leu Glu Leu Ile Val Asp Pro Met Pro Asn Leu Tyr Phe Thr Arg
145                 150                 155                 160
```

```
Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Val Asn Thr Pro Trp Tyr Tyr Asp Pro Ala Glu
        195                 200                 205

Gly Leu Ser Ile Glu Gly Gly Asp Val Phe Ile Tyr Asn Asn Asp Thr
    210                 215                 220

Leu Val Val Gly Val Ser Glu Arg Thr Asp Leu Gln Thr Ile Thr Leu
225                 230                 235                 240

Leu Ala Lys Asn Ile Lys Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Asp
    290                 295                 300

Ala Pro Gln Pro Val Asp Asn Gly Leu Pro Leu Glu Asp Leu Leu Lys
305                 310                 315                 320

Ser Ile Ile Gly Lys Lys Pro Thr Leu Ile Pro Ile Ala Gly Ala Gly
                325                 330                 335

Ala Ser Gln Ile Asp Ile Glu Arg Glu Thr His Phe Asp Gly Thr Asn
            340                 345                 350

Tyr Leu Ala Val Ala Pro Gly Ile Val Ile Gly Tyr Ala Arg Asn Glu
        355                 360                 365

Lys Thr Asn Ala Ala Leu Glu Ala Ala Gly Ile Thr Val Leu Pro Phe
    370                 375                 380

Arg Gly Asn Gln Leu Ser Leu Gly Met Gly Asn Ala Arg Cys Met Ser
385                 390                 395                 400

Met Pro Leu Ser Arg Lys Asp Val Lys
                405

<210> SEQ ID NO 28
<211> LENGTH: 410
<212> TYPE: PRT
<213> ORGANISM: Artificial Sequence
<220> FEATURE:
<223> OTHER INFORMATION: Artificial full length of Mycoplasma
      phocicerebrale

<400> SEQUENCE: 28

Met

```
            100                 105                 110
Ala Val Arg Lys Phe Leu Thr Ser Arg Lys Thr Arg Glu Met Val
            115                 120                 125
Glu Phe Met Met Ala Gly Ile Thr Lys Tyr Asp Leu Gly Ile Glu Ala
            130                 135                 140
Asp His Glu Leu Ile Val Asp Pro Met Pro Asn Leu Tyr Phe Thr Arg
145                 150                 155                 160
Asp Pro Phe Ala Ser Val Gly Asn Gly Val Thr Ile His Tyr Met Arg
                165                 170                 175
Tyr Lys Val Arg Gln Arg Glu Thr Leu Phe Ser Arg Phe Val Phe Ser
                180                 185                 190
Asn His Pro Lys Leu Val Lys Thr Pro Trp Tyr Tyr Asp Pro Ala Met
                195                 200                 205
Lys Met Ser Ile Glu Gly Gly Asp Val Phe Ile Tyr Asn Asn Asp Thr
            210                 215                 220
Leu Val Val Gly Val Ser Glu Arg Thr Asp Leu Glu Thr Ile Thr Leu
225                 230                 235                 240
Leu Ala Lys Asn Ile Lys Ala Asn Lys Glu Val Glu Phe Lys Arg Ile
                245                 250                 255
Val Ala Ile Asn Val Pro Lys Trp Thr Asn Leu Met His Leu Asp Thr
                260                 265                 270
Trp Leu Thr Met Leu Asp Lys Asp Lys Phe Leu Tyr Ser Pro Ile Ala
            275                 280                 285
Asn Asp Val Phe Lys Phe Trp Asp Tyr Asp Leu Val Asn Gly Gly Ala
            290                 295                 300
Glu Pro Gln Pro Lys Glu Asn Gly Leu Pro Leu Glu Gly Leu Leu Gln
305                 310                 315                 320
Ser Ile Ile Asn Lys Lys Pro Val Leu Ile Pro Ile Ala Gly Asn Asn
                325                 330                 335
Ala Ser His Ile Asp Ile Glu Arg Glu Thr His Phe Asp Gly Thr Asn
                340                 345                 350
Tyr Leu Ala Ile Lys Pro Gly Val Val Ile Gly Tyr Ala Arg Asn Glu
                355                 360                 365
Lys Thr Asn Ala Ala Leu Ala Ala Gly Ile Lys Val Leu Pro Phe
            370                 375                 380
His Gly Asn Gln Leu Ser Leu Gly Met Gly Asn Ala Arg Cys Met Ser
385                 390                 395                 400
Met Pro Leu Ser Arg Lys Asp Val Lys Trp
                405                 410

<210> SEQ ID NO 29
<211> LENGTH: 410
<212> TYPE: PRT
<213> ORGANISM: Artificial Sequence
<220> FEATURE:
<223> OTHER INFORMATION: Artificial full length of Mycoplasma gateae

<400> SEQUENCE: 29

Met Ser Val Phe Asp Ser Lys Phe Asn Gly Ile His Val Tyr Ser Glu
1               5                   10                  15
Ile

```
            50                  55                  60
Leu Lys Ala Asn Asp Ile Asn Val Val Glu Leu Thr Asp Leu Val Thr
 65                  70                  75                  80

Glu Thr Tyr Asp Leu Ala Ser Gln Glu Ala Lys Asp Asn Leu Ile Glu
                 85                  90                  95

Glu Phe Leu Glu Asp Ser Glu Pro Val Leu Thr Glu Glu Leu Lys Ser
            100                 105                 110

Val Val Arg Thr Tyr Leu Lys Ser Ile Lys Ser Thr Arg Glu Leu Ile
            115                 120                 125

Gln Met Met Met Ala Gly Ile Thr Lys Tyr Asp Leu Gly Ile Glu Ala
130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Val Asn Thr Pro Trp Tyr Tyr Asp Pro Ser Leu
            195                 200                 205

Lys Leu Ser Ile Glu Gly Gly Asp Val Phe Ile Tyr Asn Asn Asn Thr
210                 215                 220

Leu Val Val Gly Val Ser Glu Arg Thr Asp Leu Glu Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
            275                 280                 285

Asn Asp Val Phe Lys Phe Trp Asp Tyr Asp Leu Val Asn Gly Gly Glu
290                 295                 300

Glu Pro Gln Pro Val Glu Asn Gly Leu Pro Leu Glu Gly Leu Leu Glu
305                 310                 315                 320

Ser Ile Ile Asn Lys Lys Pro Ile Leu Ile Pro Ile Ala Gly Glu Gly
                325                 330                 335

Ala Ser Gln Ile Asp Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
            355                 360                 365

Lys Thr Asn Ala Ala Leu Glu Ala Ala Gly Ile Lys Val Leu Pro Phe
370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 30
<211> LENGTH: 410
<212> TYPE: PRT
<213> ORGANISM: Artificial Sequence
<220> FEATURE:
<223> OTHER INFORMATION: Artificial full length of Mycoplasma phocidae

<400> SEQUENCE: 30

Met Ser Val Phe Asp Ser Lys Phe Asn Gly Ile His Val Tyr Ser Glu
```

```
1               5                   10                  15
Ile Gly Glu Leu Gln Thr Val Leu Val His Glu Pro Gly Arg Glu Ile
                20                  25                  30
Glu Tyr Ile Thr Pro Ala Arg Leu Asp Glu Leu Leu Phe Ser Ala Ile
                35                  40                  45
Leu Glu Ser His Asp Ala Arg Lys Glu His Gln Glu Phe Val Ala Glu
50                  55                  60
Leu Lys Lys Asn Asn Ile Asn Val Val Glu Leu Thr Asp Leu Val Ser
65                  70                  75                  80
Glu Thr Tyr Asp Met Val Ser Lys Glu Lys Gln Glu Lys Leu Ile Glu
                85                  90                  95
Glu Phe Leu Glu Asp Ser Glu Pro Val Leu Ser Glu Glu His Lys Gly
                100                 105                 110
Leu Val Arg Lys Phe Leu Lys Ser Leu Lys Ser Ser Lys Glu Leu Ile
                115                 120                 125
Gln Tyr Met Met Ala Gly Ile Thr Lys His Asp Leu Asn Ile Glu Ala
            130                 135                 140
Asp His Glu Leu Ile Val Asp Pro Met Pro Asn Leu Tyr Phe Thr Arg
145                 150                 155                 160
Asp Pro Phe Ala Ser Val Gly Asn Gly Val Thr Ile His Tyr Met Arg
                165                 170                 175
Tyr Lys Val Arg Gln Arg Glu Thr Leu Phe Ser Arg Phe Ile Phe Ala
                180                 185                 190
Asn His Pro Lys Leu Met Asn Thr Pro Leu Tyr Tyr Asn Pro Asp Met
                195                 200                 205
Lys Leu Ser Ile Glu Gly Gly Asp Val Phe Val Tyr Asn Asn Glu Thr
210                 215                 220
Leu Val Val Gly Val Ser Glu Arg Thr Asp Leu Asp Thr Ile Thr Leu
225                 230                 235                 240
Leu Ala Lys Asn Ile Lys Ala Asn Lys Glu Arg Glu Phe Lys Arg Ile
                245                 250                 255
Val Ala Ile Asn Val Pro Lys Trp Thr Asn Leu Met His Leu Asp Thr
                260                 265                 270
Trp Leu Thr Met Leu Asp Lys Asp Lys Phe Leu Tyr Ser Pro Ile Ala
                275                 280                 285
Asn Asp Val Phe Lys Phe Trp Asp Tyr Asp Leu Val Asn Gly Gly Asp
                290                 295                 300
Glu Pro Gln Pro Lys Val Asn Gly Leu Pro Leu Glu Lys Leu Leu Glu
305                 310                 315                 320
Ser Ile Ile Asn Lys Lys Pro Ile Leu Ile Pro Ile Ala Gly Thr Ser
                325                 330                 335
Ala Ser Asn Ile Asp Val Glu Arg Glu Thr His Phe Asp Gly Thr Asn
                340                 345                 350
Tyr Leu Ala Ile Ala Pro Gly Val Val Ile Gly Tyr Ser Arg Asn Val
                355                 360                 365
Lys Thr Asn Glu Ala Leu Glu Ala Ala Gly Ile Lys Val Leu Pro Phe
                370                 375                 380
Lys Gly Asn Gln Leu Ser Leu Gly Met Gly Asn Ala Arg Cys Met Ser
385                 390                 395                 400
Met Pro Leu Ser Arg Lys Asp Val Lys Trp
                405                 410

<210> SEQ ID NO 31
```

```
<211> LENGTH: 410
<212> TYPE: PRT
<213> ORGANISM: Mycoplasma salivarium

<400> SEQUENCE: 31

Met Ser Val Phe Ser Ser Lys Phe Asn Gly Ile His Val Tyr Ser Glu
1               5                   10                  15

Ile Gly Glu Leu Glu Thr Val Leu Val His Glu Pro Gly Lys Glu Ile
            20                  25                  30

Asp Tyr Ile Thr Pro Ser Arg Leu Asp Glu Leu Leu Phe Ser Ala Ile
        35                  40                  45

Leu Glu Ser His Asp Ala Arg Lys Glu His Gln Glu Phe Val Ala Thr
    50                  55                  60

Leu Lys Lys Glu Lys Ile Asn Val Val Glu Leu Thr Asp Leu Val Thr
65                  70                  75                  80

Glu Thr Tyr Asp Leu Val Asp Gln Lys Thr Lys Asp Lys Leu Ile Asp
                85                  90                  95

Glu Phe Leu Glu Asp Ser Glu Pro Val Leu Thr Ala Glu Leu Lys Ala
            100                 105                 110

Thr Val Lys Lys Phe Leu Lys Ser Phe Lys Glu Thr Arg Lys Leu Ile
        115                 120                 125

Glu Val Met Met Ala Gly Ile Thr Lys Tyr Asp Leu Gly Ile Lys Ala
    130                 135                 140

Asp Arg Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Ile Phe Asn
            180                 185                 190

Asn His Pro Lys Leu Val Lys Thr Pro Trp Tyr Tyr Asp Pro Ala Met
        195                 200                 205

Lys Met Ser Ile Glu Gly Gly Asp Val Phe Ile Tyr Asn Asn Asp Thr
    210                 215                 220

Leu Val Val Gly Val Ser Glu Arg Thr Asp Leu Asp Thr Ile Thr Leu
225                 230                 235                 240

Leu Ala Lys Asn Ile Lys Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Ile Phe Lys Phe Trp Asp Tyr Asp Leu Val Asn Gly Gly Ala
    290                 295                 300

Asn Pro Gln Pro Lys Asp Asn Gly Leu Pro Leu Asp Lys Leu Leu Lys
305                 310                 315                 320

Ser Ile Ile Gly Lys Glu Pro Val Leu Ile Pro Ile Ala Gly His His
                325                 330                 335

Ala Thr Glu Ile Glu Val Ala Arg Glu Thr His Phe Asp Gly Thr Asn
            340                 345                 350

Tyr Leu Ala Ile Arg Pro Gly Val Val Ile Gly Tyr Ala Arg Asn Glu
        355                 360                 365

Lys Thr Asn Glu Ala Leu Lys Asp Ala Gly Ile Thr Val Leu Pro Phe
    370                 375                 380

Lys Gly Asn Gln Leu Ser Leu Gly Met Gly Asn Ala Arg Cys Met Ser
```

```
385                 390                 395                 400

Met Pro Leu Ser Arg Lys Asp Val Lys Trp
                405                 410

<210> SEQ ID NO 32
<211> LENGTH: 411
<212> TYPE: PRT
<213> ORGANISM: Mycoplasma spumans

<400> SEQUENCE: 32

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
                20                  25                  30

Asp Tyr Ile Thr Pro Ala Arg Leu Asp Glu Leu Leu Phe Ser Ala Ile
                35                  40                  45

Leu Glu Ser His Asp Ala Arg Lys Glu His Lys Gly Phe Val Ala Glu
        50                  55                  60

Leu Lys Lys Gln Asn Val Asn Val Ile Glu Leu Thr Asp Leu Val Ala
65                  70                  75                  80

Glu Thr Tyr Glu Leu Ala Ser Lys Glu Ala Gln Ala Lys Leu Ile Glu
                85                  90                  95

Asp Phe Ile Glu Asp Ser Glu Pro Val Leu Asn Ala Glu Ala Gln
            100                 105                 110

Ala Val Arg Lys Phe Leu Ser Glu Arg Lys Ser Thr Arg Glu Met Val
            115                 120                 125

Glu Tyr Met Met Ser Gly Leu Thr Lys Tyr Glu Leu Gly Leu Glu Ser
        130                 135                 140

Ala Asp Arg Glu Leu Ile Val Asp Pro Met Pro Asn Leu Tyr Phe Thr
145                 150                 155                 160

Arg Asp Pro Phe Ala Ser Val Gly Asn Gly Val Thr Ile His Tyr Met
                165                 170                 175

Lys Tyr Lys Val Arg Gln Arg Glu Thr Leu Phe Ala Lys Phe Val Phe
                180                 185                 190

Ser Asn His Pro Lys Leu Val Asn Thr Pro Arg Tyr Tyr Asp Pro Ser
            195                 200                 205

Met Lys Leu Pro Ile Glu Gly Gly Asp Val Phe Ile Tyr Asn Asn Glu
        210                 215                 220

Thr Leu Val Val Gly Cys Ser Glu Arg Thr Glu Leu Glu Thr Ile Thr
225                 230                 235                 240

Leu Leu Ala Lys Asn Ile Lys Ala Asn Lys Glu Val Glu Phe Lys Arg
                245                 250                 255

Ile Val Ala Ile Asn Val Pro Lys Trp Thr Asn Leu Met His Leu Asp
                260                 265                 270

Thr Trp Leu Thr Met Leu Asp Lys Asp Lys Phe Leu Tyr Ser Pro Ile
        275                 280                 285

Ala Asn Asp Val Phe Lys Phe Trp Asp Tyr Asp Leu Val Asn Gly Gly
        290                 295                 300

Glu Glu Pro Gln Pro Val Glu Asn Gly Leu Pro Leu Glu Glu Leu Leu
305                 310                 315                 320

Ala Ser Ile Ile Asn Lys Lys Pro Thr Leu Ile Pro Ile Ala Gly Glu
                325                 330                 335

Gly Ala Thr His Ile Asp Val Glu Arg Glu Thr His Phe Asp Gly Thr
                340                 345                 350
```

```
Asn Tyr Leu Ala Ile Ala Pro Ala Leu Ile Ile Gly Tyr Ser Arg Asn
            355                 360                 365

Glu Lys Thr Asn Ala Ala Leu Glu Lys Ala Gly Ile Thr Val Leu Pro
    370                 375                 380

Phe His Gly Asn Gln Leu Ser Leu Gly Met Gly Asn Ala Arg Cys Met
385                 390                 395                 400

Ser Met Pro Leu Ser Arg Lys Asp Val Lys Trp
                405                 410

<210> SEQ ID NO 33
<211> LENGTH: 410
<212> TYPE: PRT
<213> ORGANISM: Mycoplasma auris

<400> SEQUENCE: 33

Met Ser Val Phe Asp Ser Lys Phe Lys Gly Ile His Val Tyr Ser Glu
1               5                   10                  15

Ile Gly Glu Leu Glu Thr Val Leu Val His Glu Pro Gly Arg Glu Ile
            20                  25                  30

Asp Tyr Ile Thr Pro Lys Arg Leu Asp Glu Leu Leu Phe Ser Ala Ile
        35                  40                  45

Leu Glu Ser His Glu Ala Arg Lys Glu His Lys Gln Phe Val Ala Glu
    50                  55                  60

Leu Lys Ala Asn Asp Ile Asn Val Val Glu Leu Thr Asp Leu Val Ala
65                  70                  75                  80

Glu Thr Tyr Asp Leu Val Ser Gln Glu Leu Lys Asp Lys Leu Ile Glu
                85                  90                  95

Glu Phe Leu Asp Asp Ser Tyr Pro Val Leu Thr Glu Glu His Lys Lys
            100                 105                 110

Ala Val Arg Ser Phe Leu Lys Ser Arg Ser Ser Thr Arg Glu Leu Ile
        115                 120                 125

Glu Tyr Met Met Ala Gly Ile Thr Lys Tyr Asp Leu Gly Ile Glu Ala
    130                 135                 140

Glu Gly Asp Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Ile Phe Asp
            180                 185                 190

Asn His Pro Lys Leu Val Asn Thr Pro Arg Tyr Tyr Asp Pro Ser Leu
        195                 200                 205

Lys Leu Ser Ile Glu Gly Gly Asp Val Phe Ile Tyr Asn Asn Asp Thr
    210                 215                 220

Leu Val Met Gly Val Ser Glu Arg Thr Asp Leu Glu Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro His Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Tyr Phe Lys Phe Trp Asp Tyr Asp Leu Val Asn Gly Gly Ala
    290                 295                 300

Glu Pro Gln Pro Val Val Asn Glu Leu Pro Leu Asp Lys Leu Leu Glu
305                 310                 315                 320
```

```
Ser Ile Ile His Lys Pro Ile Leu Ile Pro Ile Ala Gly Glu Gly
            325                 330                 335

Ala Ser Gln Ile Asp Leu Glu Arg Glu Thr His Phe Asp Gly Thr Asn
            340                 345                 350

Tyr Leu Val Leu Arg Pro Gly Val Val Gly Tyr Ala Arg Asn Glu
            355                 360                 365

Lys Thr Asn Ala Ala Leu Glu Ala Val Gly Ile Lys Val Leu Pro Phe
    370                 375                 380

Tyr Gly Asn Gln Leu Ser Leu Gly Met Gly Asn Ser Arg Cys Met Ser
385                 390                 395                 400

Met Pro Leu Ser Arg Lys Asp Val Lys Trp
            405                 410

<210> SEQ ID NO 34
<211> LENGTH: 410
<212> TYPE: PRT
<213> ORGANISM: Mycoplasma hyosynoviae

<400> SEQUENCE: 34

Met Ser Val Phe Asn Ser Lys Phe Lys Gly Ile His Val Tyr Ser Glu
1               5                   10                  15

Ile Gly Asp Leu Glu Ser Val Leu Val His Glu Pro Gly Lys Glu Ile
            20                  25                  30

Asp Tyr Ile Thr Pro Ser Arg Leu Asp Glu Leu Leu Phe Ser Ala Ile
            35                  40                  45

Leu Glu Ser Asn Asp Ala Arg Lys Glu His Lys Glu Phe Val Glu Ile
50                  55                  60

Leu Lys Lys Glu Gly Val Asn Val Val Glu Leu Val Asp Leu Ile Ala
65                  70                  75                  80

Glu Thr Ile Asp Leu Val Asp Ala Lys Lys Glu Ala Leu Ile Asp
            85                  90                  95

Glu Tyr Ile Glu Asp Ser Glu Pro Val Val Asp Ala Lys Val Lys Pro
            100                 105                 110

Leu Val Lys Lys Leu Leu Leu Gly Ile Lys Asp Thr Lys Glu Leu Val
            115                 120                 125

Lys Leu Met Met Ala Gly Ile Thr Lys Tyr Asp Leu Glu Ile Glu Ser
    130                 135                 140

Glu Lys Glu Leu Ile Ile Asp Pro Met Pro Asn Leu Tyr Phe Thr Arg
145                 150                 155                 160

Asp Pro Phe Ala Ser Val Gly Asn Gly Val Thr Ile His Tyr Met Arg
            165                 170                 175

Tyr Lys Val Arg Gln Arg Glu Thr Leu Phe Ser Arg Phe Val Phe Arg
            180                 185                 190

Asn His Pro Lys Leu Thr Ser Thr Pro Trp Tyr Tyr Asp Pro Ala Met
    195                 200                 205

Lys Leu Ser Ile Glu Gly Gly Asp Val Phe Ile Tyr Asn Asn Asp Thr
    210                 215                 220

Leu Val Val Gly Val Ser Glu Arg Thr Asp Leu Asp Thr Ile Thr Leu
225                 230                 235                 240

Leu Ala Lys Asn Ile Lys Ala Asn Lys Glu Cys Glu Phe Lys Arg Ile
            245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
```

-continued

```
                275                 280                 285
Asn Asp Ile Phe Lys Phe Trp Asp Tyr Asp Leu Val Asn Gly Gly Ser
290                 295                 300

Glu Pro Gln Pro Lys Asp Asn Gly Leu Pro Leu Glu Lys Leu Leu Glu
305                 310                 315                 320

Ser Ile Ile Gly Lys Pro Val Leu Ile Pro Ile Ala Gly Cys Cys
                325                 330                 335

Ala Ser Asp Ile Glu Ile Ala Arg Glu Thr His Phe Asp Gly Thr Asn
                340                 345                 350

Tyr Leu Ala Ile Lys Pro Gly Val Val Ile Gly Tyr Ala Arg Asn Glu
                355                 360                 365

Lys Thr Asn Lys Ala Leu Glu Lys Ala Gly Ile Lys Val Leu Pro Phe
370                 375                 380

Lys Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 35
<211> LENGTH: 409
<212> TYPE: PRT
<213> ORGANISM: Mycoplasma cloacale

<400> SEQUENCE: 35

Met Ser Val Phe Asp Lys Arg Phe Lys Gly Ile His Val Tyr Ser Glu
1               5                   10                  15

Ile Gly Glu Leu Gln Thr Val Leu Val His Glu Pro Gly Arg Glu Ile
                20                  25                  30

Asp Tyr Ile Thr Pro Ala Arg Leu Asp Glu Leu Leu Phe Ser Ala Ile
                35                  40                  45

Leu Glu Ser His Asp Ala Arg Lys Glu His Lys Glu Phe Val Lys Ile
                50                  55                  60

Leu Glu Ser Gln Gly Ile Asn Val Val Glu Leu Thr Asp Leu Ile Ala
65                  70                  75                  80

Glu Thr Tyr Glu Leu Ala Ser Glu Glu Ala Lys Asp Asn Leu Ile Glu
                85                  90                  95

Glu Phe Leu Asp Glu Ser Glu Pro Val Leu Ser Glu Glu His Arg Ile
                100                 105                 110

Leu Val Arg Asn Phe Leu Lys Gly Ile Thr Lys Thr Lys Glu Leu Val
                115                 120                 125

Lys Met Met Met Ala Gly Ile Thr Lys Tyr Asp Leu Gly Ile Glu Ala
                130                 135                 140

Asp Arg Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Ile Phe Glu
                180                 185                 190

Asn His Pro Lys Leu Val Ser Thr Pro Ile Tyr Tyr His Pro Ser Gln
                195                 200                 205

Gly Leu Ser Ile Glu Gly Gly Asp Val Phe Ile Tyr Asn Asn Asp Thr
                210                 215                 220

Leu Val Val Gly Val Ser Glu Arg Thr Asp Leu Gln Thr Ile Thr Leu
225                 230                 235                 240
```

Leu Ala Lys Asn Ile Lys Ala Asn Glu Glu Cys Glu Phe Lys Arg Ile
              245                 250                 255

Val Ala Ile Asn Val Pro Lys Trp Thr Asn Leu Met His Leu Asp Thr
        260                 265                 270

Trp Leu Thr Met Leu Asp Lys Asn Lys Phe Leu Tyr Ser Pro Ile Ala
            275                 280                 285

Asn Asp Val Phe Lys Phe Trp Asp Tyr Asp Leu Val Asn Gly Gly Asp
        290                 295                 300

Glu Pro Gln Pro Val Asp Asn Gly Leu Pro Leu Asn Glu Leu Leu Ala
305                 310                 315                 320

Ser Ile Ile Gly Glu Glu Pro Val Leu Val Pro Ile Ala Gly Glu Gly
                325                 330                 335

Ala Ser Lys Met Asp Ile Glu Arg Glu Thr His Phe Asp Gly Thr Asn
            340                 345                 350

Tyr Leu Ala Ile Ala Pro Gly Val Val Gly Tyr Ser Arg Asn Glu
        355                 360                 365

Lys Thr Asn Ala Ala Leu Glu Lys Ala Gly Ile Lys Val Leu Pro Phe
    370                 375                 380

Lys Gly His Gln Leu Ser Leu Gly Met Gly Asn Ala Arg Cys Met Ser
385                 390                 395                 400

Met Pro Leu Tyr Arg Lys Asp Val Lys
            405

<210> SEQ ID NO 36
<211> LENGTH: 412
<212> TYPE: PRT
<213> ORGANISM: Mycoplasma alkalescens

<400> SEQUENCE: 36

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly His Glu Ile
            20                  25                  30

Asp Tyr Ile Thr Pro Ser Arg Leu Asp Glu Leu Leu Phe Ser Ala Met
        35                  40                  45

Leu Glu Ser His Asp Ala Arg Lys Glu His Lys Gln Phe Val Ala Glu
    50                  55                  60

Leu Lys Ala Asn Asn Val Asn Val Ile Glu Leu Thr Asp Leu Val Ala
65                  70                  75                  80

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu Glu Asn Lys Ile
            100                 105                 110

Ala Val Arg Asp Phe Leu Lys Ser Arg Lys Thr Thr Arg Glu Leu Ile
        115                 120                 125

Glu Val Met Met Ala Gly Ile Thr Lys Tyr Asp Leu Gly Ile Lys Asn
    130                 135                 140

Cys Lys Cys Gln Asp Leu Val Val Asp Pro Met Pro Asn Leu Tyr Phe
145                 150                 155                 160

Thr Arg Asp Pro Phe Ala Ser Val Gly Asn Gly Ile Thr Ile His Tyr
                165                 170                 175

Met Arg Tyr Lys Val Arg Gln Arg Glu Thr Leu Phe Ser Arg Phe Ile
            180                 185                 190

Phe Ala Asn His Pro Lys Leu Val Asn Thr Pro Ile Tyr Tyr His Pro
        195                 200                 205

```
Ser Leu Lys Leu Ser Ile Glu Gly Gly Asp Val Phe Ile Tyr Asn Asn
    210                 215                 220

Asp Thr Leu Val Val Gly Val Ser Glu Arg Thr Asp Leu Glu Thr Ile
225                 230                 235                 240

Thr Leu Leu Ala Lys Asn Ile Val Ala Asn Lys Glu Cys Glu Phe Lys
                245                 250                 255

Arg Ile Val Ala Ile Asn Val Pro Lys Trp Thr Asn Leu Met His Leu
                260                 265                 270

Asp Thr Trp Leu Thr Met Leu Asp Lys Asp Lys Phe Leu Tyr Ser Pro
            275                 280                 285

Ile Ala Asn Asp Val Phe Lys Phe Trp Asp Tyr Asp Leu Val Asn Gly
        290                 295                 300

Gly Ala Glu Pro Lys Pro Val Glu Asn Gly Ser Ser Leu Glu Ala Ile
305                 310                 315                 320

Leu Glu Ser Ile Ile His Lys Lys Pro Ile Leu Ile Pro Ile Gly Gly
                325                 330                 335

Asp Ser Ala Ser Gln Ile Glu Val Glu Arg Glu Thr His Phe Asp Gly
                340                 345                 350

Thr Asn Tyr Leu Ala Ile Arg Pro Gly Val Val Ile Gly Tyr Ser Arg
            355                 360                 365

Asn Val Lys Thr Asn Ala Ala Leu Glu Ala Ala Gly Ile Lys Val Ile
        370                 375                 380

Pro Phe His Gly Asn Gln Leu Ser Leu Gly Met Gly Asn Ala Arg Cys
385                 390                 395                 400

Met Ser Met Pro Leu Ser Arg Lys Asp Val Lys Trp
                405                 410

<210> SEQ ID NO 37
<211> LENGTH: 401
<212> TYPE: PRT
<213> ORGANISM: Mycoplasma iners

<400> SEQUENCE: 37

Met Ser Lys Ile Asn Val Tyr Ser Glu Ile Gly Val Leu Lys Glu Val
1               5                   10                  15

Leu Val His Thr Pro Gly Asp Glu Ile Arg Arg Ile Ala Pro Ser Arg
            20                  25                  30

Leu Asp Glu Leu Leu Phe Ser Ala Ile Leu Glu Pro Ser Ala Ala Ile
        35                  40                  45

Gln Glu His Lys Ser Phe Leu Lys Ile Leu Gln Asp Arg Gly Ile Lys
    50                  55                  60

Thr Ile Gln Leu Ser Asp Leu Val Ala Glu Thr Tyr Lys His Tyr Ala
65                  70                  75                  80

Ser Glu Ala Glu Lys Glu Ala Phe Ile Glu Lys Tyr Leu Asp Glu Ala
                85                  90                  95

Thr Pro Val Leu Ser Lys Asp Met Arg Ala Lys Val Lys Asn Tyr Ile
            100                 105                 110

Leu Ser Met Gln Gly Glu Pro Val Lys Met Val Arg Thr Met Met Ala
        115                 120                 125

Gly Val Ser Lys Gln Glu Leu Asn Val Glu Ser Glu Val Glu Leu Ile
    130                 135                 140

Val Asp Pro Met Pro Asn Leu Tyr Phe Thr Arg Asp Pro Phe Ala Ser
145                 150                 155                 160

Ala Gly Asn Gly Ile Ser Leu Asn Asn Met Lys Tyr Val Val Arg Lys
```

```
                165                 170                 175
Arg Glu Thr Ile Phe Ala Glu Phe Ile Phe Ser Ile His Pro Glu Tyr
            180                 185                 190

Lys Lys Thr Pro His Trp Phe Asp Arg Leu Asp Asn Gly Ser Ile Glu
        195                 200                 205

Gly Gly Asp Val Phe Ile Tyr Asn Lys Asp Thr Leu Val Ile Gly Val
    210                 215                 220

Ser Glu Arg Thr Asn Lys Glu Ala Ile Ile Thr Ile Ala Lys His Ile
225                 230                 235                 240

Gln Asp Asn Lys Glu Ala Gln Phe Lys Lys Ile Val Ala Ile Asn Val
                245                 250                 255

Pro Pro Met Pro Asn Leu Met His Leu Asp Thr Trp Leu Thr Met Val
            260                 265                 270

Asp Lys Asn Lys Phe Leu Tyr Ser Pro Asn Met Leu Ser Val Leu Lys
        275                 280                 285

Val Trp Glu Ile Asp Leu Ser Lys Pro Ile Glu Met Val Glu Thr Asn
    290                 295                 300

Lys Pro Leu Ala Glu Val Leu Glu Ser Ile Ile Gly Glu Lys Pro Ile
305                 310                 315                 320

Leu Ile Pro Ile Ala Gly Lys Asp Ala Thr Gln Leu Asp Ile Asp Ile
                325                 330                 335

Glu Thr His Phe Asp Gly Thr Asn Tyr Leu Thr Ile Ala Pro Gly Val
            340                 345                 350

Val Val Gly Tyr Ser Arg Asn Val Lys Thr Glu Ala Ala Leu Arg Ala
        355                 360                 365

Ala Gly Val Thr Val Leu Ser Phe Glu Gly Asn Gln Leu Ser Leu Gly
    370                 375                 380

Met Gly Ser Ala Arg Cys Met Ser Met Pro Leu Val Arg Glu Asp Val
385                 390                 395                 400

Lys

<210> SEQ ID NO 38
<211> LENGTH: 401
<212> TYPE: PRT
<213> ORGANISM: Mycoplasma gallinarum

<400> SEQUENCE: 38

Met Ser Lys Ile Arg Val Tyr Ser Glu Ile Gly Asn Leu Lys Lys Val
1               5                   10                  15

Leu Val His Thr Pro Gly Asp Glu Ile Arg Arg Ile Ser Pro Ser Arg
            20                  25                  30

Leu Glu Glu Leu Leu Phe Ser Ala Val Leu Glu Pro Asn Ala Ala Ile
        35                  40                  45

Glu Glu His Lys Arg Phe Val Lys Leu Leu Glu Asp Arg Gly Ile Gln
    50                  55                  60

Ala Ile Gln Leu Ser Asp Leu Val Ala Glu Thr Tyr Val Lys Tyr Ala
65                  70                  75                  80

Thr Ala Glu Gln Lys Ala Ala Phe Ile Glu Lys Tyr Leu Asp Glu Ala
                85                  90                  95

Thr Pro Ala Leu Ser Ala Glu Asn Arg Glu Arg Ala Lys Lys Tyr Ile
            100                 105                 110

Leu Ser Leu Glu Met Gln Pro Val Lys Met Ile Arg Thr Met Met Ala
        115                 120                 125

Gly Leu Ser Lys Tyr Glu Leu Asn Val Glu Ser Asn Ile Glu Leu Ile
```

-continued

```
                130                 135                 140
Ile Asp Pro Met Pro Asn Leu Tyr Phe Thr Arg Asp Pro Phe Ala Ser
145                 150                 155                 160

Ala Gly Asn Gly Ile Ser Leu Asn Asn Met Lys Tyr Val Val Arg Lys
                165                 170                 175

Arg Glu Thr Ile Phe Ala Glu Phe Ile Phe Ala Ile His Pro Glu Tyr
                180                 185                 190

Lys Glu Thr Pro His Trp Phe Asp Arg Leu Asp His Gly Ser Ile Glu
                195                 200                 205

Gly Gly Asp Val Phe Val Tyr Asn Lys Asp Thr Leu Val Ile Gly Val
                210                 215                 220

Ser Glu Arg Thr Asn Lys Glu Ala Ile Ile Thr Ile Ala Lys His Ile
225                 230                 235                 240

Gln Asp Asn Lys Glu Ala Glu Phe Lys Lys Ile Val Ala Ile Asn Val
                245                 250                 255

Pro Pro Met Pro Asn Leu Met His Leu Asp Thr Trp Leu Thr Met Val
                260                 265                 270

Asp Lys Asn Lys Phe Ile Tyr Ser Pro Asn Met Leu Ser Val Leu Lys
                275                 280                 285

Ile Trp Glu Ile Asp Leu Ala Lys Pro Ile Glu Met Val Glu Ser Asn
                290                 295                 300

Lys Ser Leu Thr Glu Val Leu Glu Ser Ile Ile Gly Glu Lys Pro Ile
305                 310                 315                 320

Leu Ile Pro Ile Ala Gly Glu Gly Ala Ser Gln Leu Asp Ile Asp Ile
                325                 330                 335

Glu Thr His Phe Asp Gly Thr Asn Tyr Leu Thr Ile Ala Pro Gly Val
                340                 345                 350

Val Val Gly Tyr Ser Arg Asn Glu Lys Thr Glu Lys Ala Leu Lys Ala
                355                 360                 365

Ala Gly Ile Thr Val Leu Ser Phe Glu Gly Asn Gln Leu Ser Leu Gly
                370                 375                 380

Met Gly Ser Ala Arg Cys Met Ser Met Pro Leu Val Arg Glu Asp Val
385                 390                 395                 400

Lys

<210> SEQ ID NO 39
<211> LENGTH: 405
<212> TYPE: PRT
<213> ORGANISM: Mycoplasma pirum

<400> SEQUENCE: 39

Met Asn Ser Asn Gln Lys Gly Ile His Val Tyr Ser Glu Ile Gly Lys
1               5                   10                  15

Leu Lys Glu Val Leu Val His Arg Pro Gly Arg Glu Leu Asp Phe Leu
                20                  25                  30

Asp Pro Thr Arg Leu Asp Glu Leu Leu Phe Ala Ala Thr Leu Glu Ala
                35                  40                  45

Glu Thr Ala Arg Leu Glu His Asp Asn Phe Thr Asn Ala Leu Lys Asn
                50                  55                  60

Gln Gly Val Thr Val Ile Glu Leu Ala Asp Leu Val Ala Gln Thr Tyr
65                  70                  75                  80

Ser Ser Ser Thr Pro Thr Ile Lys Ala Ala Phe Ile Asn Lys Tyr Leu
                85                  90                  95

Asp Glu Ala Thr Pro Ala Leu Thr Thr Lys Leu Arg Thr Leu Val Lys
```

```
                100             105             110
Asp Phe Leu Thr Lys Gln Lys Ser Val Arg Lys Met Val Asp Tyr Met
            115                 120                 125

Ile Gly Gly Ile Leu Ser Thr Asp Leu Asn Ile Lys Gly Lys Pro Glu
130                 135                 140

Leu Ile Val Glu Pro Met Pro Asn Ala Tyr Phe Thr His Asp Pro Phe
145                 150                 155                 160

Ala Ser Val Gly Asn Gly Val Thr Leu His Tyr Met Lys His Asn Val
                165                 170                 175

Arg Arg Arg Glu Val Leu Phe Ser Glu Phe Ile Phe Asn Asn Asn Glu
            180                 185                 190

Arg Phe Gln Asn Thr Pro Arg Tyr Ile Val Pro Thr Lys Gly Leu Asp
        195                 200                 205

Ile Glu Gly Gly Asp Val Phe Val Tyr Asn Lys Asn Thr Leu Val Val
    210                 215                 220

Gly Val Ser Glu Arg Thr Lys Met Val Thr Ile Lys Glu Leu Ala Lys
225                 230                 235                 240

Asn Ile Leu Lys Asn Lys Glu Cys Leu Phe Lys Lys Ile Tyr Ala Ile
                245                 250                 255

Asn Val Pro Lys Met Pro Asn Leu Met His Leu Asp Thr Trp Leu Thr
            260                 265                 270

Met Leu Asp His Asn Lys Phe Leu Tyr Ser Pro Asn Met Leu Ser Val
        275                 280                 285

Leu Lys Ile Trp Glu Ile Asp Ile Ser Ser Gly Lys Ser Ile Ser Ser
    290                 295                 300

Pro Lys Glu Leu Asn Met Asp Leu Ser Lys Ala Leu Ser Ile Ile Ile
305                 310                 315                 320

Gly Lys Lys Pro Ile Leu Ile Pro Val Ala Gly Glu Asn Ala Ser Gln
                325                 330                 335

Ile Asp Ile Asn Ile Glu Thr Asn Phe Asp Ala Thr Asn Tyr Leu Val
            340                 345                 350

Thr Gln Pro Gly Val Val Val Gly Tyr Ser Arg Asn Lys Lys Thr Glu
        355                 360                 365

Ala Ala Leu Ile Lys Ala Gly Ile Glu Val Ile Pro Phe Gln Gly Asn
    370                 375                 380

Gln Leu Ser Leu Gly Met Gly Ser Ala Arg Cys Met Ser Met Pro Leu
385                 390                 395                 400

Ile Arg Glu Asp Val
            405

<210> SEQ ID NO 40
<211> LENGTH: 404
<212> TYPE: PRT
<213> ORGANISM: Mycoplasma primatum

<400> SEQUENCE: 40

Met Ser Lys Ser Lys Ile Asn Val Tyr Ser Glu Tyr Gly Asn Leu Lys
1               5                   10                  15

Glu Val Leu Val His Thr Pro Gly Asp Glu Ile Arg Arg Ile Thr Pro
            20                  25                  30

Ser Arg Leu Asp Glu Leu Leu Phe Ser Ala Ile Leu Glu Pro Lys Ser
        35                  40                  45

Ala Ile Ala Glu His Lys Ser Phe Cys Gln Ile Leu Lys Asp Asn Lys
    50                  55                  60
```

```
Val Lys Ala Ile Gln Leu Asp Glu Leu Val Ala Thr Tyr Lys Gly
 65                  70                  75                  80

Val Ser Glu Ser Val Gln Asn Ser Phe Val Arg Trp Leu Asp Glu
                 85                  90                  95

Cys Glu Pro Lys Leu Glu Asn Asn Val Arg Pro Ile Val Lys Glu Tyr
            100                 105                 110

Leu Leu Lys Ala Ala Glu Gln Ser Val Lys Lys Met Ile Arg Ile Met
            115                 120                 125

Met Ala Gly Ile Asp Lys Arg Glu Ile Gly Val Ser Glu Val Asp
    130                 135                 140

Phe Ile Val Asp Pro Met Pro Asn Leu Tyr Phe Thr Arg Asp Pro Phe
145                 150                 155                 160

Ala Ser Val Gly Asn Gly Ile Thr Leu His His Met Lys Tyr Val Val
                165                 170                 175

Arg Gln Arg Glu Thr Leu Phe Ser Glu Phe Ile Phe Asp Asn His Pro
            180                 185                 190

Asp Tyr Lys Phe Val Pro Arg Tyr Phe Arg Asp Asp Glu Gly Lys
            195                 200                 205

Ile Glu Gly Gly Asp Val Phe Ile Tyr Asn Ser Lys Thr Leu Val Val
210                 215                 220

Gly Ile Ser Glu Arg Thr Asn Lys Asp Ala Ile Arg Ile Val Ala Lys
225                 230                 235                 240

Lys Ile Gln Ala Asn Ala Asp Ala Lys Phe Glu Lys Ile Phe Ala Ile
                245                 250                 255

Asn Val Pro Pro Met Pro Asn Leu Met His Leu Asp Thr Trp Leu Thr
            260                 265                 270

Met Leu Asp Ser Asn Lys Phe Leu Tyr Ser Pro Asn Met Leu Ser Val
    275                 280                 285

Leu Lys Val Trp Glu Ile Asn Leu Asp Asp Pro Ala Leu Glu Trp Lys
    290                 295                 300

Glu Ile Ser Gly Ser Leu Glu Glu Ile Leu Thr Tyr Ile Ile Gly Lys
305                 310                 315                 320

Lys Pro Ile Leu Ile Pro Ile Ala Gly Lys Gly Ala Ser Gln Phe Glu
                325                 330                 335

Ile Asp Ile Glu Thr His Phe Asp Gly Thr Asn Tyr Leu Ala Ile Ala
            340                 345                 350

Pro Ser Val Val Ile Gly Tyr Ser Arg Asn Glu Leu Thr Glu Lys Ala
            355                 360                 365

Leu Lys Lys Ala Gly Val Lys Val Leu Ser Leu Asp Gly Asn Gln Leu
    370                 375                 380

Ser Leu Gly Met Gly Ser Ala Arg Cys Met Ser Met Pro Leu Ile Arg
385                 390                 395                 400

Glu Asp Val Lys

<210> SEQ ID NO 41
<211> LENGTH: 401
<212> TYPE: PRT
<213> ORGANISM: Mycoplasma lipofaciens

<400> SEQUENCE: 41

Met Ser Lys Ile Asn Val Tyr Ser Glu Val Gly Val Leu Lys Glu Val
1               5                   10                  15

Leu Val His Thr Pro Gly Asp Glu Ile Arg Arg Val Ala Pro Ser Arg
                20                  25                  30
```

Leu Asp Glu Leu Leu Phe Ser Ala Ile Leu Glu Pro Gln Asp Ala Ile
            35                   40                  45

Ala Glu His Lys Arg Phe Ile Lys Ile Leu Glu Asp Asn Asn Ile Lys
 50                      55                  60

Val Ile Gln Leu Asp Glu Leu Val Ser Glu Thr Trp Glu Lys Ala Thr
 65                  70                  75                  80

Ala Glu Gln Arg Asp Ala Phe Ile Glu Lys Trp Leu Asp Glu Ala Glu
                 85                  90                  95

Pro Val Leu Asp Ala Lys Leu Arg Glu Thr Val Lys Lys Tyr Leu Leu
                100                 105                 110

Ser Leu Asn Pro Val Lys Lys Met Val Arg Thr Met Met Ala Gly Ile
            115                 120                 125

Asp Lys Lys Glu Leu Lys Ile Glu Leu Asp Arg Asp Leu Val Val Asp
130                 135                 140

Pro Met Pro Asn Leu Tyr Phe Thr Arg Asp Pro Phe Ala Ser Ala Gly
145                 150                 155                 160

Asn Gly Ile Ser Leu Asn Asn Met Lys Tyr Val Thr Arg Lys Arg Glu
                165                 170                 175

Thr Ile Phe Ala Glu Phe Ile Phe Asn Ile His Pro Asp Tyr Lys Thr
                180                 185                 190

Thr Pro His Trp Phe Asp Arg Leu Asp Lys Gly Asn Ile Glu Gly Gly
            195                 200                 205

Asp Val Phe Ile Tyr Asn Lys Asp Thr Leu Val Leu Gly Val Ser Glu
            210                 215                 220

Arg Thr Asn Lys Asp Ala Val Met Thr Ile Ala Lys His Ile Gln Ser
225                 230                 235                 240

Asn Glu Gln Ala Lys Phe Lys Leu Val Ala Ile Asn Val Pro Pro
                245                 250                 255

Met Pro Asn Leu Met His Leu Asp Thr Trp Leu Thr Met Val Asp His
            260                 265                 270

Asp Lys Phe Leu Tyr Ser Pro Asn Met Leu Ser Val Leu Lys Ile Trp
            275                 280                 285

Glu Ile Asp Leu Thr Pro Gly Lys Glu Ile Glu Met Val Glu Ser Thr
290                 295                 300

Lys Ser Leu Ser Asp Met Leu Glu Ser Ile Ile Gly Lys Lys Pro Val
305                 310                 315                 320

Leu Ile Pro Ile Ala Gly Lys Asp Ala Ser Gln Leu Asp Ile Asp Ile
                325                 330                 335

Glu Thr His Phe Asp Gly Thr Asn Tyr Leu Thr Ile Arg Pro Gly Val
            340                 345                 350

Val Val Gly Tyr Ser Arg Asn Cys Leu Thr Glu Gln Ala Leu Lys Asp
            355                 360                 365

Ala Gly Val Thr Val Leu Ser Phe Asp Gly Asn Gln Leu Ser Leu Gly
            370                 375                 380

Met Gly Ser Ala Arg Cys Met Ser Met Pro Leu Val Arg Glu Asp Ile
385                 390                 395                 400

Lys

<210> SEQ ID NO 42
<211> LENGTH: 405
<212> TYPE: PRT
<213> ORGANISM: Mycoplasma felifaucium

<400> SEQUENCE: 42

```
Met Asn Lys Ile Asn Val Tyr Ser Glu Ile Gly Lys Leu Lys Glu Val
1               5                   10                  15
Leu Val His Thr Pro Gly Asn Glu Ile Arg Arg Ile Ser Pro Ser Arg
            20                  25                  30
Leu Asp Glu Leu Leu Phe Ser Ala Leu Leu Glu Pro Asn Phe Ala Ala
        35                  40                  45
Lys Glu His Thr Ala Phe Cys Glu Ile Leu Lys Glu Asn Gly Ile Lys
        50                  55                  60
Ala Ile Gln Leu Val Asp Leu Val Ser Asp Thr Trp Arg Ile Ala Ser
65                  70                  75                  80
Glu Lys Ala Lys Thr Glu Phe Ile Glu Arg Trp Leu Asp Glu Cys Glu
                85                  90                  95
Pro Lys Leu Asp Ser Asn Leu Arg Glu Ile Val Arg Lys His Ile Tyr
            100                 105                 110
Ala Ile Glu Lys Arg Ser Val Lys Arg Met Val Lys Thr Met Met Ala
            115                 120                 125
Gly Ile Glu Arg Arg Glu Leu Pro Val Thr Ser Lys Glu Val Ala Arg
        130                 135                 140
Glu Leu Val Val Asp Pro Met Pro Asn Leu Tyr Phe Thr Arg Asp Pro
145                 150                 155                 160
Phe Ala Ser Val Gly Asn Gly Ile Ser Leu His His Met Lys Tyr Val
                165                 170                 175
Thr Arg Gln Arg Glu Thr Ile Phe Ala Glu Phe Val Phe Gly Asn His
            180                 185                 190
Pro Asp Tyr Ile Asp Thr Pro Arg Trp Phe Asp Arg Ser Asp Asp Gly
            195                 200                 205
Arg Ile Glu Gly Gly Asp Val Phe Ile Tyr Gly Ser Lys Thr Leu Val
        210                 215                 220
Ile Gly Val Ser Glu Arg Thr Asn Lys Glu Ala Ile Lys Val Met Ala
225                 230                 235                 240
Lys Lys Ile Gln Ala Asn Lys Glu Ala Thr Phe Glu Lys Ile Tyr Ala
                245                 250                 255
Ile Asn Val Pro Pro Met Pro Asn Leu Met His Leu Asp Thr Trp Leu
            260                 265                 270
Thr Met Leu Asp Lys Asn Lys Phe Leu Tyr Ser Pro Asn Met Leu Ala
        275                 280                 285
Val Leu Gln Val Trp Glu Ile Asp Leu Lys Asp Pro Glu Leu Thr Trp
        290                 295                 300
His Glu Leu Ser Gly Ser Leu Glu Glu Ile Leu His Lys Ile Ile Gly
305                 310                 315                 320
Arg Lys Pro Ile Leu Ile Pro Ile Ala Gly His Gly Ala Gln Gln Ile
                325                 330                 335
Asp Ile Asp Ile Glu Thr His Phe Asp Gly Thr Asn Tyr Leu Ala Ile
            340                 345                 350
Ala Pro Gly Val Val Gly Tyr Asn Arg Asn Val Leu Thr Glu Arg
            355                 360                 365
Ala Leu Lys Lys Ala Gly Ile Lys Val Leu Ser Phe Glu Gly Asn Gln
        370                 375                 380
Leu Ser Leu Gly Met Gly Ser Ala Arg Cys Met Ser Met Pro Leu Ile
385                 390                 395                 400
Arg Glu Asn Leu Lys
            405
```

```
<210> SEQ ID NO 43
<211> LENGTH: 404
<212> TYPE: PRT
<213> ORGANISM: Mycoplasma imitans

<400> SEQUENCE: 43

Met Phe Asn Lys Ile Lys Val Tyr Ser Glu Ile Gly Arg Leu Arg Lys
1               5                   10                  15

Val Leu Val His Thr Pro Gly Lys Glu Leu Glu Tyr Val Thr Pro Gln
            20                  25                  30

Arg Leu Asp Glu Leu Leu Phe Ser Ser Leu Leu Asn Pro Val Lys Ala
        35                  40                  45

Arg Gln Glu His Glu Ala Phe Ile Lys Ile Leu Gln Asp Gln Gly Val
    50                  55                  60

Glu Cys Val Gln Leu Thr Thr Leu Thr Ala Gln Thr Phe Gln Ser Ala
65                  70                  75                  80

Thr Ser Glu Val Lys Glu Lys Phe Ile Asn Arg Trp Leu Asp Glu Cys
                85                  90                  95

Leu Pro Lys Leu Ser Asp Asp Asn Arg Ile Lys Val Tyr Ala Tyr Leu
            100                 105                 110

Lys Asp Leu Ser Ser Asp Pro Glu Val Met Ile Arg Lys Met Met Ser
        115                 120                 125

Gly Ile Leu Ala Lys Glu Val Asn Val Gln Ser Asp Val Glu Leu Ile
    130                 135                 140

Ala Asp Pro Met Pro Asn Leu Tyr Phe Thr Arg Asp Pro Phe Ala Ser
145                 150                 155                 160

Ile Gly Lys Gly Val Thr Leu His Ser Met Phe His Pro Thr Arg Lys
                165                 170                 175

Arg Glu Thr Ile Phe Ala Asp Phe Val Phe Ser His His Pro Glu Tyr
            180                 185                 190

Lys Gln Thr Pro Lys Tyr Tyr Ser Arg Leu Asn Glu Tyr Ser Ile Glu
        195                 200                 205

Gly Gly Asp Leu Phe Val Tyr Asp Asp Lys Thr Leu Val Ile Gly Val
    210                 215                 220

Ser Glu Arg Thr Glu Lys Lys Ala Ile Gln Phe Leu Ala Glu Lys Leu
225                 230                 235                 240

Arg Glu Asn Tyr Glu Thr Thr Phe Glu Lys Ile Tyr Ala Ile Asn Val
                245                 250                 255

Pro Lys Met Ser Asn Leu Met His Leu Asp Thr Trp Leu Thr Met Leu
            260                 265                 270

Asp Tyr Asp Lys Phe Leu Tyr Ser Pro Asn Met Met Gly Val Leu Lys
        275                 280                 285

Ile Trp Glu Ile Asp Leu Thr His Glu Gln Leu Ser Trp Arg Glu Leu
    290                 295                 300

Asn Glu Ser Leu Glu Glu Phe Leu Ser Met Val Ile Gly Lys Lys Ala
305                 310                 315                 320

Thr Thr Ile Pro Val Ala Gly Glu Asp Ser Thr Gln Ile Glu Ile Asp
                325                 330                 335

Val Glu Thr Asn Phe Asp Ala Thr Asn Phe Leu Val Ile Gln Pro Gly
            340                 345                 350

Val Val Val Gly Tyr Asp Arg Asn Tyr Lys Thr Asn Gln Ala Leu Val
        355                 360                 365

Asn Ala Gly Ile Lys Val Leu Ser Trp Asn Gly Asp Gln Leu Ser Leu
    370                 375                 380
```

```
Gly Met Gly Ser Ala Arg Cys Met Ser Met Pro Leu Tyr Arg Asp Pro
385                 390                 395                 400

Ile Lys Lys Gly

<210> SEQ ID NO 44
<211> LENGTH: 401
<212> TYPE: PRT
<213> ORGANISM: Mycoplasma opalescens

<400> SEQUENCE: 44

Met Ser Lys Ile Asn Val Tyr Ser Glu Ile Gly Thr Leu Lys Glu Val
1               5                   10                  15

Leu Val His Thr Pro Gly Asp Glu Ile Arg Arg Val Ala Pro Ala Arg
            20                  25                  30

Leu Asp Glu Leu Leu Phe Ser Ala Ile Leu Glu Pro Asn His Ala Ile
        35                  40                  45

Ala Glu His Lys Ala Phe Ile Lys Ile Leu Glu Asp Asn Gly Ile Lys
    50                  55                  60

Val Ile Gln Leu Asp Glu Leu Val Val Gln Thr Trp Asn Gln Val Asp
65                  70                  75                  80

Glu Ala Thr Arg Lys Ala Phe Val Thr Lys Trp Leu Asp Glu Cys Glu
                85                  90                  95

Pro Lys Leu Glu Ser Asn Val Arg Val Glu Val Glu Lys Tyr Ile Tyr
            100                 105                 110

Ser Leu Ala Lys Glu Pro Lys Lys Met Val Arg Thr Met Met Ala Gly
        115                 120                 125

Ile Ser Lys Glu Glu Leu Pro Leu Asn Val Asn Arg Pro Leu Val Val
130                 135                 140

Asp Pro Met Pro Asn Leu Tyr Phe Thr Arg Asp Pro Phe Ala Ser Val
145                 150                 155                 160

Gly Thr Gly Ile Ser Leu His His Met Lys Tyr Val Thr Arg Gln Arg
                165                 170                 175

Glu Thr Ile Phe Ala Gln Phe Val Phe Asp Asn His Lys Asp Tyr Asn
            180                 185                 190

Thr Val Pro Arg Trp Phe Asp Asn Lys Asp Gln Gly Arg Ile Glu Gly
        195                 200                 205

Gly Asp Val Phe Ile Tyr Asn Thr Lys Thr Leu Val Ile Gly Val Ser
210                 215                 220

Glu Arg Thr Asp Lys Asp Ala Ile Lys Ile Met Ala Lys Lys Ile Gln
225                 230                 235                 240

Ala Asp Lys Asn Cys Lys Phe Glu Lys Ile Phe Ala Ile Asn Val Pro
                245                 250                 255

Pro Met Pro Asn Leu Met His Leu Asp Thr Trp Leu Thr Met Val Asp
            260                 265                 270

Arg Asn Lys Phe Leu Tyr Ser Pro Asn Met Leu Ser Val Leu Lys Val
        275                 280                 285

Trp Glu Ile Asp Leu Lys Asp Ala Ser Leu Ala Trp Lys Glu Ile Glu
        290                 295                 300

Gly Ser Leu Ser Gln Ile Leu Glu Lys Ile Ile Gly Glu Lys Pro Ile
305                 310                 315                 320

Leu Ile Pro Ile Ala Gly Glu Asn Ala Ser Gln Leu Asp Ile Asp Ile
                325                 330                 335

Glu Thr His Phe Asp Gly Thr Asn Tyr Leu Thr Ile Ala Pro Gly Val
            340                 345                 350
```

Val Val Gly Tyr Ser Arg Asn Val Lys Thr Glu Gln Ala Leu Lys Ala
            355                 360                 365

Ala Gly Val Lys Val Leu Ser Phe Glu Gly Asn Gln Leu Ser Leu Gly
370                 375                 380

Met Gly Ser Ala Arg Cys Met Ser Met Pro Leu Ile Arg Glu Asp Leu
385                 390                 395                 400

Lys

<210> SEQ ID NO 45
<211> LENGTH: 425
<212> TYPE: PRT
<213> ORGANISM: Mycoplasma moatsii

<400> SEQUENCE: 45

Met Lys Lys Asn Ala Ile Asn Val Tyr Ser Glu Ile Gly Lys Leu Lys
1               5                   10                  15

Lys Val Leu Val His Arg Pro Gly Asp Glu Leu Lys Tyr Val Thr Pro
            20                  25                  30

Gln Arg Met Asp Glu Leu Leu Met Ser Ala Ile Ile Glu Leu Glu Gln
        35                  40                  45

Ala Lys Glu Glu His Asp Ala Phe Thr Lys Ile Leu Arg Asp Asn Gly
    50                  55                  60

Val Glu Val Ile Glu Leu Ala Asp Leu Thr Ala Glu Met Tyr Asp Ser
65                  70                  75                  80

Leu Thr Pro Ser Glu Lys Asp Ala Phe Leu Asn Gln Trp Val Lys Glu
                85                  90                  95

Ala Ser Trp Gly Lys Lys Ser Ser Ile Asp Ala Leu Lys Ile Lys Lys
            100                 105                 110

Asn Leu Ser Lys Lys Val Phe Asp Tyr Val Lys Ser Ile Lys Pro Thr
        115                 120                 125

Arg Lys Met Ile Asp Lys Leu Met Ala Gly Val Leu Leu Ser Glu Ile
130                 135                 140

Gly Glu Lys Ser Ile Ile Leu Asn Lys Asp Lys Lys Asn Glu Met Val
145                 150                 155                 160

Ile Asp Leu Val Val Asp Pro Met Pro Asn Leu Tyr Phe Thr Arg Asp
                165                 170                 175

Pro Phe Ala Ser Val Gly Asn Gly Ile Thr Leu His Asn Met Lys Tyr
            180                 185                 190

Pro Thr Arg Lys Arg Glu Thr Ile Phe Ala Gln Trp Ile Phe Asn Lys
        195                 200                 205

His Pro Glu Tyr Lys Asp Val Pro Gln Phe Ile Ser Lys Arg Asp Gly
    210                 215                 220

Lys Glu Thr Ile Glu Gly Gly Asp Val Phe Ile Tyr Thr Lys Asp Val
225                 230                 235                 240

Leu Ala Ile Gly Val Ser Glu Arg Thr Asn Met Glu Ala Ile Leu Arg
                245                 250                 255

Ile Ala Thr Asn Ile Lys Lys Asp Lys Asn Cys Glu Phe Lys Lys Ile
            260                 265                 270

Val Ala Ile Asn Val Pro Pro Met Gly Asn Leu Met His Leu Asp Thr
        275                 280                 285

Trp Leu Thr Met Leu Asp Lys Asp Leu Phe Leu Tyr Ser Gly Asn Ile
    290                 295                 300

Lys Ser Ala Leu Lys Val Trp Glu Ile Asp Leu Thr Lys Pro Ile Thr
305                 310                 315                 320

```
Pro Lys Ser Pro Lys Leu Ser Thr Ala Lys Leu Ala Asp Ile Leu Ala
            325                 330                 335

Lys Ile Val Gly Lys Val Arg Met Ile Pro Ile Gly Gly Lys Asp
        340                 345                 350

Gly Asn Gln Met Asp Ile Asp Ile Glu Thr His Phe Asp Gly Thr Asn
            355                 360                 365

Tyr Leu Ala Ile Ala Pro Gly Val Val Gly Tyr His Arg Asn Arg
        370                 375                 380

Lys Thr Gln Lys Ala Leu Glu Glu Ala Gly Val Lys Val Leu Ala Phe
385                 390                 395                 400

Gln Gly Asn Gln Leu Ser Leu Gly Met Gly Ser Ala Arg Cys Met Ser
            405                 410                 415

Met Pro Leu Val Arg Glu Glu Val Lys
        420                 425

<210> SEQ ID NO 46
<211> LENGTH: 399
<212> TYPE: PRT
<213> ORGANISM: Mycoplasma elephantis

<400> SEQUENCE: 46

Met Ser Gln Ile Asn Val Phe Ser Glu Ile Gly Gln Leu Lys Glu Val
1               5                   10                  15

Leu Val His Thr Pro Gly Asp Glu Ile Arg Arg Ile Ser Pro Lys Arg
            20                  25                  30

Tyr Asn Glu Leu Leu Phe Ser Ala Ile Leu Glu Ala Asp Val Ala Ile
        35                  40                  45

Lys Glu His Lys Ser Phe Val Lys Ile Leu Glu Glu Asn Asn Val Lys
    50                  55                  60

Val Ile Gln Leu Lys Asp Ile Leu Leu Glu Thr Trp Asn Ile Cys Ser
65                  70                  75                  80

Lys Glu Ala Lys Asn Ile Phe Ile Asn Lys Trp Ile Glu Glu Ala Gln
            85                  90                  95

Pro Val Ile His Ser Ser Leu Lys Glu Lys Ile Lys Leu Phe Leu
        100                 105                 110

Lys Ser Lys Thr Pro Leu Glu Ile Ile Asp Ile Met Met Lys Gly Ile
        115                 120                 125

Leu Lys Gln Glu Leu Gly Ile Glu Tyr Lys His Glu Leu Ile Ile Asp
        130                 135                 140

Pro Met Pro Asn Leu Tyr Phe Thr Arg Asp Pro Phe Thr Ser Met Gly
145                 150                 155                 160

Ser Gly Ile Thr Ile Asn Asn Met Lys Tyr Gln Thr Arg Lys Arg Glu
            165                 170                 175

Thr Ile Phe Ser Glu Phe Ile Phe Asn Asn His Pro Lys Tyr Lys Asn
        180                 185                 190

Thr Pro Arg Trp Phe Asp Arg Phe Asp Ser Gly Asn Ile Glu Gly Gly
        195                 200                 205

Asp Leu Phe Val Tyr Thr Lys Glu Thr Ile Val Val Gly Val Ser Glu
    210                 215                 220

Arg Thr Lys Lys Lys Ala Ile Leu Lys Ile Ala Lys Asn Ile Gln Glu
225                 230                 235                 240

Asn Asn Asn Ser Phe Lys Lys Ile Val Val Ile Lys Val Pro Ile Met
            245                 250                 255

Gln Asn Leu Met His Leu Asp Thr Trp Ile Val Met Val Asp Phe Asp
        260                 265                 270
```

```
Lys Phe Ile Tyr Ser Pro Asn Val Thr Lys Ser Leu Lys Phe Trp Glu
            275                 280                 285

Ile Asp Leu Thr Lys Lys Pro Lys Phe Ile Gln Leu Lys Asn Glu Thr
        290                 295                 300

Leu Glu Asp Val Leu Tyr Arg Val Ile Gly Lys Lys Pro Ile Leu Ile
305                 310                 315                 320

Pro Val Ala Gly Glu Asn Ala Asn Gln Ile Asp Ile Asp Val Glu Thr
                325                 330                 335

His Phe Asp Ala Thr Asn Tyr Leu Thr Ile Arg Pro Gly Val Val Val
            340                 345                 350

Gly Tyr Ser Arg Asn Lys Lys Thr Glu Glu Ala Leu Ile Asn Ala Gly
                355                 360                 365

Val Lys Val Tyr Ala Phe Glu Gly Asn Gln Leu Ser Leu Gly Met Gly
            370                 375                 380

Ser Ala Arg Cys Met Ser Met Pro Leu Ile Arg Glu Asp Ile Ile
385                 390                 395

<210> SEQ ID NO 47
<211> LENGTH: 399
<212> TYPE: PRT
<213> ORGANISM: Mycoplasma testudinis

<400> SEQUENCE: 47

Met Lys Asn Ile Asn Val Tyr Ser Glu Val Gly Lys Leu Lys Glu Val
1               5                   10                  15

Val Val His Thr Pro Gly Glu Glu Leu His Asn Val Ala Pro Ser Arg
            20                  25                  30

Leu Gln Glu Leu Leu Thr Ser Ala Val Leu Glu Pro Glu Val Ala Arg
        35                  40                  45

Lys Glu His Leu Lys Phe Ile Lys Ile Leu Asn Asp Tyr Gly Val Lys
    50                  55                  60

Val Ile Gln Ile Val Asp Leu Ile Thr Glu Thr Tyr Glu Ala Val Asp
65                  70                  75                  80

Ser Asn Lys Lys Glu Ala Phe Ile Asn Asn Trp Leu Asp Asn Ser Val
                85                  90                  95

Pro Lys Leu Thr Asp Lys Asn Arg Met Ile Leu Arg Asn Tyr Leu Thr
            100                 105                 110

Gln Phe Ser Thr Lys Ala Met Ile Arg Lys Met Ile Ser Gly Ile Arg
        115                 120                 125

Ala Lys Glu Leu Asn Leu Lys Thr Pro Ser Ala Leu Leu Val Asp Pro
    130                 135                 140

Met Pro Asn Leu Cys Phe Ala Arg Asp Thr Phe Ala Cys Val Gly Ser
145                 150                 155                 160

Ala Ile Ser Leu Ser Thr Met Lys His Pro Thr Arg Arg Glu Ala
                165                 170                 175

Leu Leu Thr Glu Phe Ile Phe Gln Asn His Pro Lys Tyr Lys Asp Val
            180                 185                 190

Ile Lys Tyr Phe Asp Ser Lys Asn Ser Lys Ala Thr Ile Glu Gly Gly
        195                 200                 205

Asp Ile Phe Val Tyr Asn Pro Lys Thr Leu Val Val Gly Asn Ser Glu
    210                 215                 220

Arg Thr Asn Met Gln Ala Cys Leu Leu Leu Ala Lys Lys Ile Gln Ser
225                 230                 235                 240

Asn Pro Asn Asn Lys Phe Glu Lys Ile Val Ile Val Asn Val Pro Pro
```

```
                       245                 250                 255
Leu Pro His Leu Met His Leu Asp Thr Trp Leu Thr Met Val Asp Tyr
            260                 265                 270

Asp Lys Phe Ile Tyr Ser Pro Asn Ile Leu His Thr Leu Lys Phe Trp
            275                 280                 285

Val Ile Asp Leu Lys Lys Arg Lys Leu Glu Ala Val Glu Lys His Asn
            290                 295                 300

Thr Leu Lys Ala Met Leu Arg Met Ile Ile Lys Lys Glu Pro Ile Leu
305                 310                 315                 320

Ile Pro Val Gly Asp Val Gly Ala Asp Gln Leu Asp Ile Asp Leu Glu
            325                 330                 335

Thr His Phe Asp Ala Thr Asn Tyr Leu Ala Leu Ala Pro Gly Val Val
            340                 345                 350

Val Gly Tyr Asp Arg Asn Ile Lys Thr Gln Arg Ala Leu Glu Lys Ala
            355                 360                 365

Gly Val Lys Val Leu Ser Phe Ser Gly Asn Gln Leu Ser Leu Ala Met
            370                 375                 380

Gly Ser Ala Arg Cys Leu Ser Met Pro Leu Ile Arg Glu Glu Asn
385                 390                 395

<210> SEQ ID NO 48
<211> LENGTH: 410
<212> TYPE: PRT
<213> ORGANISM: Mycoplasma canadense

<400> SEQUENCE: 48

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Lys Gln Phe Val Ser Glu
        50                  55                  60

Leu Lys Ala Asn Asp Ile Asn Val Val Glu Leu Thr Asp Leu Val Ala
65                  70                  75                  80

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu His Lys Ala
            100                 105                 110

Ile Val Arg Lys Tyr Leu Lys Gly Ile Gln Pro Thr Lys Leu Ile
            115                 120                 125

Glu Met Met Met Ala Gly Ile Thr Lys Tyr Asp Leu Gly Ile Glu Ala
            130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
            165                 170                 175

Tyr Lys Val Arg Gln Arg Glu Thr Leu Phe Ser Arg Phe Val Phe Ser
            180                 185                 190

Asn His Pro Lys Leu Val Asn Thr Pro Trp Tyr Tyr Asp Pro Ser Leu
            195                 200                 205

Lys Leu Ser Ile Glu Gly Gly Asp Val Phe Val Tyr Asn Asn Asp Thr
            210                 215                 220
```

```
Leu Val Val Gly Val Ser Glu Arg Thr Asp Leu Gln Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Ser
    290                 295                 300

Glu Pro Gln Pro Val Glu Asn Gly Leu Pro Leu Glu Gly Leu Leu Glu
305                 310                 315                 320

Ser Ile Ile Asn Lys Lys Pro Ile Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
        355                 360                 365

Lys Thr Asn Ala Ala Leu Glu Ala Ala Gly Ile Lys Val Leu Pro Phe
    370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 49
<211> LENGTH: 409
<212> TYPE: PRT
<213> ORGANISM: Mycoplasma anseris

<400> SEQUENCE: 49

Met Ser Val Phe Asp Lys Arg Phe Lys Gly Ile His Val Tyr Ser Glu
1               5                   10                  15

Ile Gly Glu Leu Gln Thr Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Ala Glu His Lys Lys Phe Val Ala Thr
    50                  55                  60

Leu Lys Glu Gln Gly Ile Asn Thr Val Glu Leu Thr Asp Leu Val Ala
65                  70                  75                  80

Glu Thr Tyr Asp Leu Ala Ser Gln Glu Ala Arg Asp Asn Leu Leu Glu
                85                  90                  95

Glu Phe Leu Asp Asp Ser Ala Pro Val Leu Ser Glu Glu His Lys Glu
            100                 105                 110

Ile Val Arg Thr Tyr Leu Lys Gly Ile Lys Gly Thr Arg Lys Leu Ile
        115                 120                 125

Glu Thr Met Met Ala Gly Ile Thr Lys Tyr Asp Leu Gly Ile Glu Ala
    130                 135                 140

Glu Gln Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Ile Phe Ser
            180                 185                 190
```

Asn His Pro Gln Leu Val Asn Thr Pro Trp Tyr Tyr Asn Pro Ala Glu
            195                 200                 205

Gly Leu Ser Ile Glu Gly Gly Asp Val Phe Ile Tyr Asn Asn Asp Thr
210                 215                 220

Leu Val Val Gly Val Ser Glu Arg Thr Asp Leu Gln Thr Ile Thr Leu
225                 230                 235                 240

Leu Ala Lys Asn Ile Lys Ala Asn Glu Glu Cys Glu Phe Lys Arg Ile
            245                 250                 255

Val Ala Ile Asn Val Pro Lys Trp Thr Asn Leu Met His Leu Asp Thr
            260                 265                 270

Trp Leu Thr Met Leu Asp Thr Asn Lys Phe Leu Tyr Ser Pro Ile Ala
            275                 280                 285

Asn Asp Val Phe Lys Phe Trp Asp Tyr Asp Leu Val Asn Gly Gly Asp
290                 295                 300

Glu Pro Gln Pro Val Asp Asn Gly Leu Pro Leu Asn Glu Leu Leu Lys
305                 310                 315                 320

Ser Ile Ile Gly Glu Glu Pro Ile Leu Ile Pro Ile Ala Gly Asp Gly
            325                 330                 335

Ala Thr Gln Ile Glu Ile Glu Arg Glu Thr His Phe Asp Gly Thr Asn
            340                 345                 350

Tyr Leu Ala Ile Ala Pro Gly Val Val Ile Gly Tyr Ser Arg Asn Glu
            355                 360                 365

Lys Thr Asn Ala Ala Leu Glu Ala Ala Gly Ile Lys Val Leu Pro Phe
370                 375                 380

Lys Gly His Gln Leu Ser Leu Gly Met Gly Asn Ala Arg Cys Met Ser
385                 390                 395                 400

Met Pro Leu Tyr Arg Lys Asp Val Lys
            405

<210> SEQ ID NO 50
<211> LENGTH: 401
<212> TYPE: PRT
<213> ORGANISM: Mycoplasma meleagridis

<400> SEQUENCE: 50

Met Ser Lys Ile Asn Val Tyr Ser Glu Ile Gly Val Leu Lys Glu Val
1 5 10 15

Leu Val His Thr Pro Gly Asp Glu Ile Arg Arg Ile Ser Pro Ser Arg
20 25 30

Leu Asp Glu Leu Leu Phe Ser Ala Ile Leu Gln Pro Glu Gln Ala Ile
35 40 45

Lys Glu His Gln Ser Phe Val Lys Ile Leu Gln Asp Arg Gly Ile Lys
50 55 60

Val Ile Gln Leu Ser Asp Leu Val Ala Glu Thr Tyr Val Lys Tyr Ala
65 70 75 80

Thr Ser Lys Glu Lys Glu Ser Phe Ile Glu Lys Trp Leu Asp Glu Ala
85 90 95

Thr Pro Ala Leu Asn Ser Glu Asn Arg Ala Arg Val Lys Asn Tyr Ile
100 105 110

Thr Ala Met Gln Gly Gln Pro Val Lys Met Val Arg Ala Met Met Ala
115 120 125

Gly Val Ser Lys Gln Glu Leu Asn Ile Glu Ser Asp Val Glu Leu Ile
130 135 140

Val Asp Pro Met Pro Asn Leu Tyr Phe Thr Arg Asp Pro Phe Ala Ser

```
                145                 150                 155                 160
Ala Gly Asn Gly Ile Ser Leu Asn Asn Met Lys Tyr Val Val Arg Lys
                    165                 170                 175

Arg Glu Thr Ile Phe Ala Glu Phe Ile Phe Ser Ile His Pro Glu Tyr
                    180                 185                 190

Lys Gln Thr Pro His Trp Phe Asp Arg Leu Asp Lys Gly Asn Ile Glu
                    195                 200                 205

Gly Gly Asp Val Phe Ile Tyr Asn Lys Asp Thr Leu Val Ile Gly Val
            210                 215                 220

Ser Glu Arg Thr Asn Lys Glu Ala Ile Leu Thr Ile Ala Glu His Ile
225                 230                 235                 240

Lys Asn Asn Lys Glu Ala Lys Phe Lys Ile Val Ala Ile Asn Val
                245                 250                 255

Pro Pro Met Pro Asn Leu Met His Leu Asp Thr Trp Leu Thr Met Val
                260                 265                 270

Asp Lys Asn Lys Phe Leu Tyr Ser Pro Asn Met Leu Ser Val Leu Lys
                275                 280                 285

Ile Trp Glu Ile Asp Leu Ser Lys Glu Ile Lys Met Val Glu Thr Ser
            290                 295                 300

Lys Pro Leu Ala Asp Val Leu Glu Ser Ile Ile Gly Glu Lys Pro Ile
305                 310                 315                 320

Leu Ile Pro Ile Ala Gly Glu Asn Ala Ser Gln Leu Asp Ile Asp Ile
                325                 330                 335

Glu Thr His Phe Asp Gly Thr Asn Tyr Leu Thr Ile Ala Pro Gly Val
                340                 345                 350

Val Val Gly Tyr Ser Arg Asn Val Lys Thr Glu Ala Ala Leu Lys Ala
            355                 360                 365

Ala Gly Val Thr Val Tyr Ser Phe Asp Gly Asn Gln Leu Ser Leu Gly
                370                 375                 380

Met Gly Ser Gly Arg Cys Met Ser Met Pro Leu Val Arg Glu Asp Val
385                 390                 395                 400

Lys

<210> SEQ ID NO 51
<211> LENGTH: 404
<212> TYPE: PRT
<213> ORGANISM: Mycoplasma alvi

<400> SEQUENCE: 51

Met Ser Ile Lys Glu Asn Gly Ile His Val Tyr Ser Glu Ile Gly Lys
1               5                   10                  15

Leu Arg Asp Val Leu Val His Arg Pro Gly Arg Glu Leu Asn Phe Leu
                20                  25                  30

Asp Pro Ser Arg Leu Asp Glu Leu Leu Phe Ala Ala Thr Leu Glu Pro
            35                  40                  45

Glu Thr Ala Arg Leu Glu His Asp Asn Phe Thr Thr Val Leu Lys Asn
        50                  55                  60

Gln Gly Val Asn Val Ile Glu Leu Ala Asp Leu Val Ser Gln Thr Tyr
65                  70                  75                  80

Ser Lys Val Asp Ser Lys Val Lys Lys Glu Phe Ile Asp Gln Tyr Leu
                85                  90                  95

Asn Glu Ala Thr Pro Lys Leu Thr Ser Glu Leu Ser Lys Lys Val Tyr
            100                 105                 110

Asp Phe Leu Thr Lys Gln Lys Ser Asn Arg Glu Met Val Asp Phe Met
```

```
            115                 120                 125
Met Gly Gly Ile Leu Ser Ser Asp Leu Asn Ile Lys Gly Gln Pro Tyr
    130                 135                 140

Leu Ile Val Glu Pro Met Pro Asn Leu Tyr Phe Thr Arg Asp Pro Phe
145                 150                 155                 160

Ala Ser Val Gly Asn Gly Ala Thr Ile His Trp Met Lys His Asn Val
                165                 170                 175

Arg Arg Arg Glu Val Leu Phe Ala Asn Phe Ile Phe Lys Tyr Asn Glu
            180                 185                 190

Arg Phe Gln Asn Thr Pro Lys Tyr Ile Thr Pro Thr Lys Gly Leu Asp
        195                 200                 205

Ile Glu Gly Gly Asp Val Phe Val Tyr Asn Lys Lys Thr Leu Val Val
    210                 215                 220

Gly Val Ser Glu Arg Thr Lys Met Glu Thr Ile Lys Glu Leu Ala Lys
225                 230                 235                 240

Asn Ile Ser Lys Asn Lys Glu Cys Thr Phe Thr Lys Ile Tyr Ala Ile
                245                 250                 255

Asn Val Pro Lys Met Pro Asn Leu Met His Leu Asp Thr Trp Leu Thr
            260                 265                 270

Met Leu Asp Tyr Asn Lys Phe Leu Tyr Ser Pro Asn Met Leu Ser Val
        275                 280                 285

Leu Lys Val Trp Glu Ile Asn Ile Ser Asn Asn Lys Val Ser Ala Pro
    290                 295                 300

Lys Glu Leu Asn Val Asn Leu Glu Lys Ala Leu Ser Met Ile Ile Gly
305                 310                 315                 320

Lys Lys Pro Ile Leu Ile Pro Val Ala Gly Ala Asn Ala Ser Gln Ile
                325                 330                 335

Asp Ile Asn Ile Glu Thr Asn Phe Asp Ala Thr Asn Tyr Leu Val Ile
            340                 345                 350

Glu Pro Gly Val Val Val Gly Tyr Ser Arg Asn Lys Lys Thr Glu Glu
        355                 360                 365

Ala Leu Val Lys Ala Gly Ile Lys Val Leu Pro Phe His Gly Asn Gln
    370                 375                 380

Leu Ser Leu Gly Met Gly Ser Ala Arg Cys Met Ser Met Pro Leu Tyr
385                 390                 395                 400

Arg Glu Asp Val

<210> SEQ ID NO 52
<211> LENGTH: 410
<212> TYPE: PRT
<213> ORGANISM: Mycoplasma penetrans

<400> SEQUENCE: 52

Met Ser Ser Ile Asp Lys Asn Ser Leu Gly Asn Gly Ile Asn Val Tyr
1               5                   10                  15

Ser Glu Ile Gly Glu Leu Lys Glu Val Leu Val His Thr Pro Gly Asp
            20                  25                  30

Glu Ile Arg Tyr Thr Ala Pro Ser Arg Leu Glu Glu Leu Leu Phe Ser
        35                  40                  45

Ala Val Leu Lys Ala Asp Thr Ala Ile Glu Glu His Lys Gly Phe Val
    50                  55                  60

Lys Ile Leu Gln Asn Asn Gly Ile Lys Val Ile Gln Leu Cys Asp Leu
65                  70                  75                  80

Val Ala Glu Thr Tyr Glu Leu Cys Ser Lys Glu Val Arg Asn Ser Phe
```

-continued

```
                85                  90                  95
Ile Glu Gln Tyr Leu Asp Glu Ala Leu Pro Val Leu Lys Lys Glu Ile
            100                 105                 110
Arg Pro Val Val Lys Asp Tyr Leu Leu Ser Phe Pro Thr Val Gln Met
            115                 120                 125
Val Arg Lys Met Met Ser Gly Ile Leu Ala Asn Glu Leu Asn Ile Lys
            130                 135                 140
Gln Asp Asn Pro Leu Ile Ile Asp Gly Met Pro Asn Leu Tyr Phe Thr
145                 150                 155                 160
Arg Asp Pro Phe Ala Ser Met Gly Asn Gly Val Ser Ile Asn Cys Met
            165                 170                 175
Lys Tyr Pro Thr Arg Lys Arg Glu Val Ile Phe Ser Arg Phe Val Phe
            180                 185                 190
Thr Asn Asn Pro Lys Tyr Lys Asn Thr Pro Arg Tyr Phe Asp Ile Val
            195                 200                 205
Gly Asn Asn Gly Thr Ile Glu Gly Gly Asp Ile Phe Ile Tyr Asn Ser
            210                 215                 220
Lys Thr Leu Val Ile Gly Asn Ser Glu Arg Thr Asn Phe Ala Ala Ile
225                 230                 235                 240
Glu Ser Val Ala Lys Asn Ile Gln Ala Asn Lys Asp Cys Thr Phe Glu
            245                 250                 255
Arg Ile Val Val Ile Asn Val Pro Pro Met Pro Asn Leu Met His Leu
            260                 265                 270
Asp Thr Trp Leu Thr Met Leu Asp Tyr Asp Lys Phe Leu Tyr Ser Pro
            275                 280                 285
Asn Met Met Asn Val Leu Lys Ile Trp Glu Ile Asp Leu Asn Val Lys
            290                 295                 300
Pro Val Lys Phe Val Glu Lys Lys Gly Thr Leu Glu Glu Val Leu Tyr
305                 310                 315                 320
Ser Ile Ile Asp Lys Lys Pro Ile Leu Ile Pro Ile Ala Gly Lys Gly
            325                 330                 335
Ala Asn Gln Leu Asp Ile Asp Ile Glu Thr His Phe Asp Gly Thr Asn
            340                 345                 350
Tyr Leu Thr Ile Ala Pro Gly Val Val Gly Tyr Glu Arg Asn Glu
            355                 360                 365
Lys Thr Gln Lys Ala Leu Val Glu Ala Gly Ile Lys Val Leu Ser Phe
            370                 375                 380
Asn Gly Ser Gln Leu Ser Leu Gly Met Gly Ser Ala Arg Cys Met Ser
385                 390                 395                 400
Met Pro Leu Ile Arg Glu Asn Leu Lys Lys
            405                 410

<210> SEQ ID NO 53
<211> LENGTH: 404
<212> TYPE: PRT
<213> ORGANISM: Mycoplasma fermentans

<400> SEQUENCE: 53

Met Lys Lys Ile Asn Val Tyr Ser Glu Tyr Gly Lys Leu Lys Glu Val
1               5                   10                  15
Leu Val His Thr Pro Gly Asp Glu Ile Arg Arg Ile Ala Pro Ser Arg
            20                  25                  30
Leu Asp Glu Leu Leu Phe Ser Ala Ile Leu Glu Pro Asp Ser Ala Ile
            35                  40                  45
```

| | | | | | | | | | | | | |
|---|---|---|---|---|---|---|---|---|---|---|---|---|
|Ala|Glu|His|Lys|Arg|Phe|Val|Gln|Leu|Leu|Lys|Asp|Asn|Gly|Ile|Lys|
|50| | | | |55| | | |60| | | | | | |

Val Ile Gln Leu Asp Glu Leu Phe Ala Lys Thr Phe Asp Leu Val Ser
65                  70                  75                  80

Glu Ser Val Lys Gln Ser Phe Ile Glu Arg Trp Leu Asp Glu Cys Glu
                85                  90                  95

Pro Lys Leu Asp Ala Thr Leu Arg Ala Lys Val Lys Glu Tyr Ile Leu
            100                 105                 110

Glu Leu Lys Ala Lys Ser Ser Lys Met Val Arg Val Met Met Ala
        115                 120                 125

Gly Ile Asp Lys Lys Glu Leu Gly Ile Glu Leu Asp Arg Asp Leu Val
    130                 135                 140

Val Asp Pro Met Pro Asn Leu Tyr Phe Thr Arg Asp Pro Phe Ala Ser
145                 150                 155                 160

Val Gly Asn Gly Ile Ser Leu His His Met Lys Tyr Val Thr Arg Gln
                165                 170                 175

Arg Glu Thr Ile Phe Ser Glu Phe Ile Phe Asp Asn Asn Leu Asp Tyr
            180                 185                 190

Asn Thr Val Pro Arg Trp Phe Asp Arg Lys Asp Glu Gly Arg Ile Glu
        195                 200                 205

Gly Gly Asp Val Phe Ile Tyr Ser Ala Asp Thr Leu Val Gly Val
    210                 215                 220

Ser Glu Arg Thr Asn Lys Glu Ala Ile Asn Val Met Ala Arg Lys Ile
225                 230                 235                 240

Ala Ala Asp Lys Glu Val Lys Phe Lys Arg Ile Tyr Ala Ile Asn Val
                245                 250                 255

Pro Pro Met Pro Asn Leu Met His Leu Asp Thr Trp Leu Thr Met Leu
            260                 265                 270

Asp Lys Asn Lys Phe Leu Tyr Ser Pro Asn Met Leu Ser Val Leu Lys
        275                 280                 285

Val Trp Arg Ile Asp Leu Asn Asp Pro Asp Phe Val Trp His Glu Ile
    290                 295                 300

Glu Gly Ser Leu Glu Glu Ile Leu Glu Gln Ile Ile Gly Met Lys Pro
305                 310                 315                 320

Ile Leu Ile Pro Ile Ala Gly Lys Gly Ala Ser Gln Leu Asp Ile Asp
                325                 330                 335

Ile Glu Thr His Phe Asp Gly Thr Asn Tyr Leu Thr Ile Ala Pro Ser
            340                 345                 350

Val Val Val Gly Tyr Ser Arg Asn Glu Lys Thr Glu Lys Ala Leu Lys
        355                 360                 365

Ala Ala Lys Val Lys Val Leu Ser Phe Glu Gly Asn Gln Leu Ser Leu
    370                 375                 380

Gly Met Gly Ser Ala Arg Cys Met Ser Met Pro Leu Ile Arg Glu Asp
385                 390                 395                 400

Ile Lys Lys Lys

<210> SEQ ID NO 54
<211> LENGTH: 404
<212> TYPE: PRT
<213> ORGANISM: Mycoplasma pneumoniae

<400> SEQUENCE: 54

Met Lys Tyr Asn Ile Asn Val His Ser Glu Ile Gly Gln Leu Gln Thr
1               5                   10                  15

-continued

Val Leu Val His Thr Pro Gly Asn Glu Ile Arg Arg Ile Ser Pro Arg
            20                  25                  30

Arg Leu Asp Asp Leu Leu Phe Ser Ala Val Ile Glu Pro Asp Thr Ala
        35                  40                  45

Ile Gln Glu His Gln Thr Phe Cys Gln Leu Leu Gln Glu Gln Asn Ile
50                  55                  60

Glu Val Val Gln Leu Thr Asp Leu Thr Ala Thr Thr Phe Asp Lys Ala
65                  70                  75                  80

Asn Ala Thr Ala Gln Asn Gln Phe Ile Glu Thr Trp Leu Asp Gln Ala
                85                  90                  95

Glu Pro Lys Leu Thr Pro Glu His Arg Lys Val Ala Lys Gln Tyr Leu
            100                 105                 110

Leu Glu Gln Lys Ala Lys Ser Thr Leu Ser Met Val Arg Ser Met Met
        115                 120                 125

Gly Gly Ile Asp Lys Arg Lys Val Ala Ala Ala Asn Thr Ile Asn Gly
        130                 135                 140

Asp Phe Leu Val Asp Pro Met Pro Asn Leu Tyr Phe Thr Arg Asp Pro
145                 150                 155                 160

Phe Ala Ser Ile Gly His Gly Ile Ser Ile Asn Arg Met Lys Tyr Leu
                165                 170                 175

Thr Arg Arg Arg Glu Thr Leu Phe Ala Ser Phe Ile Phe Ala Asn His
            180                 185                 190

Pro Ile Ile Ala Ala Arg Lys Phe Tyr Phe Lys Pro Ile Asp Met Gly
        195                 200                 205

Thr Ile Glu Gly Gly Asp Ile Phe Val Tyr Asp Gln Gln Thr Val Val
    210                 215                 220

Met Gly Leu Ser Glu Arg Thr Thr Glu Ala Ala Ile Asn Val Leu Ala
225                 230                 235                 240

Lys Lys Ile Gln Gln Asp Ser Ser Thr Ser Phe Lys Arg Ile Phe Val
                245                 250                 255

Ile Asn Val Pro Gln Leu Pro Asn Leu Met His Leu Asp Thr Trp Leu
            260                 265                 270

Thr Met Leu Asp Arg Asn Lys Phe Leu Tyr Ser Pro Asn Met Leu Ala
        275                 280                 285

Val Leu Lys Ala Trp Arg Ile Asp Phe Thr Asp Pro Ala Leu Lys Trp
    290                 295                 300

Asn Glu Ile Ala Gly Asp Leu Ser Thr Ile Leu His Thr Ile Ile Gly
305                 310                 315                 320

Gln Lys Pro Met Leu Ile Pro Ile Ala Gly Ala Asp Ala Asn Gln Thr
                325                 330                 335

Glu Ile Asp Ile Glu Thr His Phe Asp Gly Thr Asn Tyr Leu Thr Ile
            340                 345                 350

Ala Pro Ser Val Val Val Gly Tyr Ala Arg Asn Lys Leu Thr His Gln
        355                 360                 365

Thr Leu Glu Ala Ala Gly Val Lys Val Ile Ala Phe Lys Gly Asn Gln
    370                 375                 380

Leu Ser Leu Gly Met Gly Ser Ala Arg Cys Met Ser Met Pro Leu Val
385                 390                 395                 400

Arg Lys Pro Leu

<210> SEQ ID NO 55
<211> LENGTH: 414
<212> TYPE: PRT
<213> ORGANISM: Mycoplasma sp. CAG:877

<400> SEQUENCE: 55

```
Met Glu Lys Ile His Val Thr Ser Glu Ile Gly Pro Leu Lys Lys Val
1               5                   10                  15

Leu Leu His Arg Pro Gly Asn Glu Leu Leu Asn Leu Thr Pro Asp Thr
            20                  25                  30

Leu Ser Arg Leu Leu Phe Asp Asp Ile Pro Tyr Leu Pro Asp Ala Ile
        35                  40                  45

Lys Glu His Asp Glu Phe Ala Asp Ala Leu Arg Ala Asn Gly Val Glu
    50                  55                  60

Val Val Tyr Leu Glu Asn Leu Met Ala Asp Val Leu Asp Leu Ser Asp
65                  70                  75                  80

Glu Ile Arg Asp Lys Phe Ile Lys Gln Phe Ile Tyr Glu Ala Gly Ile
                85                  90                  95

Arg Thr Pro Lys Tyr Lys Tyr Leu Val Phe Asp Tyr Leu Asp Gln Ile
            100                 105                 110

Thr Asn Ser Lys Lys Leu Val Leu Lys Thr Met Glu Gly Ile Gln Ile
        115                 120                 125

Ser Asp Ile Pro Arg Arg Lys Arg Glu Ile Glu Lys Ser Leu Val Asp
    130                 135                 140

Leu Ile Glu Thr Glu Asp Glu Phe Ile Ala Asp Pro Met Pro Asn Leu
145                 150                 155                 160

Tyr Phe Thr Arg Asp Pro Phe Ala Ser Val Gly Glu Gly Ile Ser Leu
                165                 170                 175

Asn Lys Met Tyr Ser Val Thr Arg Asn Arg Glu Thr Ile Tyr Ala Glu
            180                 185                 190

Tyr Ile Phe Lys Tyr His Pro Asp Tyr Lys Asp Gln Ala Arg Leu Tyr
        195                 200                 205

Tyr Asp Arg Tyr Asn Pro Tyr His Ile Glu Gly Gly Asp Val Leu Asn
    210                 215                 220

Ile Asn Asp His Val Leu Ala Ile Gly Ile Ser Gln Arg Thr Thr Ala
225                 230                 235                 240

Glu Ala Ile Asp Gln Ile Ala Lys Asn Leu Phe Lys Asp Pro Glu Cys
                245                 250                 255

Lys Ile Asp Thr Ile Leu Ala Phe Asn Ile Pro Glu Ser Arg Ala Phe
            260                 265                 270

Met His Leu Asp Thr Val Phe Thr Gln Val Asp Tyr Asp Lys Phe Thr
        275                 280                 285

Tyr His Pro Gly Ile Met Gly Thr Leu Gln Val Phe Glu Ile Thr Glu
    290                 295                 300

Gly Asp Asp Pro Asn Ser Asp Glu Asp Leu Thr Val Thr Glu Ile Asn
305                 310                 315                 320

Ala Pro Leu Glu Glu Ile Leu Thr Lys Tyr Val Gly Arg Lys Val Thr
                325                 330                 335

Leu Ile Pro Cys Ala Gly Gly Asp Lys Val Ser Ala Glu Arg Glu Gln
            340                 345                 350

Trp Asn Asp Gly Ser Asn Thr Leu Cys Ile Ala Pro Gly Val Val Val
        355                 360                 365

Val Tyr Asp Arg Asn Asn Leu Thr Asn Ala Val Leu Arg Ser Tyr Gly
    370                 375                 380

Leu Lys Val Ile Glu Ile His Gly Ala Glu Leu Ser Arg Gly Arg Gly
385                 390                 395                 400

Gly Pro Arg Cys Met Ser Met Pro Leu Val Arg Glu Asp Ile
```

<210> SEQ ID NO 56
<211> LENGTH: 408
<212> TYPE: PRT
<213> ORGANISM: Mycoplasma sp. CAG:472

<400> SEQUENCE: 56

Met His Val Thr Ser Glu Ile Lys Lys Leu Lys Lys Val Leu Val His
1               5                   10                  15

Arg Pro Gly Lys Glu Leu Leu Asn Leu Thr Pro Asp Thr Leu Gly Arg
            20                  25                  30

Leu Leu Phe Asp Asp Ile Pro Tyr Leu Lys Asp Ala Ile Leu Glu His
        35                  40                  45

Asp Glu Phe Cys Gln Ile Leu Arg Asp Asn Asp Val Glu Val Val Tyr
    50                  55                  60

Leu Glu Asp Leu Met Ala Glu Thr Leu Asp Glu Asn Pro Gln Val Lys
65                  70                  75                  80

Pro Ser Phe Ile Arg Gln Phe Ile Tyr Glu Ala Gly Val Arg Thr Pro
                85                  90                  95

Lys Tyr Lys Asp Leu Leu Phe Asp Tyr Leu Met Ser Tyr Thr Asn Asn
            100                 105                 110

Lys Glu Leu Val Leu Lys Thr Met Glu Gly Ile Lys Val Ser Glu Val
        115                 120                 125

His Arg Asn Lys Gln Asp Ser Glu Tyr Ser Leu Val Asp Gln Ile Ser
    130                 135                 140

Glu Glu Thr Lys Phe Leu Ala Glu Pro Met Pro Asn Leu Tyr Phe Thr
145                 150                 155                 160

Arg Asp Pro Phe Ala Ser Val Gly Asp Gly Ile Ile Leu Asn Lys Met
                165                 170                 175

His Ser Val Thr Arg Ser Arg Glu Thr Ile Tyr Ala Tyr Tyr Ile Phe
            180                 185                 190

Asn Tyr His Pro Asp Tyr Met Asp Lys Val Pro Lys Tyr Tyr Asp Arg
        195                 200                 205

Glu Asn Pro Phe Ser Ile Glu Gly Gly Asp Val Leu Asn Leu Asn Glu
    210                 215                 220

His Thr Leu Ala Ile Gly Ile Ser Gln Arg Thr Ser Ala Glu Ala Ile
225                 230                 235                 240

Asp Leu Val Ala Lys Asn Met Phe Asn Asp Glu Lys Cys Asn Ile Asp
                245                 250                 255

Thr Ile Leu Ala Phe Lys Ile Pro Glu Cys Arg Ala Phe Met His Leu
            260                 265                 270

Asp Thr Val Phe Thr Gln Ile Asp Ile Asp Lys Phe Thr Tyr His Pro
        275                 280                 285

Gly Ile Met Asp Thr Leu Glu Val Phe Glu Ile Thr Lys Asn Glu Asp
    290                 295                 300

Asp Leu Asp Glu Val Arg Val Ile Lys Lys Glu Gly Ser Leu Glu Asn
305                 310                 315                 320

Ile Leu Glu Glu Tyr Leu Gly Ile Asp Ile Thr Leu Ile Pro Cys Ala
                325                 330                 335

Gly Gly Asp Lys Ile Ala Ser Glu Arg Glu Gln Trp Asn Asp Gly Thr
            340                 345                 350

Asn Thr Leu Cys Ile Ala Pro Gly Val Val Val Tyr Asn Arg Asn
        355                 360                 365

```
Asn Ile Thr Asn Glu Val Leu Arg Glu Lys Gly Ile Lys Val Ile Glu
    370                 375                 380
Met Asn Ser Ala Glu Leu Ser Arg Gly Arg Gly Gly Pro Arg Cys Met
385                 390                 395                 400
Ser Met Pro Leu Glu Arg Glu Asp
                405
```